(12) United States Patent
Shouldice et al.

(10) Patent No.: US 11,364,362 B2
(45) Date of Patent: Jun. 21, 2022

(54) METHODS AND SYSTEMS FOR SLEEP MANAGEMENT

(71) Applicant: RESMED SENSOR TECHNOLOGIES LIMITED, Clonskeagh (IE)

(72) Inventors: Redmond Shouldice, Clonskeagh (IE); Colin Lawlor, Wicklow (IE); Matthew Norton, Dublin (IE); David Mulligan, Dublin (IE); Stephen McMahon, Dublin (IE); Paul Phillips, Donaghadee (GB); Damien O'Rourke, Dublin (IE); Luke Gahan, Dublin (IE); Marc Lavelle, Dublin (IE); Conor Heneghan, San Diego, CA (US); Alberto Zaffaroni, Dublin (IE); Gareth McDarby, Wicklow (IE)

(73) Assignee: ResMed Sensor Technologies Limited

( * ) Notice: Subject to any disclaimer, the term of this patent is extended or adjusted under 35 U.S.C. 154(b) by 299 days.

(21) Appl. No.: 16/516,992

(22) Filed: Jul. 19, 2019

(65) Prior Publication Data

US 2020/0009349 A1 Jan. 9, 2020

Related U.S. Application Data

(60) Division of application No. 14/900,532, filed as application No. PCT/US2014/045814 on Jul. 8, 2014, (Continued)

(30) Foreign Application Priority Data

Jul. 8, 2013 (AU) ................................ 2013902516

(51) Int. Cl.
*A61M 21/02* (2006.01)
*A61B 5/00* (2006.01)
(Continued)

(52) U.S. Cl.
CPC ............. *A61M 21/02* (2013.01); *A61B 5/486* (2013.01); *A61B 5/4806* (2013.01); *G10L 15/26* (2013.01);
(Continued)

(58) Field of Classification Search
CPC ............. A61M 21/00–02; A61B 5/4806–4818
See application file for complete search history.

(56) References Cited

U.S. PATENT DOCUMENTS

D443,931 S 6/2001 Davey
6,468,234 B1 10/2002 Van der Loos et al.
(Continued)

FOREIGN PATENT DOCUMENTS

CN 101310690 A 11/2008
CN 101489478 A 7/2009
(Continued)

OTHER PUBLICATIONS

US 9,750,909 B2, 09/2017, Rapoport et al. (withdrawn)
(Continued)

*Primary Examiner* — Thaddeus B Cox
(74) *Attorney, Agent, or Firm* — Botos Churchill IP Law LLP

(57) ABSTRACT

A processing system includes methods to promote sleep. The system may include a monitor such as a non-contact motion sensor from which sleep information may be determined. User sleep information, such as sleep stages, hypnograms, sleep scores, mind recharge scores and body scores, may be recorded, evaluated and/or displayed for a user. The system may further monitor ambient and/or environmental conditions corresponding to sleep sessions. Sleep advice may be generated based on the sleep information, user queries and/or environmental conditions from one or more sleep sessions. Communicated sleep advice may include content (Continued)

to promote good sleep habits and/or detect risky sleep conditions. In some versions of the system, any one or more of a bedside unit 3000 sensor module, a smart processing device, such as a smart phone or smart device 3002, and network servers may be implemented to perform the methodologies of the system.

43 Claims, 59 Drawing Sheets

Related U.S. Application Data now Pat. No. 10,376,670, which is a continuation-in-part of application No. 29/490,436, filed on May 9, 2014, now Pat. No. Des. 765,256.

(60) Provisional application No. 62/018,289, filed on Jun. 27, 2014.

(51) Int. Cl.
*H04R 3/00* (2006.01)
*G10L 15/26* (2006.01)
*H04R 5/04* (2006.01)
*H04R 29/00* (2006.01)
*A61M 21/00* (2006.01)
*G10L 25/78* (2013.01)
*G10L 15/22* (2006.01)

(52) U.S. Cl.
CPC ........ *H04R 3/00* (2013.01); *A61B 2560/0242* (2013.01); *A61M 2021/0027* (2013.01); *A61M 2021/0083* (2013.01); *A61M 2021/0088* (2013.01); *A61M 2205/18* (2013.01); *A61M 2205/3303* (2013.01); *A61M 2205/3306* (2013.01); *A61M 2205/3368* (2013.01); *A61M 2205/3375* (2013.01); *A61M 2205/3584* (2013.01); *A61M 2205/502* (2013.01); *A61M 2205/52* (2013.01); *A61M 2205/581* (2013.01); *A61M 2205/583* (2013.01); *A61M 2205/80* (2013.01); *A61M 2230/40* (2013.01); *A61M 2230/63* (2013.01); *G10L 25/78* (2013.01); *G10L 2015/223* (2013.01); *H04R 5/04* (2013.01); *H04R 29/00* (2013.01); *H04R 2430/01* (2013.01)

(56) References Cited

U.S. PATENT DOCUMENTS

| | | |
|---|---|---|
| 6,878,121 B2 | 4/2005 | Krausman et al. |
| 6,928,031 B1 | 8/2005 | Kanevsky et al. |
| D598,551 S | 8/2009 | Miwa et al. |
| D603,515 S | 11/2009 | Blackwell et al. |
| D605,305 S | 12/2009 | Carter |
| 7,674,230 B2 | 3/2010 | Reisfeld |
| 7,720,531 B2 | 5/2010 | Schieb |
| 7,785,265 B2 | 8/2010 | Schätzl |
| 7,996,076 B2 | 8/2011 | Burns et al. |
| 8,083,682 B2 | 12/2011 | Dalal et al. |
| 8,280,501 B2 | 10/2012 | Guo et al. |
| 8,398,546 B2 | 3/2013 | Pacione et al. |
| D679,800 S | 4/2013 | Gusky et al. |
| D693,710 S | 11/2013 | Bachel et al. |
| 8,577,472 B2 | 11/2013 | Mashiach |
| 8,608,655 B2 | 12/2013 | Izumi |
| D700,343 S | 2/2014 | Liu |
| D707,827 S | 6/2014 | Tseng et al. |
| 8,956,295 B2 | 2/2015 | Ni et al. |
| D724,970 S | 3/2015 | Hasegawa et al. |
| 8,983,569 B2 | 3/2015 | Lee |
| D731,906 S | 6/2015 | Troutman et al. |
| 9,168,344 B2 | 10/2015 | Rapoport et al. |
| D753,313 S | 4/2016 | Kim et al. |
| 9,314,583 B2 | 4/2016 | Gavish |
| D765,256 S | 8/2016 | Bates et al. |
| 9,430,938 B2 | 8/2016 | Proud |
| 9,474,876 B1 | 10/2016 | Kahn et al. |
| 9,687,177 B2 | 6/2017 | Ramanan et al. |
| 9,993,166 B1 | 6/2018 | Johnson et al. |
| 10,004,451 B1 | 6/2018 | Proud |
| 10,009,581 B2 | 6/2018 | Proud |
| D834,200 S | 11/2018 | Bates et al. |
| 10,832,813 B2 | 11/2020 | Schätzl |
| 2006/0019224 A1 | 1/2006 | Behar et al. |
| 2008/0200869 A1 | 8/2008 | Bedingfield |
| 2008/0306351 A1 | 12/2008 | Izumi |
| 2009/0203972 A1 | 8/2009 | Heneghan et al. |
| 2009/0240311 A1* | 9/2009 | Andersen ............... H05B 47/16 607/90 |
| 2010/0099954 A1 | 4/2010 | Dickinson et al. |
| 2010/0102971 A1 | 4/2010 | Virtanen et al. |
| 2010/0131028 A1* | 5/2010 | Hsu ..................... A61B 5/7225 607/42 |
| 2010/0168812 A1 | 7/2010 | Blomqvist et al. |
| 2011/0015495 A1 | 1/2011 | Dothie et al. |
| 2011/0230790 A1 | 9/2011 | Kozlov |
| 2012/0092171 A1 | 4/2012 | Hwang et al. |
| 2012/0125337 A1 | 5/2012 | Asanoi |
| 2012/0296156 A1 | 11/2012 | Auphan |
| 2013/0310662 A1 | 11/2013 | Tsutsumi et al. |
| 2014/0024917 A1 | 1/2014 | Mcmahon et al. |
| 2014/0088373 A1 | 3/2014 | Phillips et al. |
| 2015/0038865 A1 | 2/2015 | Shigeto et al. |
| 2015/0230750 A1 | 8/2015 | Mcdarby et al. |
| 2016/0015315 A1 | 1/2016 | Auphan et al. |
| 2016/0151603 A1 | 6/2016 | Shouldice et al. |
| 2016/0157780 A1 | 6/2016 | Rimminen |
| 2016/0220783 A1 | 8/2016 | Garcia et al. |
| 2016/0239609 A1 | 8/2016 | Vuong et al. |
| 2016/0262690 A1 | 9/2016 | Chen et al. |
| 2016/0270716 A1 | 9/2016 | Heneghan et al. |
| 2016/0270718 A1 | 9/2016 | Heneghan et al. |
| 2016/0287168 A1 | 10/2016 | Patel et al. |
| 2016/0296164 A1 | 10/2016 | Garcia |
| 2017/0035351 A1 | 2/2017 | Prerau et al. |
| 2017/0055898 A1 | 3/2017 | Bandyopadhyay et al. |
| 2017/0055899 A1 | 3/2017 | Bandyopadhyay et al. |
| 2017/0127967 A1 | 5/2017 | Garcia et al. |
| 2017/0215789 A1 | 8/2017 | Mahadevan et al. |
| 2017/0224289 A1 | 8/2017 | Yamaji et al. |
| 2017/0312476 A1 | 11/2017 | Woo |
| 2018/0078198 A1 | 3/2018 | Reich et al. |

FOREIGN PATENT DOCUMENTS

| | | |
|---|---|---|
| CN | 104095615 A | 10/2014 |
| CN | 104720748 A | 6/2015 |
| CN | 105496356 A | 4/2016 |
| CN | 105748043 A | 7/2016 |
| CN | 105764409 A | 7/2016 |
| CN | 106419893 A | 2/2017 |
| CN | 106983515 A | 7/2017 |
| CN | 107106085 A | 8/2017 |
| EP | 2897526 A1 | 7/2013 |
| EP | 2830484 A1 | 2/2015 |
| EP | 3200691 A1 | 8/2017 |
| EP | 3232913 A1 | 10/2017 |
| EP | 3286577 A1 | 2/2018 |
| JP | 2001061819 A | 3/2001 |
| JP | 2004503284 A | 2/2004 |
| JP | 2007319238 A | 12/2007 |
| JP | 2009233027 A | 10/2009 |
| JP | 2011036649 A | 2/2011 |
| JP | 2013094340 A | 5/2013 |
| WO | 2007143535 A2 | 12/2007 |
| WO | 2008037020 A1 | 4/2008 |
| WO | 2008057883 A2 | 5/2008 |
| WO | 2010036700 A1 | 4/2010 |
| WO | 2010098836 A2 | 9/2010 |
| WO | 2012073183 A1 | 6/2012 |

(56) References Cited

FOREIGN PATENT DOCUMENTS

| | | | |
|---|---|---|---|
| WO | 2013086161 | A3 | 8/2013 |
| WO | 2013144893 | A1 | 10/2013 |
| WO | 2014047310 | A1 | 3/2014 |
| WO | 2016051305 | A1 | 4/2016 |
| WO | 2016076253 | A1 | 5/2016 |
| WO | 2016170005 | A1 | 10/2016 |
| WO | 2016193030 | A1 | 12/2016 |
| WO | 2017076324 | A1 | 5/2017 |
| WO | 2017093098 | A1 | 6/2017 |
| WO | 2017132726 | A1 | 8/2017 |
| WO | 2017134681 | A2 | 8/2017 |
| WO | 2017156421 | A1 | 9/2017 |
| WO | 2017185539 | A1 | 11/2017 |
| WO | 2018004279 | A1 | 1/2018 |
| WO | 2018053085 | A1 | 3/2018 |

OTHER PUBLICATIONS

Office Action for Japanese Patent Application No. 2019-230391, dated Sep. 8, 2021.
Office Action for Japanese Patent Application No. 2019-230391, dated Dec. 25, 2020.
"Extended European Search Report (includes Supplementary European Search Report and Search Opinion) received for European Patent Application No. 14823491.7, dated Feb. 3, 2017", 9 pages.
"International Search Report and Written Opinion received for PCT Patent Application No. PCT/US2014/045814, dated Dec. 31, 2014", 23 pages.
"Office Action received for Chinese Patent Application No. 201480049512.5, dated Dec. 1, 2017", 8 pages. (2 pages of English Translation and 6 pages of official copy).
"Office Action received for Corresponding Japanese Application No. 2016525436, dated Dec. 4, 2018", 14 pages. (9 pages of English Translation and 5 pages of Official Copy).
"Office Action received for Corresponding Japanese Application No. 2016-525436, dated May 8, 2018", 8 pages. (3 pages of English Translation and 5 pages of official copy).
Akerstedt, et al., "Sleep and Sleepiness in Relation to Stress and Displaced Work Hours", Physiology & Behavior, vol. 92, No. 1-2, 2007, pp. 250-255.
Buysse, et al., "Can an Improvement in Sleep Positively Impact on Health?", Sleep Medicine Reviews, vol. 14., 2010, pp. 405-410.
Dijk, Derk-Jan, "Slow-Wave Sleep Deficiency and Enhancement: Implications for Insomnia and its Management", The World Journal of Biological Psychiatry, vol. 11, No. (S1), May 31, 2010, pp. 22-28.
Epstein, Lawrence, "Improving Sleep a Guide to a Good Night's Rest", The Harvard Medical School Guide to a Good Night's Sleep, 2006, 48 pages.
Iber, et al., "The AASM Manual for the Scoring of Sleep and Associated Events", AASM Manual for Scoring Sleep, 2007, 51 pages.
O'Brien, Jennifer, "First Human Gene Implicated in Regulating Length of Human Sleep", UCSF, Aug. 13, 2009, 4 pages.
Ostrow, Nicole, "Not Enough Sleep Leads to Diabetes and Obesity", Available Online at: <http://www.idependent.ie/lifestyle/health/not-enough-sleep-leads-to-diabetes>, Dec. 24, 2012, 2 pages.
Patel, et al., "Association between Reduced Sleep and Weight Gain in Women", American Journal of Epidemiology, vol. 164, No. 10, Nov. 15, 2006, 14 pages.
Webster, Molly, "Can You Catch Up on Lost Sleep?", Available Online at: <https://www.scientificamerican.com/article/fact-or-fiction-can-you-catch-up-on-sleep/>, Scientific American, May 6, 2008, 2 pages.
Young, et al., "Epidemiology of Obstructive Sleep Apnea", American Journal of Respiratory and Critical Care Medicine, vol. 165, 2002, pp. 1217-1239.
Office Action for Chinese Patent Application No. 202010266854X, dated Mar. 30, 2022.

\* cited by examiner

 REPORT FOR YOUR FAMILY PRACTITIONER (PRIMARY CARE PHYSICIAN)

Name: Josephine Mary Smyth
Email: sample.email@gmail.com
DOB: 5th Apr 1963. Gender: F.
Prepared: 12th May 2014.
Sleep Period: Sun 28th Apr '14 to Sun 11th May '14 (two weeks)

SUMMARY

- You may be suffering from sleep apnea – you answered "yes" to 3 of 7 questions
- Your bedtime varies widely – poor sleep habits (sleep hygiene)
- You sleep 6hrs 40 mins on average – shorter than recommended

QUALITATIVE

You answered "yes" to:
You feel very tired during the day
Your neck size is greater than 16 inches
You snore You answered "no" to:
You do not have high blood pressure.
You have not been told that you stop breathing during sleep.
You do not suffer from any illness or condition that disturbs your sleep at night
You have not been told that you move a lot during your sleep.

You answered "no" to:
You do not have high blood pressure.
You have not been told that you stop breathing during sleep.
You do not suffer from any illness or condition that disturbs your sleep at night

BMI

Your BMI is 28.3 (weight 165 lbs, height 5' 4")

You may be suffering from sleep apnea

Sleep apnea is a significant health problem and, when left untreated, affects many serious chronic conditions including drug-resistant hypertension, heart disease, and diabetes. The good news is that treating sleep apnea has been shown to improve patients' quality of life and may help improve glucose control, lower blood pressure, and improve heart health. Talk to your doctor if your lack of sleep is affecting your lifestyle, especially if you suffer from any of these conditions.

Fig. 54a

 REPORT FOR YOUR FAMILY PRACTITIONER (PRIMARY CARE PHYSICIAN)

HABITS/LIFESTYLE

- You smoke 5-10 cigarettes on average each day.
- Number of times in a week you exercise for at least 30 minutes, 1-2 times (gentle intensity, and sometimes within three hours of going to bed).
  -- Your nightly sleep survey indicates 10 min exercise on average in the last two weeks.
- After lunchtime, you normally drink 3-4 caffeinated drinks
  -- Your nightly sleep survey indicates 1-2 caffeinated drinks on average in the last two weeks.
- You regularly consume alcohol. You normally consume 1-2 drinks in the evening.
  -- Your nightly sleep survey indicates 0-1 drinks on average in the last two weeks.

ENVIRONMENT

Your bedroom assessment noted that your bedroom was very warm at 81°F

STRESSORS

You noted that you feel stressed regularly.
Your nightly sleep survey indicates you have been highly stressed in the last two weeks.

BEDTIME

You noted that you take too long to fall asleep, and wake up in the middle of the night
Your bedtime varies from week to week.
You currently taking over the counter (OTC) medication to help you sleep 1-2 times per week.
You do not nap during the day

QUANTITATIVE

Bedtime
Your bedtime is varying widely. You should try to maintain a regular sleep schedule

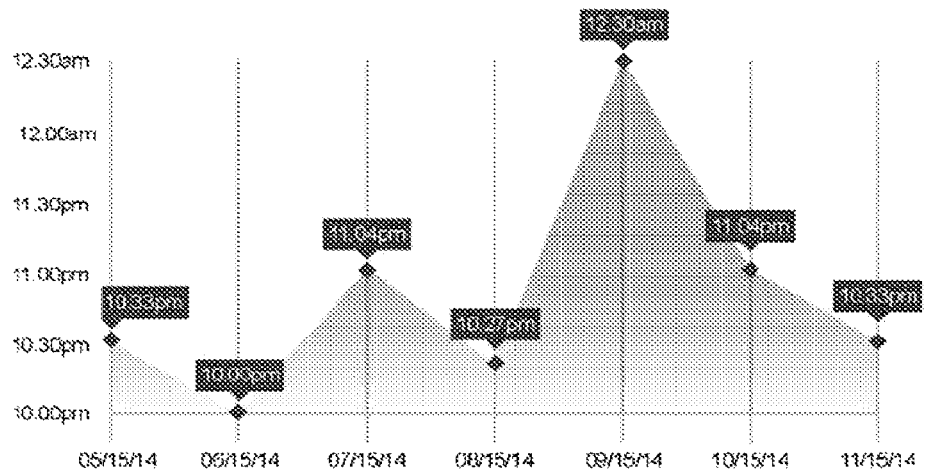

Fig. 54b

METHODS AND SYSTEMS FOR SLEEP MANAGEMENT

CROSS-REFERENCE TO RELATED APPLICATIONS

This application is a divisional of U.S. patent application Ser. No. 14/900,532 filed Dec. 21, 2015, now U.S. Pat. No. 10,376,670, which is a national phase entry under 35 U.S.C. § 371 of International Application No. PCT/US2014/045814 filed Jul. 8, 2014, published in English, which claims priority from U.S. Provisional Patent Application No. 62/018,289 filed on Jun. 27, 2014, and claims priority to U.S. Design Patent Application No. 29/490,436, filed on May 9, 2014, now U.S. Pat. No. D834,200,and which claims the benefit of the filing date of Australia Provisional Patent Application No. AU 2013902516 filed Jul. 8, 2013, all of the disclosures of which are incorporated herein by reference.

FIELD OF THE TECHNOLOGY

The present technology relates to systems and methods for sleep management and, may concern systems and methods for assisting a user to fall asleep.

BACKGROUND OF THE TECHNOLOGY

Poor sleep is a significant issue globally and impacts up to 60% of the adult population. The insufficient rest leads to underperformance at the work place. A tired person is also more likely to cause an accident, both in and outside of the workplace.

Sleep can be characterized by four distinct stages (phases) which change throughout the night. Sleepers move between the states, usually in an order.

There are typically several cycles of states (three to five a night) moving from NREM Stages 1 through 3 to REM, and then repeating. Each cycle lasts about 90-110 minutes. As it would be discussed later in the text, REM stage may be characterised by the so called Rapid Eye Movement of the user.

Stages 1-3 are known as non-REM (NREM) or quiet sleep. The new American Academy of Sleep Medicine guidelines groups NREM into three stages: N1, N2, and N3 (Iber et al. 2007). Usually a sleeper ascends from deep sleep briefly to light sleep before going into REM. These stages may be understood as follows:

Stage 1 ("N1"):
Transition between being awake and being asleep.
You lose awareness of your surroundings (feels like drowsiness when you are not completely awake), and can be easily woken from this state.
May experience generalized or localized muscle contraction associated with vivid visual imagery.
Sleep onset usually lasts 5-10 minutes.
Stage 2 ("N2"):
Sleeping, but not particularly deeply (easy to wake from this stage).
Usually lasts 10-25 minutes at a time.
Typically, you spend about half the night sleeping in this state.
Your heart rate, breathing, and brain activity slows down in this sleep stage and your body completely relaxes
Stages 3 ("N3")—SWS, formerly known as stages 3&4 (Iber et al. 2007):
Deep, slow wave sleep (SWS). This is believed to be the time where your body renews and repairs itself.
After falling asleep it might take up to half an hour to reach this deepest part of your sleep. It takes far more effort to wake you up.
Your breathing becomes more regular, blood pressure falls, and pulse rate slows.
The amount of deep sleep varies with age (Dijk 2010).
As you get older there is a decrease in deep sleep (and increase in lighter sleep).
You tend to sleep for a shorter length of time as you age. Therefore, you are more likely to wake up during the night as you get older (i.e., you are in light sleep for longer, from which you can more easily be disturbed by noise, movement of a bed partner, discomfort etc.). This is normal, and most older adults continue to enjoy their sleep.
Rapid Eye Movement (REM):
Your eyes move beneath closed lids, and you have most of your dreams. Your mind races, while your body is virtually paralyzed.
It is believed this stage facilitates learning and memory.
If you wake from this state, you tend to remember that you were dreaming. This can happen particularly as REM is followed by light sleep (i.e., starting a new cycle).
The first period of REM may only last 5 minutes or so, but progressively lasts longer over the course of a night, with the last period being up to 30 mins long.
REM sleep dominates in the final third of the night.
There are more changes in breathing pattern in REM as compared to slow wave sleep.
Healthy Sleep Healthy sleep is essential to a healthy life. Insufficient sleep for an extended period of time increases your risk for diabetes, obesity, depression, high blood pressure and even stroke.

Most healthy adults require 7-9 hours of sleep, with experts recommending 8 hours. Some people require only 6 hours, but others may require 10 hours of quality sleep. A University of California study from 2009 suggests that genetically some people can get by on 6 hours sleep—but this only applies to 3% of the population (O'Brien 2009). Most people experience difficulty getting to sleep or staying asleep at some point in their lives, particularly during times of stress or change. It is normal to have about 5% wakefulness during the night. All stages of sleep are important. However, a balance of deep, light and REM sleep is needed to feel at our best in the morning (Epstein & Mardon 2006).

A graph of sleep stages is referred to as a hypnogram (sometimes called 'sleep architecture' as the outline looks like the silhouette of a city skyline).

"Sleep Efficiency" provides a metric of how well a person has slept. This may be understood as working out the percentage of time spent in bed asleep each night. If a person spends 8 hours in bed, but only 4 of those hours are spent asleep, then the sleep efficiency may be very low at 50%. Sleep efficiency is based on the assumption that people go to bed in order to sleep.

Impacts on Sleep

A large number of publications have been dedicated to issues associated with sleep. Lack of sleep can affect important things like your personal relationships, productivity, and your overall mood. Lack of sleep can make people obese, and lead to health complications such as diabetes (Ostrow 2012; Patel 2006). If deep sleep is restricted, a person may wake up un-refreshed—no matter how long they have been in bed. It is believed that if you are sleep deprived, you tend to pass through light sleep rapidly to deep sleep, and spend more time in restorative deep sleep. If sleep is undisturbed after being deprived of REM sleep, a person will tend to enter REM earlier (and stay in this state for longer).

The literature notes that exercise is the only known way for an adult to increase the amount of deep sleep they get (Epstein & Mardon 2006).

Alcohol can make you drowsy and help you fall asleep, but suppresses REM sleep and is metabolised after a few hours so you may have more wakefulness.

It is thought that you can reach a point of severe tiredness where you no longer feel tired (but your decision making can be impaired). It may be possible to operate in this state, but your overall health could be affected.

Buysse et al. (2010) in "*Can an improvement in sleep positively impact on health?*", Sleep Medicine Reviews 14, notes; "Reports from a large number of studies document significant associations between sleep duration and various health problems such as cardiovascular events, risk of stroke, incident artery calcification, changes in inflammatory markers and many more." . . . . "There is a need for more detailed investigation into long-term outcomes and the potential for causality."

Åkerstedt et al. (2007) in "*Sleep and sleepiness in relation to stress and displaced work hours*", Physiology & Behavior 92 notes: "Sleep is an important factor in relation to accidents, long-term health and mortality." . . . "We have also looked at the concept of sleep quality and found it dependent on sleep duration, sleep continuity and content of sleep stages 3 and 4. Sleep is also clearly disturbed in people on long-term sick leave for burnout or in individuals with high burnout scores, in particular sleep fragmentation is increased and sleep efficiency and sleep stages 3 and 4 (SWS—deep sleep) decreased."

Dijk (2010), "*Slow-wave sleep deficiency and enhancement: Implications for insomnia and its management*", The World Journal of Biological Psychiatry; 11(S1) notes: "An age-related decline in SWS and SWA (slow-wave activity) is well established. In some studies, apprehension, depression and insomnia have been associated with reductions in SWS and SWA. Experimental reductions of SWS through SWS deprivation (without altering total sleep time or REM duration) have been reported to lead to an increase in daytime sleep propensity and reductions in performance. SWS and SWA are therefore thought to contribute to the recovery processes that occur during sleep."

Various methods of improving users sleep include physical exercise, breathing exercises and optimising the user's ambient conditions such as music, light, temperature etc. For example, the following approach may be taken to improve sleep:

1. Avoid caffeine at least four hours before bedtime as it can remain in the body for many hours.
2. Avoid smoking (or chewing tobacco) before bedtime and/or if you wake up during the night.
3. Avoid alcohol around bedtime; it may help you get to sleep, but it can also wake you up later in the night and disrupt REM sleep.
4. A light snack at bedtime may promote sleep—but avoid heavy meals. Foods containing high levels of tryptophan such as nuts, bananas, dairy, green leafy veg, eggs and soya products will promote good sleep.
5. Avoid vigorous exercise within two or so hours of bedtime (this may be subject dependent).
6. Keep your bedroom calm and comfortable, and at a comfortable temperature (e.g., between 65 deg F. and 75 deg F.).
7. Minimize noise and light in the bedroom; take advantage of light during the day—it will help regulate your body clock. Excessive light before bed may impact melatonin production.
8. Keep your bedroom mainly for sleeping and sex; try to avoid watching television, using your tablet or smartphone, listening to the radio, or eating in your bedroom.

A Regular Sleep Schedule

Normally, people should try to maintain a regular sleep schedule. For instance, if a person stays up late on Friday, sleeps late on Saturday, they are set up to sleep even later on Saturday night. This can give rise to 'Sunday night insomnia'.

In practice, this means trying to get up at the same time every day, even after a late night party. It also suggests that "sleeping in" at the weekend to make up sleep debt (Webster 2008) from the week may not be completely effective—especially if encountering 'Sunday night insomnia'.

Insomnia

Insomnia means that the sleep problem is chronic (persisting for at least a month), and interferes with your day-to-day activities, perhaps through fatigue, irritability, or just a persistent feeling of being fed-up with things.

There are four main insomnia symptoms:
Problems getting to sleep
Problems staying asleep
Waking up too early in the morning (and unable to get back to sleep)
Not feeling refreshed in the morning
Sleep deprivation can lead to:
Poor immune system
High blood pressure
Greater incidence of traffic and workplace accidents.

Sleep Disordered Breathing

The term sleep-disordered breathing (SDB) can refer to conditions where apnoeas (e.g., cessation of airflow for ten seconds or more) and hypopnoeas (e.g., decrease in airflow that is at least 30% for 10 seconds or more with an associated oxygen desaturation or arousal) are present during sleep. It is estimated that one in every five adults has SDB (Young et al. 2002).

A variety of monitoring and sleep improvement products have been (or are) on the market, including wearable devices such as wristwatches, armbands, head mounted devices, and non-contact products. Examples of these are the following brands: Sleeptracker watch (monitors sleep stages throughout the night and uses that data to determine the exact moment when a person should be awoken helping the person feel refreshed and energetic), Lark (provides sleep assessment and coaching), Larklife (a product similar to Lark, but in the form of a wristband), Jawbone Up (wristband, tracks hours slept, light and deep sleep, time of awakening), Nike Fuelband (wristband, activity and sleep tracker), Bodymedia (armband, tracks duration and quality of sleep), Zeo (Headband Sleep Management System allows for creating a chart of the quality of the user's sleep patterns and provides a daily personalised assessment and expert advice), Omron Sleepdesign (wireless, a full picture of sleep health is provided, alongside a customized summary of health tips and advice), Gear 4 Renew Sleepclock (similar to Omron's Sleepdesign, +optimised wakeup).

SUMMARY OF THE TECHNOLOGY

A system and a method of the present technology may detect sleep and provide feedback to a user concerning sleep.

Some versions of the technology may optionally include a device with any one or more of the following features:

It may sit by the user's bedside and unobtrusively record and analyze the user's sleep environment (light, sound and temperature, as well as humidity and/or air quality)

It may monitor and analyze the user's sleeping, breathing and heart rate patterns (sleep and cardiorespiratory patterns)

It may actively assist the user to get to sleep and stay asleep, by way of generating calming sounds to help adjust the user's breathing and ease the user to sleep. It may intelligently detect sleep conditions and gently switch off the sounds, after the user falls asleep.

It may chart the user's sleep patterns and send personalized recommendations via text or email to help improve the user's sleep. These customised advice "nuggets" are designed to help the person sleep better and may be based on clinical research.

It may provide expert advice articles and access to moderated forums.

It may communicate with the user's Smartphone to use its processing power for various levels of data processing, as well as to deliver the information to the user.

Examples of the technology may help users achieve noticeably better sleep by providing a system of sleep management. Some of the included features may include: recording of sleep patterns and bedroom environment; offering personalized recommendations to help improve the user's sleep environment and habits; offering personalized recommendations with regards to the user's day and evening routines with a customized personal advice program to help set the user up for better sleep; offering specific recommendations to the user in order to allow the user to relax more easily and fall asleep; waking up the user in a way that allows the user to feel more refreshed and/or connecting the user to resources should the user need further help.

In some of its more specific aspects, the proposed technology helps the user relax by tracking user's breathing (also respiration) rate and guiding the user to reduce their breathing rate. Such an encouragement helps the user to slow their breathing, fall asleep faster and better recover from the stresses of the day. A 'Mind Clear' feature helps the user to clear their mind of thoughts that might otherwise keep the user awake. The system can record the user's sleep, breathing and heart rate patterns using a bio motion sensor, thus allowing a review of the user's level of physical (generally associated with the amount of deep sleep) & mental (generally associated with the amount of REM sleep) recharge. This can be then visualised by a simple number or by a chart plot on the screen of a PC or a smart device, such as a phone or a tablet. The system and method measure environmental parameters of the bedroom using sensors such as light, sound, temperature, humidity and/or air quality. The proposed system and method also deliver customised personal advice to help improve the user's sleep based on personal sleep data, trended data, de-identified population data, bedroom environment data and external environmental data.

An overall sleep management system and method is proposed that can assist in monitoring and improving the user's sleep.

Some versions of the present technology may be implemented as medical devices used in the diagnosis, amelioration, treatment, and/or prevention of sleep and/or respiratory disorders and may have one or more of improved comfort, cost, efficacy, ease of use and manufacturability.

Some versions of the present technology may include an apparatus for inducing relaxation in a user. The apparatus may include a speaker to play a sound of a sound file; and a processor coupled with the speaker. The processor may be configured to repeatedly play the sound file through the speaker and to repeatedly adjust a period of the sound file. The sound file may include an exhalation cue portion and an inhalation cue portion. The exhalation cue portion and the inhalation cue portion may be in a fixed ratio throughout repeated playing and repeated adjustment of the sound file. A ratio of the exhalation cue to the inhalation cue may be about 1 to 1.4. In some cases, the repeated playing and the repeated adjustment of the sound file may comprise initially playing the sound file with the sound file set to a first time length for a first period of playing time and thereafter increasing the first time length of the file to a second longer time length and repeatedly playing the sound file with the second longer time length for a second period of playing time.

The apparatus may be configured to repeatedly play and repeatedly adjust the sound file until the adjustment of the period of the sound file meets a threshold. The threshold may comprise a repetition per minute minimum threshold. The processor may be further configured to gradually reduce volume of the played sound file through the speaker during a further period of time, after the adjustment of the period of the sound file meets the threshold.

The apparatus may further include a movement sensor and the processor may be further configured to determine a measure of respiration with the movement sensor, and/or to set the period of the sound file as a function of the determined measure of respiration.

In some cases, the processor may set a period of the sound file as a function of the measure of respiration once only, before initiating the repeated adjusting of the period of the sound file; and/or the repeated adjusting of the period of the sound file may include an adjustment of the period of the sound file by a fixed predetermined change.

Optionally, the processor may be further configured to determine a measure of sleep or wake of the user, with the movement sensor. The processor may be further configured to gradually reduce volume of the played sound file through the speaker during a further first period of time, if sleep is detected, and either delay a gradual reduction in volume or gradually reduce volume of the played sound file through the speaker during a further second period of time, if awake is detected, the further second period of time being different from the further first period.

In some cases, each adjustment of the period of the sound file may substantially maintain pitch of any sounds of the sound file.

Some versions of the present technology may include a method of a processor for an apparatus for inducing relaxation in a user. The method may include with a processor, repeatedly playing a sound file through a speaker and repeatedly adjusting a period of the sound file. The sound file may include an exhalation cue portion and an inhalation cue portion, the exhalation cue portion and the inhalation cue portion being in a fixed ratio throughout repeated playing and repeated adjustment of the sound file. The ratio of the exhalation cue to the inhalation cue may be about 1 to 1.4. The repeated playing and the repeated adjusting of the sound file may comprise initially playing the sound file with the sound file set to a first time length for a first period of playing time and thereafter increasing the first time length of the file to a second longer time length and repeatedly playing the sound file with the second longer time length for a second period of playing time. The processor may repeatedly play and repeatedly adjust the sound file until the adjustment of the period of the sound file meets a threshold. The threshold comprises a repetition per minute minimum threshold. The processor may gradually reduce volume of the played sound file through the speaker during a further period of time after the adjustment of the period of the sound file meets the threshold. The processor may determine a measure of respiration with a movement sensor, and the processor may set a period of the sound file as a function of the determined measure of respiration. Optionally, the processor may set a period of the sound file as a function of the measure of respiration once only, before initiating the repeated adjusting of the period of the sound file and wherein the repeated adjusting of the period of the sound file comprises an adjustment of the period of the sound file by a fixed predetermined change.

In some cases, the processor may determine a measure of sleep or wake of the user with a movement sensor, and the processor may gradually reduce volume of the played sound file through the speaker during a further first period of time, if sleep is detected; and either gradually reduce volume of the played sound file through the speaker during a further second period of time, the further second period being different from the further first period, or delays a gradual reduction in volume, if awake is detected. Optionally, in some/any cases each adjustment of the period of the sound file may maintain pitch of any sounds of the sound file.

Some versions of the present technology may include an apparatus to promote sleep of a user. The apparatus may include a microphone to sense voice of the user. It may include a processor coupled with the microphone and configured to receive signals generated by a sensor and indicative of motion of a user. The processor may be further configured to analyze the received signals and detect sleep information from the signals, and, upon receiving an activation signal, to record a voice sound message of the user and store data of the voice sound message in a memory coupled to the processor, whereby a user may record thoughts so as to clear a mind of the user and promote sleep.

In some cases, the processor may be further configured to play the recorded voice sound message with a speaker of the apparatus. The processor may be further configured to control a conversion of the voice sound message to a text message and store it as data in the memory. The processor may be configured to initiate transfer of the text message to the user. The transfer may comprise an SMS or an email communication. In some cases, the activation signal comprises a voice activation signal, whereby the processor, with the microphone, detects a voice command of the user to initiate a voice recording process.

Some versions of the present technology may include a method of a processor for promoting sleep of a user. The method may involve with a processor, analyzing signals from a motion sensor to detect sleep information from the signals. The method may involve with the processor, upon receiving an activation signal, recording by a microphone a voice sound message of the user and storing data of the voice sound message in a memory coupled to the processor. The method may permit a user to record thoughts so as to clear a mind of the user and promote sleep. The method may involve playing, with the processor, the recorded voice sound message through a speaker. The method may involve with a processor controlling a conversion of the voice sound message to a text message and storing it as data in the memory. The method may involve with a processor initiating a transfer of the text message to the user. The transfer may be an SMS or an email communication, for example. In some cases of the method the activation signal may comprise a voice activation signal, whereby the processor detects, with a microphone, a voice command of the user to initiate a voice recording process.

Some versions of the present technology include an apparatus to promote sleep of a user. The apparatus may include an alarm device to generate an alarm to wake user. The apparatus may include a processor configured to prompt a user to input a wake-up time and a wake-up time window, the wake-up time window ending with the wake-up time. The processor of the apparatus may be configured to receive signals from a motion sensor, the signals being indicative of motion of the user. The processor of the apparatus may be configured to detect sleep information with an analysis of the received signals indicative of motion. The processor of the apparatus may be configured to trigger activation of the alarm device as a function of the sleep information and a function of the wake-up window and the wake-up time, wherein the function of the sleep information and the function of the wake-up window and the wake-up time comprise detecting the user being in a light sleep stage during the wake-up window.

In some cases, the function of the sleep information may further comprise presence in a light sleep stage for at least a certain length of time or number of epochs. The function of the sleep information may further comprise satisfying a minimum amount of total sleep time. Optionally, the processor may be further configured to trigger activation of the alarm device with a probability function configured to randomize activation of the alarm. The processor may be further configured to trigger activation of the alarm device upon detection of absence of the user during the wake-up window. The processor may be further configured to trigger activation of the alarm device upon detection of an awake state of the user during the wake-up window. The alarm device may be configured to generate any one or more of an audible sound alarm and a visible light alarm. The function of the wake-up window and the wake-up time may comprise a plurality of comparisons of current time with the wake-up window and the wake-up time to ensure triggering of the alarm within the wake-up window and by the wake-up time.

Some versions of the present technology may involve a method of processor to promote sleep of a user. The method may involve with a processor coupled, e.g., wirelessly, with a motion sensor prompting a user to input a wake-up time and a wake-up time window, the wake-up time window ending with the wake-up time. The method may involve with the processor receiving signals from a motion sensor, the signals being indicative of motion of the user. The method may involve with the processor detecting sleep information with an analysis of the signals indicative of motion. The method may involve with the processor triggering activation of an alarm device as a function of the sleep information and a function of the wake-up window and the wake-up time. The function of the sleep information and the function of the wake-up window and the wake-up time may comprise detecting the user being in a light sleep stage during the wake-up window.

In some cases, the function of the sleep information may further comprise presence in a light sleep stage for at least a certain length of time. The function of the sleep information further may comprise satisfying a minimum amount of total sleep time. The method may involve the processor triggering activation of the alarm device with a probability function that randomizes activation of the alarm. The processor may evaluate whether to trigger activation of the alarm device with detection of absence of a user during the wake-up window. The processor may evaluate whether to trigger activation of the alarm device with detection of an awake state of the user during the wake-up window. The alarm device may generate any one or more of an audible sound alarm and a visible light alarm. Optionally, the function of the wake-up window and the wake-up time may involve a plurality of comparisons of current time with the wake-up window and the wake-up time to ensure triggering of the alarm within the wake-up window and by the wake-up time.

Some versions of the present technology may include an apparatus to promote a user's sleep. The apparatus may include a processor adapted to access measured data representing user movement detected by a movement sensor. The processor may be configured to process the measured data and determine sleep factors with features derived from the measured data. The processor may be further configured to generate one or more indicators including a sleep score indicator, mind recharge indicator and body recharge indicator based on the determined sleep factors. The apparatus may include a display for displaying the one or more indicators. The processor may be configured to control the display of the sleep score and wherein the sleep factors from which the sleep score is based may be include two or more of total sleep time, deep sleep time, REM sleep time and light sleep time, wake after sleep onset time and sleep onset time. In some cases, the features may include time domain statistics and/or frequency domain statistics.

Optionally, the sleep score may include a total having a plurality of component values, each component value determined with a function of a measured sleep factor and a predetermined normative value for the sleep factor. The function may include a weighting variable varying between 0 and 1 and wherein the weighting is multiplied by the predetermined normative value. The function of at least one sleep factor for determining a component value may be an increasing function of the measured sleep factor such as when the at least one sleep factor is one of total sleep time, deep sleep time, REM sleep time and light sleep time. In some cases, the function of at least one sleep factor for determining a component value may be an initially increasing and subsequently decreasing function of the measured sleep factor, such as when the at least one sleep factor is REM sleep time. The function of at least one sleep factor for determining a component value may be a decreasing function of the measured sleep factor, such as, when the at least one sleep factor is one of sleep onset time and wake after sleep onset time.

Optionally, the display of the sleep score may include displaying a sleep score total. The display of the sleep score may include displaying a graphic pie chart, the graphic pie chart divided about its periphery into segments, each segment size about the periphery being attributed to a predetermined normative value for each sleep factor, each segment being filled radially in accordance with a function of a respective measured sleep factor and the predetermined normative value for the respective sleep factor. Optionally, in some cases, a predetermined normative value for total sleep time is 40, a predetermined normative value for deep sleep time is 20, a predetermined normative value for REM sleep time is 20, a predetermined normative value for light sleep time is 5, a predetermined normative value for wake after sleep onset time is 10 and/or a predetermined normative value for sleep onset is 5.

In some cases, the processor may be further configured to access detected ambient parameters including ambient light and or sound, to adjust settings of the apparatus during at least some operations of the apparatus, the adjusted settings comprising screen brightness and/or sound volume. The processor may control a display of the mind recharge indicator, the mind recharge indicator being based on REM sleep time. The mind recharge indicator may include a function of a REM sleep factor and a predetermined normative value for the REM sleep factor. The function of the REM sleep factor and a predetermined normative value for the sleep factor may include an increasing and decreasing function of REM sleep time.

In some cases, the mind recharge indicator may be displayed as a graphic indicator relating measured REM sleep time to a normative REM sleep time as a percentage, the graphic indicator having an appearance of a segmented battery proportionally filled according to the percentage. The processor may be control a display of the body recharge indicator and the body recharge indicator may be based on deep sleep time. Optionally, the body recharge indicator may include a function of a deep sleep factor and a predetermined normative value for the deep sleep factor. The function of the deep sleep factor and a predetermined normative value for the deep sleep factor may include an increasing function of deep sleep time. The body recharge indicator may be displayed as a graphic indicator relating measured deep sleep time to predetermined normative deep sleep time as a percentage, the graphic indicator having an appearance of a segmented battery proportionally filled according to the percentage.

Some versions of the present technology may involve a method to promote sleep with a processor adapted to access measured data representing user movement detected by a movement sensor. The method may involve processing the measured data and determining sleep factors with features derived from the measured data. The method may involve generating one or more indicators including a sleep score indicator, mind recharge indicator and body recharge indicator based on the determined sleep factors. The method may involve controlling a display of the one or more indicators.

The display may include the sleep score and wherein the sleep factors from which the sleep score is based include two or more of total sleep time, deep sleep time, REM sleep time and light sleep time, wake after sleep onset time and sleep onset time. Optionally, the features may include time domain statistics and frequency domain statistics. The sleep score may include a total having a plurality of component values, each component value determined with a function of a sleep factor and a predetermined normative value for the sleep factor. The function may include a weighting variable varying between 0 and 1 and wherein the weighting is multiplied by the predetermined normative value. The function of at least one sleep factor for determining a component value may be an increasing function, such as when the at least one sleep factor is one of total sleep time, deep sleep time, REM sleep time and light sleep time. The function of at least one sleep factor for determining a component value may be an increasing and decreasing function, such as when the at least one sleep factor is REM sleep time. The function of at least one sleep factor for determining a component value may be a decreasing function, such as when The at least one sleep factor is one of sleep onset time and wake after sleep onset time.

The method may involve displaying the sleep score that includes a sleep score total. The displayed sleep score may involve displaying a graphic pie chart, the graphic pie chart divided about its periphery into segments, each segment size about the periphery being attributed to a predetermined normative value for each sleep factor, each segment being filled radially in accordance with a function of each sleep factor and the predetermined normative value for the sleep factor. Optionally, in some cases a predetermined normative value for total sleep time is 40, a predetermined normative value for deep sleep time is 20, a predetermined normative value for REM sleep time is 20, a predetermined normative value for light sleep time is 5, a predetermined normative value for wake after sleep onset time is 10 and/or a predetermined normative value for sleep onset is 5.

The method may involve a display including the mind recharge indicator where the mind recharge indicator may be based on measured REM sleep time. The mind recharge indicator may be determined as a function of a measured REM sleep factor and a predetermined normative value for the REM sleep factor. The function of the REM sleep factor and a predetermined normative value for the sleep factor may include an initially increasing and subsequently decreasing function of the measured the measured REM sleep time. The mind recharge indicator may be a graphic indicator relating measured REM sleep time to a normative REM sleep time as a percentage. The graphic indicator optionally may have an appearance of a segmented battery proportionally filled according to the percentage.

The display may include the body recharge indicator, the body recharge indicator optionally being based on measured deep sleep time. The body recharge indicator may be determined as a function of a measured deep sleep factor and a predetermined normative value for the deep sleep factor. The function of the deep sleep factor and a predetermined normative value for the deep sleep factor may include an increasing function of deep sleep time. The body recharge indicator may be a graphic indicator relating measured deep sleep time to predetermined normative deep sleep time as a percentage. The graphic indicator may have an appearance of a segmented battery proportionally filled according to the percentage.

Some versions of the present technology may involve an apparatus to promote sleep with one or more processors. The one or more processors may be configured to access measured data representing user movement detected by a movement sensor. The one or more processors may be configured to process the measured data and determine sleep factors with features derived from the measured data. The one or more processors may be configured to access detected environmental condition data from one or more environmental sensors. The one or more processors may be configured to generate and display a sleep hypnogram. The sleep hypnogram may plot sleep stages over time for a sleep session. The sleep hypnogram may further include at least one detected environmental condition plotted in temporal association with a sleep stage or a transition between sleep stages. The detected environmental condition may include any one of a light event, a sound event and a temperature event. The detected environmental condition may include an event that corresponds to a detected sleep disturbance. The detected sleep disturbance may include a wake after sleep onset period. The apparatus may further include the movement sensor and/or the one or more environmental sensors, the sensor(s) coupled, such as wirelessly, with the processor to transfer data representing detected signals from the sensor(s) to the processor.

Some versions of the present technology may involve a method of a processor for promoting sleep. The method may involve receiving, from a movement sensor, measured data representing user movement. The method may involve processing the measured data and determining sleep factors with features derived from the measured data. The method may involve accessing detected environmental condition data from one or more environmental sensors. The method may involve generating a sleep hypnogram, the sleep hypnogram plotting sleep stages over time for a sleep session. The method may involve controlling a display to present the sleep hypnogram.

Optionally, the method may involve presenting information of the detected environmental condition in temporal association with a sleep stage in the hypnogram. The detected environmental condition may include any one of a light event, a sound event and a temperature event. The detected environmental condition may include an event that corresponds to a detected sleep disturbance. The detected sleep disturbance may include a wake after sleep onset period. The method may further involve detecting the user movement with the movement sensor and/or detecting the environmental condition with the one or more environmental sensors.

Some versions of the present technology may involve an apparatus to promote sleep. The apparatus may include a display. The apparatus may include a processor coupled with the display. The processor may be configured to access measured data representing user movement detected by a movement sensor. The processor may be configured to process the measured data and determine sleep factors with features derived from the measured data. The processor may be further configured to prompt for input of user parameters comprising one or more of daily caffeine consumption, daily alcohol consumption, daily stress level and daily exercise amount. The processor may be further configured to display a temporal correlation for a plurality of sleep sessions between one or more determined sleep factors and one or more of the input user parameters. In some cases, the processor may be configured to prompt the user to select the one or more sleep factors and the one or more input user parameters for the display. Optionally, one of the determined sleep factor may include a total sleep time for a sleep session. In some cases, the processor may be further configured to display a temporal correlation for a plurality of sleep sessions between one or more determined sleep factors and environmental data representing one or more ambient sleep conditions including ambient sound level, ambient light level, ambient temperature level, ambient air pollution level and weather conditions at a location of the user. The processor may be further configured to access weather data based on detecting a location of the apparatus. In some versions, the apparatus may be further configured to generate the temporal correlation for a plurality of sleep sessions between one or more determined sleep factors, one or more input user parameters and one or more ambient sleep conditions, including ambient sound level, ambient light level, ambient temperature level, ambient air pollution level and weather conditions at a location of the user.

Some versions of the present technology may involve a method of a processor to promote sleep. The method may involve with a processor accessing measured data representing user movement detected by a movement sensor. The method may involve with the processor processing the measured data to determine sleep factors with features derived from the measured data. The method may involve with the processor prompting for input of user parameters comprising one or more of daily caffeine consumption, daily alcohol consumption, daily stress level and daily exercise amount. The method may involve with the processor displaying on a display a temporal correlation for a plurality of sleep sessions between one or more determined sleep factors and one or more of the input user parameters.

Optionally, the method may involve with the processor prompting the user to select the one or more input user parameters for displaying of the temporal correlation. The determined sleep factor may include a total sleep time for a sleep session. The method may involve generating the temporal correlation for a plurality of sleep sessions between one or more determined sleep factors, one or more of the input user parameters and one or more ambient sleep conditions including ambient sound level, ambient light level, ambient temperature level, ambient air pollution level and weather conditions at a location of the user.

Some versions of the present technology may involve a system to promote sleep. The system may include one or more processors, such as one or more processors of a server(s), as one or more processors of a smart device(s) (e.g., mobile phone), as one or more processors of computer(s) or any combination of such processors. The one or more processors may be configured to access measured sleep data representing user movement detected by a movement sensor, and to process the measured sleep data to determine sleep factors with features derived from the measured data. The one or more processors may be configured to access measured environmental data representing ambient sleep conditions. The one or more processors may be configured to prompt for input of user lifestyle data on a sleep session-by-sleep session basis. The one or more processors may be configured to evaluate the sleep factors to detect a sleep issue. The system may optionally include a transmitter configured to transmit at least some of at least one of: the measured sleep data, data of the determined sleep factors, the measured environmental data and the input user lifestyle data, so as to facilitate evaluation of the transmitted data and selection of a likely cause, or a most likely cause, of the detected sleep issue. The system may optionally include a receiver configured to receive one or more advice messages associated with the selected cause, the advice messages including advice content for promoting sleep. The system may optionally include a display to display the received one or more advice messages to a user.

Optionally, one or more advice messages may comprise a series of advice messages over time consecutively generated upon continued detection of the sleep issue. The measured environmental data may comprise one or more of detected light, detected sound and detected temperature. The sleep factors may comprise one or more of sleep latency, REM sleep time, deep sleep time and number of sleep interruptions. A detected sleep issue may comprise any one or more of a REM time too short condition, a REM time too long condition, a REM time fragmented condition, a Deep sleep time too short condition, a Deep sleep time too long condition and a Deep sleep time fragmented condition. A detected sleep issue may be that a user's sleep had too many interruptions. In some cases, the evaluation of the measured environmental data and the input user lifestyle data to select one as a most likely cause of the detected sleep issue may involve calculating probabilities. Optionally, in the system, generation of an advice message may include triggering a push notification. In some cases, the selected most likely cause of the detected sleep issue, associated with the received advice, may be further based on an evaluation of historical sleep data to detect a sleep trend.

In some cases, the one or more processors and/or the receiver may be configured to receive data indicative of a result of a triage process. The triage process may involve a probability determination based on the detected sleep issue to determine a risky sleep condition. The probability determination may include calculating a probability of one or more of a risk of sleep apnea, a risk of snoring and a risk of chronic insomnia. In some cases, the one or more processors and/or the receiver may be further configured to receive a generated report with information concerning the risky sleep condition to facilitate access to a sleep health specialist. In some versions, the one or more processors and/or the transmitter may be further configured to transmit data indicative of a user's location and receive one or more advice messages based on the transmitted location data. Optionally, a received advice message may include jet lag advice.

Some versions of the present technology may involve a method for an electronic system to promote sleep with one or more processors. The one or more processors may be in a server(s), a smart device(s) (e.g., mobile phone), a computer(s) or any combination of such processors. The method may include accessing measured data representing user movement detected by a movement sensor. The method may include processing the measured data to determine sleep factors with features derived from the measured data. The method may include accessing measured environmental data representing ambient sleep conditions. The method may include prompting for input of user lifestyle data on a sleep session-by-sleep session basis. The method may include evaluating the sleep factors to detect a sleep issue. The method may include transmitting to a remote location at least some of at least one of the following types of data: the measured data, data of the determined sleep factors, the measured environmental data and the input user lifestyle data, to facilitate evaluation of the transmitted data and selection of a likely cause, or a most likely cause, of the detected sleep issue. The method may include receiving one or more generated electronic advice messages associated with the selected cause. The advice messages may include advice content for promoting sleep. The method may include displaying the received electronic advice messages.

Optionally, the environmental data may include one or more of detected light, detected sound and detected temperature. The sleep factors may include one or more of: REM sleep time; deep sleep time; too many sleep interruptions; a REM time too short condition; a REM time too short or too long condition; a REM time fragmented condition; a Deep sleep time too short condition; a deep sleep time too long condition; and a deep sleep time fragmented condition. The evaluation of the measured environmental data and the input user lifestyle data to select one as a most likely cause of the detected sleep issue may further include evaluating historical sleep data to detect a sleep trend.

The method may include executing a triage process. The triage process may involve determining probabilities based on the detected sleep issue to determine a risky sleep condition. The determined probabilities may include a probability of one or more of a risk of sleep apnea, a risk of snoring and a risk of chronic insomnia. The method may include receiving a report indicative of a result of a triage process. The report may include information concerning the risky sleep condition to facilitate access to a sleep health specialist. In some cases, at least one of the one or more advice messages is based on a detected location or on a detected change in location. Optionally, a generated advice message may include jet lag advice.

Some versions of the present technology may include a method for an electronic system to promote sleep. The method may involve accessing, with one or more processors, measured data representing user movement detected by a movement sensor, and/or sleep factors with features derived from the measured data. The method may involve accessing, with one or more processors, measured environmental data representing ambient sleep conditions. The method may involve accessing, with one or more processors, input user lifestyle data obtained on a sleep session-by-sleep session basis. The method may involve evaluating, with one or more processors, the sleep factors to detect a sleep issue. The method may involve evaluating, with one or more processors, the measured environmental data and the input user lifestyle data to select one as a most likely cause of the detected sleep issue. The method may involve generating one or more electronic advice messages associated with the selected one, the advice messages including advice content for promoting sleep.

Optionally, the generating one or more advice messages may involve generating a series of advice messages over time consecutively upon continued detection of the sleep issue. The environmental data may include one or more of detected light, detected sound and detected temperature and wherein the sleep factors comprises one or more of sleep latency, REM sleep time, deep sleep time and number of sleep interruptions. A detected sleep issue may include any one or more of: a REM time too short condition; a REM time too long condition; a REM time fragmented condition; a Deep sleep time too short condition; a deep sleep time too long condition; deep sleep time fragmented condition; and too many sleep interruptions. The evaluating of the measured environmental data and the input user lifestyle data to select one as a most likely cause of the detected sleep issue may involve calculating probabilities. The generating of the advice message may include triggering a push notification. The method may be executed by processes of one or more networked servers.

The evaluating of the measured environmental data and the input user lifestyle data to select one as a most likely cause of the detected sleep issue may further include evaluating historical sleep data to detect a sleep trend. The method may further involve executing a triage process. The triage process may include determining probabilities based on the detected sleep issue to determine a risky sleep condition. The determined probabilities may include a probability of one or more of a risk of sleep apnea, a risk of snoring and a risk of chronic insomnia. Optionally, the triage process may trigger generation of a report with information concerning the risky sleep condition to facilitate access to a sleep health specialist. The triage process may trigger generation of a report based on a comparison of a threshold with a calculated probability value. The method may involve generating one or more of the advice messages based on a detected location or detected change in location. The method may involve
a generated advice message that includes jet lag advice.

Some versions of the present technology may include an electronic system to promote sleep. The system may include one or more processors. The one or more processors may be in a server(s), a smart device(s) (e.g., mobile phone), a computer(s) or any combination of such processors. The one or more processors may be configured to access measured sleep data representing user movement detected by a movement sensor, and/or sleep factors with features derived from the measured sleep data. The one or more processors may be configured to access measured environmental data representing ambient sleep conditions. The one or more processors may be configured to access input user lifestyle data collected on a sleep session-by-sleep session basis evaluate the sleep factors to detect a sleep issue. The one or more processors may be configured to evaluate one or more of: the measured sleep data, data of the sleep factors, the measured environmental data and the input user lifestyle data, to select a likely cause, or a most likely cause, of the detected sleep issue. The one or more processors may be configured to generate one or more advice messages associated with the selected cause, the advice messages including advice content for promoting sleep. Optionally, the one or more processors may be configured to transmit (or display) the generated one or more advice messages to a display device associated with the user.

Optionally, the generated one or more advice messages may include a series of advice messages (or different advice messages) over time consecutively generated upon continued detection of the sleep issue. In some cases, an evaluation of the measured environmental data and the input user lifestyle data to select one as a most likely cause of the detected sleep issue may involve calculating probabilities. Optionally, generation of an advice message may include triggering a push notification by the system. In some versions, an evaluation of the measured environmental data and the input user lifestyle data to select one as a most likely cause of the detected sleep issue further includes an evaluation of historical sleep data to detect a sleep trend.

The system may optionally include one or more processors are configured to execute a triage process. The triage process may include a probability determination based on the detected sleep issue to determine a risky sleep condition. The probability determination may involve calculating a probability of one or more of a risk of sleep apnea, a risk of snoring and a risk of chronic insomnia. Optionally, the triage process may trigger generation of a report with information concerning the risky sleep condition to facilitate access to a sleep health specialist. The triage process may trigger generation of a report based on a comparison of a threshold with a calculated probability value. In some cases, at least one of the generated one or more advice messages may be based on a detected location and/or change in location. In some versions, at least one generated advice message may include jet lag advice.

Some versions of the present technology may include a system to promote sleep comprising a processor. The processor may be configured to receive a measured sleep data associated with user movement data during a sleep session. The processor may be configured to process the movement data to determine sleep factors with features derived from the movement data. The processor may be configured to measure ambient sleep conditions with one or more environmental sensors. The processor may be configured to create a sleep record for the sleep session with sleep factors and the ambient sleep conditions. The processor may be configured to display the sleep factors on a display coupled to the processor. The processor may be configured to transmit the sleep record to a server.

In some versions, processor control instructions of the processor may further control the processor of a device in execution of an autostart process to: evaluate the movement data transmitted from a sensor module to determine presence or absence of a user based on a detection quality of sensed respiration; and on detection of presence of the user, initiating a sleep session information gathering process.

In some versions, processor control instructions of the processor may further control the processor of a device in execution of an autostop process to: evaluate the movement data transmitted from a sensor module to determine presence or absence of a user; and on detection of a sustained absence of a user, terminate a sleep session information gathering process. The detection of the sustained absence of the user may determine the sustained absence in relation to an expected wake up time.

In some cases, a sensor module may further include a receiver to receive control commands and processor control instructions may further control the processor to transmit a terminate command to the receiver of the sensor module. Optionally, the system may include processor control instructions configured to control the processor of a device to detect environmental parameters and/or location of the device, and based on at least a detected environmental parameter or the location of the device, adjust a parameter of a sleep session information gathering process. Optionally, the environmental parameter may include a light setting and/or sound setting for the device. In some cases, the parameter may be adjusted upon determination of a local time at a detected location. Processor control instructions may also be configured in the system to control the processor of a device to generate a user interface for selectively controlling activation and deactivation of the one or more environmental sensors. In some version, included processor control instructions may be configured to control the processor of a device to generate an alarm to remind a user to go to sleep. Included processor control instructions may also be configured to control the processor of a device to generate the alarm upon detection of a time to sleep. The time to sleep may be a calculated optimal nap time. In some versions, the one or more environmental sensors may include a humidity sensor, a sound sensor, a light sensor and an air quality sensor.

Some versions of the present technology may include a method for executing, with a processor, a sleep session information gathering process in a device. The method may involve receiving movement data transmitted from a sensor module. The method may involve processing the movement data to determine sleep factors with features derived from the movement data. The method may involve measuring ambient sleep conditions with one or more environmental sensors. The method may involve creating a sleep record for a sleep session with sleep factors and the ambient sleep conditions. The method may involve displaying the sleep factors on a display coupled to the processor. The method may involve transmitting the sleep record to a server.

In some cases, the method may involve with the processor executing an autostart process. The process may involve evaluating the movement data transmitted from the sensor module to determine presence or absence of a user based on a detection quality of sensed respiration, and on detection of presence of the user, initiating a sleep session information gathering process.

In some cases, the method may involve with the processor, executing an autostop process. The process may involve evaluating the movement data transmitted from the sensor module to determine presence or absence of a user, and on detection of a sustained absence of a user, terminating a sleep session information gathering process. Detection of the sustained absence of the user may involve determining the sustained absence in relation to an expected wake up time. In some versions, the sensor module may further include a receiver to receive control commands, and the method may further include transmitting a terminate command to the receiver of the sensor module.

The method may involve detecting environmental parameters and/or a location of the device, and based on at least a detected parameter or a detected location of the device, adjusting a parameter of the sleep session information gathering process. The parameter may include a light setting and/or sound setting for the device. The parameter may be adjusted upon determination of a local time at a detected location.

The method may involve generating a user interface for selectively controlling activation and deactivation of the one or more environmental sensors. The method may involve generating an alarm to remind a user to go to sleep. The alarm may be generated by detecting a time to sleep. The time to sleep may be detected when a clock time satisfies a calculated optimal take a nap time. The method may further include calculating the optimal take a nap time such that the optimal take a nap time may be based on processing logged wake up times. In some cases, the one or more environmental sensors may include a humidity sensor, a sound sensor, a light sensor and an air quality sensor.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE DRAWINGS

Aspects of the present technology will now be described with reference to the accompanying drawings, by way of example, and not by way of limitation, in which like reference numerals refer to similar elements:

FIG. 54a-d shows an example output report that may be generated with a processor of the present technology.

DETAILED DESCRIPTION

Figure 1:
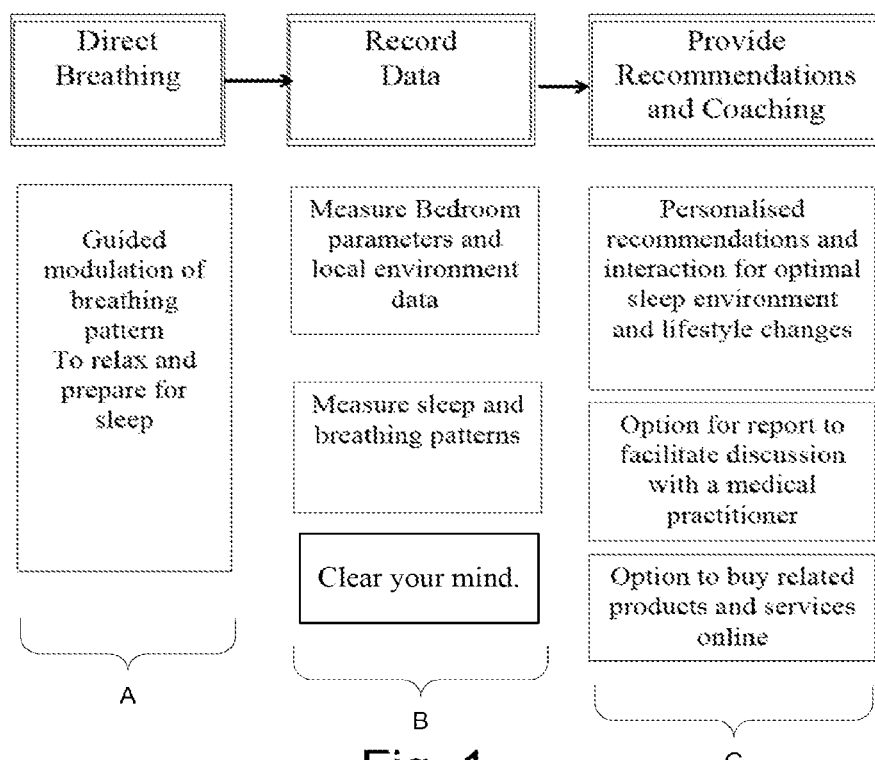
FIG. 1 shows an overview of aspects of the present technology.

The present technology relates to methods and systems that may enable a user to achieve a better sleep. The system may record sleep patterns and bedroom environment parameters. Further parameters, such as location of the user, for example in the form of GPS coordinates, time of the day, time of the year etc. may also be recorded. With such information, the system may generate sleep related output as well personalised recommendations, such as regarding the user's day and evening routines, and connection to various information resources, in order to help improve the user's sleep environment and habits. As well as monitoring a user's environment and sleep pattern which contribute to the personalized recommendations, the system can help the user to clear their mind of thoughts that might otherwise keep the user awake and assist in inducing sleep. Along with promoting better sleep, the system can also provide a method to assist in falling asleep, waking up, and do such that the user wakes in a state that the user feels as refreshed as possible.

The users sleep environment can divert from the users optimal sleep pattern required for achieving restful sleep. Therefore, the users sleep environment can be monitored for the duration of the sleep session. These measurements can be collected and processed by the "RM20" Library process (a sleep library of software processing functions and procedures that detects sleep related data from sensed motion signals) and contribute to the advice engine functioning. They can trigger specific sleep hygiene advice, as well as identify a link between the user's sleep and data obtained by the environmental sensors. The system may at appropriate intervals register, record or monitor and display bedroom events which could cause disturbances. The ambient light and temperature sensors will provide the absolute level of the light falling upon the BeD (the bedside device) (e.g., 0 to 100 Lux) with a resolution of 1 Lux and the temperature of the air around the BeD (e.g., +5 degrees to +35 degrees centigrade) with an accuracy of 1 degree centigrade and a resolution of (for example) 0.25 degree centigrade.

To monitor the users sleep environment, the system may utilize any one or more of;

Continuous sound, temperature and light monitoring and/or recording during a sleep session.

Optional filter to separate the 5 loudest sounds during the night.

Annotation of the environmental conditions on hypnogram.

The room environment conditions can be linked to periods of awakenings

Local storage of annotations on sleep session data

Note whether the room temperature, light levels or sounds and/or light are non-conducive to sleep The technology described herein, including a system and a method, represents a non-pharmacological sleep aid. The technology combines a relaxation program, customized to the breathing pattern of the user, with environmental (i.e., sleeping area) monitoring, sleep monitoring, 'mind clear' notes feature and other sleep assisting features. It does not require any mechanical contact with the user, so that the user does not have to wear any wires or sensors which may disturb the user's sleep (e.g., it does not require wearing a headband or having a phone placed on the mattress). It also alleviates the need to use sensing mattresses, which can be uncomfortable, as they still depend on direct contact with the user's body. The technology provides customized rather than generic advice based on data from the user, local environment and other sources. A larger number of different types of parameters can be analysed, allowing for a much broader picture of the user's sleep health to be assembled—e.g., sleep interruptions could be linked to allergy based on seasonal factors/local weather forecast.

Thus, the system may use wireless sensors to monitor breathing patterns and movement without the need for wearable attachments or any direct contact with the user's body. One realization shall use a non-contact bio-motion sensor for monitoring user's physiological parameters and movement, the detailed operation of which is described in detail in the above mentioned international patent applications WO2007/143535, WO2008/057883, WO2010/098836 and WO2010/036700. The system provides real-time feedback to the user (or to an application software) following analysis of raw sensor data of the user's breathing and/or movement with the non-contact bio-motion monitoring (e.g., ResMed's "SleepMinder" radio frequency device or other). Other non-contact (e.g., passive infra-red) or contact wearable (e.g., accelerometer- or piezoelectric mattresses-) based devices could also be used. The system also uses additional sensors, such as one or more microphones, photodetectors and/or thermometers (e.g., thermistor(s)), to track the presence and potential impacts of factors, such as light, noise and ambient temperature on the user's sleep. Apart from monitoring the bedroom environment, the system may have knowledge of the time of year and the specific location of the user, and be able to link to geographic and season-adjusted weather conditions, ask the user targeted questions, receive user's answers by way of a keyboard, touch sensitive pad or speech recognition software, and cross correlate all the collected information to the sleep parameters and trends detected for the individual consumer. Statistical data from general population and/or other users may also be used.

The system works silently (except when the user has deliberately chosen to use the alarm or calming sounds) and unobtrusively from the user's bedside table or similar. The system does not produce any light or sound during the sleeping period, unless it is being brought in a "wake-up" mode (unless a specific feature such as "lucid dreaming" is initiated based on sleep stage).

The example contactless biosensor can measure various physiological parameters of the user, such as a breathing rate and various sleep parameters. These may be processed to determine specific sleep stages of the user's sleep and the time the user spends in each of these stages. As discussed in more detail herein, the sleep staging analysis evaluates outputs of user presence/absence and multi-epoch analysis to generate a hypnogram, sleep parameters and sleep scores. A decision may be made for every epoch (e.g., 30 second interval or other suitable time period) to indicate if the user is asleep (deep, light or REM), awake or absent. Such data may be presented to a user to provide a feedback to the user regarding the user's mental and physical recovery (recharge) rate, portrayed in the sleep score as discussed later and hypnograph (hypnogram). The system is able to monitor and, in real time or otherwise, display to the user the sleep parameters by visualization on a screen of a bedside portable monitoring unit, a personal computer or a communication device, such as a smartphone. Other parameters, such as snoring or sleep disorder breathing (apnoea or apnoea-hypopnea index) may also optionally be monitored, recorded and presented to the user. (Detail on conducting such sleep and Sleep disordered breathing (SDB) measurements are disclosed in US 2009/0203972, which is incorporated here in its entirety by reference).

The processing of the data can be implemented either on a recording bedside table device itself or at a separate location (e.g., offline processing device with data storage—smartphone or website) before presentation of the sleep data to the user.

The system may also be used in a mode where the measured parameters are fed back to the system and processed in order to obtain a feedback on the basis of which the system will decide whether to continue with a specific set of parameters or to either automatically change, or make a recommendation to the user to change one or more of the system parameters. These parameters may include the nature of the sounds, the tempo of a specific rhythm, the loudness of the played music or the presence of any other sound in the room, the setting/brightness, the volume level for recording messages etc. In addition, the user has full access to the data and can review their sleep and/or environmental data through mediums such as the app or website.

The user can process the data and decide to, or be prompted to, change one or more environmental parameters. For instance, the user may be prompted to change the lighting or the temperature in the room or the volume setting of the TV set or other environmental factors. If, for example, the user's sleep pattern suggests that the user may be waking because of occasional noises around 5 am, the system may suggest reducing the noise level by closing the window or wearing ear plugs. If the user's bedroom is currently 80° F. but previous data shows that the user sleeps better when it's cooler, the system may prompt the user to reduce the room temperature by opening a window or turning on the air conditioning to lower the temperature to (say) 66° F. If on the last night it took the user unusually long to fall asleep, or if the system currently detects that the user is taking too long to fall asleep and the user is still in an awake state, the system may prompt the user to use a breathing relaxation techniques or relieve the user's mind by recording any thoughts that may be keeping the user awake, as discussed earlier in the text.

An alarm notification may be implemented to prompt the user to conduct breathing exercises, such if the user is taking too long to fall asleep (e.g., a time period commencing with the start of a sleep session during a continued absence of detection of sleep onset compared to a threshold). A personalised alarm, in the form of an email, "sms" (short message service) text message (or push notification or other), playing of a pre-recorded message or predetermined music, can be created to alert the user to perform a specific relaxation breathing exercise in the hours before sleep time.

The rationale is that if a user is in a 'stressed' condition lying in bed, they may find it very difficult to unwind and relax at that time—even with customised breathing exercises or advice. In order to address this need—which may be communicated by the user, or automatically determined based on an observed long duration sleep latency (lengthy time to sleep)—the system can recommend scheduling a series of breathing exercises in the hours before going to bed such as the 'assisted mediation' feature. The system may also accept input from the user of possible times of the evening to implement the breathing exercise programme in order to suit the user's schedule.

In order to automatically detect the above need, the system measures objective sleep measures (such as sleep latency, sleep duration, number of interruptions, type and duration of various sleep stages (light, deep, REM), and sleep quality) and subjective measures (such as perceived stress level, time taken to sleep—which may be entered via a simple questionnaire). For example, if a user typically goes to bed at say 11 pm, but is seen to take 30 mins to fall asleep, has many interruptions and reports being stressed/"mind racing" in bed, the system may recommend a breathing programme at 10 pm. This could be related to the user by way of a reminder alert on the smartphone (app alert, email, text, audio sound, or other means). This programme might consist of deep breathing exercises lasting 15 minutes, with biofeedback utilising the non-contact sensor. A period of gentle music may follow. The purpose is to relax the user in this time, and prepare them gently for sleep. Optionally, the system may monitor the user's heart rate, and heart rate variability in order to estimate their level of stress. A lower average heart, and/or increased variability in heart rate, can be promoted by such breathing exercises, and relaxing sounds.

Apart from the system prompting the user to undertake a specific action, the user can also access and change, on the user's own accord or when prompted, the current environmental parameters (the nature of the played sounds, the frequency of a specific rhythm, the loudness of the played music, the setting/brightness of the lighting, the temperature in the room etc.). The user is also able to select alternatives to the current settings, as well as to review and amend any future settings, for example proposed for implementation for the coming night of for future one or more nights.

In summary, the system may include any one or more of the following features:

(1) With the non-contact bio-motion sensor, so that the user's sleep is completely uninterrupted, the system can measure/monitor and learn the user's personal sleep pattern.

(2) The system can use environmental sensors to monitor the user's bedroom environment, such as light, sound, temperature, humidity, and/or air quality. The system can also evaluate other relevant factors, such as user's geographic location or altitude, time of the year etc.

(3) The result of the monitoring of the user biomotion data and environmental parameters may be processed and related to the user by way of a personal electronic device, such as a PC (or a tablet) or a communication device, such as a smart phone. At least some or all of the processed data can also be sent to a remote server. Apart from uploading data to a system server, the system may also be arranged to upload data to the user's personal webpage, to enable visual analysis and comparison to benchmarks.

(4) All measurements and recordings of data are "opt-in" and the user may be notified and in control when data is being collected.

(5) A pause feature (e.g., a "privacy" button) to halt recording of one or more sensor inputs. For example, a graphic user interface on the PC, tablet, smart phone or other electronic device (SmD) used to interface with the user, may permit a user to temporarily disable certain sensors from a list of sensors (e.g., microphone, temperature, motion, etc.). This might also be enabled a privacy switch on the BeD.

(6) The Bedside Device (BeD) and/or the SmD may perform automated self-checks on a regular basis, such as each evening, and be capable of resetting itself if required, such as if a fault is detected.

(7) The system is configured to prompt the user to record other data, such as the use of caffeine, alcohol, exercise, sleep pills, as well as further details related to any taken substances, such as the relevant amount, strength/brand, when (relate back to sleep patterns) etc. To avoid an unwanted burden, the user has control of how many prompts and how much data is requested and recorded.

(8) An easily selectable "airplane" mode on a smart device to quickly disengage, when required.

(9) Range gating capabilities of the sensors allow the system to work with two people in the bed, by monitoring the closest person, without impacting the accuracy of the measurement.

(10) Two sensors can be used in the bedroom (to monitor each bed partner) without impacting the accuracy of the system.

(11) The sensor of the system may be configured to continue to record, even when the user forgets to connect the smart device, so that it will store the data for up to, for example, 7 nights. The process of syncing back the stored data is straightforward (e.g., just plug it in or other simple process) and reasonably quick (e.g., 15-30 seconds to transfer and process).

(12) The sensor device (e.g., bed table device) may include a charging port for a smart device. The user may be reminded, such as by an electronic message on the SmD, to plug in their smart device, as the device needs to last the entire night.

(13) The system may be used by multiple users over time, or by a single user on multiple devices over a period of time, each user being able to access their complete record.

(14) User remains able to use phone as normal (receive texts and phone calls, browse web etc.) while the sensor working.

System Architecture—Overview

Figure 2:
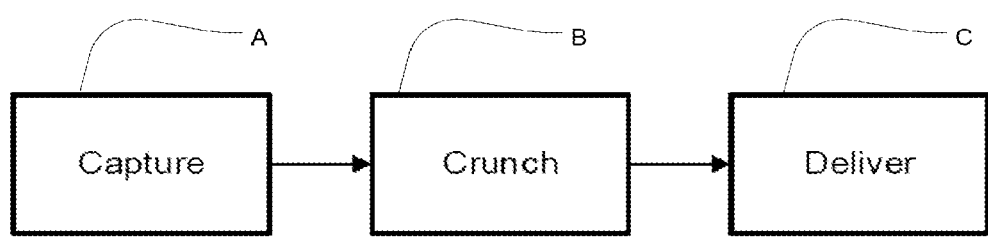
FIG. 2 is an example diagram of the processing of data generated by sensors associated with an example system of the present technology; this diagram illustrates the movement of the sleep data. Initially, collected by the various sensors from the user in the "capture" stage, the data is processed, during the "crunch" stage. During this processing various characteristics and trends in the data, possibly identifying sleep characteristics and patterns, are identified.

As shown in FIG. 1, in one view the system can be divided conceptually in three categories or stages—e.g., providing sleep assistance (by guiding the user towards relaxation) in stage A, sleep data recording and analysis in Stage B, and providing sleep recommendations and coaching in Stage C. The interconnection between these stages may be understood with reference to FIG. 2 showing a progression of sleep data. Initially collected by the various sensors from the user in the "capture" stage, the data is processed, during the "crunch" stage. During this processing various characteristics and trends in the data, sleep characteristics and patterns are identified. On the basis of these features and trends, the proposed system and method provide recommendations and coaching to the user, in the "deliver" stage (see, e.g., FIG. 36).

At a high level, data is gathered from one or more sensors, such as a biomotion sensor (e.g., a radio frequency movement sensor), from room environmental sensors such as of light, sound, temperature and humidity. In addition, localisation data may be used to check online services for local weather patterns. The data may be input into an advice engine which analyses the parameters (environment, biomotion, etc.) in conjunction with previous user data, including population normative data. The output generator may include information concerning sleep (e.g., a sleep score) and/or advice such as from an advice engine that will be discussed in more detail herein.

Figure 3:
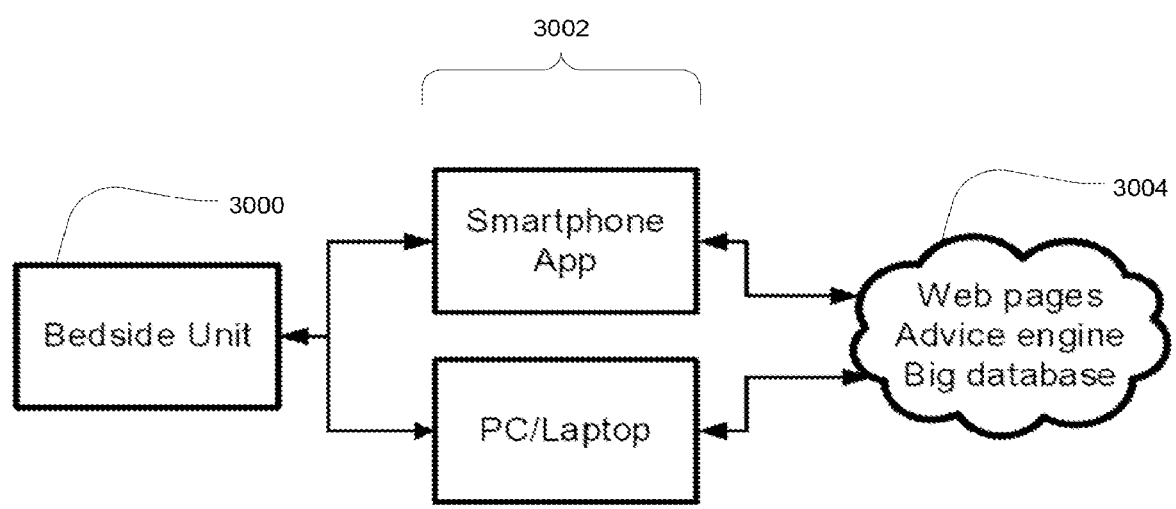
FIG. 3 is a block diagram of example physical components that may be implemented in some versions of the present technology; in one example, the system may use a bedside unit, including a sensor, a software mobile "App" or software running on a computer, and a server (e.g., a web based cloud service) with a database.

Example components of the system may be considered in reference to FIG. 3. The system may include a bed side unit, such as the biomotion sensor. Some of the key sleep features identified with data from the biomotion sensor may include sleep quality, sleep duration, awake, light sleep, deep sleep, REM sleep, number of interruptions, respiration rate, duration of movement, and intensity of movement.

Figure 3A:
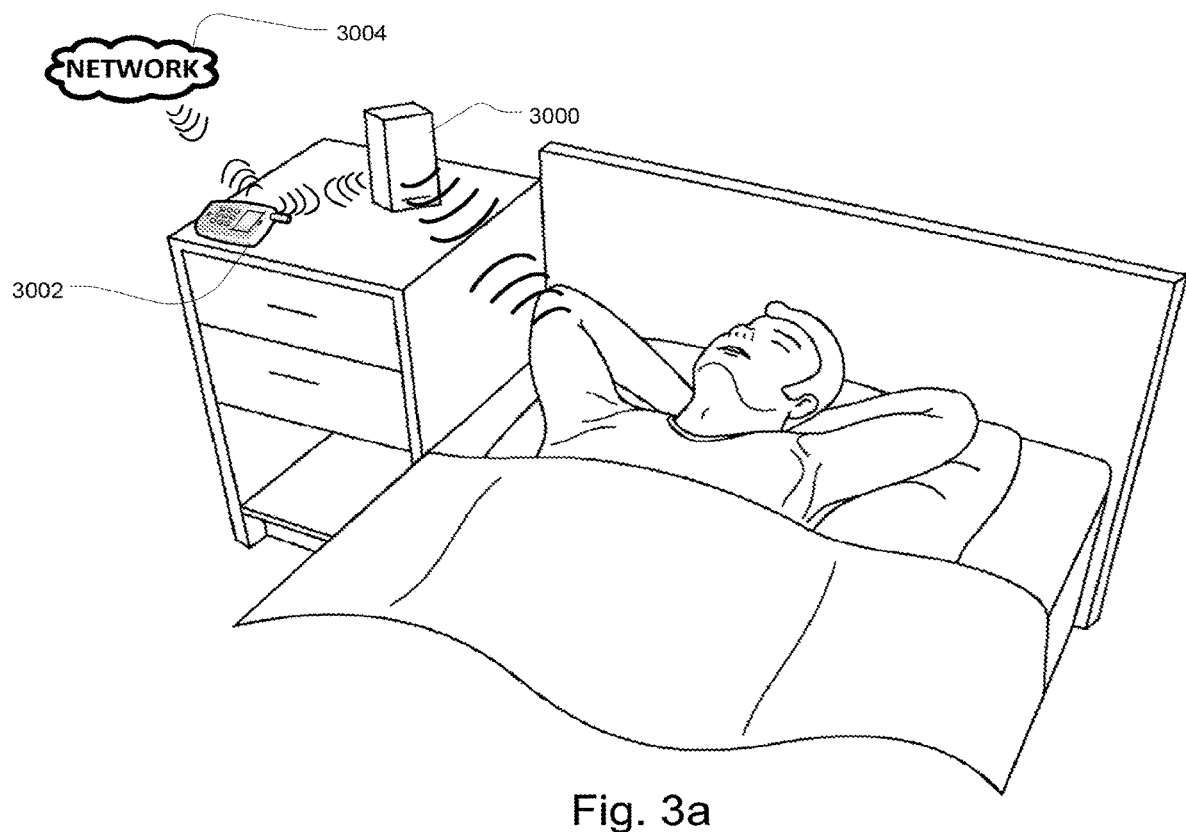
FIG. 3a illustrates an example version of the present technology of FIG. 3.

In one example, the system may use a bedside unit, including a sensor, a software mobile "App" or software running on a computer or other smart/programmable processing device (e.g., tablet, phone laptop etc.), and a server (e.g., a web based cloud service) with a database. The bedside unit 3000 is a device placed on a bedside table, bedside locker, stand, or other supporting means located near the user when they are in bed. This device contains the biomotion sensor and other environmental sensor(s), and a wired or wireless (e.g., Bluetooth) link to an app on a smart device 3002 (e.g., smartphone or tablet). The sleep data processing may be split between the bedside unit and the smart device, or even concentrated in the smart device, to keep the data payload as small as possible, whilst leveraging the processing power available on the smart device. Further processing, such as by an advice engine, may be implemented as a module on one or more servers 3004, typically implemented on a cloud platform. The smart device and server communicate via a data connection. For example, as illustrated in FIG. 3a, the data from the bedside unit 3000 sensors, which may be determined from Doppler radio frequency motion sensors, may be transferred from the bedside device to a smartphone, tablet or PC via a wireless link (such as Bluetooth) and then transferred to a cloud service where an advice engine is running. The advice may be delivered back to the user via their smart device 3002.

System Architecture—Main Elements

Figure 4:
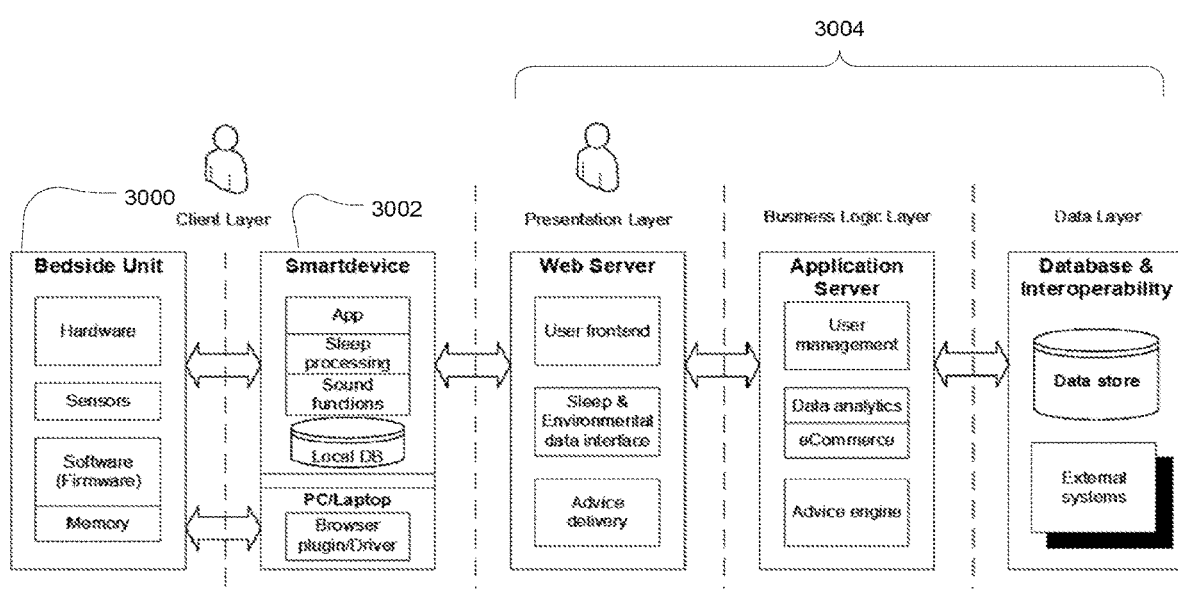
FIG. 4 shows a block diagram of hardware components and the resulting movement of data from a bedside unit to an online database.

The system may be further considered in reference to FIG. 4, and may be capable of logging data on the bedside unit 3000 (BeD) and/or on a smart device 3002 (SmD), and transferring data to computer system such as a PC/laptop, smart device, server 3004 and/or 'cloud' service.

In the example of FIG. 4, the system includes:
Bedside unit 3000 (e.g., standalone mains powered bedside device)
Communications link from bedside unit to a smart device or PC
Smart device 3002 application (e.g., Apple and Android implementations)
Communications link from Smart device or PC to Cloud
Cloud services (shown as servers 3004) including, Backend, Consumer frontend, Advice generation, Advice delivery engine, Analytics.

An example of such a system is provided in the following table:

| Element | Type |
| --- | --- |
| 1. Bedside unit (standalone mains powered bedside device) | Device (full industrial design) |
| 2. Communications links from (a) bedside unit to smart device, (b) bedside unit to PC | Comms link |
| 3. Smart device application (Apple and Android) | App (multiple platforms) |
| 4. Communications links from (a) smart device to Cloud, (b)PC browsers (including upload of data from PC) to Cloud | Comms link |
| 5. Cloud service (with backend, consumer frontend and analytics & advice generation & advice delivery engine, analytics). | Cloud software as a service |

The FIG. 4 block diagram is one example implementation of the system. Generally, in such a system, the bedside unit carries out, such as with its hardware and/or processor, most of the user and environmental monitoring, and contains memory storage. This device then communicates with a processing device or computer (e.g., PC or smart device/cell phone) via a wired (e.g., USB) or wireless (e.g., Bluetooth, Wi-FI, NFC or other) link. The computer then communicates with a series of servers implementing sleep advice analysis applications, data storage and connections to other systems via a network, such as the Internet. It should be noted that the series of indicated optional servers may be implemented in one or more actual hardware servers/devices. The communications may be via wired or wireless means. It should be noted that the system can function with either PC or smart device, although greater functionality is available if the user has a supported smart device. The systems can still function without the connection to the webserver, but a connection is preferable and may be employed via any number of methods to transfer the data between the computer/smart device ("SmD") and the cloud servers. The cloud may include of the backend server which contains an advice engine that can then generate one or more 'nugget(s)' of advice as discussed in more detail herein.

FIGS. 5-10 provide further detail on the main blocks identified in FIG. 4.

System Architecture—Hardware—the Bedside Unit ("BeD")

Figure 5:
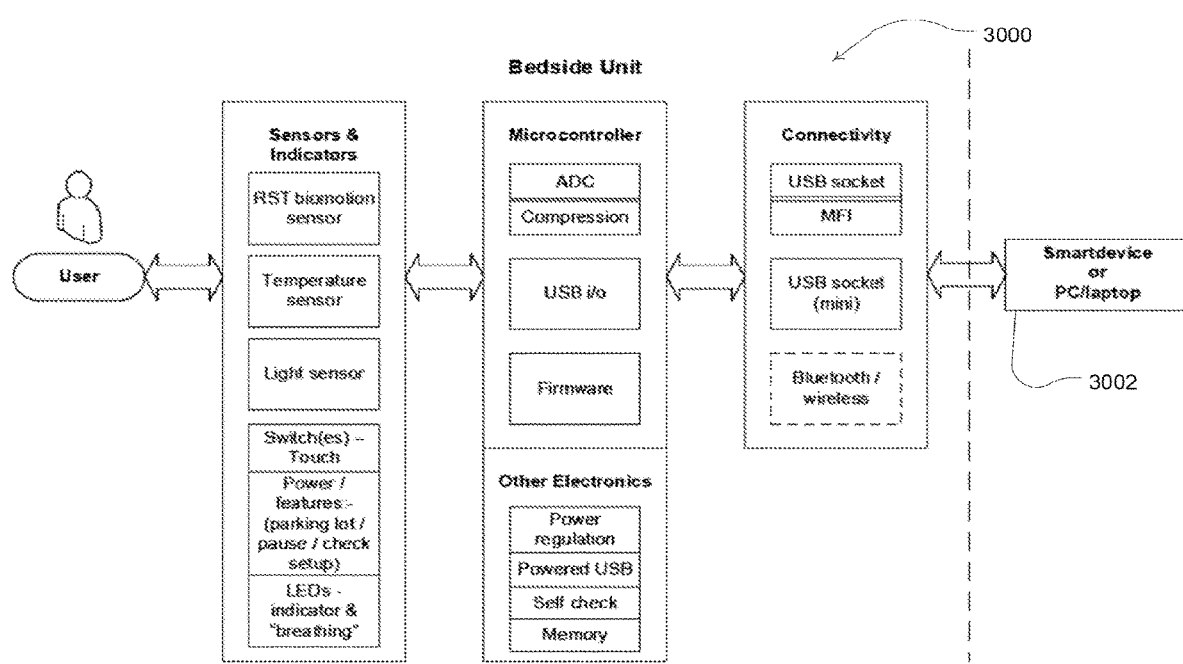
FIG. 5 shows conceptual diagram of hardware components in a bedside unit and its interaction with a PC.
Figure 10A:
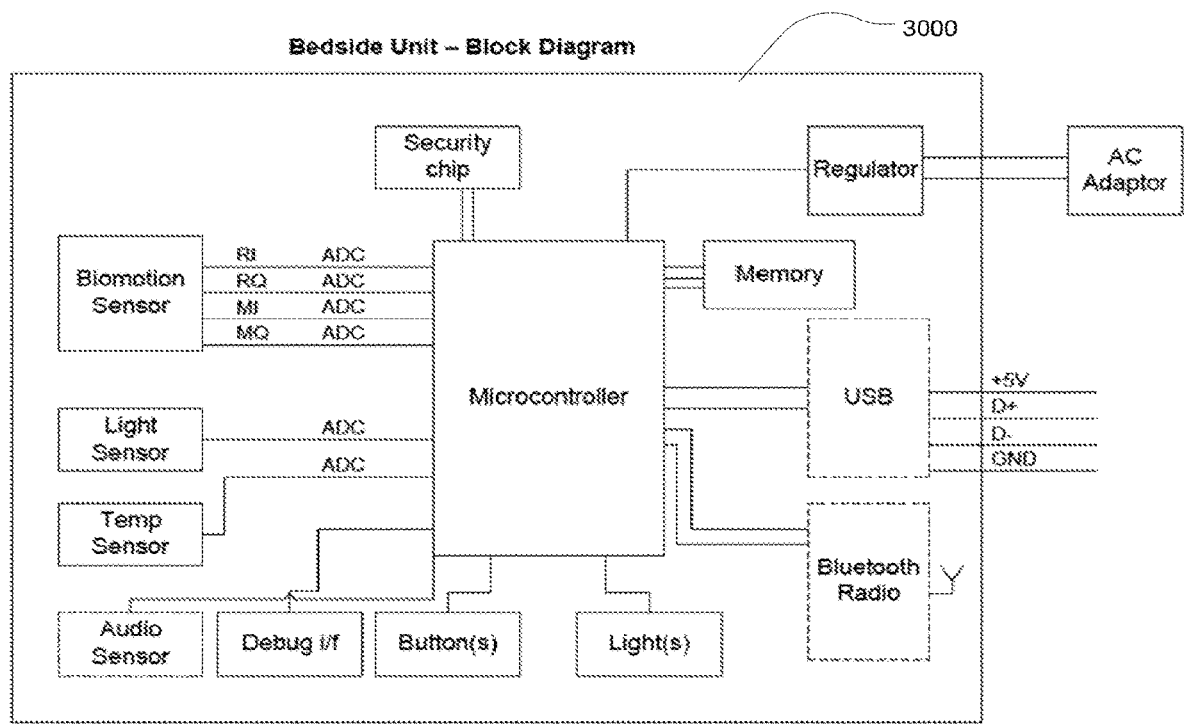
FIG. 10a shows a block diagram of an example implementation of a bedside unit.
Figure 10B:
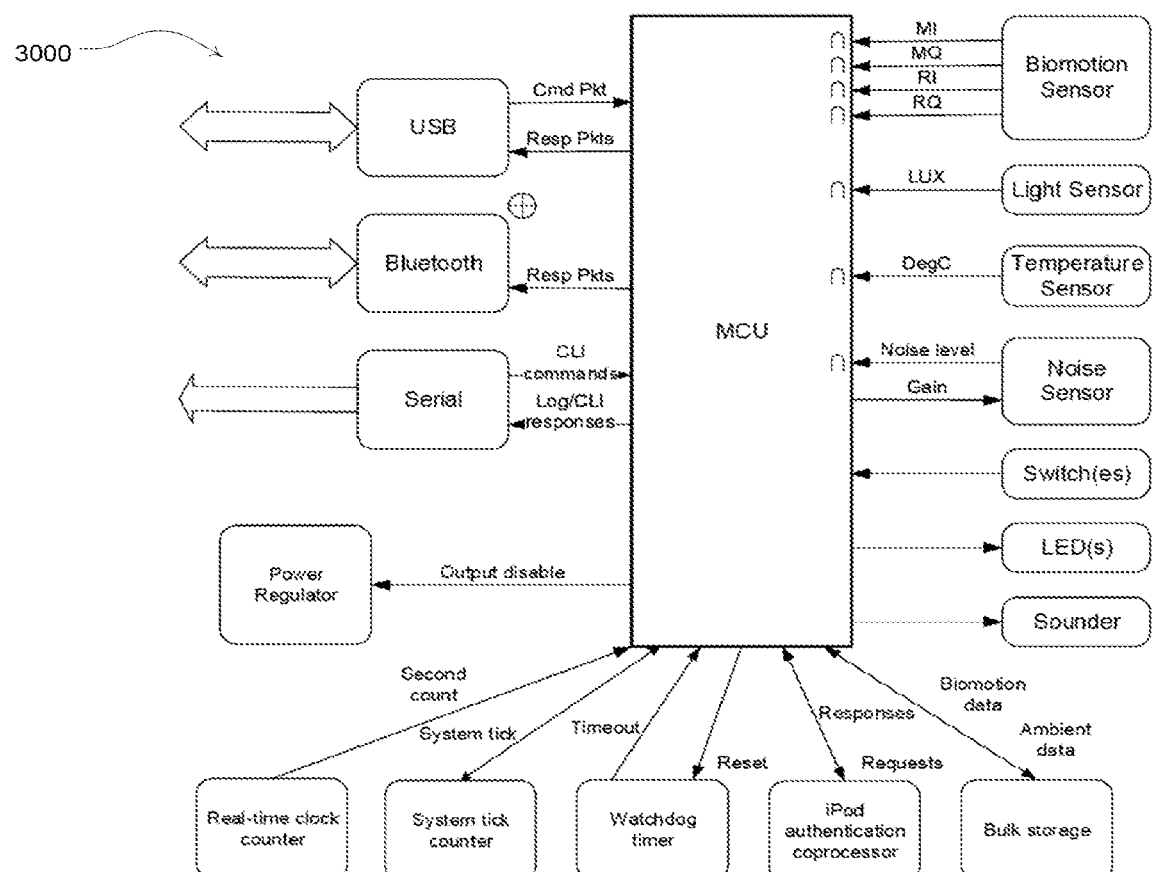
FIG. 10b shows a block diagram of another example implementation of a bedside unit; in this example, a microcontroller runs a firmware program in order to sample data from the various sensors (biomotion, light, temperature etc.) The design may include button and light interfaces, memory for storing data when an external communication link is not available, a security chip to manage the data communications, and USB (universal serial bus) and Bluetooth (wireless) interfaces. The USB port may be for charging only, or be configured as USB OTG (On-The-Go), i.e., to have a hosting role or act as a normal USB device when attached to another host.

FIG. 5 shows one possible block diagram of a Bedside Unit 3000. Other conceptual diagrams for the Bedside Unit 3000 are shown in FIG. 10a or 10b. The illustrated design of FIG. 5 contains sensors such as biomotion, temperature, light, humidity and/audio. The sound sensor, typically a microphone, could be implemented on the smart device rather than on the bedside unit. Functions such as power on/power off and privacy (suspend logging) can be implemented by switches, such as micro-switches or touch switch/es—e.g., capacitive touch on either device, but are preferably included in the SmD. Indicators (such as single, bi-colour or RGB LEDs) provide a visual indication of the status of the device. These indicators may turn off during the sleeping period such that the user is not disturbed by unnecessary "light pollution" in the bedroom. The lights may vary in colour and/or intensity based on the detected respiratory rate/respiratory waveform of the user, to indicate the state of activity of the device. A full display with graphics could also be provided on the device in another version. The Bedside Unit may incorporate memory to store data for later retrieval by the smart device. More details for the design illustrated in FIG. 13 will be provided further in the text. Example BeD units are also illustrated in U.S. Design patent application Ser. No. 29/490,436, filed on May 9, 2014, the entire disclosure of which is incorporated herein by reference.

System Architecture—Smart device/PC/Laptop —("SmD")

Figure 6:
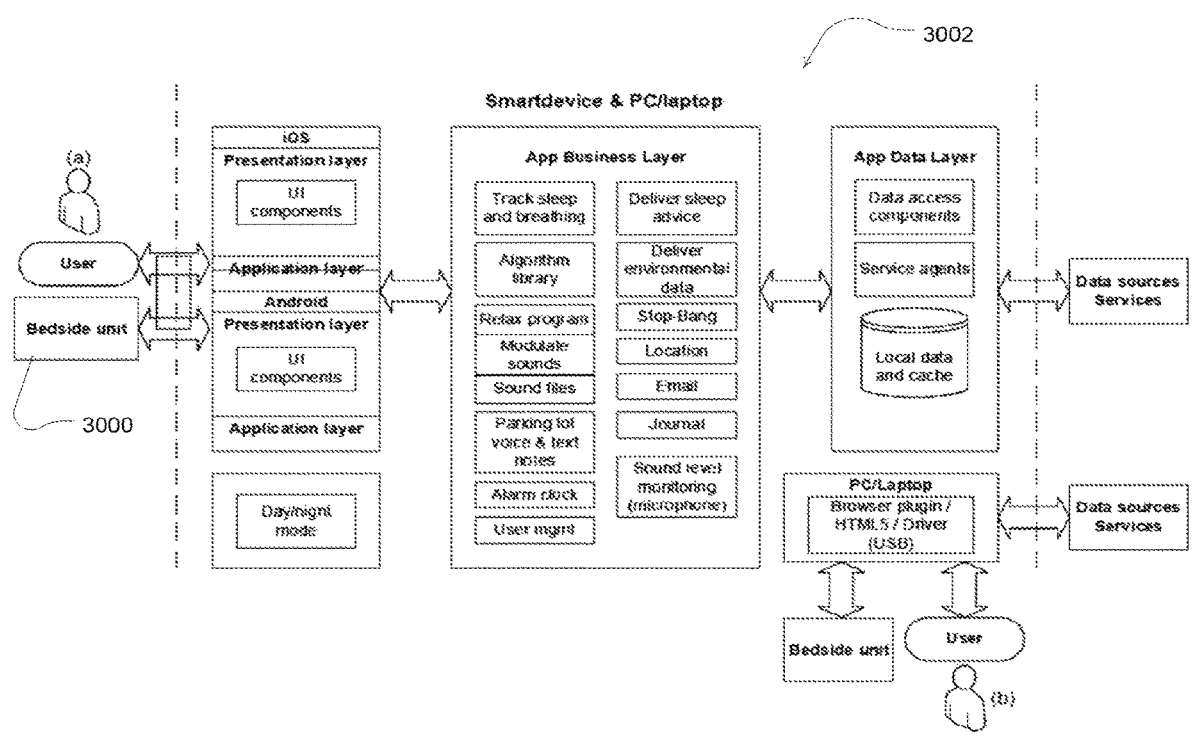
FIG. 6 shows a block diagram of one implementation of an application for Apple, Android or other smart device.

FIG. 6 is a block diagram of the processes (i.e., "app") of the smart device 3002 or PC. For example, it illustrates (a) an application running on either an Apple, Android or other smart device and (b) PC/laptop web view of data/upload of data from the bedside unit. The app "business layer" performs processing of the sensor data received from the Bedside Unit. Additionally, audio processing can be performed by the app, including monitoring of background sounds (e.g., snoring of the user, traffic noise, other background noises such as the trash truck, car horns etc.— manifesting in the audio signal). Sound data can be delivered via the app—either through the Smart device's internal speaker or via an external speaker (e.g., connected via Bluetooth, cable etc.). Local storage in a database on the Smart device is used to cache data, and provide local storage for quick display of statistics, graphs and advice delivered from the web server/cloud across a data connection—and allow for the case where a data connection is not available between cloud and the App. The app can gather location data from GPS or other means in order to enhance the advice delivered (e.g., user to cross reference with weather forecasting, pollen alerts, jet lag, etc.). By using/obtaining/recording location data, advice can be linked to actual sunrise time at the user location, check if the user is travelling and offer appropriate advice to manage jetlag or their new room environment. It can recommend advice on diet.

An optional PC application or HTML 5 (or other) based website can provide an alternative means of viewing statistics, graphs and advice concerning sleep data and advice.

The SmD is a central component in the overall system design. (although, the SmD functionality could be replicated in the BeD with a suitable display, processor and other components in another version). It may be responsible for the following: BeD control and BeD interface; cloud interface; Push notifications interface; DSP (digital signal processing) and Sound acquisition. Input to the processor of the SmD may include the following. The BeD interface enables communication between the SmD and BeD of: raw biomotion data; compressed biomotion data; temperature data (e.g., Celsius) and/or light data (e.g., Luminance). The SmD's cloud interface enables exchange between the BeD and the cloud/servers of: user data; processed sleep data (states, scores, etc.); annotated advice ("nuggets"). Sound Acquisition of the SmD may involve input of microphone power level sample. The SmD may receive Push Notifications that may include sleep related advice. The BeD Interface of the SmD may output control signals to control operations of the BeD and firmware updates for updating the BeD. The cloud interface of the SmD may output User data (e.g., account information etc.), processed sleep data, raw sleep data, advice feedback, sound data, Celsius temperature data and/or Luminance light data.

Sound may be recorded on the SmD throughout a sleep tracking session. Environmental sound monitoring may incorporate the following process. The sound content need not be stored. User may be prompted for permission to record sound events. The sound volume may be sampled at 1 Hz (or at other rates, e.g., 16 kHz or other). In one configuration, only some sounds, such as sound greater than a certain threshold, may be saved. At the end of the night, the loudest sounds (e.g., 5 sound events but this number may be set by a user as a software setting to any different number of events) can be stored and the remaining sound events deleted. The frequency of the sound may also be analysed using an FFT (Fast Fourier Transform) and other time domain measures such as zero crossing, peak detection, run length averaging to identify specific components, such as snoring, high, mid, and low frequency sound events— whether they be of short or longer duration.

System Architecture—Web Server/Cloud Service

Figure 7:
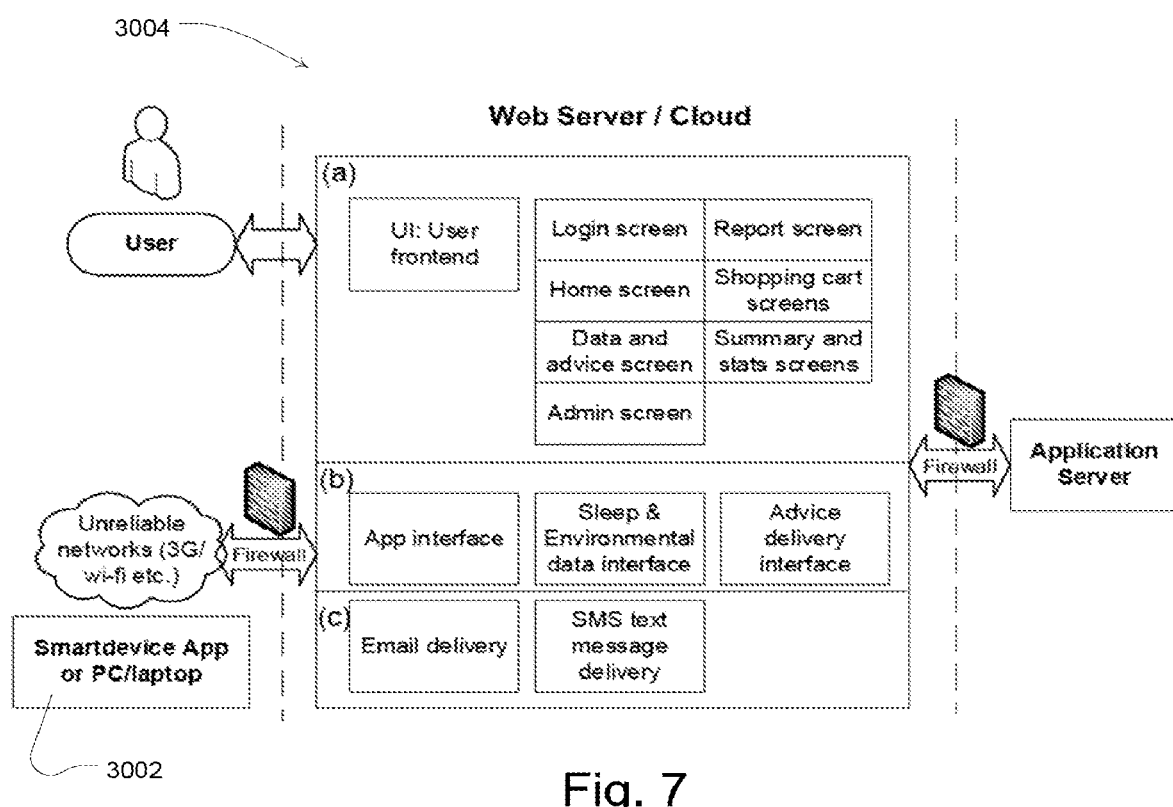
FIG. 7 shows a logic outline of a web server/cloud and of its data links with the smart device app or PC/laptop and an application server; this shows a web server outline for one or more of: (a) user's web pages and (b) for the data link between either the smart device app or PC/laptop, and (c) external delivery of email/communications outputs. The user interface allows a user to access various screens to manage their account, view their sleep and environmental data, and sleep advice delivered from the advice engine.

FIG. 7 shows a web server logic processes for one or more of: (a) user's web pages and (b) for the data link between either the smart device app or PC/laptop, and (c) external delivery of email/communications outputs. The user interface allows a user to access various screens to manage their account, view their sleep and environmental data, view their personal goals and achievements, their progress against their peers, and sleep advice delivered from the advice engine.

System Architecture—Application Server/Cloud Service/Personalized Advice

Figure 8:
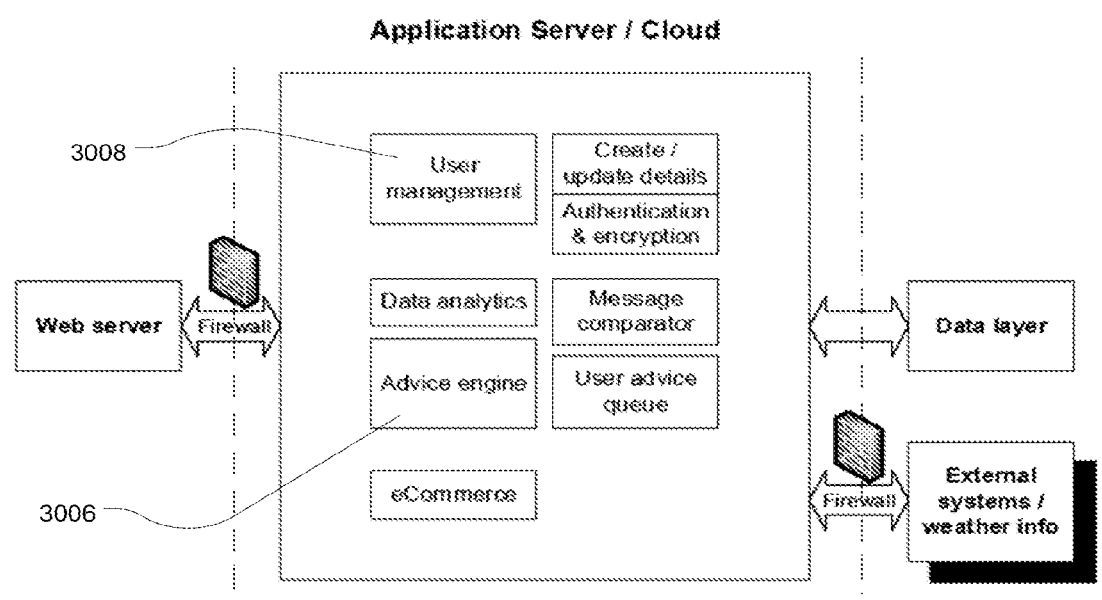
FIG. 8 shows logic units (including advice engine and user data management) of the application server (or cloud implementation of same)

FIG. 8 illustrates the main business logic processes (including advice engine 3006 and user data management 3008) being carried out by the application server (or cloud implementation of same). The advice engine 3006 may generate advice as described in more detail herein such as sleep related message for sleep improvement based on recorded/detected user sleep data.

The backend cloud software may have discrete modules including a user backend and advice engine. These modules may share common business logic and a one or more database(s). The database can be separated into two different schemas: one for user data and one for advice data. Both modules can be accessible through a service layer, this is discussed as part of the Advice engine in more detail herein.

The cloud user backend contains the data and business logic for serving the SmD. Communication with the SmD may be via the client-server model pattern. The user backend may be responsible for client backup service; to synchronise user data to multiple devices; to maintain historical data (e.g., user and sleep data). Input to the cloud user backend via the SmD interface may include User data, Processed sleep data, Raw sleep data, Sound data, Celsius temperature data and/or Luminance light data. Output from the cloud user backend to the SmD interface may include User data and/or Processed sleep data, Advice data etc.

System Architecture—Data Store and Links to External Systems (Application Programming Interfaces—APIs)

Figure 9:
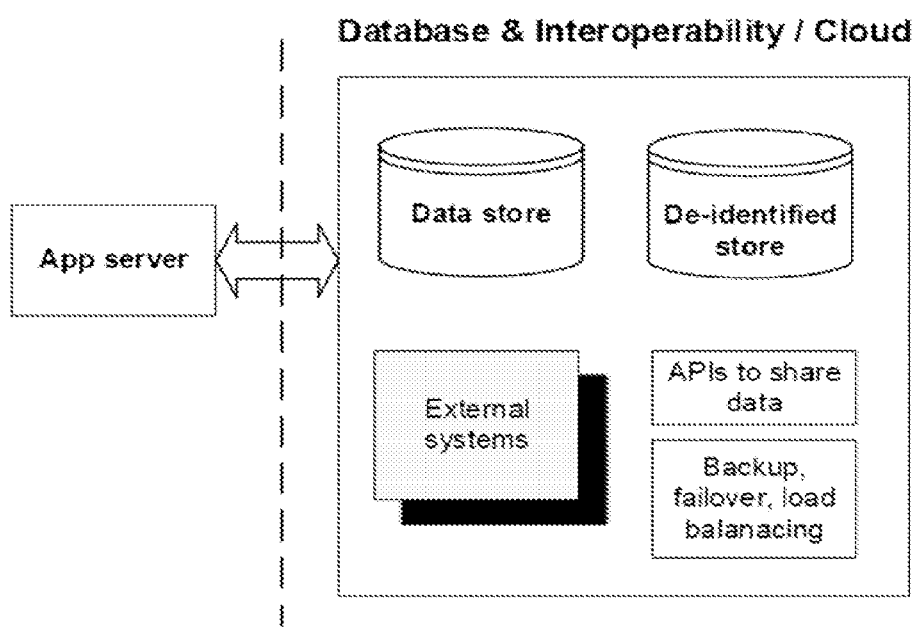
FIG. 9 shows one implementation of data layer that could comprise a main database and links to external systems (e.g., APIs to interoperate with other systems)

FIG. 9 illustrates the data layer comprising a main database and links to external systems (e.g., APIs to interoperate with other systems). These may be accessible to the server(s) 3004 and/or the smart device 3002. Data utilized in the processes of the system may be stored and organized in these components of the system.

Hardware—Exemplar Embodiments—Bedside Unit (BeD) Block Diagram

Returning now to the reference design of Bedside Unit 3000, several examples are illustrated with reference to FIGS. 10a and 10b. In the example shown in FIG. 10a, a microcontroller (MCU) or other processor runs a firmware program in order to sample data from the various sensors (for biomotion, light, temperature, noise/sound etc.) The design may include button and light interfaces, memory for storing data when an external communication link to the smart device is not available, a security chip to manage the data communications, an universal serial bus USB and/or Bluetooth (wireless) interfaces. The USB port may be for charging only, or be configured as USB OTG (On-The-Go), i.e., to have a hosting role or act as a normal USB device when attached to another host. Thus, the device is configured with components to perform the functions described in more detail throughout this specification.

The BeD can, for example, operate in one of 2 states: (a) Out-of-session and (b) In-session. While in the out-of-session state the BeD will not respond to any remote procedure calls ("RPCs") apart from a session open request. It will respond to all such RPCs with a failure response. Following power up or reset the initial state will be out-of-session. RPC 16 (request session) is used with this feature. Exiting the in-session state will trigger the generation and storage of appropriate notifications. Notifications are generated and either sent to a connected and in-session SmD or queued for later transmission. All communications with SmDs may utilise a packet-protocol. When the BeD is in the Sleep Session Breathing state, the LED brightness may be varied to reflect the ambient light levels. The LED brightness can be reduced to zero after a predetermined time (for example, between 5 and 30 seconds, say 15 seconds). For example, when a low ambient light is detected, it can be assumed that it is night time and the user may be preparing for sleep or be temporarily woken from their sleep. Thus it makes sense to use much lower screen intensity so as to avoid disturbing the user or they partner. Similarly, different volume may be used for the generated sounds, depending on the measured noise background. Such settings of adjustable screen brightness and/or sound volume may be used for all device functions or for some device functions, such as "Smart alarm" and "Mind Clear" which will be discussed later in the text.

The BeD also has the facility to accept firmware updates from the SmD. It is also able to send notifications to the smart device when certain environmental and internal events occur. The BeD shall be configured to provide a Bluetooth connectivity to ensure good connectivity to the SmD in a room. Typically, the BeD will be implemented for signal acquisition, compression and to provide an interface to the SmD device. Input to the processor (MCU) of the BeD will include sensed Biomotion data (4 channels from its sensors including Breathing and Motion; ambient temperature data, light data, sound data (in some configurations); Control signals and/or firmware updates. The processor of the BeD may then output raw biomotion data, such as for further processing by the SmD, compressed biomotion data; converted temperature data (e.g., Celsius) and/or converted light data (e.g., Luminance).

System Architecture—Exemplar Embodiment

Figure 11:
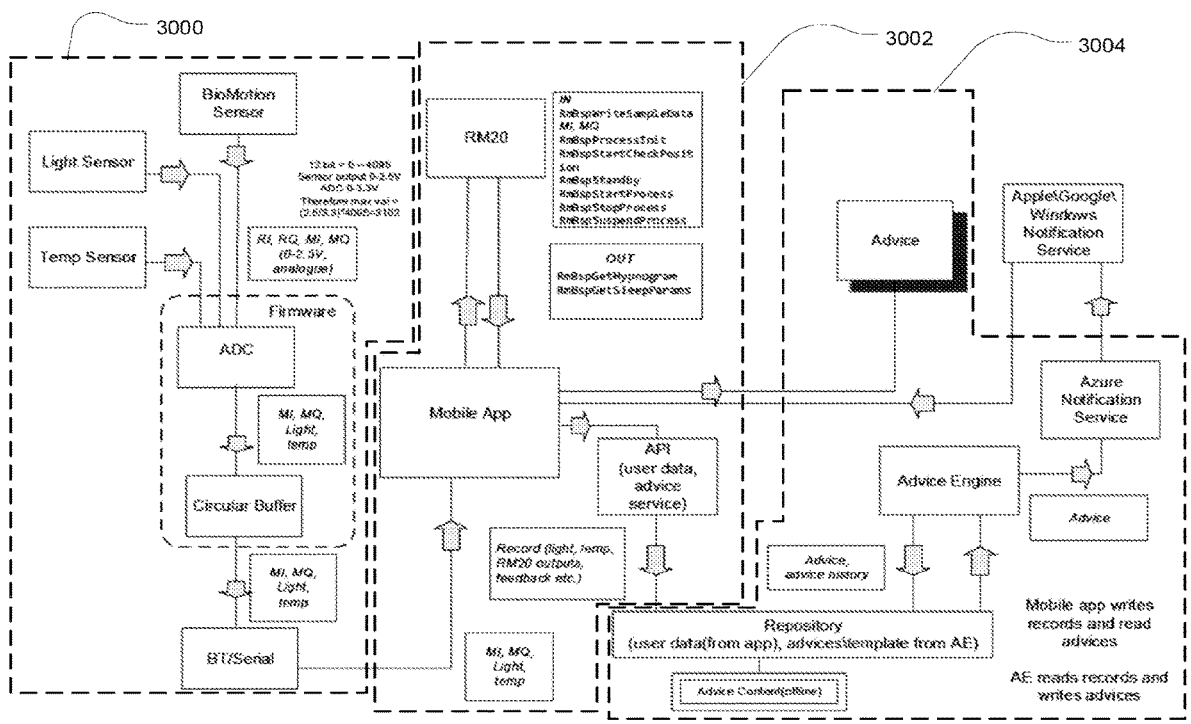
FIG. 11 shows a block diagram of example components of a system including an example advice delivery data pathway perspective; RM20 may be understood as a process for 'sleep processing'. The data is captured by the sensors, crunched by the RM20 library and then delivered to the user, these include sleep scores and hypnograms. This data is transferred to the advice engine. The advice engine is able to draw from the user's history such as previous sleep histories, previous advice given to the user, pre-sleep questionnaire to tailor the advice and generate the most appropriate advice for the user. The advice is then relayed to the user. One such embodiment of this delivery method is a push notification service utilizing the smart devices operating system.
Figure 12:
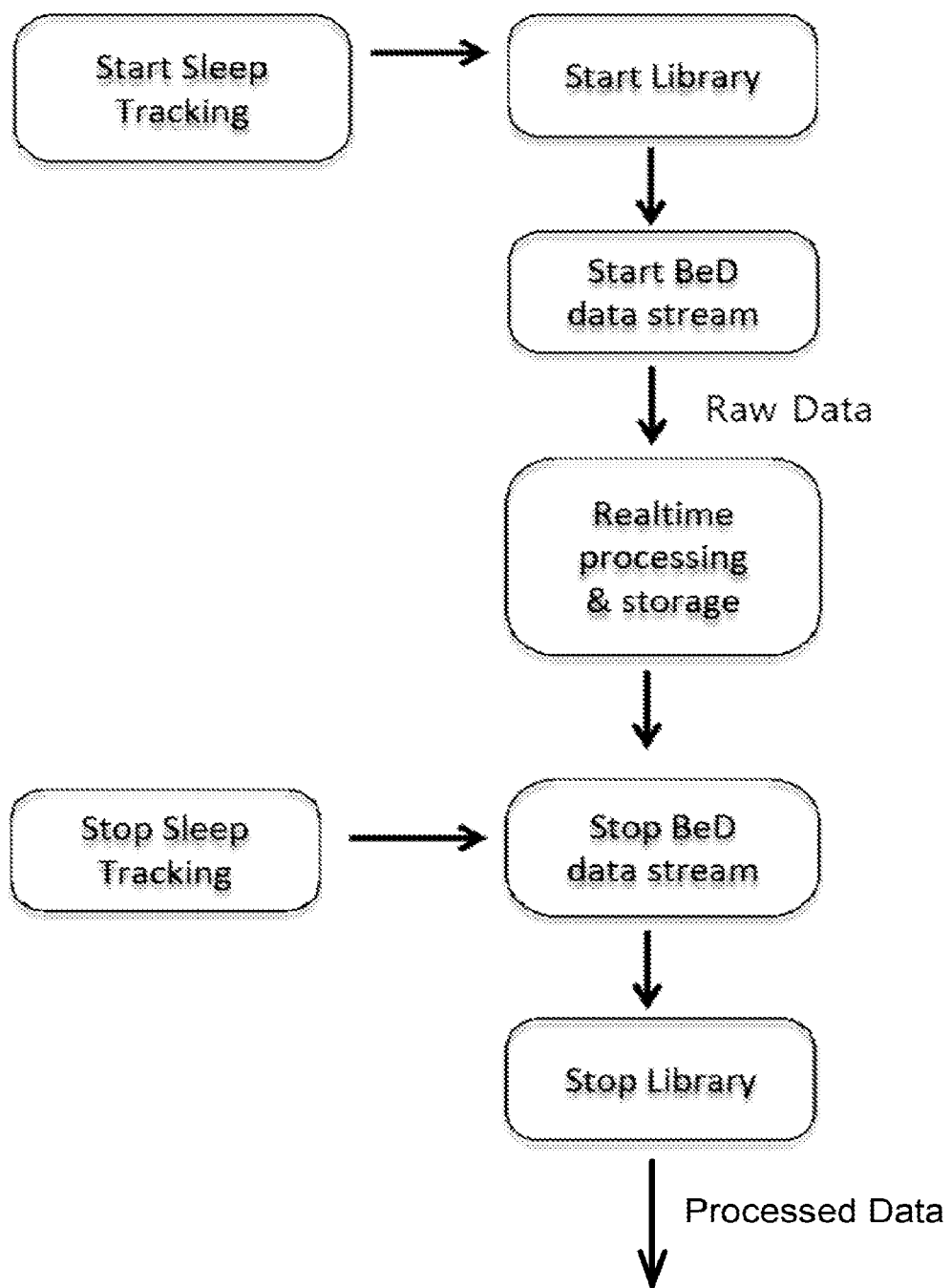
FIG. 12 illustrates a methodology for sleep tracking such as with a connected accessory processing device (e.g., motion sensor monitor and smart phone) during a sleep session; in this example, sleep tracking with phone connected occurs, and remains connected for the full sleep session. Once the Bed Side (BeD) device starts tracking sleep and a smart device remains connected, the RM20 library located in the smart device process data it receives in near real-time. Once the sleep tracking is terminated, the processed data provides the user with information on their sleep, giving the user a clear breakdown of their results such as a sleep score, hypnogram and pie chart.

An advice delivery data pathway may be considered with reference to FIG. 11. The data is captured by the sensors of the BeD device (bedside unit 3000). The data is transmitted to the processor of the SmD (smart device 3002). In this example, the RM20 'sleep processing' functions are performed by the SmD processor. Thus, the sensor data is processed/evaluated by the RM20 library and the result(s) of the processing are then delivered to the user by the SmD processor. Such output data may include sleep scores and hypnograms as described in more detail herein. This data may then be transferred by the SmD device to the Advice engine of the cloud service server(s) 3004. The Advice engine is able to draw from the user's history such as previous sleep histories, previous advice given to the user and pre-sleep questionnaires answered by the user on the SmD device. With this data, the advice engine can tailor the most appropriate advice for the user. The advice is then relayed back to the user such as by transmitting the advice to the SmD. One such embodiment of this delivery method is a push notification service utilising the SmD's operating system).

System—Exemplar Embodiments of Sleep Tracking (Handling of Sleep Sessions, Data Download "Onboarding", Reconnecting)

In one example of the system, an application on the SmD may have a sleep screen (graphic user interface). The screen may optionally show that monitoring/recording is in process if sleep tracking with the SmD and BeD is taking place. Optionally, it may show a real time or near real time movement signal and/or respiration signal detected by the BeD. Once a 'Sleep' option on the SmD activates, signifying that the user wants to initiate going to sleep and activate the sleep tracking, a 'pre-sleep questionnaire' screen is presented to the user so that the user may answer the questionnaire discussed in more detail in this specification. Upon completion of the questionnaire, the SmD may send a request to the BeD to stream data. Once data streaming begins the SmD may initiate processing with the RM20 process described in more detail herein. The SmD processor then continues to request data from the BeD over the course of the night, during this time, the RM20 process may function in several ways. When a sleep session is initiated, the lights on the BeD and SmDs are turned off to minimize disruption to the user. Alternatively, instead of the sleep data being continuously transmitted from the BeD to the SmD, the data may be saved temporarily at the BeD and transmitted to the SmD in transmission sessions periodically through the night or in the morning, when the user terminates the sleep session.

A sleep record is generated after processing one sleep session following the stopping of the sleep tracking. Such records may be deleted after a period of time (e.g., 1 year). The following strategy is employed to ensure the record arrives at the cloud server(s):

(1) Upload sleep data record after generation.

(2) If record fails to upload, a background service of the SmD may attempt to upload the record at various intervals while the app is inactive.

(3) If more than one record has failed to upload, the records will be queued, with one record uploaded per attempt.

FIGS. 12-16 may be considered in conjunction with the management of the transfer of detected sensor information on the BeD device and its transfer to the SmD device. As shown in FIG. 1, a sleep tracking session may be initiated while the SmD device is "connected" for communications purposes with the BeD device. Such a communications connection preferably exists during the entirely of the sleep tracking/detection session. The RM20 library is initiated and a stream or raw movement data is transmitted from the BeD to the SmD. Once the Bed Side device starts tracking sleep and a smart device remains connected, the RM20 library located in the smart device processes data it receives in near realtime. Once the sleep tracking is terminated at the end of a sleep session such as by the user turning off the tracking, the processed data provides the user with information on their sleep, giving the user a clear breakdown of their results such as a sleep score, hypnogram and a pie chart, which will be described in more detail later in the text.

Figure 13:
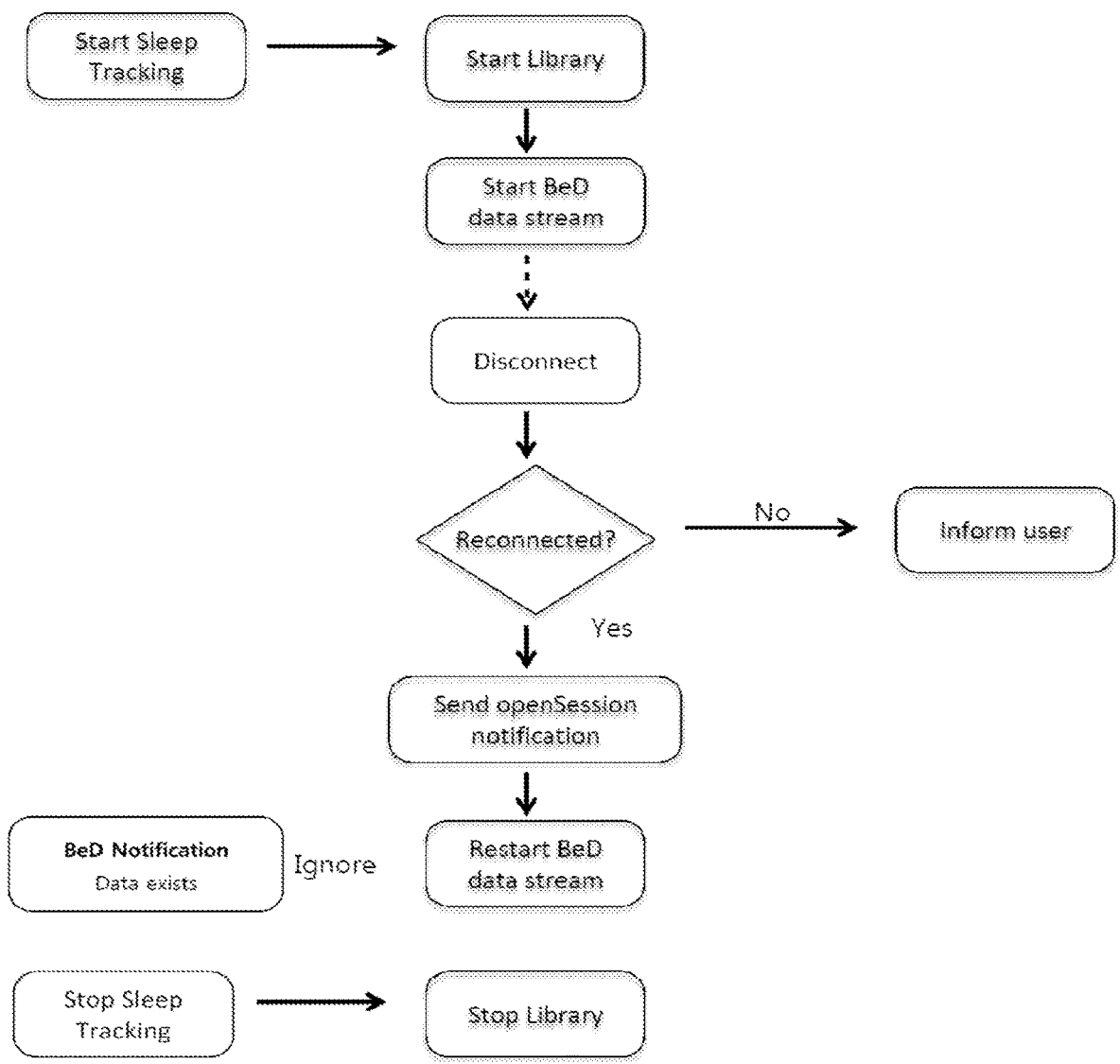
FIG. 13 shows a methodology for sleep tracking such as with an intermittently connected accessory processing device (e.g., motion sensor monitor and smart phone) during a sleep session; in this example, start sleep tracking with SmD (smart phone/tablet etc.) connected occurs, and SmD disconnects and reconnects during the sleep session. The library stops processing data, as it no longer is receiving real time data streaming form the BeD. The post processing results are generated for the user and the user is informed. One such method to inform the user could include a notification on the device. The SmD will try to reconnect to the BeD. If a reconnection is successful, then data streaming and processing will resume from where it left off. The data remaining on the BeD is transferred for processing can the sleep session tracking continues on as normal and the notification can be ignored.

As shown in FIG. 13, during an initiated sleep session after data streaming has initiated, the SmD to BeD connection may be lost ("disconnected"). The library stops processing data, as it no longer is receiving realtime data streaming form the BeD. The post processing results are generated for the user and the user is informed. One such method to inform the user could include a notification on the SmD device such as a software pop up window. The SmD can attempt to reconnect to the BeD. If a reconnection is successful, then data streaming and processing will resume from where it left off. During the disonnect, the BeD may continue to queue detected sensor data. The queued data remaining on the BeD after reconnect may then be transferred for processing by the SmD and further sleep session tracking continues as normal to the completion of the sleep session and the notification can be ignored.

Figure 14:
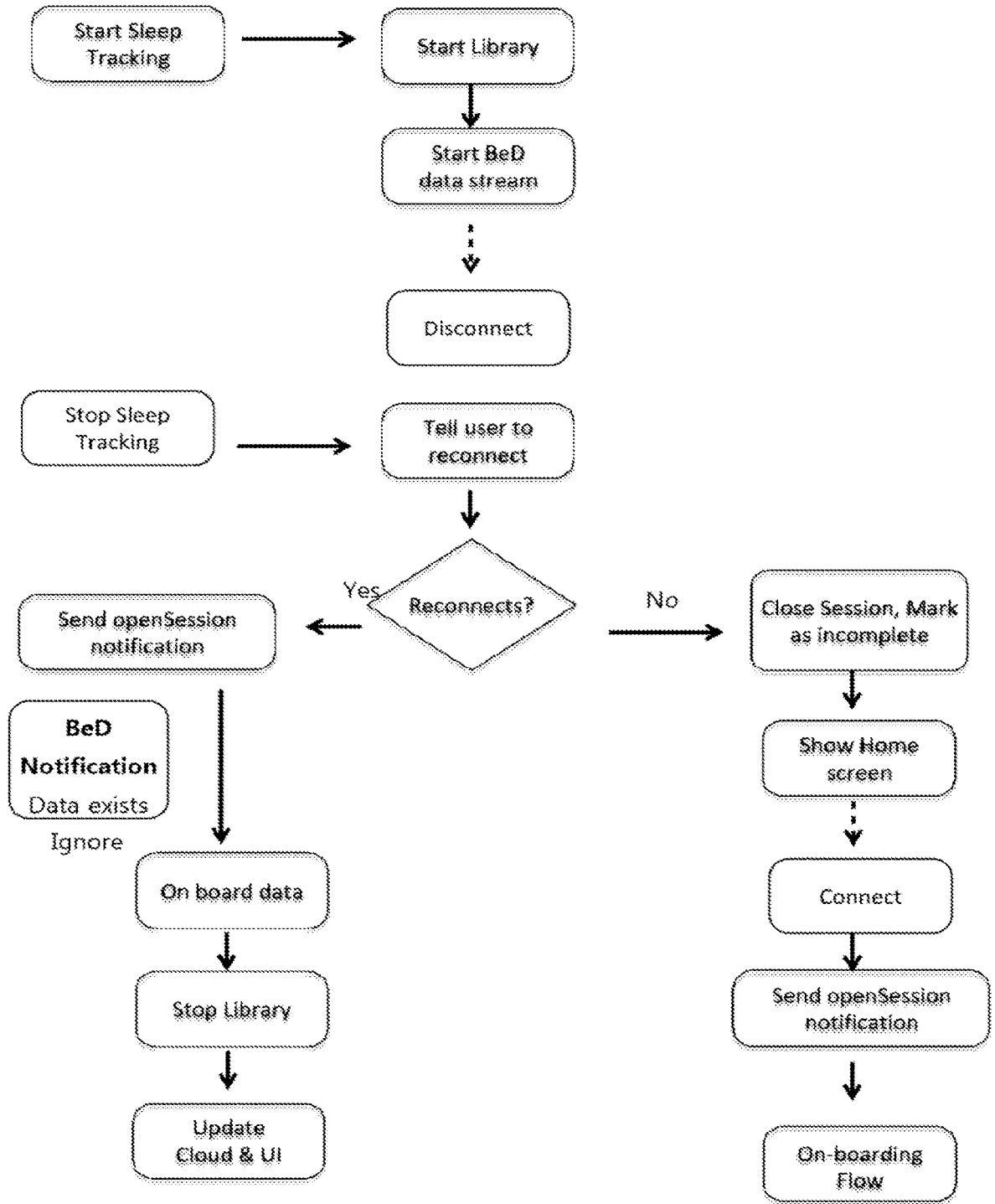
FIG. 14 is another methodology for sleep tracking such as with an intermittently connected accessory processing device (e.g., sleep sensor monitor and smart phone) during a sleep session; in this example, the start sleep tracking occurs with SmD connected, then the SmD disconnects, for example Bluetooth connection is lost. Bluetooth connection can be re-established by itself but if the 'stop sleep tracking' button is pressed before reconnection is established the 'app' offers the option to reconnect. If the user decides not to reconnect then the sleep session will close and the data will remain on the device for a later time. However, if the user decides to re-establish the connection the data on the BeD can be transferred to the SmD for processing and upload to the cloud. This is the on-boarding flow.

In the transfer process of FIG. 14, a disconnect event occurs and a user is provided an opportunity to terminate reconnection. Thus, the start of the sleep tracking with SmD connected may occur as usual. Thereafter, if the SmD disconnects, for example the Bluetooth connection is lost, a notification is presented to the user on the SmD. The connection can be re-established by itself but if a 'stop sleep tracking' button is activated by the user before reconnection is established the SmD application then offers the option to the user to reconnect. If the user decides not to reconnect then the sleep session will close and any queued data will remain on the BeD device for a later time. However, if the user decides to re-establish the connection, the queued data on the BeD can be transferred to the SmD for processing and upload to the cloud servers.

Figure 15:
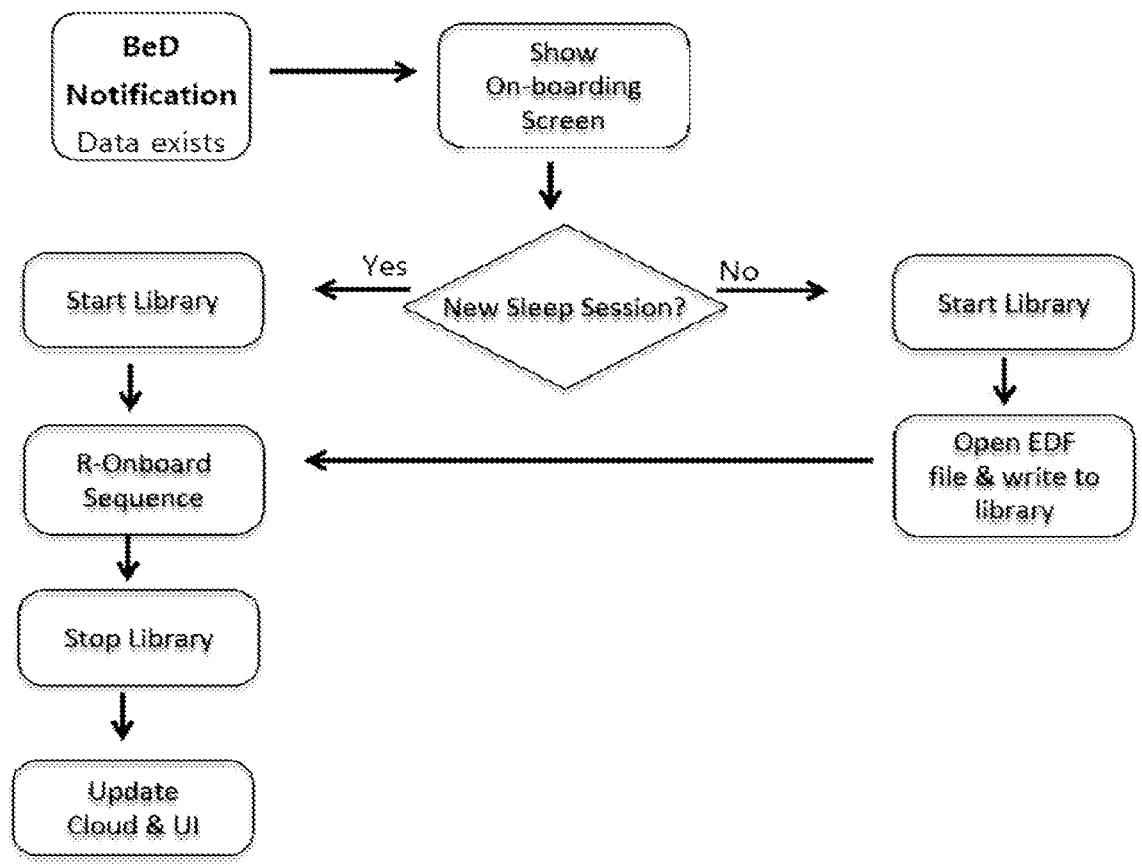
FIG. 15 shows a methodology for transfer of data for sleep session management between hardware device (motion detector with sensors) and smart processing device (e.g., smart phone or computer); this example is of the On-boarding Flow. When a new sleep session is initiated, library processing is initiated, the pre-existing data is transferred from the BeD to the SmD if this data exists. On boarding is required when a loss of connection between the two devices occurs. It occurs once connection is re-established. One embodiment of this occurs when a new sleep session is initiated by the user; library processing is initiated, data on boarding occurs. Once the library is stopped, the sleep data is processed and is available to the user. It is also uploaded to the cloud to contribute to the user data available. This enables the advice engine processing. If a new sleep session is not initiated and reconnection is established after connection loss, for example Bluetooth connection, once reconnection is re-established data on boarding can be performed. The data left on the device can now be transferred to the smart device for processing. European Data Format (EDF) is a standard file format designed for exchange and storage of data time series and may be implemented in this process.

FIG. 15 illustrates an "on-boarding" flow process that addresses how the device manages queued data on the BeD. Such an Onboarding process is necessary when a loss of connection between the two devices occurs. A BeD notification may be provided by the BeD that identifies to the SmD that queued data exists and onboarding should proceed upon connection. The data may be transferred depending on whether a new sleep session is initiated or not. Generally, the RM20 library can manage the transfer and will be initiated after the BeD notification. Any pre-existing/queued data is transferred from the BeD to the SmD via an "R-Onboard" sequence if this data exists and a new session is not initiated (i.e., a session is continued). Such on-boarding will typically occur once connection is re-established. If a new sleep session is initiated by the user and library processing is initiated and the queued data may not be transferred. When the queued data is transferred, the data left on the device may be transferred in a standard file format designed for exchange and storage of data time series such as European Data Format (EDF) via the R-Onboard Sequence. Once the library is stopped, the processed sleep data is available to the user. It can also be uploaded to the cloud servers to contribute to the user data history available. This data then enables the advice engine processing.

Figure 16:
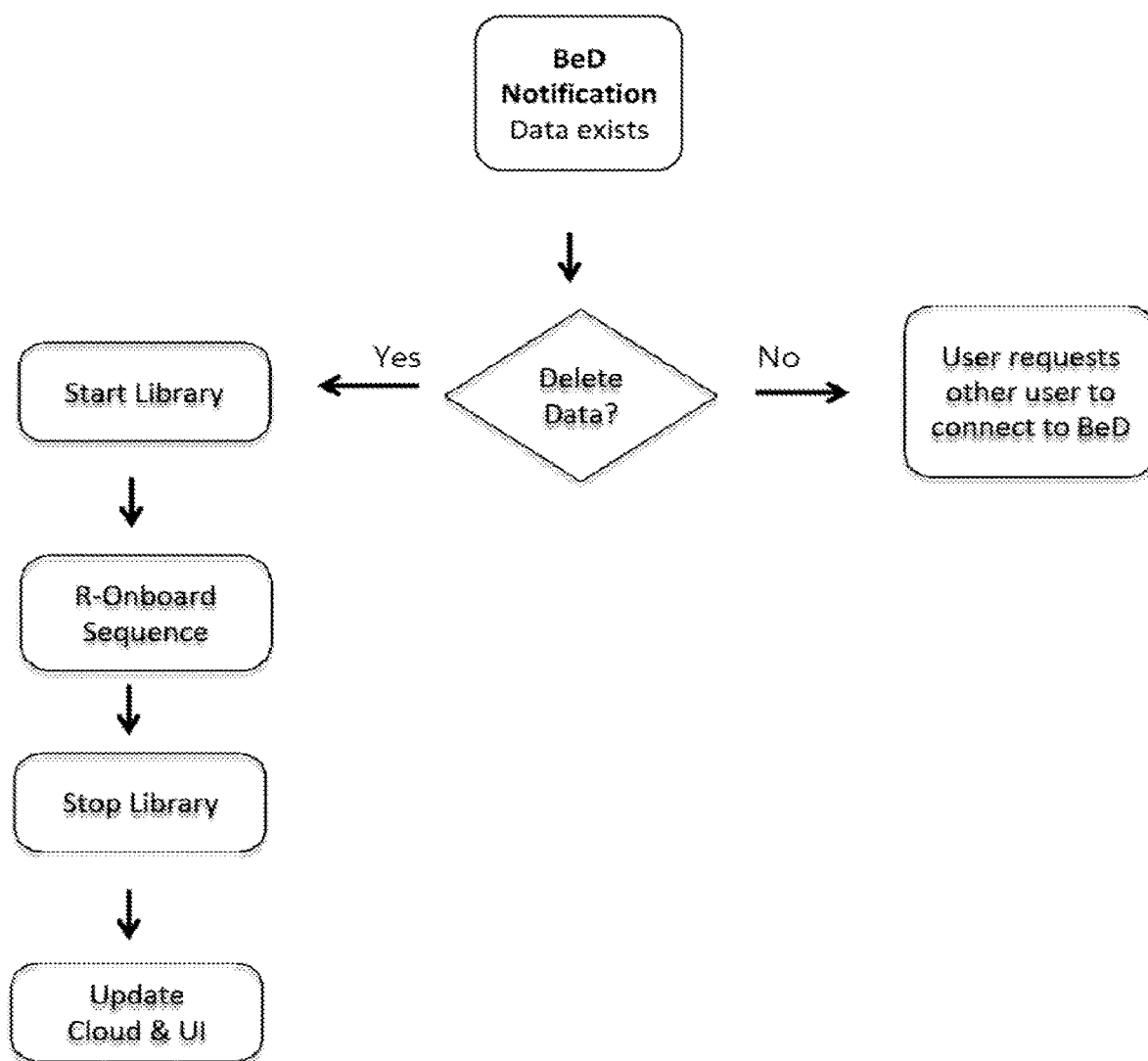
FIG. 16 shows a methodology for deleting data for sleep session management between hardware device (motion detector with sensors) and smart processing device (e.g., smart phone or computer); On-boarding Flow with respect to a different user. Data may remain on the BeD if an unexpected disconnection occurs, such as Bluetooth connection loss. This embodiment gives the option to the user to delete data that remains on the BeD prior to another user connecting to the BeD. If the user decided to remove the data that is stored locally on the BeD, the user must start the library to allow near real time data transfer and processing. Once the library is stopped the data can be viewed by the user following post data processing. And it is also uploaded to the cloud for the back end server to process, the Advice Engine processing.

In the example of FIG. 16, the onboarding process may provide the user the option to delete queued data. If Data remains on the BeD from an unexpected disconnection, such as Bluetooth connection loss, a BeD notification is generated. This process prompts the user to delete data that remains on the BeD prior to another user connecting to the BeD so that the data from different users is not commingled. If the current user decides to keep the data that is stored on the BeD, then a new session will be initiated by starting the library to allow near real time data transfer of the queued data and its processing. Once the library is stopped the data can be viewed by the user following post data processing. And it is also uploaded to the cloud for the back end server to process and the advice engine processing.

System—Exemplar Embodiments of Sleep Tracking—Auto Stop/Start

An auto start and auto stop function can be implemented for the non-contact sensor (BeD)—to ensure that the user does not forget to start and/or stop the sensor. This will ensure that the sensor records regularly the relevant sleep data, whilst no irrelevant data of an empty bed during the day is recorded. The auto-start and auto-stop features may be executed together, separately, or not at all. For some users there may be value in enabling the auto-stop feature only; if they feel that there is a behaviour benefit in associating the depression of the button of the device with the onset of the sleeping phase.

Figure 17:
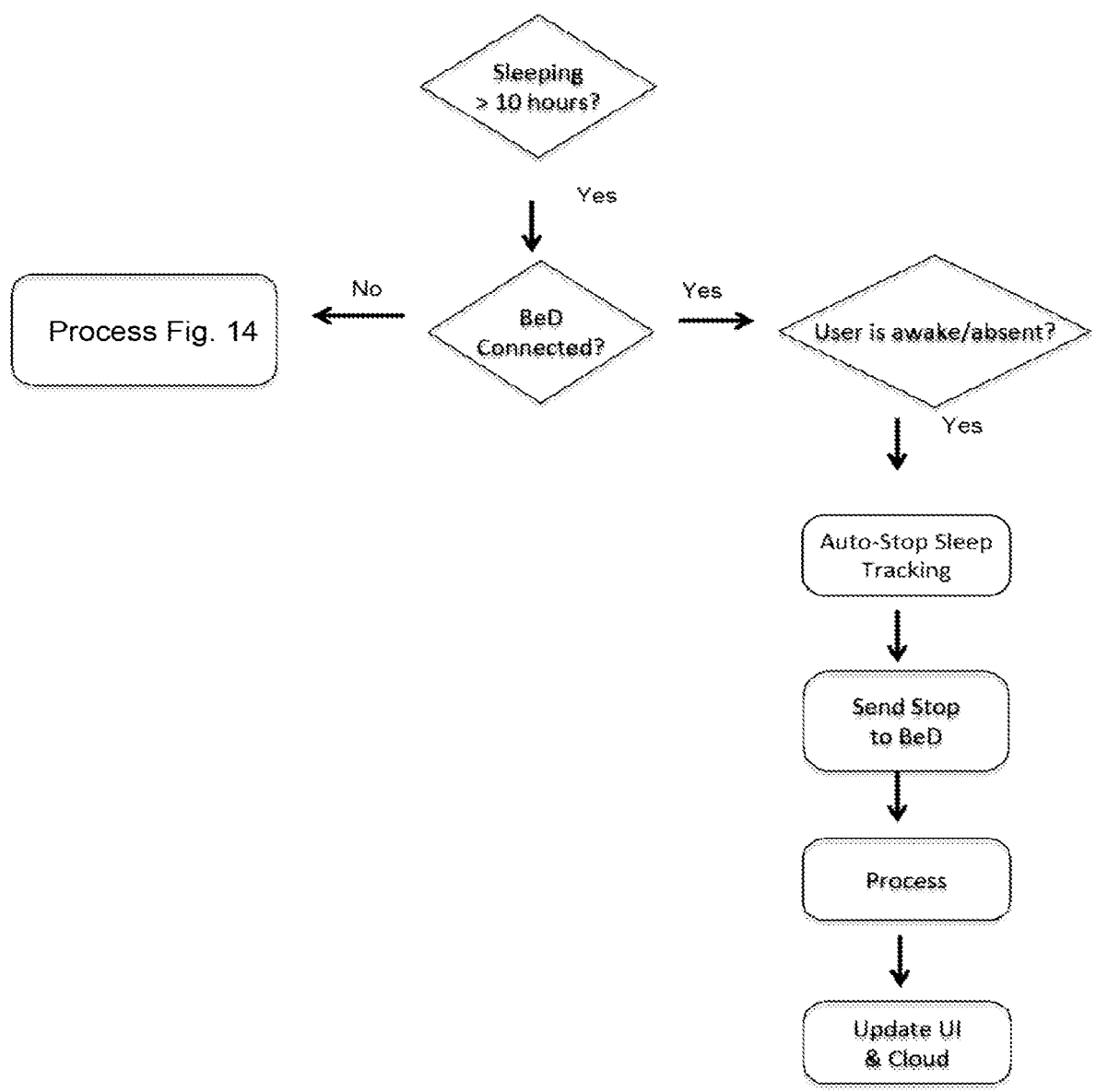
FIG. 17 illustrates a methodology for ceasing sleep session logging such as when a user is not within range of a motion sensor; such an auto stop logic can stop logging data when user is not within range. A probability of the user's absent/presence is determined based on the detection of characteristic breathing signals and/or gross large scale movements. Auto stop is a mechanism for stopping the BeD from over-recording. If the user is deemed to be awake or absent, the SmD will stop monitoring/recording and the data is processed by the RM20 library. The post process data will become available for the user to assess. The data is upload to the cloud for implementation by the advice engine.

FIG. 17 illustrates a process for control of automated termination of the BeD device. This auto stop process can stop data logging such as when user is not within range of the sensors of the BeD. The processor of the SmD by review of sleep data may initially determine if total sleep time is greater than a threshold (e.g., any one of 8, 9 or 10 hours or other). If the BeD is connected to the SmD, the SmD processor by evaluation of the data from the sensor of the BeD may calculate a probability of the user's absence or presence. This may be determined based on the detection of characteristic breathing signals and/or gross large scale movements in the data from the sensor. Auto stop is a mechanism for stopping the BeD from over-recording. If the user is deemed to be awake or absent, the SmD will send a control signal to the BeD to stop the BeD's monitoring/recording process. The SmD then completes its processing of sensed data with the functions of the RM20 library. The post processed data then will be available for the user to view (e.g., in the form of sleep score and/or hypnogram). The data will then also be uploaded to the cloud servers for evaluation by the advice engine. In the event that the BeD is no longer connected, the SmD will attempt to reconnect. This process may be considered with reference to the methodology shown in FIG. 14.

Other versions of auto stop function may also be implemented. In some cases, an autostart function may be implemented. Such auto-start and auto-stop functions allow the automatic recording of data and presenting the "sleep" aspects to the user in a plausible manner. For example, the extraction/determination of "user absent"/"user present" status information from the movement data can form a list of absent/present labels (e.g., on a 30 second epoch basis). The Presence/Absence detection module (e.g., a process of the SmD device) can make a causal decision (e.g., using 64 second windows, 1 second steps) to indicate if the subject is present within the field of the sensor or if the signal is background noise signal; the latter indicating that the subject is absent. The Presence/Absence detection methodology can make a decision based on signal power levels, signal morphology and movement detections. A probability of the user's absence/presence can be determined based on the detection of characteristic breathing signals and/or gross large scale movements. Hysteresis can be used to reject the case where the user (or a pet or child for example) enters the room for a brief period during the day and then leaves again. Other versions may use the main user's characteristic breathing and/or heart rate patterns to distinguish the user from another user's signals (e.g., bed partner).

As an example, when a user enters a bedroom first, they may be seen to move into and out of range of the sensor, or be at the periphery of the sensing range. Additionally, larger movement signatures may be captured during this time as the user prepares for bed. The sleep/wake analysis engine will note a higher percentage of good quality breathing signal, with less movement, as the user prepares for sleep; when these conditions are met, a "present" state may be recorded. The notion that the user is deemed not to be awake is based on a reduction in movement levels (both intensity and duration) being detected and also by the increased regulation in the breathing pattern detected by the BeD. The auto-start event then may be taken as the initiation of a sleep session or the attempt to go to sleep. Auto stop is a mechanism for stopping the BeD from over-recording. If the user has been sleeping for more than a certain period of time (e.g., 10 hours, 16 hours or other) as previously discussed.

Thus, the triggering of sleep session initiation or termination of sleep session may be based on any of the following data parameters: the peak power level in the frequency domain (e.g., using a Fast Fourier Transform); the ratio of in-respiratory-band to out-of-respiratory-band frequencies (to isolate a clear breathing frequency, even in low amplitude signals); Peak or zero crossing detection on the time domain signal (to help characterise movements), and the root mean square (RMS—or quadratic mean) of the time domain signal—a statistical measure of magnitude of a varying signal (indicating movement).

These measures may be performed on overlapping or non-overlapping epochs of data (typically of 30 sec length), and post processing may be performed to reject isolated "false" breathing detection (e.g., in a "true absence" case, some background movement or small periodic signal could raise the probability of a particular epoch being classified as "presence", but if the surroundings epochs have a low calculated probability of "presence", then the epoch under question can be rescored as "absence").

For the "auto-stop" feature, a primary feature may be based on a sustained period of absence, optionally based around the expected user wake time. The system may scan a large portion of absence/presence annotations to avoid tagging an "auto-stop" event when, for example, the user has gone to the bathroom during the night, or gone to the kitchen for a snack.

Optionally, a light sensor can be used, in isolation or in combination with the above described criteria, to detect if the room light is switched on or off, and compared to the user specific habits. Optionally, this may be stored as historical data, by uploading to the cloud, which data the device then can draw upon to determine these user specific habits. This can also contribute to the personalized advice generation. Also optionally, the system can be provided with a 'target time' related to the user going to bed and/or waking up to reduce the search window for the auto-start and/or auto-stop feature.

The auto-start/auto-stop feature may be configured to not "lose" data; for example, if the data is displayed on a device, it may be possible for the user to over-ride the automatically tagged events.

Figure 18A:
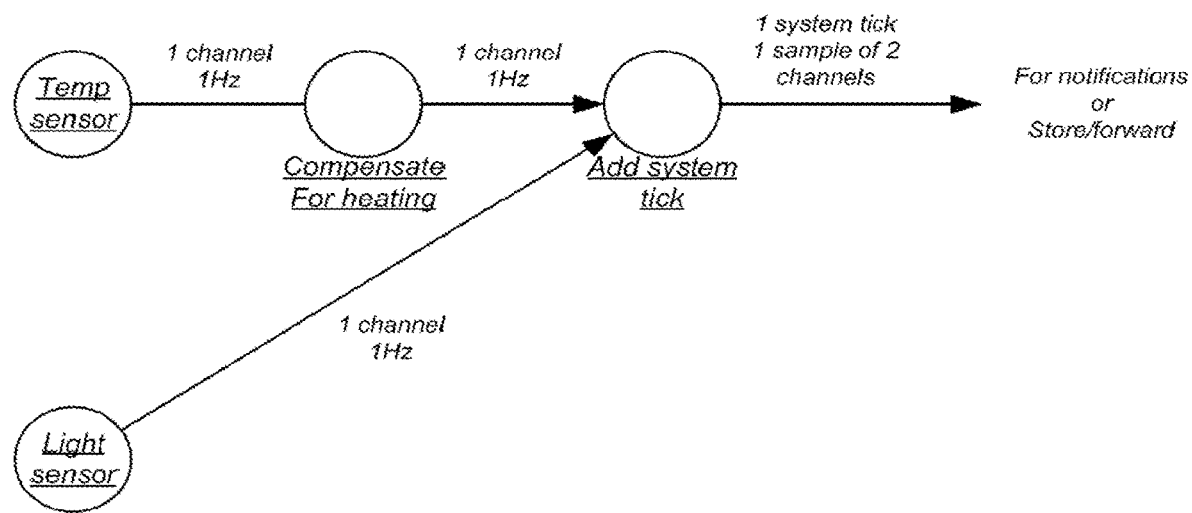
FIGS. 18a and 18b illustrate notification pathways that may be provided by a device of the present technology when implementing real-time bio-motion/environmental signals processing and storage; in this example, temperature compensation is applied to correct for self heating. Also, an antialiasing filter and resampling operation is depicted.
Figure 18B:
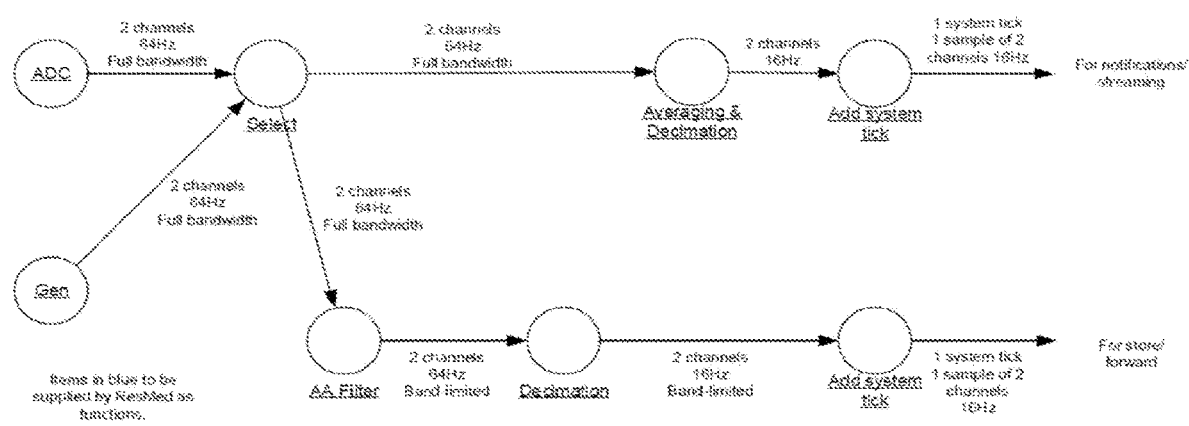

Hardware/Firmware—Exemplar Embodiment—Environmental and Biomotion Data Acquisition FIGS. 18a and 18b iillustrate a "Notification Path" provided by real-time bio-motion/environmental signal processing and storage implemented by the BeD. As illustrated in FIG. 18a, a temperature sensor generates an ambient temperature signal that may be compensated for self-heating (internal temperature). Temperature compensation is applied to correct for self heating. The signal may be combined with a light sensor signal and supplied to the processor (e.g., microcontroller (MCU)) where notifications based thereon may be generated or the data therefrom stored. A similar flow path may occur for the generation of a raw movement signal from the bio-motion sensors of the BeD.

Thus, temperature and light are recorded by the BeD. The BeD may record these data at 1 Hz and down sample to $\frac{1}{30}$ Hz. The SmD may stores 1 light and 1 temperature sample for every 30 second epoch of sensor movement data.

Software—Sleep Staging

As previously mentioned the SmD device may employ RM20 processing functions. The processing functions provided by the RM20 module may include, for example, a relax-to-sleep function, sleep score generation function, hypnogram generation function, smart alarm function and all features that require information processing. RM20 library allows the user to assess their sleep on a night by night basis. As such, the RM20 module may implement a sleep staging process. This process evaluates data obtained from the sensors (e.g., biomotion or otherwise).

Some processes of the RM20 library may include the following:

1. Analysis of raw sensor data: Raw non-contact biomotion data is passed into the RM20 library. This data is processed and a hypnogram (sampled at, e.g., 30 seconds) and sleep parameters (sleep efficiency, total sleep time, etc.) are calculated and can be retrieved from the library such as via API calls. These black box outputs are referred to as Post Analysis Engine (PAE) outputs, or 'end of night' outputs.

2. Provide real time outputs: If the raw data is written to the RM20 library incrementally, then (semi) real-time outputs will be made available. These will include respiration rate, signal quality, sleep state, smart alarm status. These could also include heart rate, and activity levels.

The RM20 algorithm processing may be specified to detect breathing rates between for example, 7.5 and 30 breaths per minute (bpm), corresponding to, for example, 0.125-0.5 Hz. This frequency band corresponds to realistic human respiration rates. Hence, the term 'in-band' refers to this frequency range.

Before the core RM20 algorithm can be implemented, sensor data may be processed using an anti-aliasing (AA) filter, decimated to 16 Hz and high pass filtered at 16 Hz—which is beneficial for activity analysis (See, e.g., FIG. 18b). Phase demodulation techniques are used to map the non-contact sensor signal (16 Hz) to activity at 1 Hz, in a causal manner. In each epoch, additional analysis is carried out to give an epoch based activity count.

Time domain statistics are calculated using 64 second overlapping data windows, with lengths 1 second steps. Computations are causal allowing real time processing, using retrospective data. Non causal methods allow for off-line processing. The sleep score may be calculated at the end of the recording, using a non-causal hypnogram methodology, for example.

The following features may then be derived for each window and each channel: Mean; Standard deviation; Range. Each 64 second window may contain 1024 (64 secs at 16 Hz) data points. Hence, the algorithm(s) may calculate a 512 point FFT for each (I and Q signal components) data window. The results of these FFTs can be used to calculate respiration rate. Data from the biomotion sensor or its signal generator can be made available in a range of rates and resolutions. Typically only one rate/resolution will be implemented within the BeD at any one time. The RF Biomotion sensor permits extraction of movement features and estimation of breathing features.

Further details of the analysis of motion signals in the detection of respiration, movement and sleep staging by the RM20 processing may be considered in reference to the disclosures of PCT/US13/060652 filed Sep. 19, 2013 and PCT/US07/70196 file Jun. 1, 2007, the entire disclosures of which are incorporated herein by reference.

Figure 19:
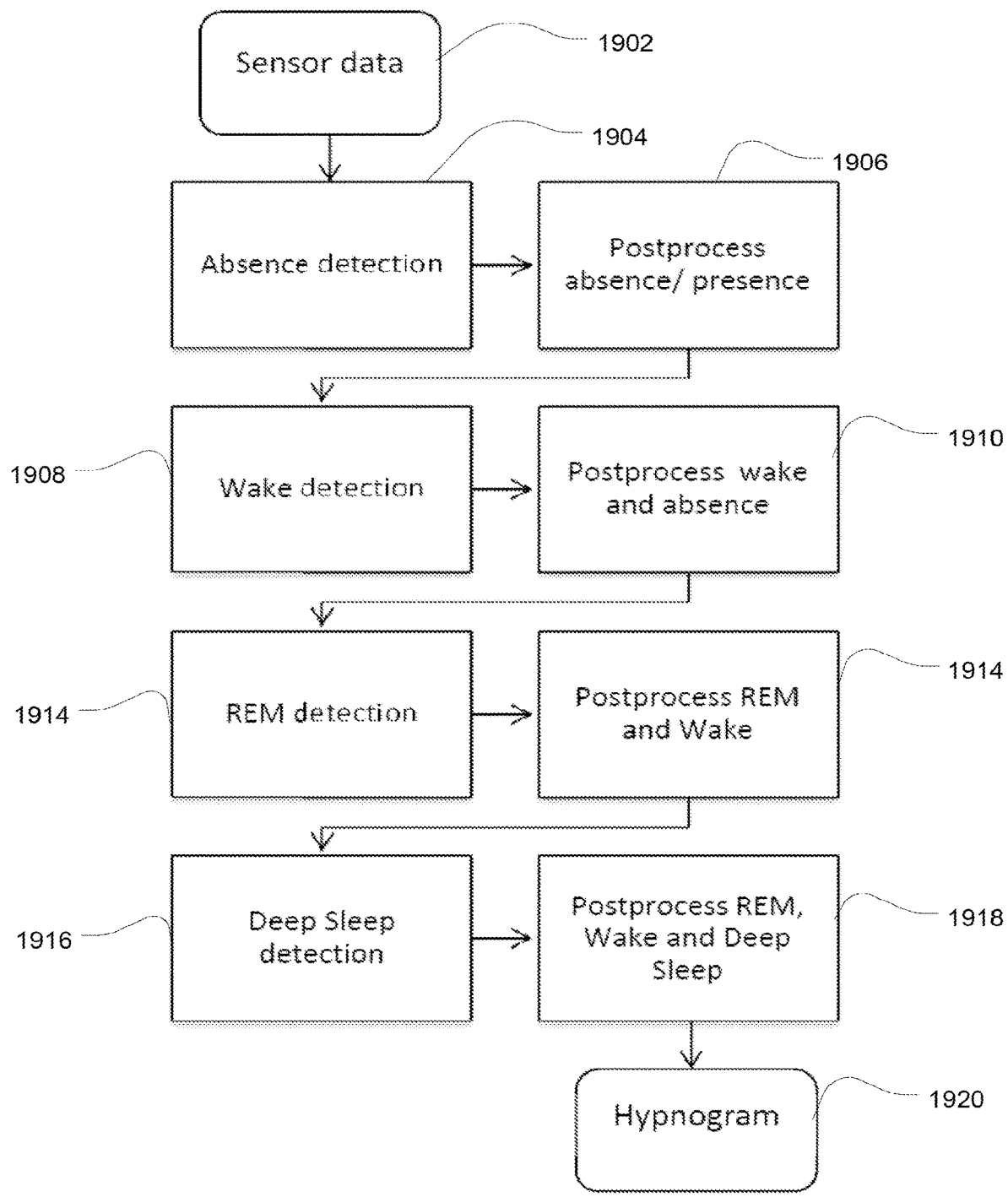
FIG. 19 is an example sleep staging methodology flow chart that may be implemented by the processing of the apparatus described herein.

The sleep staging process may then be considered in reference to FIG. 19. Sensor data is received at 1902. Absence detection and presence detection processing is made at 1904 and 1906. Wake and Absence detection processing is made at 1908 and 1910. REM detection and Wake detection processing is made at 1912 and 1914. Deep Sleep detection and REM, Wake and Deep Sleep processing is made at 1916 and 1918. A Hypnogram is then generated at 1920.

Thus, the SmD may determine and display sleep related data and stages of sleep over time of a sleep session such as wake, absent, light sleep, deep sleep and REM sleep.

Figure 20:
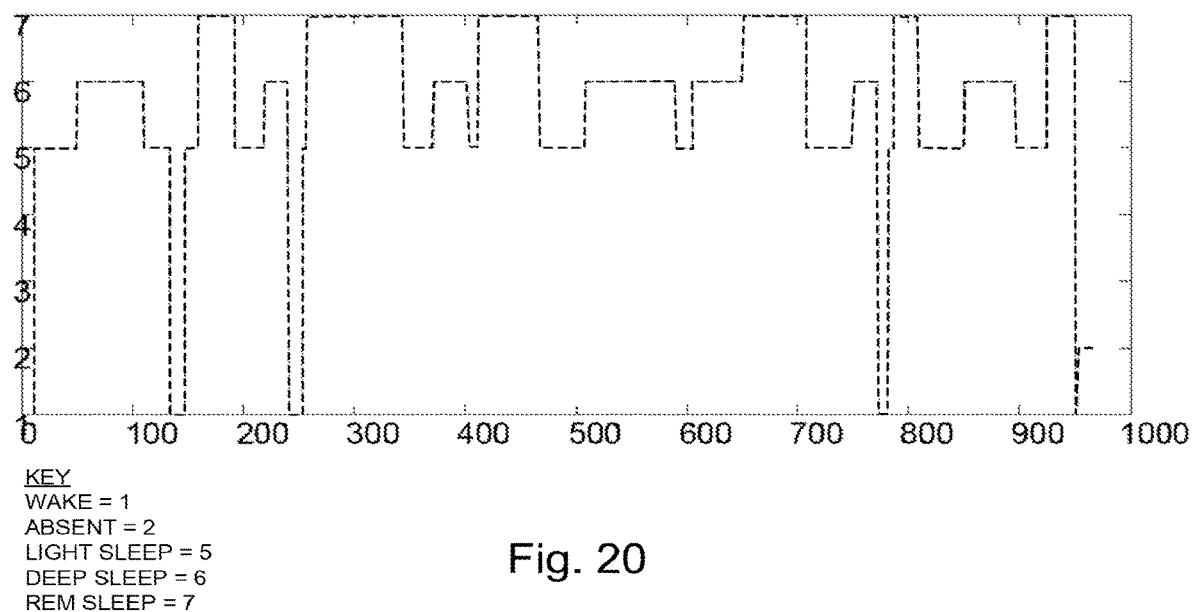
FIG. 20 illustrates example sleep staging processing output such as in the form of a hypnogram.

A suitable example hypnogram with such data over time is illustrated in the graph of FIG. 20. Typical information captured on the hypnogram may be the indication of any one or more periods of a) Deep Sleep, b) REM sleep c) Light Sleep d) Awake periods e) Absent Sections f) Events Annotation (e.g., detected Light, Noise and Temperature events and/or such events may have disturbed sleep and be displayed in association with wake periods); g) Sleep Score h) indication of a level of Body Recharge and/or Mind Recharge; j) Date and Time Information. A typical data flow that may be involved with the hypnogam may include: 1. Generation of analog data from the bio-motion sensor of the BeD; digitizing the generated data via a ADC; 3. Data arrives in a circular buffer; 4. transmission to the SmD; 5. Processing with the RM20 library of the SmD; 6. Generate hypnogram & Sleep Synopsis information, displayed on SmD; 7. forward to the network server (the Advice Engine and store on the Cloud Repository); and 7. Advice engine generates and returns advice nugget(s) back to SmD based on hypnogram and sleep synopsis information.

Thus, a hypnogram may be provided as a feedback report to indicate whether the subject's status at the respective period is that of deep sleep, light sleep, REM sleep, wake or absent for every 30 seconds of the recording. There can be multiple (e.g., two types) hypnograms provided: a pseudo (as it requires a number of surrounding Epochs) real-time hypnogram and a post processed hypnogram (which makes use of a whole recording as can be seen in sleep history). The hypnogram may therefore be based on: (1) An activity and movement detection module that determines whether the subject had a gross body movement or lay motionless; (e.g. Displacement 16 Hz); (2) a presence detection module which determines whether the subject is present or absent; and/or (3) Sleep staging algorithm for Sleep/Wake detection, REM detection, Deep sleep detection and/or Light Sleep detection.

Sleep/Wake at 1908 and Post-Process Wake and Absence at 1910

A filter is used to update activity counts throughout the night. A threshold for wake detection is applied to the output of the filter. This threshold is combined with a ramp function, which accounts for Wake being more likely to occur at the beginning of the night, decreasing in likelihood for the initial part of the night and then reaching a plateau. It may be assumed that no "absence" status exists at the beginning and end of the data recording—absence in these sections is rescored as wake. Periods of absence must be surrounded by periods of wake.

REM Identification at 1912 and Post-Process REM and Wake at 1914

To identify sections of REM, a threshold for REM detection is applied to the normalized respiration rate variation. This threshold may be combined with a ramp function for the threshold, which accounts for why REM is more likely to occur during the latter part of the night. REM typically cannot be preceded by Wake. Short Wake sections within long REM sections may be removed.

Deep Sleep Identification at 1916 and Post-Process REM, Wake and Deep Sleep at 1918

To identify sections of deep sleep, a threshold for deep sleep detection is applied to the normalized respiration rate variation. This threshold may be combined with a ramp function for the threshold, which accounts for deep sleep being less likely to occur beyond a certain portion of the night. Sections of deep sleep which are close to sections of wake at the beginning and end of night may be removed. A check may be performed to determine if deep sleep follows too soon after REM. If it does, the end of REM section and first portion of deep section may be rescored.

Figure 21:
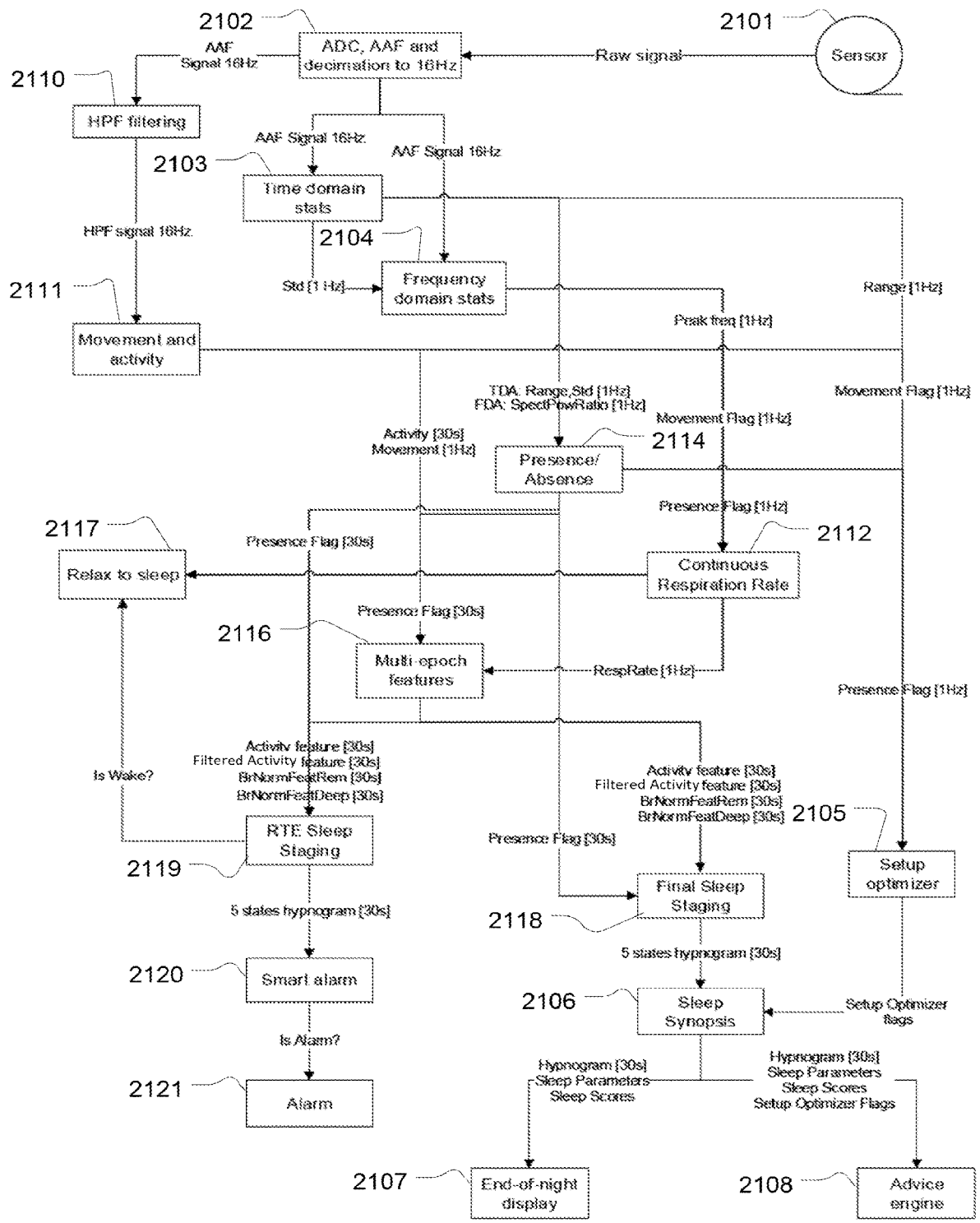
FIG. 21 is another detailed example of a sleep staging process that may be implemented by one or more processors of the devices of the present technology.

Software—Specific Embodiment—System Flow of Sleep Staging, Relax to Sleep, Sleep Score, Smart Alarm, Advice Engine Example processing of the RM20 functions are illustrated with reference to FIG. 21. The sensor at 2101 generates a raw motion signal. The signal is digitized, subject to anti-aliasing and decimated at 2102. Time domain statistics and/or frequency domain statistics can be determined from the processed signal. Time domain statistics and frequency domain statistics are determined at 2103 and 2104 respectively. Range, movement and presence information is supplied to a setup optimizer at 2105 where flags are generated for sleep synopsis at 2106. In some versions, the setup optimizer may execute the processes described in more detail in the following specification. The filtered signal of the sensor is also supplied to high pass filtering process of 2110. The resulting signal is supplied to movement and activity detection process at 2111. Frequency statistic information is supplied to a continuous respiration detection process at 2112. Time domain statistics are supplied to presence absence detection process at 2114. The respiration rate may be applied to a "relax to sleep" process at 2117. Presence, activity, movement and respiration information is supplied to multi-epoch features process at 2116. The epoch features are then supplied to final sleep staging process at 2118 which provides hypnogram output for the sleep synopsis process 2106. The epoch features are also supplied to the real time sleep staging process at 2119, which provides sleep information for a smart alarm process 2120 for triggering an alarm at 2121. The output sleep synopsis information may then be provided to an advice engine at 2108 and an end-of-night display process at 2107.

In summary, the RM20 library can process the biomotion sensor data in real time and also at the end of a recording. This library allows the estimation of sleep quality metrics on a night by night basis. There are also product specific modules to support certain features. For example, the Relax-to-Sleep feature relies on respiration rate capture in real time. Similarly, smart alarm processing considers sleep staging estimation in real-time and provides a logic for ensuring users are not woken up while in deep sleep within a chosen time window.

The following represents the current outputs provided by the RM20 processing:

(a) A 5-states (3 stages of sleep) hypnogram. This indicates whether the current subject's status is that of deep sleep (N3 sleep stage), light sleep (N1-N2 sleep stage), REM sleep (N4 stage) or REM stage, wake or absent for every 30 seconds of the recording. There are two type of hypnograms provided: a pseudo (as it requires a small number of surrounding epochs) real-time hypnogram and a post processed hypnogram (which makes use of a whole or more complete recording). Optionally, an extra state could be included, whereby light sleep stages N1 and N2 are separated into two states. To facilitate the hypnogram, the following are evaluated:

(1) An activity and movement detection module which estimates gross body motion;

(2) A presence detection module which estimates presence or absence;

(3) A module capable of returning respiration rate throughout the night;

(4) Certain multi-epoch features obtained from respiration rate and activity levels;

(5) Sleep staging algorithm (Sleep/Wake; REM detection; Deep sleep detection)

(b) Relax: Processed respiration rate data is provided as an input to the Relax feature.

(c) Real-time sleep staging: this output and a heuristic logic aim to wake the user within a user-defined time window, while not in deep sleep.

(d) Sleep score: A score is provided at the end of the recording to indicate how well the user slept overall, based on sleep staging information.

Most processing employed in the RM20 algorithm module is conducted using causal methods for real time processing, and also using non-causal methods for off-line post-processing. Functions may be either real-time, requiring retrospective data only, or off-line non-causal, requiring the full signal being available prior to analysis. Various processing methods are described in detail in the sections to follow.

Time domain statistics at 2103 of the process may be calculated using 64 second data windows, overlapping with 1 second steps. Computations are causal, using retrospective data. The following features may then be derived for each window and each channel: Mean, Standard deviation and/or Range.

Frequency domain statistics at 2104 may be calculated using 64 second overlapping data windows, with 1 second step length. Computations are causal, using retrospective data. The process may detect breathing rates within a certain breathing rate window. For example, this amounts to 7.5 to 30 breaths per minute (bpm), corresponding to 0.125-0.5 Hz. This frequency band corresponds to realistic human breathing rates. Hence, in this document the term 'in-band' refers to the frequency range 0.125-0.5 Hz. Each 64 second window may contain 1024 (64 seconds at 16 Hz) data points. Hence, the algorithm calculates a 512 point (N/2) FFT for each (I and Q) data window. The results of these FFTs are used to calculate in-band spectral peak (which may subsequently be used to determine respiration rate), as described below. The in-band frequency range is used to calculate respiration rate for each 64 second window, as described below. An alternative frequency band can also be considered for typical heart rate (e.g., where a HR of 45 beats per minute to 180 beats per minute corresponds to 0.75-3 Hz).

The spectral peak ratio may also be determined at 2104. The maximum in-band and outside-band peaks are identified, and used to calculate the spectral peak ratio. This may be understood to be the ratio of the maximum in-band peak, to the maximum outside-band peak.

The In-band variance may also be determined at 2104. The in band (0.125 Hz-0.5 Hz) variance quantifies the power in the frequency band between 0.125 and 0.5 Hz. This is used in the presence/absence detection module.

The spectral peak is identified at 2104 in the frequency band of interest through the implementation of a figure of merit which combines spectral power level at each bin, as well as distance from adjacent peaks and frequency of bin. The bin with the highest value for the above described figure of merit.

Activity Estimation and Movement Detection at 2111

Phase demodulation techniques are used to map the non-contact sensor signal (16 Hz) to activity at 1 Hz, in a causal manner. In each epoch, additional analysis is carried out to give an epoch based activity count. One example methodology follows:

Phase Between I & Q Channels:

Phase is found by mapping the ratio between I and Q sample to the closest value in a pre-defined matrix of arc-tangent values.

Initial Activity Analysis:

Initially the activity counter is set to zero: ActCount=0

Check that I and Q signals are both above the noise threshold (0.015)

If yes: ActCount=ActCount+8 (but never >16)

If no: ActCount=ActCount−1 (but never <0)

If ActCount(i)>=9, and ActCount(i−1)<9, the $i^{th}$ data point recorded as the start of a movement.

While no movement started, velocity=0 Displacement analysis (only while movement detected, ActCount>=9):

Velocity is calculated as the change in phase between consecutive points; i.e. the instantaneous phase delta.

Displacement (16 Hz)=abs(Velocity).

Final Activity Analysis:

Activity (1 Hz)=mean displacement for each second.

For computational efficiency, activity is then mapped to the closest value on a pre-defined matrix In each 30 second epoch, Activity is summed, and limited to a maximum of 30.

Presence/Absence Detection at 2114

The Presence/Absence detection module makes a causal decision (using 64 second windows, 1 second steps) to indicate if the subject is present within the field of the sensor or if the signal is purely noise; the latter indicating that the subject is absent. The presence/absence detection algorithm makes a decision based on signal power levels, signal morphology and movement detections. For absence detection, the maximum in-band power between the I and Q signal channels from the sensor is identified. A threshold is then applied to this value to identify absence and presence sections. Absence is detected if the in-band variance is less than a threshold, and no 'twitches' are detected (twitches are identifies when the range in a given second is greater than a pre-defined threshold). Presence is detected otherwise.

Following presence/absence detection, several post-processing steps are implemented. The following steps account for periods of data at the beginning and end of the recording where the user may be moving in and out of the field of the sensor: (i) Find all sections of presence greater than 15 minutes; (ii) Mark all epochs before beginning of first as absence; (iii) Mark all epochs after end of last as absence. Detected absences are padded out to the previous and following detected movement, provided it is contained within a 5 minutes window from the boundary of the absence detection.

Real Time Respiration Rate Estimation at 2112

The module processes the respiration rate vector (1 Hz), previously calculated through spectral analysis, to exclude values which deviate too far from the previous mean, and output a vector of breathing rates at 1/30 Hz:

The system has 3 main modes of operation:

Init mode
- The initial 'best respiration rate' is taken as the mean of the initial respiration rate values for I and Q channels Fast output mode
- For each new data point, the updated mean of the signal is calculated and compared with the previous mean. The I or Q (in-phase or quadrature) respiration rate value which is closest to the previous mean value is used.

Safe output mode
- Like fast output mode. As an additional condition, for each sample (one sample/second), the algorithm checks if the new mean respiration rate is within a certain band (e.g. +/−30%). If this is the case, the new value is assumed to be an anomaly and is replaced by NaN (not-a-number).
- In case no output is returned consecutively for more than a certain amount of time (in one embodiment 120 s) of presence and no movement, due to the condition on the maximum allowed against currentMean, the system is set to InitMode.

The resulting respiration rate vector is used in all further analysis; and in the SmD App to run the Relax-to-sleep feature.

Multi-Epoch Analysis at 2116

In this section of the algorithm, data is processed using 30 second non-overlapping epochs.

Activity count—causal and non-causal:
- Epoch-based activity counts are used here. A filter using 21 (non-causal) or 11 (causal) empirically derived coefficients is used to provide the final estimation of activity in each epoch.

Respiration rate variability analysis:
- De-trend the respiration rate signal by subtracting the moving average (using a pre-defined window size to generate REM and Deep Sleep respiration rate variability features) of the respiration rate signal.
- Find the local variation signal by calculating the moving standard deviation of the de-trended respiration rate signal.
- Using shorter windows (half as long), select sections of the moving standard deviation signal; Take the minimum standard deviation in each window as the final local variability of respiration rate.

Sleep Staging at 2119 and 2118

The sleep staging module uses the outputs of the presence/absence and multi-epoch analysis modules to generate a hypnogram, sleep parameters and sleep scores. A decision is made for every 30 second epoch to indicate if the subject is asleep (deep, light or REM), awake, absent. A block diagram of the sleep staging algorithm is shown in more detail in FIG. 19.

Smart Alarm Flowchart of Logic

The system may include a smart alarm which may assist user with waking up during optimal wakeup/time state to ensure most restful sleep and waking. This seeks to sound the alarm when the user is in an awake, aroused, or light or REM sleep state. In some configurations, REM sleep stages may also be avoided by the smart alarm. The system will alarm at the end of the pre-programmed time window (e.g., sound an alarm at the optimal time within a defined wake-up window), regardless of the sleep state, in order that the user definitely is woken. The alarm can be set once, daily, or on selected days such as weekdays only. The user can also choose to set a time window before the alarm time where the sleep monitor device can decide to wake the user, along with an audio sound chosen from a list provided by the application or from a file on the SmD to set the audible alarm sound. The optimal wake time may be determined based on near real-time sleep staging analysis by the processing library.

The user may select a time for the alarm to fire/trigger and an alarm window, which proceeds the alarm time. The system looks for a suitable sleep stage during the time window and wakes the user when one is detected. A user can query if an alarm is set. The user can query the current set alarm time. The user can disable the alarm, if set.

If the user is within deep sleep during the alarm window, the system will wait for up to, for example, 20 minutes (or so) before beginning to ramp an audio alarm/music very gradually in order to lead the user into a light sleep, and then into a wake state. The predefined time may not be 20 minutes and may depend on the length of the alarm window. The system will sound the alarm at the end of the alarm window regardless of the sleep state, in order that the user definitely be woken.

This feature differs from the classic alarm which is set to a specific time in the morning with the opportunity to snooze for another fixed period of time, the smart alarm, offers the user the option to have the app attempt to awaken them at a time more suitable to a comfortable awakening. The smart alarm uses the real time processed data to intelligently select a time with which to sound the alarm. The period with which this alarm could fire is selected by the user the previous night or according to a schedule. Once the alarm window is reached the smart alarm feature will select a sufficiently lengthy period of light sleep or wake to sound the alarm. If a period of light sleep or wake cannot be found the alarm defaults to firing at the very end of the window.

The optimal time is determined based on near or real-time sleep staging analysis. The RM20 library contains the logic about whether the alarm should be fired or not. The application passes the Current Epoch, the Epoch number of the start of the window, and the Epoch Number of the end of the window to the RM20 library. It preforms its logic internally and passes a flag back to the app. This flag is a go/no go for the alarm sound.

An example use of the smart alarm may be considered in reference to the following table. Consider a sleeper, George. George goes to bed. He logs onto the SmD application and sets the Smart Alarm window to end at 7:30 am with a length of 30 mins. He chooses the Alarm Sound and he then starts his Sleep Session.

| # | Use Case | Outcome |
| --- | --- | --- |
| 1 | If George is in Deep Sleep | Smart alarm waits for George to have 1 epoch of wake or 4 epochs of light sleep before activating* |
| 2 | If George is in Light Sleep | Smart alarm waits for George to have 1 epoch of wake or 4 epochs of light sleep before activating* |
| 3 | If George is awake | Smart alarm fires immediately |
| 4 | If George is absent | Smart alarm fires immediately |

-continued

| # | Use Case | Outcome |
|---|---|---|
| 5 | If George is in REM | Smart alarm waits for George to have 1 epoch of wake or 4 epochs of light sleep before activating* |

*activating means that the Smart Alarm logic proceeds to the probability function as opposed to firing where firing is understood to mean that the alarm is activated to wake the user immediately. This logic has a weighted probability of waking the user towards the end of the smart alarm window.

Typical pre-requisites for proper function of the Smart Alarm may include:
  The BeD is set up and powered on—Smart alarm cannot activate without a functioning system (but the alarm will fail safe trigger at the end of the alarm window to wake the user)
  The BeD is getting sufficient bio-sensor signals (but the alarm will fail safe trigger at the end of the alarm window to wake the user—see also the conditions where the user is wake or absent)
  The user sets the smart alarm—if the user forgets or doesn't set it or doesn't set it up correctly, the smart alarm will not activate (unless the smart alarm is on a daily, weekly or other repeat cycle)
  The user activates a sleep session—if the user doesn't start a sleep session, the smart alarm will not activate
  In order to wake user at an appropriate phase of sleep, the user should be asleep up to and during the smart alarm window—if user is awake or absent the smart alarm will default to immediate activation i.e. no smarts just alarm
  Volume is set sufficiently high to wake the user—if the volume has been turned down then the amplitude of the alarm may not be sufficient to wake the user (unless the smart alarm is configured to override the volume setting).
  Alarm scheduling is set up correctly (for example, weekdays, everyday etc)—if the scheduling is incorrect then the item for the smart alarm to activate will also be incorrect.
  Alarm sounds for sufficient length to wake the user—if the alarm length is too short it may not wake the user. If it doesn't turn off automatically then it requires user interaction and could run indefinitely.

Figure 22:
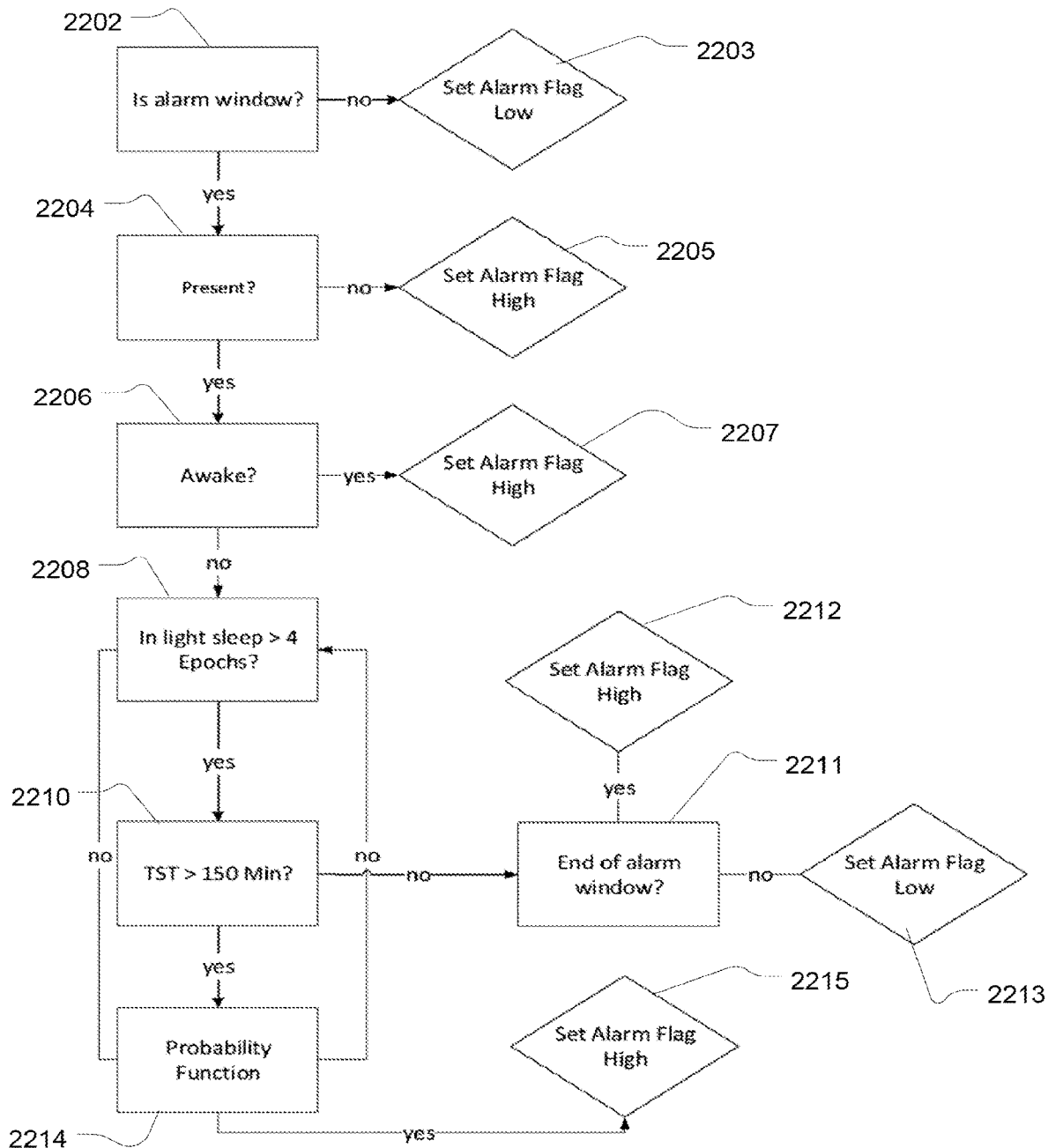
FIG. 22 is an example methodology for a wake alarm in some versions of the present technology.

A processing methodology for operation of the smart alarm by a processor of the SmD may be considered in reference to FIG. 22. At 2202, the processor determines if the current time is within the set wake up alarm window. If no at 2203, the alarm flag is set low preventing the alarm from sounding. If yes, at 2204 the processor determines with movement data analysis if the user is present. If no, the alarm flag is set high, thereby sounding the alarm. If present at 2206, the processor determines if user is awake with movement data analysis and sleep staging information. If yes, the alarm flag is set high at 2207 sounding the alarm. If no, the processor determines at 2208 if the user is in a light sleep stage for a least a certain number of epochs (e.g., 4 or more), if no, a probability function is evaluated at 2214. Based on the probability function at 2214 the alarm may be set high at 2215 or maintained low by returning to the light sleep evaluation at 2208. If in light sleep for sufficient epochs at 2208, the total sleep time of the sleep session is evaluated at 2210. If sufficient sleep exists (e.g., by comparing with a threshold of for example, 150 minutes) the probability function at 2214 will again be evaluated. If sleep is not sufficient at 2210, the end of alarm window time will be evaluated at 2211. If at end of the alarm window the alarm flag is set high at 2212 sounding alarm. If not, the alarm flag will be set low at 2213 and process will return to 2208 or 2210.

At 2214 the evaluation of the probability function provides a randomised time delay aiming to avoid waking the user at the same time every morning. The probability of the alarm triggering with the function will increase with time. A threshold of the process at 2214 is set as a function of the start of the alarm window (this value is relative to the start of the recording session e.g., 600 epochs from the beginning of the night), and may be for example:

$$threshold = modulus(startAlarmWindow, 10)$$

The variable is obtained by monitoring the current Epoch as follows:

$$\text{current probability vale} = \left( \frac{currentEpoch - startAlarmWindow}{endAlarmWindow - startAlarmWIndow} \right)^2 \times 10$$

If this current probability value is below the previously defined threshold, we can set the alarm flag high otherwise it will remain low. Other randomizers may be employed at 2214.

Figure 23:
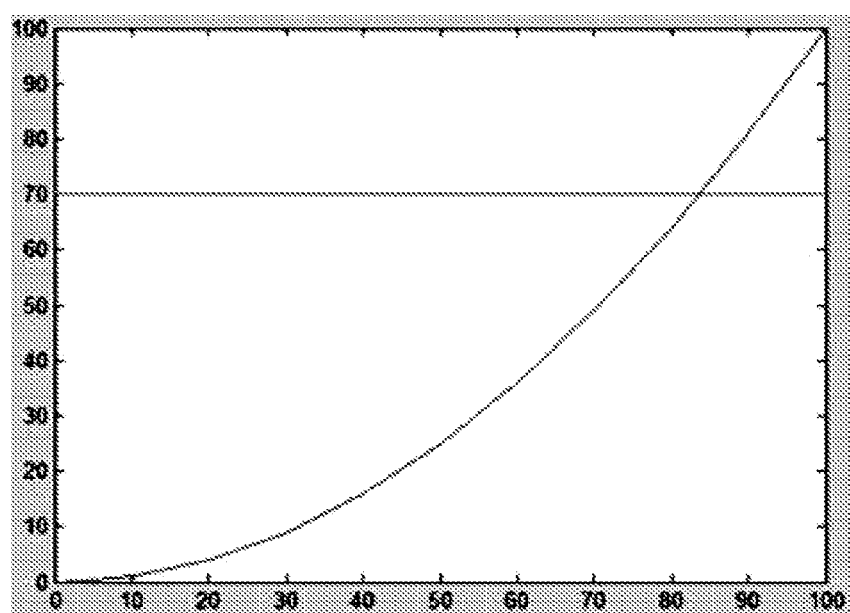
FIG. 23 is an example of a probability function that is a continuously increasing function with respect to a fixed threshold, the illustrated example of probability function being used in some embodiments of the described technology.

FIG. 23 illustrates the function at 2214. The plot above the curved line represents the varying probability function while the horizontal line represents a fixed threshold. This threshold is randomized by the fact that the startAlarmWindow value will vary from night to night. This is flat randomization, all values for the threshold are equally probable. The variable could be linear and the smart alarm would also have a flat probability of firing. To skew the data toward the end of the night, the variable is quadratic. Preferably, this probability function is evaluated once the processor has detected that the user has obtained at least 2.5 hours of sleep, 4 epochs of light sleep, and the subject is not already awake. Other suitable minimums may be applied.

Software—Example Embodiment—Sleep Analysis Feedback

Sleep Score, Mind and Body Recharge

It is normal to have about 5% wakefulness during the night. All stages of sleep are important. However, a balance of deep, light and REM sleep is needed to feel at our best in the morning. Processing may be performed by the system herein in order to provide feedback to a user concerning the quality of their sleep. This may be provided as a sleep score, a mental recharge indicator and/or a body/physical recharge indicator. Such feedback may be considered generally with reference to the examples of FIGS. 24, 25a and 25b.

There can be three scores; overall, mind and body recharge scores. These can be determined or calculated, such as by the SmD device, with the RM20 library processing. The normative parameters, from which the scores may be based, may be located in the normative database which has been generated for the advice engine and reside in the cloud servers. An extensible normative database has been generated for the Advice Engine. It may be derived from the mean and standard deviations (in percentage terms) for the sleep parameters that are measured across a broad population with 120 breakdowns including age and sex, for example. These normative values may optionally be enhanced or updated by the inclusion of a user's own data. A user's score for each element may be calculated. This may be done by comparing a measured sleep parameter for that user with the normal distribution for a person of that age and sex. The score for each of these factors is obtained by comparing a user's sleep factors with those of the general population (normative data). For example, if a user gets less sleep than most people of their age and gender then they will get a low score for sleep duration (e.g., 7/40).

It is desirable to provide such feedback so that it is (a) Easy to see connection between sleep score, nights sleep, body and mind charge; (b) Easy to represent visually; (c) Aligns with normative database in Advice Engine; (d) Built in comparison to norms; (e) Easily extensible to make sleep tab a set of buttons lining to more data on each parameter.

Sleep Score

Following a night's sleep it is useful to be able to provide a user with some feedback on the measurements made on their sleep. The sleep score is one of the mechanisms to meet this need. In some cases, a sleep score may be derived from an unbounded equation that tries to weight different measured sleep parameters so as to produce a number that somehow reflects how a person has slept. The reason the equation is unbounded is to allow for the user to exceed a 'norm' and that somehow this is something that the user can respond to positively. However, users may be found to be confused by a score exceeding 100, and alternative approaches can be implemented. Thus, in some versions, a sleep score may represent the quality of the user's sleep and it may be a value on a scale of 0 through 100. It can be presented as a representation of the different stages of sleep. The sleep score may compile a series of additive elements with each element being associated with a sleep parameter that is measured. A user's score for each element is calculated. This can be done by using the user's data alone or in comparison with previous sleep data of the same user. Alternatively, this can be done by comparing what is measured as a sleep parameter for that user against the normal distribution for a person of that age and sex. The further a person is from the norm the more their score drops (allowing for a range of values one standard deviation from the normal mean for each parameter). In the case of a measurement like REM, a deviation from the norm can be both positive and negative to reflect the fact that too little and too much REM can be problematic.

Some of the parameters are weighted more than others. Parameters like Deep, Rem and Total Sleep time may have a higher weighting than Onset, Light and No. of Awakenings. Scores may be based on a weighted summation of one or more of the following six bins: Bin 1: Sleep Onset; Bin 2: Light Sleep; bin 3: Total Sleep Time (Tst); Bin 4: Deep Sleep; Bin 5:REM Sleep; Bin 6: Wake After Sleep Onset (WASO). These may be considered with reference to the graphs of FIGS. 26-31. These graphs each illustrate a function to relate the measured value with respect to the normative value (vertical line) for determining the portion of the particular contribution to the sleep score.

In the example, the sleep score may be a value out of 100 which represents the quality of sleep. Six sleep factors contribute towards this score, each contributing different amounts, see Table SS below. The specific contribution of each factor to the overall score can be obtained on the basis of general population (normative) data and may be independent of the user's sleep data. The below values are examples that may be modified in some embodiments.

TABLE SS

| Factors contributing to sleep score. | |
|---|---|
| Total sleep time (TST) | 40 |
| Deep sleep time | 20 |

TABLE SS-continued

| Factors contributing to sleep score. | |
|---|---|
| REM sleep time | 20 |
| Light sleep time | 5 |
| Wake after sleep onset (WASO) time | 10 |
| Sleep onset (time to fall asleep) | 5 |
| Total | 100 |

The user's score for each of these factors is obtained by comparing each sleep factor with those of the general population. For example, if a user gets less sleep than most people of the same age and gender then they will get a low score for sleep duration (e.g. 7/40). Thus, the sleep score may be: Sleep Duration: A maximum of 40/100 towards the sleep score; Deep Sleep: A maximum of 20/100 towards the sleep score; Rem Sleep: A maximum of 20/100 towards the sleep score; Light Sleep: A maximum of 5/100 towards the sleep score; Wake during the night: A maximum of 10/100 towards the sleep score; Sleep onset (time to fall asleep): A maximum of 5/100 towards the sleep score.

These six factors divide into two different groups, positive and negative. This reflects the behaviour of the score. The positive scores begin at zero and increase to X. For example, the sleep duration score begins at zero, as you get more sleep the score increases. With sleep onset the score begins at five and decreases as the duration of sleep onset increases.

Positive: TST, deep sleep, REM sleep and light sleep.
Negative: WASO and sleep onset.

Studies have shown that too much REM can have a detrimental effect on sleep quality. For this reason too little or too much REM sleep will result in a low REM score. As seen by the function in FIG. 29, the REM score starts at zero and increases to 20 as the amount of REM sleep increases. After the score reaches 20 it then begins to decrease slowly in order to reflect the negative affect of too much REM on sleep quality. 'Bins' for each sleep factor are calculated using probability distributions.

To obtain a sleep score, the sum of the products of each bin with its associated weight and the total weight (sum of all individual weights) provides the score for each sleep factor, Table SS. Body and mind score may also be provided, based on deep sleep and REM respectively, Table SS.

Figure 24:
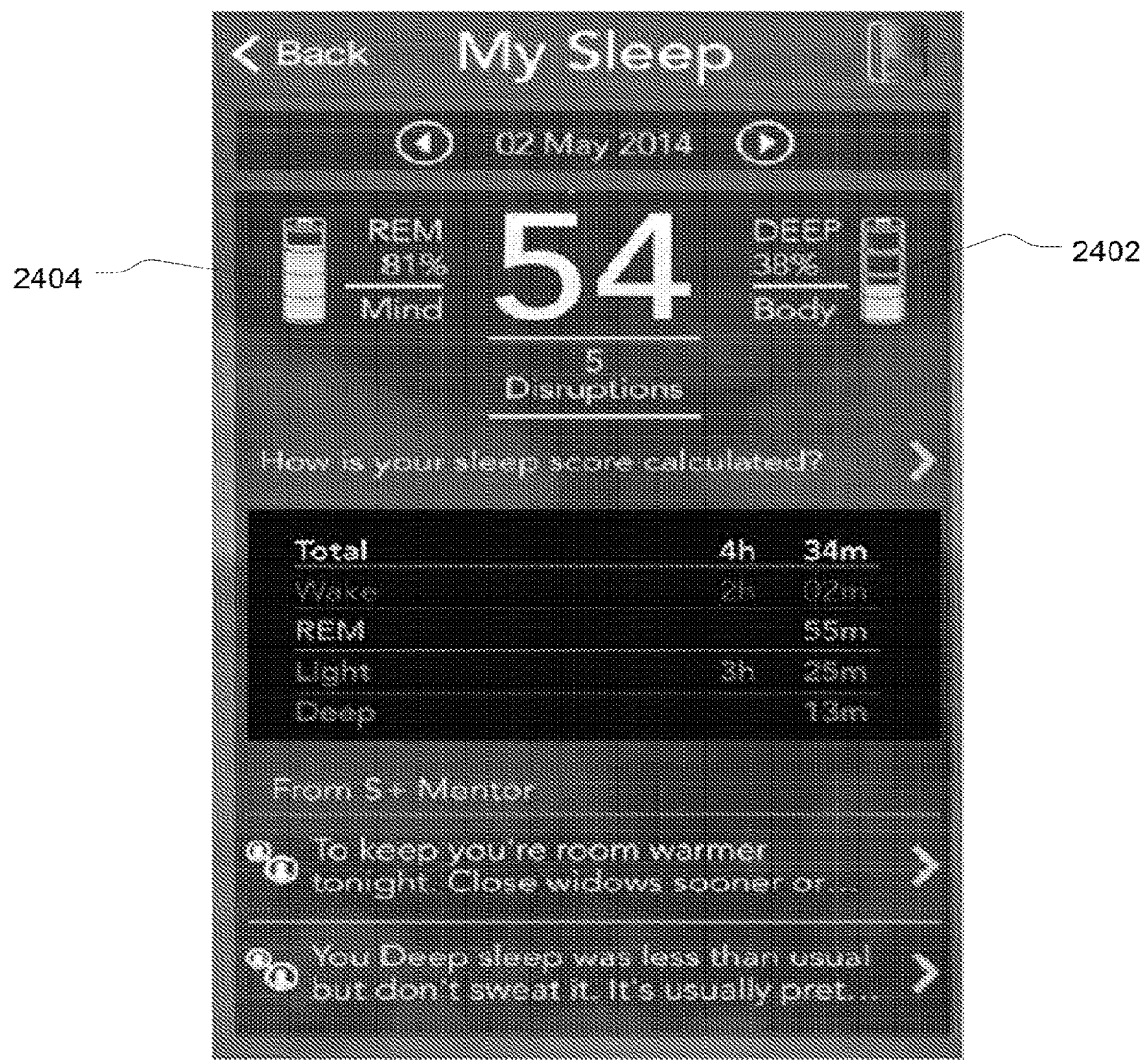
FIG. 24 show an example output report with example mind and body sleep indicators that may be generated in some embodiments of the present technology.
Figure 25A:
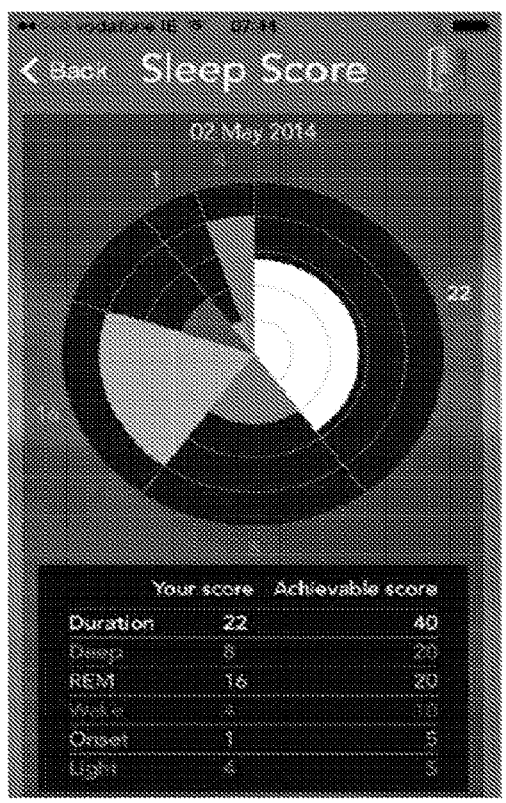
FIGS. 25a and 25b show example output report with an example sleep score that may be generated in some embodiments of the present technology.
Figure 25B:
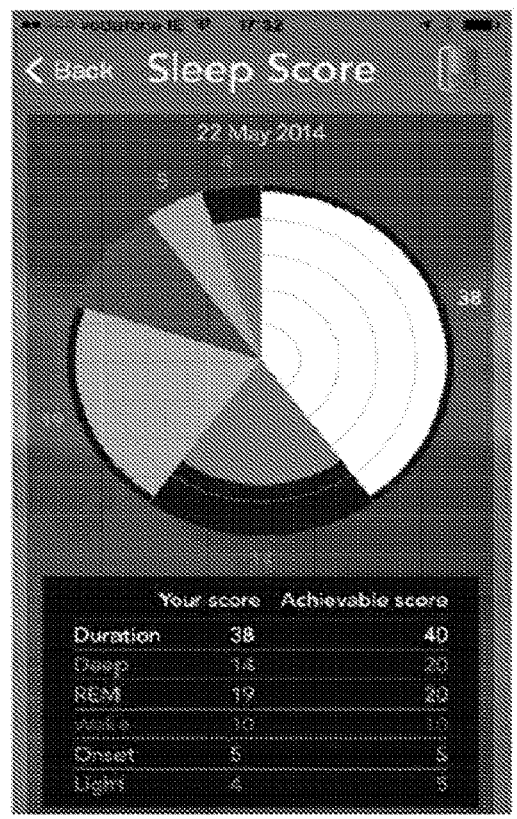
Figure 26:
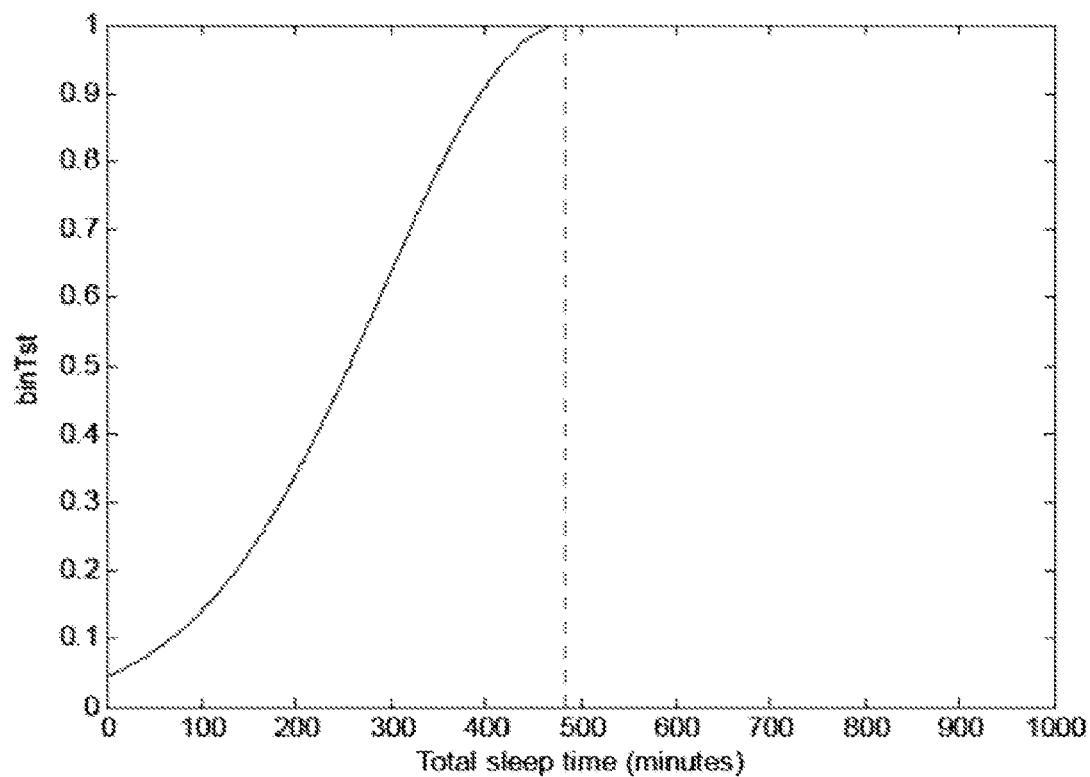
FIG. 26 is a graph illustrating total sleep time verses bin total sleep time.
Figure 27:
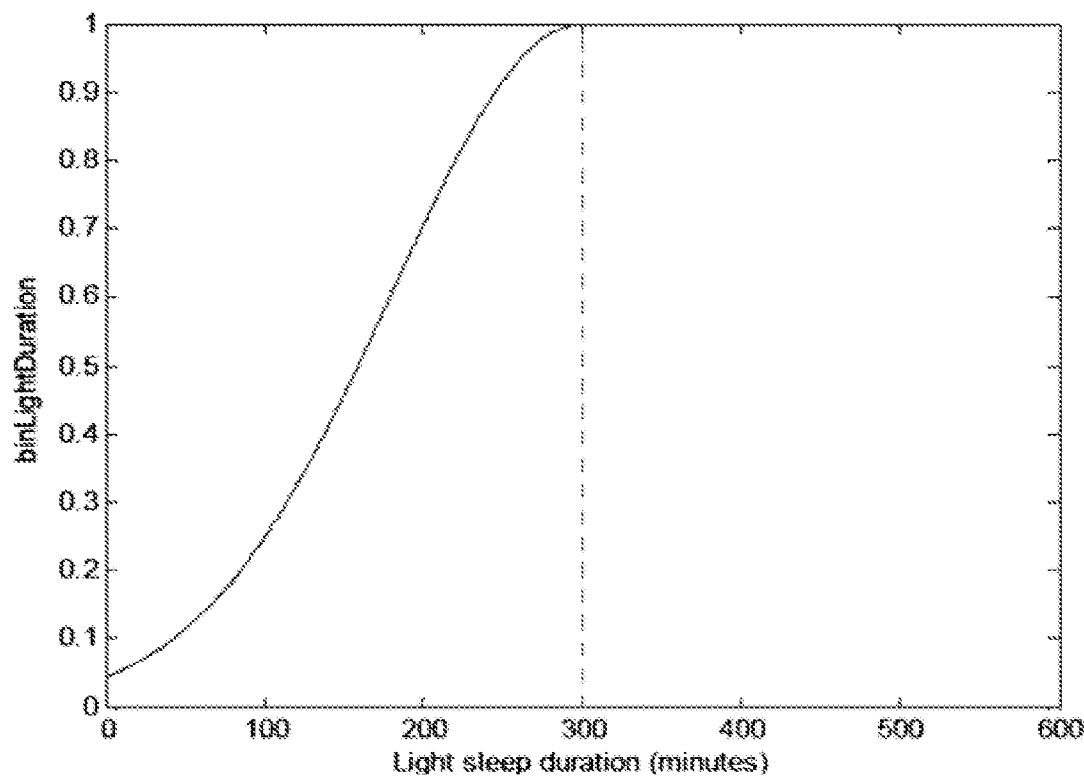
FIG. 27 is a graph illustrating light sleep duration verses bin light sleep duration.
Figure 28:
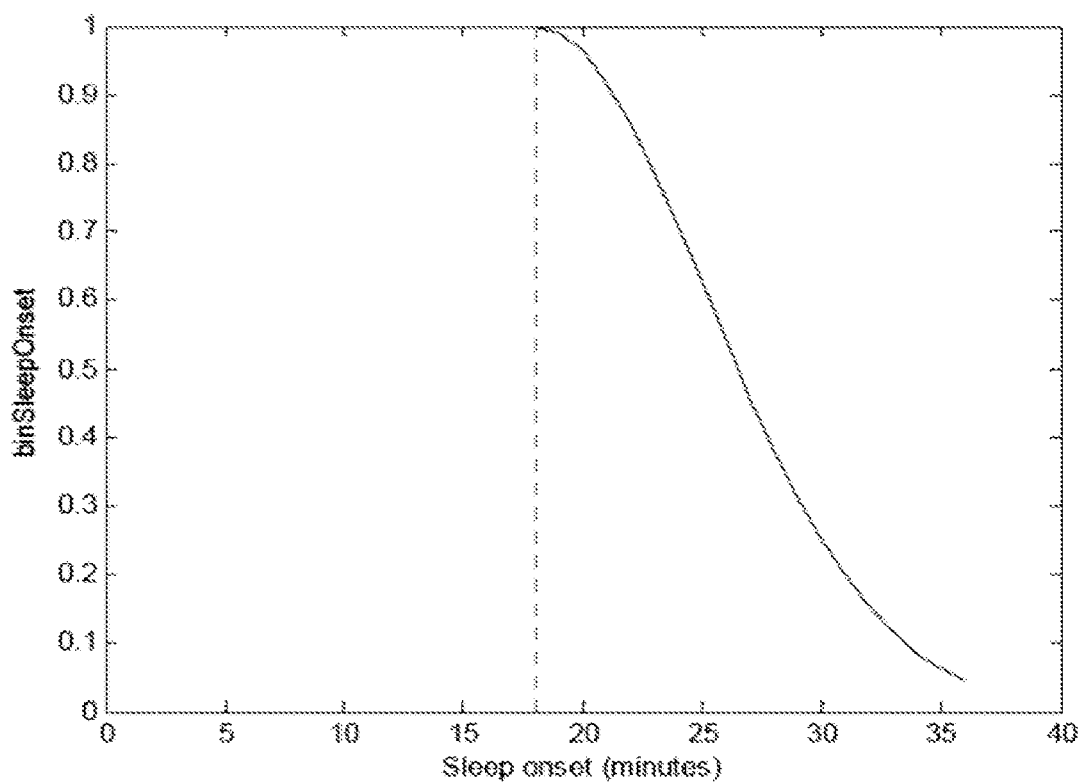
FIG. 28 is a graph illustrating sleep onset time verses bin sleep onset.
Figure 29:
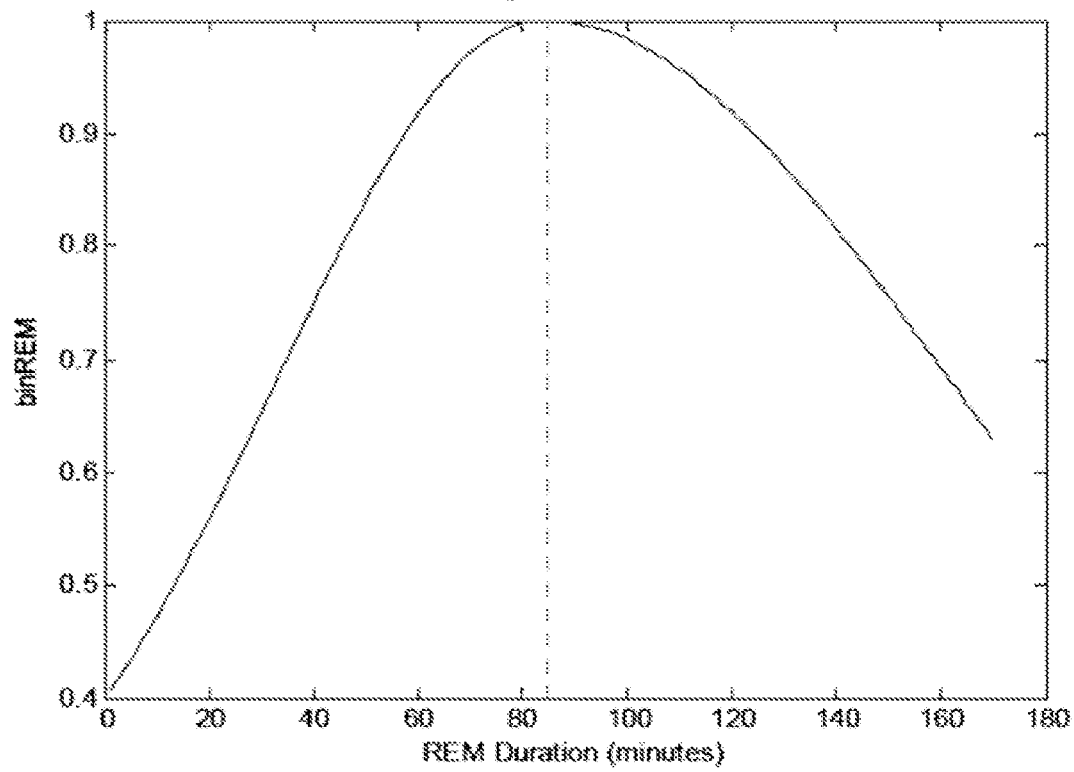
FIG. 29 is a graph illustrating REM duration verses bin REM.
Figure 30:
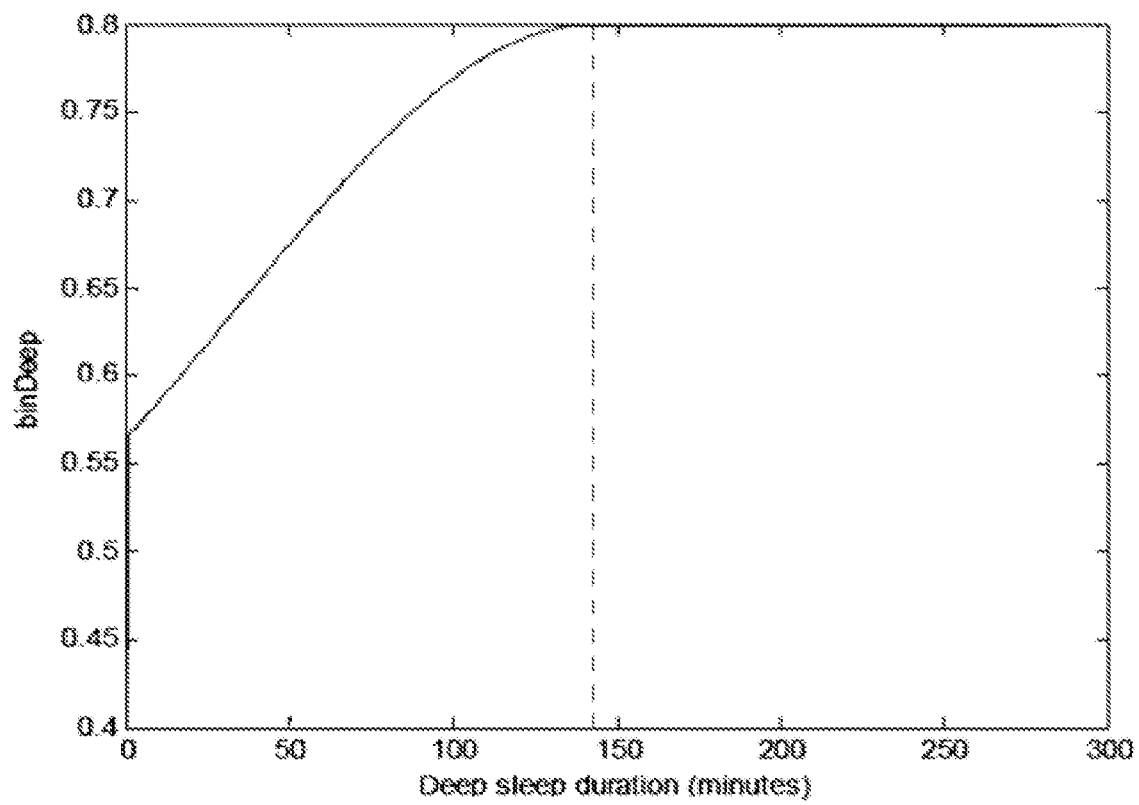
FIG. 30 is a graph illustration deep sleep duration verse bin Deep.
Figure 31:
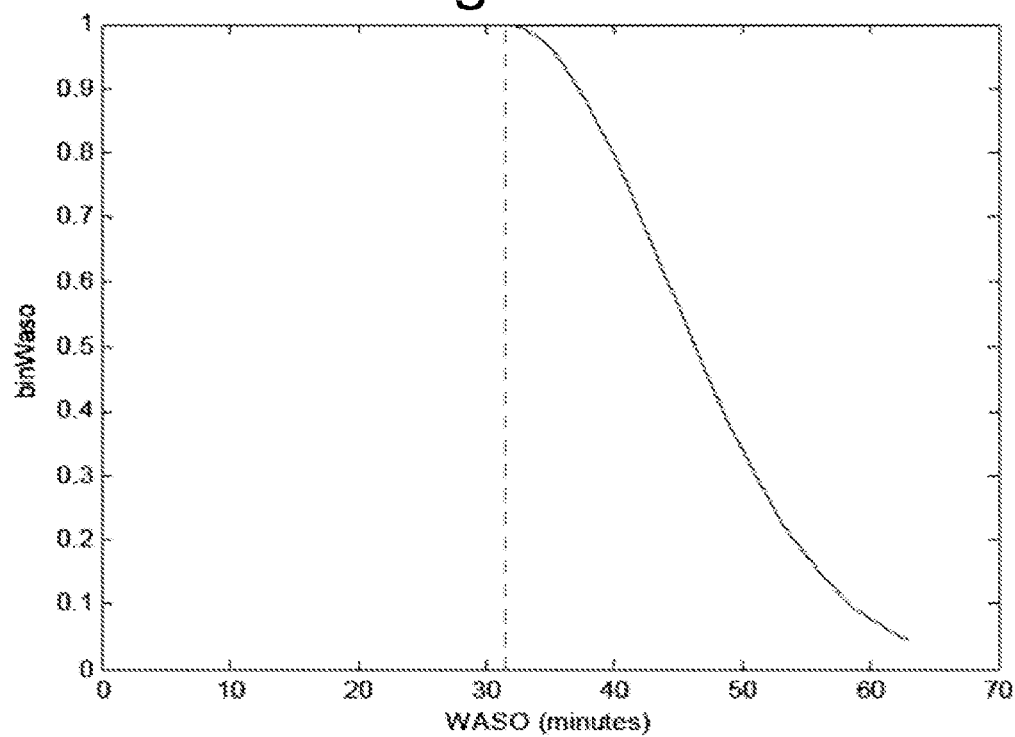
FIG. 31 is a graph illustrating WASO (wake after sleep onset) duration verses bin WASO.

As illustrated in FIG. 24, the sleep score may be displayed by the SmD as a number (in this case this is the number 54). Time totals for the different sleep stages may also be displayed. FIGS. 25a and 25b illustrate a display of the SmD showing a breakdown of the sleep score given the factors of table SS showing a comparison of the achieved score in relation to the achievable (normative) score. The pie graph also illustrates the breakdown of the score. The pie charts generated give the user a clear graphical breakdown of the users total sleep score. Moving around the periphery of the pie chart, the segments of each circle are fixed according to the contributions of Table SS. Each segment is then filled in radial direction progressively by animation, from the center outwards—according to the achieved score for the respective sleep factor. For example, in FIG. 25a, the bright white segment indicating the sleep factor "Duration of sleep" takes 40% of the entire 360 circle periphery (as per Table SS) and is filled in slightly more than half (22 out of 40) based on the ratio of the user's duration of sleep when compared to a normative value obtained from the general population.

These may be considered a morning report to inform the user on how they slept the night before, giving them an overall score as well as one for body and mind charge as portrayed in the hypnogram and radial pie charts. A radial pie chart can provide such a graphical breakdown of the sleep score.

Recharge

In some versions of determining a "mental recharge" and "physical recharge" as well as detailed sleep analysis, the following signal processing can be performed: (a) Sleep latency estimation and/or (b) REM sleep separation.

The biomotion sensor of the BeD discussed above is capable of detection of movement—both gross body movement and the movement of the chest (of a human or animal such as a dog, horse, cow, etc.) due to the physiological action of breathing. Alternative examples include infra-red- or accelerometer-based devices. Groups of algorithms can be used to distinguish fiducial patterns in both time and frequency domain representations of the sensor signal, and provide an output of the probability of being in a particular sleep stage (wake or absent) as previously discussed. A filter bank and associated signal processing block is used to separate higher frequency movement signals and those signals representing the motion of the chest.

For (a)—sleep latency estimation (i.e., the time to sleep measure) is for example used to fade out the sound sequence, an aspect that can be implemented in the discussed 'relax to sleep' feature: The desired output is to detect the change from wakefulness to "stage 1" light sleep and to calculate a sleep latency (time to sleep) parameter. Stage 1 sleep can be considered to be the transition period between wakefulness and sleep. For example, time to sleep may be determined by the SmD processor as the time the user activates the "relax to sleep" feature or initiates a sleep session to the time that the system detects an initial sleep state. Some specific parameters that may be estimated and analysed relate to the frequency, amplitude, and "burstiness" (occurring in bursts) of higher frequency (faster) movements as a subject moves from wakefulness to the twilight stage of stage 1 sleep. The combined nature of movement pattern and breathing rate value and waveform shape may be used to classify sleep onset. Over time, the system may adapt to subject specific data in order to increase the accuracy of this classification (e.g., the typical baseline breathing rate and amount of movement of the subject—i.e., how much the move around in bed/fidget as they are falling asleep) may be learned and employed in the estimation process.

For (b)—REM sleep separation: Classification knowledge of a subject specific and population average of breathing rate and waveform shape (morphological processing) may be used to capture a baseline wakefulness signal type. This may be characterized by a regularly irregular or irregularly irregular breathing rate (increased information content), and sporadic movement bursts (i.e., during wake). The regularity (reduced information content) is used as a secondary benchmark state. REM sleep is separated by a marked change in movement frequency, intensity and burstiness as compared to the wake state. In addition, REM sleep is paradoxically denoted by breathing features similar to those seen by the subject during the wake state.

It should also be noted that during REM sleep, a lower level of movement flags may be observed than during wake periods. Thresholds can adapt to the analysed subject data under inspection. In some cases, the thresholds can adapt based on subject specific historical data stored in a database (e.g., if a subject had an elevated baseline breathing rate or unusual breathing dynamics, the system would still be able to extract sleep stage information for that subject). In other examples, the thresholds can adapt based on population average values of respiration dynamics. Optionally, the relative inspiration/expiration respiratory waveform can be considered in the analysis block as another measure of regularity of the signal.

The REM algorithm may use a time/frequency methodology for extraction of the respiratory and movement signals known as discrete wavelet analysis to "decompose" the signal epochs. This can either replace or augment processes such as an approximate entropy measure.

If body temperature measurements are available (either contact or non-contact sensing), these can be introduced into the system in an early integration or late integration fashion to augment the sleep staging decision.

If audio recording is available, the system can optionally detect characteristic patterns of snoring, snuffling, coughing or breathing difficulties in the non-contact motion movement and respiration patterns. Optionally, sound can be detected by a microphone, and analyzed in conjunction with the non-contact sensor and/or the body temperature measurements. The system can provide an analysis of the data under analysis, and trend over multiple nights. As discussed herein, specific audio events can also be detected.

"Recharge" may also be related to the proportion of deep sleep ("physical recharge") and REM sleep ("mental recharge") that are recorded during the night. The user see a physical recharge and mental recharge score based on their comparative level of these sleep states versus population norms for their age (and also linked to their perceived feeling the next day, and based on their past sleep performance). Thus, the system provides the user with an overview of their level or rate of physical recharge (indicated by the amount of obtained deep sleep) & mental recharge (indicated by the amount of obtained REM sleep) as represented by the level of charge of two battery type indicators (i.e. Mind and Body batteries). Data may be viewable over a day, week, month or longer time-scales. This could be enabled by displaying a summary of sleep data (for example represented by, such as, a hypnograph, pie chart, sleep score) on a smart device (e.g., cell phone or tablet) or on a PC.

Thus, the level of recharge may be relayed to the user during or after the users sleep session in an easy to understand way. This may be implemented by UI (user interface) of the SmD with animated graphics showing sleep and mind re-charge values. For example, as seen in FIG. 24 a mind recharge indicator 2404 shows a percentage of mind recharge and a body recharge indicator 2402 shows a percentage of body recharge. As previously mentioned, body and mind recharge score may be based on deep sleep time and REM time respectively, in accordance with the calculations described in relation to Table SS.

However, in some versions, the three sleep scores may be given by the following:

Overall Sleep Score (%):((0.5×bin1+0.5×bin2+4× bin3+2×bin4+2×bin5+bin6))*10)

Mind Charge Score (%):(bin5)×100

Body Charge Score (%):(bin4)×100

All three scores may be bounded between [0,100] %. The bin# may be any of the sleep related parameters such as the parameters of table SS. Additionally, these weightings (multiplication factors) can be re-weighted in a dynamic manner to account for different user behaviour (for example by adjusting the weighting). Each of the six measured sleep parameters above from the user are measured and compared against the normative database for a user of that age and sex. For example, if the measurement is within one standard deviation of the mean, that bin may be filled. Otherwise its distance from the interval is calculated (this yields a number between 0 and 1) and the bin is filled with the appropriate amount. The overall sleep-score is calculated as the sum of the weight bins giving you a number between 0 and 100%.

Software—Specific Embodiment—Sleep Trend (Correlator)

Figure 32:
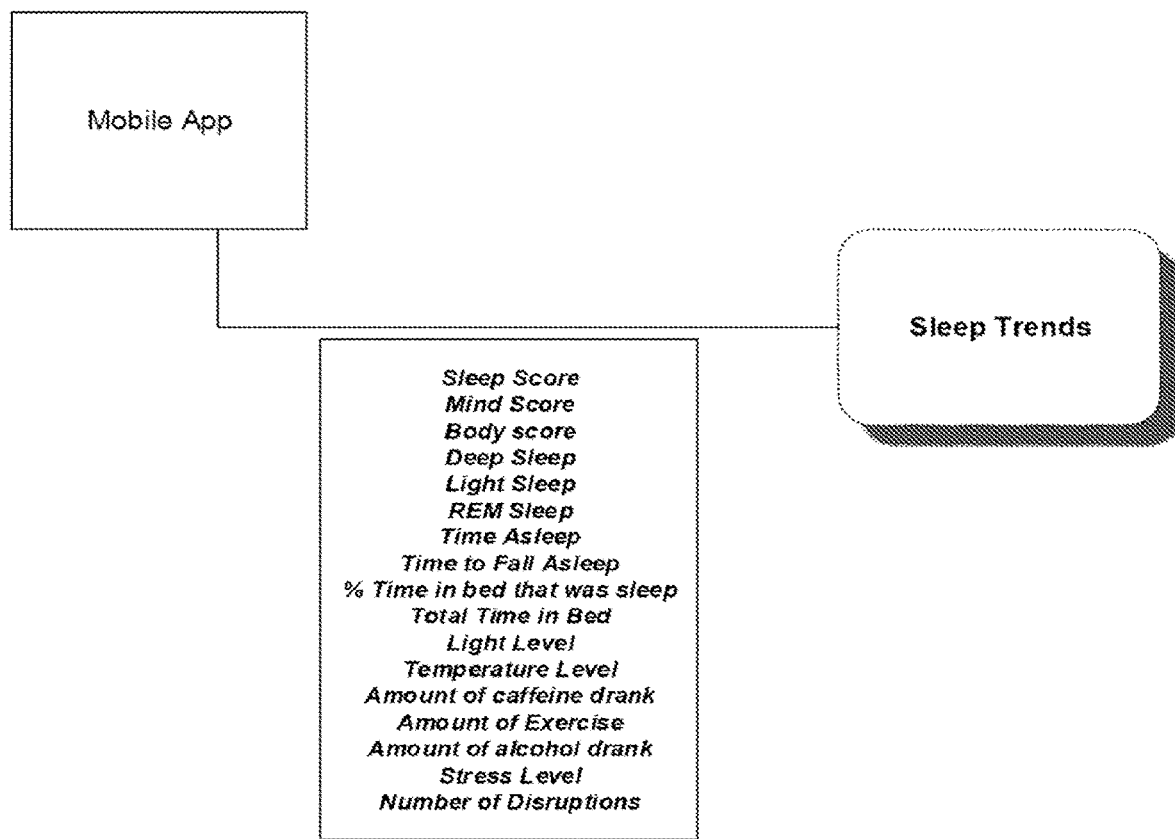
FIG. 32 illustrates example output indicators that may be generated by a processing apparatus of the technology such as a processor of a smart phone.

As illustrated in FIG. 32, the system may provide feedback concerning sleep trends. Sleep Trends provides a graphical view of results the 'app' or SmD device has generated for the user over time overlayed with variables affected by user that the user can change. These can be viewed on various devices; an example of this would be a smart device/PC, website. The graphs can represent input from data processed after a sleep recording. Other data may require further processing before it can be inputted into the sleep trend analysis such as % of time in bed that was sleep. Other data provided in the pre-sleep questionnaire, that can prompt the user on a nightly basis for daytime sleep related information, can also be included such as caffeine consumption. In response to the questionnaire, users may input amount of caffeine drank during a day, amount of exercise, stress etc. As identified in FIG. 32, the historic trend display of information may include any one or more of sleep score, mind score/recharge, body score/recharge, deep sleep time, light sleep time, REM sleep time, total time asleep, time to fall asleep, % time in bed that was sleep, total time in bed, ambient sound level, ambient light level, ambient temperature level, ambient air pollution level, number of sleep disruptions, amount of caffeine consumed, amount of exercise, amount of alcohol consumed, and/or stress level. These latter four factors may be determined by the SmD device in a pre-sleep questionnaire prompting the user to provide the information. If air quality, humidity or other sensors, or heart rate values are available or otherwise implemented, information from these may be included.

All of the information that the process uses may be stored in the memory of SmD over time so the access to information is very convenient. Moreover, a user may select, such as with a user interface generated by a processor, any two or more of the different monitored information so a display showing their temporal association or temporal correlation may be generated by a processor for viewing such as on the SmD or from a webpage of the cloud service. Such a trend plotting of information may include, for example:

Selectable Graphs for results from app (Sleep Score, Amount of REM Sleep etc.) overlaid by graphs of user driven variables (caffeine drank, exercise etc.)

Scalability of graphs to show variable time scales

Graphical design to make it easy to use and read without appearing too complicated to naive users.

Efficient layout to make it easy to read and make the graph as large and easy to read as possible.

Graphs of variables that line up with how the advice engine uses these same variables (e.g. if the advice engine uses an average from the night of light and temperature then the graphs may show an average).

A user of such a trend plotting feature can gain new insight by plotting different variables. For example, a user interface for a correlation process can present the user with the option to select to plot alcohol consumption (from nightly questionnaire) and change in REM sleep over time. It could also display all advice given by the system on REM sleep to the user for easy reference. A user could then see that, for example, a reduction or cessation of alcohol consumption is associated with an increase of REM sleep duration. They might also see that they had been given correct advice about the impact of alcohol consumption on REM sleep quality (if such a nugget had been provided to them with that content). Similarly, daily caffeine consumption may be plotted in temporal association with daily sleep information (e.g., total sleep time and/or deep sleep time) so that a user may visibly see the changes that different amounts of caffeine consumption may have on sleep information over time.

Software—Example Embodiment—Relax to Sleep

Some versions of the present technology may include a "relax to sleep" process. Generally, a user's breathing rate BR can be captured by a biomotion sensor in a device (e.g., BeD). Music or other sound can be played as a function of a predetermined maximum rate (measured in breaths per minute (BPM)). That is, the time length of the sound file is set so that it will match a desired breath time length. After an initial period during which the system captures the user's breathing rate, the music can be aligned with the measured breathing rate of the user. The new/adjusted BPM of the music when played will be tuned to the user's breathing rate. If the users breathing rate is greater than the maximum breathing rate then the music can initially be set at the maximum rate. In some cases, the music BPM may follow a predetermined reduction pathway.

Background—Entrained Reduction of Breathing Rate to Guide the User to Sleep

Thus, one aspect of the proposed system and method provides relaxation techniques that help the user to get to sleep by producing calming sounds, the nature, volume and rhythm of which may be chosen by the user or adjusted automatically to help the user change their own breathing rhythms (i.e., a relaxation programme customised to the user's breathing pattern). This is the 'relax-to-sleep' feature which is activated/chosen by the user.

Figure 33A:
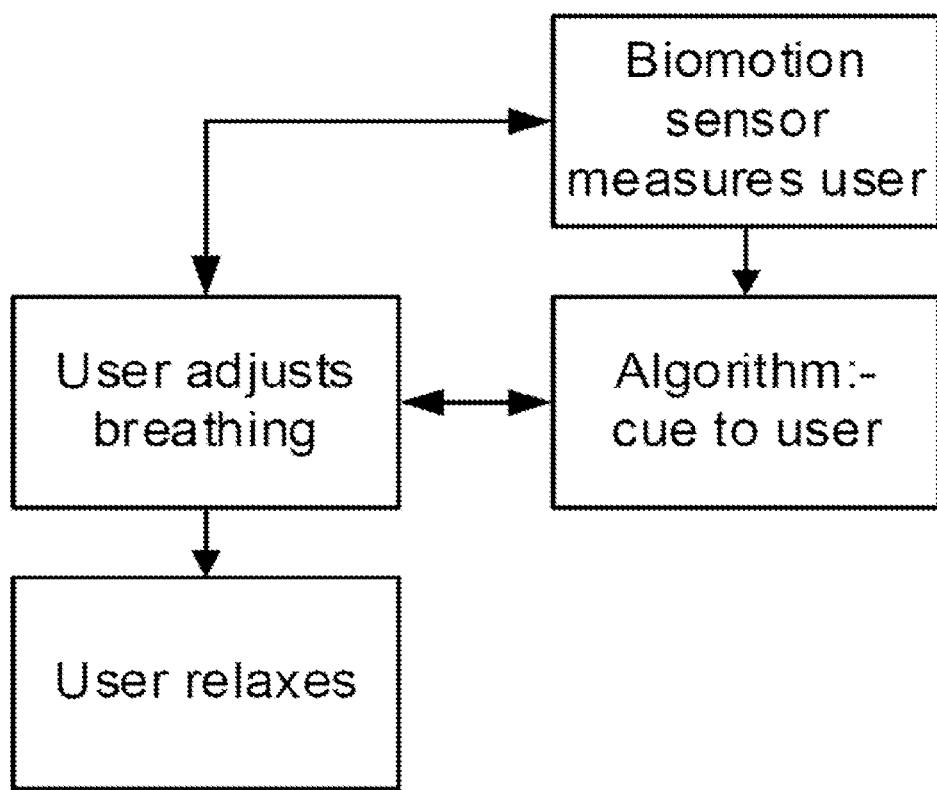
FIG. 33a shows an example diagram of a process of guided breathing according to an implementation of the proposed technology, from a user's perspective.

The premise is that a pleasant, cyclic sound acts like a metronome and the user's breathing rate would tend to synchronise with that sound rate. Such a process may be considered in reference to FIG. 33a. A contactless sensor can give real-time feedback on both breathing rate and awake/sleep status. The sensor feedback could be used to control the sound's cyclic rate, gradually slowing it down. If the subject's breathing rate is "captured", slowing the breathing rate down could relax the subject and hasten the onset of sleep. Once the user is deemed not to be awake, the audio volume could be turned off. The soothing sound volume can also be reduced to zero gradually, rather than suddenly as the sudden change in audio environment could re-awake the subject.

The Relax to Sleep feature may use a spot or continuous respiration analysis. For example, a respiration determination function of the RM20 process (algorithm) can be accessed once at the beginning of a relax to sleep process, to facilitate the selection of the starting repetition rate of the calming sound chosen by the user (out of a selection of several sound files provided by the app of the SmD or from a music library). Thus, the system can track the breathing pattern, and modulate the sound files such as only at the beginning of the feature and then adjust the sound according to a set pattern (such as described below). The idea is that the user naturally entrains their breathing to the sound pattern, but is not directed to do so. This differs from a meditation feature which may more actively direct the user to breath at a specific rate to relax, which requires conscious engagement with the device thus keeping the user awake.

After the initial 'capture' of breathing rate to set the modulation (audio playback rate) rate to an initial value, the breathing rate might not be tracked and the system may proceed with a reduction in the modulation frequency (audio BPM) along a predetermined curve to a minimum lower value (BPM). The frequency of modulation may then be reduced in step wise manner to reach the desired lower value (e.g., six breaths per minute). This reduction encourages the user to reduce their breathing rate and thus enter a more relaxed state to fall asleep more easily. The step wise function allows the user some time to consolidate their breathing rate at a particular playback rate. Once the system detects that the user is not awake it optionally reduces the volume of the sound to zero in a fashion which doesn't wake the user, such as by a gradual shutdown rather than an abrupt silence.

The implementation of such a process may include:

(1) Selectable high quality sound files (e.g., file type is AAC);

(2) option to download additional sound files;

(3) a user interface to select and play the different sound files;

(4) volume control, returns to default value if the feature completes or user stops it; Return volume to default value if user interacts with App during session (5) routing of audio to speakers (external if connected or integrated);

(6) a measure of real-time breathing;

(7) a maximum playtime (e.g., 60 minutes from the time the minimum breathing rate is reached).

In a particular example, the maximum modulation frequency can be 14 BPM. The default BPM play rate function may follow a stepped reduction (in BPM): 14 to 12 to 10 to 8 to 6. However, if the process returns a value of 11.5 BPM, such as from the detection of breathing rate, for example, this then changes the measured frequency and from there it resumes the step wise reduction by 2 BPMs. In the discussed case, this will result in the following change (in BPM): 14 to 11.5 to 9.5 to 7.5 to 6. The jumps or steps from the penultimate rate to the minimum rate (e.g., 6 BPM) can be less than the 2 BPM step of the previous example. The maximum rate may be for example, 14 BPM. If the user is detected to be breathing at a greater rate than 14 BPM, the process might not increase the playback rate of the sound sample to match the user's breathing rate, but may maintain the playback rate at the predetermined max (e.g., 14 BPM) and start the rate reduction function from there. The minimum reduced rate can be 6 BPM. If the user is determined to be breathing at a less than the predetermined minimum rate, the process may start the playback at the predetermined minimum rate (e.g., 6 BPM). This can lead directly to a period of play (e.g., 10 minute) at the minimum 6 BPM rate (i.e. additional time may be added (e.g., 2 minutes) at this minimum rate). The total playtime is variable but may be for example approximately 60 minutes. The full length may depend on when and if the algorithm detects a breathing rate.

Figure 33B:
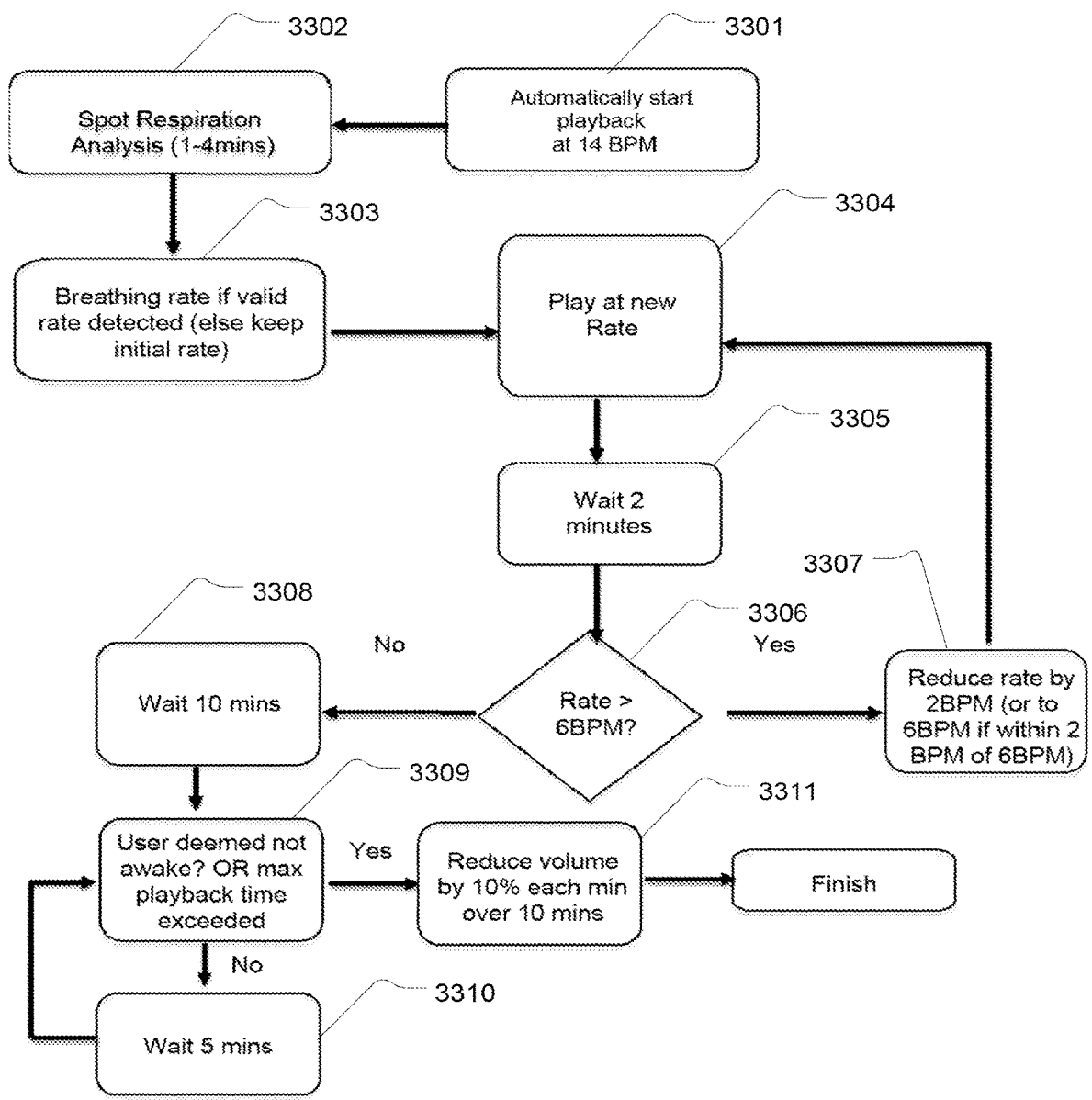
FIG. 33b shows another example methodology of a processor such as for guided breathing to induce sleep that may be implemented in a processing device of the present technology; in one example, the recorded rate is 7 BPM (br/min). Playback starts at 14 Br/min. The user's breathing rate will be captured by the biomotion sensor, the music will originally play at a predetermined maximum BPM but will align with the user's breathing after this initial capture period. This initial capture period will be affected by when the user stops moving—as no value will be returned if they keep moving. The new rate will be played and will be in tune to the user's breathing rate. If the user's breathing rate is greater than the maximum breathing rate then this embodiment will initially be set at the maximum rate. It will then follow its predetermined BPM reduction pathway.

The above example process may be considered in reference to the methodology of FIG. 33*b*. At 3301 a music/sound play process is initiated by a user selecting the relax to sleep operation of the SmD. Initially, a sound file is repeatedly played as an initial rate (e.g., 14 BPM), for example by playing the sound file 14 repetitions per minute. At 3302, during playing of the sound file respiration is measured. At 3303, the detected rate is evaluated to ensure a valid rate is detected. If the rate is in a range (e.g., 14 to 6 BPM) the sound file's period is adjusted so that it may be played repeatedly so as to conform to the detected rate. The sound may undergo further processing to ensure that the pitch of the sounds in the sound file is substantially maintained, in order to sound natural. If the detected user rate is invalid, the initial music BPM is maintained. If the detected rate is below the range, the sound period of the file is adjusted so that it may be played at a rate conforming to the minimum of the range. At 3304 the sound file is played at the period determined at 3303. At 3305, a two minute timer interval is permitted to run while playing of the sound file is repeated. At 3306, the current sound file play rate is checked to determine if the current rate of the sound file is greater than a minimum. If it is greater, at 3307, the rate is reduced by a step amount (e.g., 2 BPM) by increasing the sound file period while maintaining pitch. This reduction of rate has a floor of the minimum from the range (e.g., 6 BMP). Repeated playback of the modified sound file then returns at 3304. If at 3306 the rate has reached its minimum of the range, playing of the sound file will continue for an additional period (e.g., 10 minutes) at 3308. At 3309, sleep information from the sensor analysis is evaluated to determine if the user is not awake or if a maximum play time has been reached. If not, a further period runs (e.g., 5 minutes) at 3310 before checking again at 3309. If asleep or the maximum time has been reached, at 3311 a volume reduction process is initiated. Volume may be progressively reduced, e.g., by a predetermined proportion (e.g., 10%) over several intervals (e.g. 10 minutes) until the sound volume is zero or off.

In another example, the sequence may follow these steps:
a. User selects Relax option
b. Audio is played at the default breathing rate of 14 breaths per minute (maximum available) while waiting for the RM20 algorithm to return a valid breathing rate.
c. The maximum time the SmD App will wait for the RM20 algorithm to return a valid value is 4 minutes. There are two possibilities therefore: i) the algorithm returns a valid value within this time or ii) it does not. In the former case steps 4 to 10 (below) are executed in order. In the latter case, i.e. where the algorithm does not return a valid value, step 4 is skipped and only steps 5 to 10 are executed.
d. Once the algorithm returns the users breathing rate, jump to that breathing rate (this allows the user to hear that the detected breathing rate/simple feedback). Remain at this rate for 2 minutes.
e. Reduce playback rate by 2 breaths every 2 minutes until the minimum rate of 6 breaths per minute is reached.
f. When the minimum breathing rate is reached remain at this rate for 10 minutes.
g. At the end of this 10 minute period, check every 5 minutes if the user is awake. If the user is deemed not to be awake at any 5 minute check point ramp down the volume of sound by 10% every minute for 10 minutes.
h. To facilitate an approximate playtime of 60 minutes, after a 50-minute period, if the user is still awake, reduce sound by 10% every minute for 10 minutes.
i. On completion, close feature (and return to sleep screen if in night mode)

As previously described, each time a sound file rate change is needed, the sound file period (time length) is adjusted (longer to slow the rate and short to increase the rate) while maintaining the sound file's pitch. By playing it repeatedly, it will have the desired rate. Changes to the sound file may be implemented by a stretcher function that can either stretch or compress the audio file length so as to effect the period change. The term "stretcher function" is used to represent both stretching and compressing depending on whether the source file is being played back slowly (stretching or lengthening) or faster (compressing or shortening).

For example: The original sound files may be recorded to be suitable for a playback rate of 7 BPM. The sound files may provide various calming sounds such as sounds from nature, for example, the sound of the sea shore and instrumental recordings. The ratio of the exhalation cue (exhalation portion of the sound file) to inhalation cue (inhalation portion of the sound file) can be set to a predetermined fixed ratio (preferably at about 1:1.4) in all files. This ratio may remain even when the period of the sound file is adjusted. This ratio was determined through experimentation with real subjects to give a more natural guidance.

The stretching process library includes algorithms implemented to stretch the time of the audio files while keeping the pitch equivalent to the original audio file. An example is the commercially available DIRAC system or other digital signal processing implementation, which is a time stretching algorithm. It is a time stretching technology which allows changes to the speed of playback of the audio file (while maintaining the sampling playback rate), in this regard to increase or reduce the sound files to match the breathing rate of the user which can then be entrained to reduce the users breathing rate. It keeps the audio file sounding natural.

The stretcher process can run in real time in the application of the SmD. It can be applied to all the sound files to stretch or contract the time of the audio files, to play at the rate desired. The 7 BPM rate of the original sound file can be maintained by setting a stretching value (a software function parameter) of 1 which is passed into the library so no altering of the file takes place. This is how the 7 BPM file remains at this 'unaltered' rate. A stretching value other than one is fed into the library to alter the sound.

Other Implementations

Different versions for playing sound to entrain user to relaxed breathing for sleep may be implemented. Any of the following features may be included in the system and method, either separately or in combination:

(1) Reproducing predetermined sounds to guide the user by encouraging an adjustment in the user's breathing rate/rhythm, to facilitate the user's transition to sleep;

(2) Tracking the user's breathing pattern whilst generating calming sounds (selected from a range of sounds according to the user's personal preference) that help slowing the user's breathing rhythm (modulation of breathing) in order to assist the user's transition to sleep more. Parameters, such as the nature, the volume, rhythm etc. of the users environment (light, sound and temperature), may be adjusted depending on the detected breathing patterns. For white-noise type sound file, this can be set to either persist or turn off. The sound may also include a single frequency sound that varies in frequency and/or volume. Such variations of the sensory output provided to the user (such as of the rhythm of a particular sound or the colour of light) are aimed at "entraining" the user's breathing rate and bringing it down together with the respective frequency of the changing colour, rhythm, volume etc.

(3) The range and the loudness of the sounds can be chosen to drown out other noises and clear the user's mind of distractions. Input may be provided based on the detected ambient noise level of the room environment.

(4) As sound preferences are highly personal, the user is made practical, helpful suggestions over a number of nights by the system, and is enabled to select optimal sounds on the basis of their own preference. For example, the SmD may detect which sound file induce sleep onset faster (e.g., on average) and inform the user.

(4) One or more sensors, preferably wireless, may be used to monitor the user's breathing rate and/or other physiological parameters. These sensors provide feedback to the controller that drives the sound and/or light input provided to the user. The system detects when a user starts to fall asleep and by adjusting the audio pattern it assists in adjusting the user's breathing. The sound is automatically faded off when the user falls asleep.

The switching off of the sound in the "relax to sleep"/"breath to sleep" function is possible for ending the "relax to sleep" session. Once the system detects that the user is not awake it can reduce the volume of the sound to zero. The notion that the user is deemed not to be awake may in some versions be based on a reduction in movement levels (both intensity and duration) being detected and normalization of breathing and/or based on processes as discussed with respect to the RM20 library. This example test can be taken as a trigger for initiating a volume ramp down over a ten minute period. After these 10 minutes, the sound can simply be turned off in a fashion that does not wake the user, a gradual shutdown rather than an abrupt silence is possible.

It is important to note that the switching off of sound in an 'assisted meditation' process (also referred to as a daytime relax process) may differ from the 'relax to sleep' process that is intended to assist the user with their night time sleep routine. For example, one difference may be that the relax process does not detect that the user is asleep before it initiates the sound volume reduction process. In the case of relax to sleep—the user's breathing and movement levels may be assessed every 5 minutes to evaluate them as awake or not awake. The volume ramp down can be initiated at any of these five minute checkpoints when the user is deemed not awake. When the user's breathing rate remains level for 10 minutes, after the minimum targeted breathing rate is achieved, the reduction of the sound can be implemented by, for example:

At the end of this 10 minute period, check every 5 minutes if the user is awake. If the user is deemed not to be awake at any 5 minute check point ramp down the volume of sound by 10% every minute for 10 minutes.

Returning now to the feature of initiating adjustment to the user's breathing rate/rhythm, the feature is associated with the fact that the breathing pattern of an anxious or stressed person can be shallow and rapid, with the upper chest and neck muscles being used for breathing, instead of the abdominal muscles. With traditional respiratory biofeedback, chest and the abdomen sensor belts enable the breathing pattern to be visualized on a computer screen, thus allowing the user to slow down their breathing rate, and focus on deep breathing. The systems of the present technology may achieve additional respiration biofeedback by instructing the user to pace their breathing based on graphical, other video and/or audio cues with parameters that may be associated, but are not identical, with the user's breathing parameters with a display on the SmD. The user need not actually monitor their breathing, but a pattern with externally defined parameters. The cues are sensory, but preferably contactless, and may include light or sound with a strong pattern (e.g., wave or surf sounds, sounds from nature or instrumental recordings), modulated such that the user subconsciously entrains their breathing to the respective pattern.

Returning to FIG. 33a, another such process may be further described as follows. The current subject's breathing rate is estimated using the biomotion sensor and processing the data by way of a time and frequency based analysis to calculate the user breathing rate. As described in the above, a rule set is used to distinguish fiducial patterns in the signals, and provide an output stage. A filter bank and associated signal processing block is used to separate higher frequency movement signals and those signals representing the motion of the chest. The primary breathing frequency can be located using a Fourier transform, and tracked at, for example, 15 or 30 second intervals. Calculation of the spectral content of the signal is performed using a Fast Fourier transform and find peak (frequency domain) or via time-frequency processing such as using the discretized wavelet transform, appropriate basis selection, and peak find. The residual low frequency components may also be processed to determine longer timescale trends. A respiration rate vector (1 Hz) may be processed.

The process may further create an adaptive baseline for a user, and look at breathing rate parameters such as median, mean, interquartile range, skewness, kurtosis, min and max breathings rates over a period of time (e.g., 24 hours), and is primarily (but not exclusively) targeted at the times when a person is asleep (or in bed). In this manner, the system may analyze and track the breathing rate, and the variation of breathing rate. In addition, the inspiration and expiration waveform shape, and short, medium and long term breathing fluctuations may be tracked.

Once the user breathing rate is calculated, audio and/or video cues are provided to the user based on the calculated rate. Alternatively, the audio and/or video cues can be provided to the user based not on a calculated, but on a predetermined rate, based on statistical data from this user, from other users of from statistical data obtained from the general population with no association to the device. The visual and sound cues are adapted to guide the user to a low and stable breathing rate. For example, this could be 6-9 breaths per minute for a typical user, but could be in the range 2-25 br/min, adapting to the detected breathing rate/amount of movement of the subject. For practical stress reduction, the highest suggested breathing rate target is 14 br/min. The light/sound sequence is created such that it gradually brings the user's breathing rate to a target level, adaptively set based on breathing rate and breathing rate trend information. Optionally, if the user is observed by the system to be unable to adjust and capture their rate below 20 br/min, this may indicate that the user is unwell or suffering from a respiratory issue and this may be brought to the user's attention in the form of a risk assessment report which is available online or through the smart device and can be saved as a PDF and used as the basis of a discussion with the users practitioner. A full sleep pattern report is available from the smart device or online. It may be presented in the form of a histogram. The sleep score is a mechanism employed to represent the feedback on the users sleep pattern following a sleep session.

Further Example

A subject is monitored over 30 s and is detected ("captured") as breathing at 17 breaths per minute. As discussed earlier in the text, the detection is achieved by the filtering and spectral and/or time domain analysis of the biomotion signal to isolate the breathing component.

Let's assume that the user is using the system for the first time, and has no "history" or trend data available. An audio sound file is generated at a target rate of, for example 14 or 15 breaths/min, which should be 5%-20%, more specifically 10%-20%, i.e. 10%, below the captured rate. In some cases, the starting rate may be confined between 12 and 14 B/min respectively. If no suitable breathing signal could be estimated, a default starting rate of 10-14 br/min may be selected. If historical user data was available, the average rate after 2 minutes of exposure to the modulated light or sound, is read from the database (data store) and used as the initial estimate value.

The particular sound sequence used can vary, but in one example is based on the sounds of a wave breaking on a beach; the sound file can be stretched and squashed (compressed) to give other cyclic rates, without the pitch content being altered.

Once the sound/music is played to the user at the initial rate, consciously or subconsciously, the subject begins to match their breathing rate to the provided reference rate. The system then slowly decreases the targeting breathing rate cue to a target breathing rate of 6 breaths/min (could be in the range 10-3 br/min, but 6 br/min is calming to many subjects as tested) over 10 minutes. The decrease can be gradual or stepwise. The system is switched off if light sleep is detected. The reduction in volume ceases if the user is not detected as falling asleep. In this case, the system will turn off after a predetermined amount of time, say one hour.

In one embodiment, it may initiate a sound ramp down after 50 minutes to turn off the sound by 60 minutes. The system may keep checking every 5 minutes between the following times; from ten minutes after target breathing rate has been reached until ten minutes before the sound volume must be turned off in order to complete the programme to facilitate maximum playtime. Upon completion the feature is closed and the application returns to the sleep screen.

The sensor feedback is used for monitoring if the user breathing rate follows the audio and/or visual cues and slows down together with them. The reduction in breathing rate is designed to be smooth in nature (i.e., no sudden jumps), and to be a predetermined % below the captured (detected) rate. However, there may be an exception if the detected user breathing rate stabilizes at a higher than the desired rate, or if suddenly increases to a previous high rate. For example, if the user had been breathing at 17 breaths/min, and guided down to 13 breaths/min, but suddenly their rate speeded up to 25 breaths/min, the system might not track this upwards rate (the faster breathing rate might tend to wake up rather relax the user). Instead, the controller may temporarily halt any change in the frequency of the audio and/or visual cues and wait until the user's rate goes back down to a level close to the last frequency of the cues, before the downward change in the frequency of the cues is resumed. Alternatively, the controller may be programmed to increase the cue frequencies so that is the same as the user's increased breathing rate, or is only a predetermined % below it (such as 10%), so as to more easily "capture" the user's breathing rate, and start again reducing the frequency from there.

The system may be programmed to run in this mode for between 2 and 20 minutes, depending on the rate of change, and then stop, regardless of the user's response. The lack of success for such a predetermined time may indicate that the user has specific difficulty with following the guiding sounds and that the continuation of the process may disturb, rather than assist, the user in falling asleep.

In another implementation, a sound sample of waves on a beach is selected that has a cyclic rate of 5 seconds (the equivalent of 12 breaths/min). The sound file can be stretched and squashed to give other cyclic rates, without the pitch content being altered.

The sound files may be incorporated into a simple app process that obtains the real time breathing rate and sleep status for feedback from a unit incorporating an RF biomotion sensor. The application may output various parameters to a CSV (comma separated value) file for post analysis. Returning again to FIG. 33a, the iteration process indicated there may include the following:

1. The cyclic sound is to lead the subject's actual breathing rate downwards towards a target breathing rate. The values of offset and epoch lengths cited below are starting points and may be amended by way of experimentation.

a) The default target is 6 breaths per minute breathing rate (BR), but the GUI (graphical user interface) is to have a user settable target BR.

b) The cyclic sound is to have a BR of 0.5 breaths per minute less than the subject's current epoch-average BR, i.e., to lead it downwards towards the target. This offset value can be set in advance or empirically defined by way of test session determining an optimum starting difference from the user's breathing rate.

c) The cyclic sound BR is to be updated (i.e., next switch up or down) on an epoch basis.

d) Start conditions: assume a BR of 13 breaths per minute for the cyclic sound. Monitor the subject's BR for 4 epochs and match the cyclic sound to the subject's BR minus the offset after this 4 epoch start condition. This is to try and "capture" the subject's BR.

e) During leading the subject's BR downwards, if the subject's epoch-average BR stays >1 breath per minute above the cyclic sound BR for >4 epochs, then allow the cyclic sound BR to be moved up to the subject's current BR minus the offset. This is in order to try and "capture" the subject BR again.

f) The overall amplitude of the cyclic sound is to decrease over time when sleep is detected, and the following go-to-sleep logic may be implemented: once asleep for 10 epochs, reduce original volume by 1/10 per epoch, if subject awakes during this period, halt volume reduction, and keep volume level until subject goes to sleep again.

Cycle Variation

In some versions, the device may use single cycle-length sound files, with a short padding in between to prevent click or jump between the end of one file and the start of the next. The cyclic sound files may be preconfigured in set lengths, equating to BR from 10 to 15 breaths per minute, in 0.5 BR steps (i.e., BR of 10; 10.5, 11.0 etc.). The short files lengths may cause small gaps between the end of one and the start of the next cycle. With this in mind each cyclic file may be concatenated into continuous sound files that have a whole number of cycles, but as close to 30 seconds long as possible. This may reduce the incidence of jumps to a minimum. The effect is dependent upon the SmD hardware and may be addressed by appropriate buffering in software (e.g., to promote seamless looping.)

Versions

Various further versions can have one or more of the following features:

user selectable target breathing rates;
capability of selecting different source sound files;
limited or full breathing coach logic as specified above;
a two-step algorithm logic pattern. The sound cyclic rate can start at 12BR and remained at that until the subject's breathing rate touched/reduced to <=12.5BR, then the sound cyclic rate is reduced to 10BR. More than two steps may also be implemented.
Using a constant sound cyclic rate, e.g. 10BR. In this case, the only use of the real time feedback from the biomotion sensor is the sleep status feedback to reduce the sound volume.

Saving Data

The data obtained during a relax session may be saved in the form of a CSV file that has the once per second data in 4 columns:

I. Date time stamp.
II. Subject status
III. Subject breathing rate
IV. Sound (target) breathing rate.

The raw biomotion sensor I/Q signal levels can also be saved, at a sample rate of 16 samples per second. The data can then be passed through application GUI to generate a sleep report. Optionally, the raw data can be stored in a compressed format, such as "zip" files.

Data Analysis

The data analysis for each subject may be saved in a spreadsheet (Excel) file, one per subject. This can include the first hour of data for each epoch extracted from the raw data files and then plotted as Subject BR, target BR and Subject sleep Status on one graph. There may be a separate graph for each night.

There may also be a summary Excel file generated that compares the average time-to-sleep (sleep latency) under each configuration, plus a summary comment from each subject, where available.

This relax process may optionally be used during the day for shorter periods to reduce stress/promote relaxation.

The heart rate of the user may also be used in conjunction with the breathing rate in order to indicate a relaxed state—for example when there is a greater coherence (e.g., calculated by time or frequency domain measure) between the two parameters indicating a more advanced state of relaxation.

Software—Specific Embodiment—Daytime Relax (Assisted Meditation)

As previously mentioned, the system may include a "daytime relax" process similar to the "relax to sleep" process and employing similar functionality as previously described. This process may be implemented by the processor of the SmD. This 'assisted meditation' process may involve guided breathing exercises which are accompanied by a selectable range of sounds and/or lights. This is intended for relaxation at any time, but in particular in the evening approaching bedtime. This relax feature may optionally use, but does not need to use, the user's breathing rate to set the initial speed of the chosen sound. As there is no requirement for the hardware biomotion sensor to be connected, the feature can be used anywhere. This relax feature follows similar logic to the Relax-to-Sleep process but with some differences. The 'relax' breathing rate reduction feature synchronises a 'relax sound' (chosen by the user from a range supplied by the app) to the users measured breathing and modulates that sound to slow the user's breathing. The volume ramp down is not determined by the user's state of wakefulness. Instead, it may follow a predetermined course. In some configurations, it requires the interaction of the user with this 'meditation' feature which may direct the user to breath at a specific rate to relax. This requires conscious engagement with the device thus keeping the user awake.

The audio rate can be initially set (e.g., at 12 BPM) (this may vary (e.g., it could be 14 BPM or some other)). The rate may then be ramped down to the targeted minimum (e.g., 6 BPM or lower) following a predetermined reduction path. Volume step ramp down may optionally occur every 2 minutes. The user may optionally set the length of the relax period and the application may then determine the rate of volume ramp down of the audio files.

If the user interacts with this process and selects a different audio file, the playback rate may be reset to the initial rate (e.g., 12) and the logic restarts (parameters are being refined). Closing the feature will also terminate playback.

Further options (as previously discussed):
Provide high quality sounds (such as file type AAC)
Facility to download additional sounds in the future.
UI to select and play different sounds
Return volume to default value (14 breaths per minute) if user interacts with process during session
Route audio to speakers (if connected)

An example process may be implemented by a processor as follows:
User selects "assisted meditation" option
Audio is played at the default breathing rate of 12 breaths per minute (i.e. 2 BPM less than the maximum available) for 2 minutes.
At the end of the two minutes from the previous step reduce the playback rate by 2 breaths every 2 minutes until the minimum rate of 6 breaths per minute is reached.
When the minimum breathing rate is reached remain at this rate for 10 minutes.
At the end of the 10 minute period from the previous step reduce volume by 10% every minute for 10 minutes.

If the user interacts with the app and selects a different audio track, the playback rate the playback rate resets to 12 and the logic restarts (parameters are being refined). Closing the process may terminate playback.

Figure 34:
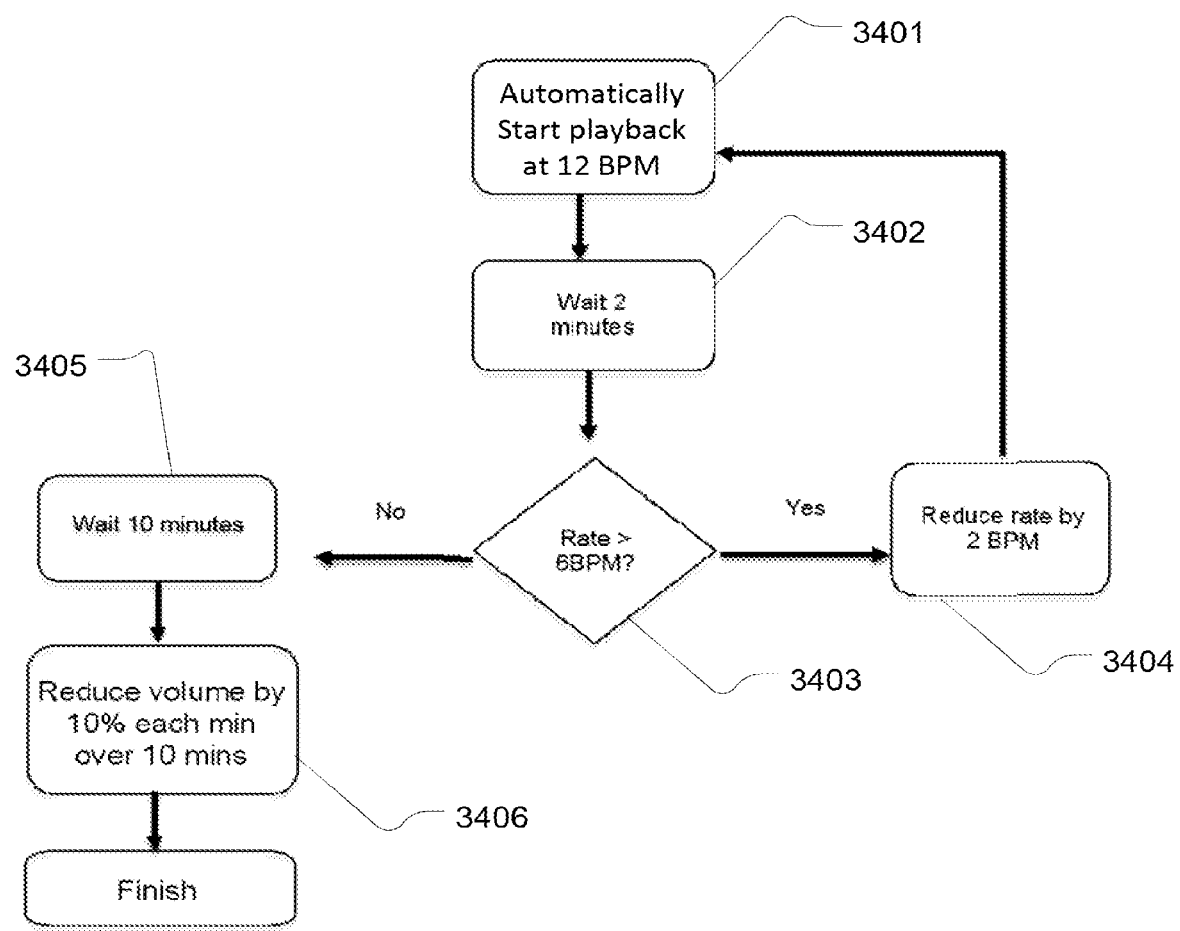
FIG. 34 shows an example methodology of a processor such as for guided breathing to relaxation that may be implemented in a processing device of the present technology.

A suitable example of this process may also be considered with reference to FIG. 34. This example does not require capturing of the user's breathing rate prior or during activation. This feature relies on conscious engagement with the process by the user. It can initiate with the default breathing rate (e.g., 12 br/min) and follow a rate reduction pathway and then a volume reduction mechanism.

Referring to the example of FIG. 34, at 3401, the processor begins repeatedly playing the sound file at an initial rate (e.g., 12 BPM). At 3402 a time period elapses during playback (e.g., a 2 minute wait). At 3403 the current playback rate is evaluated. If it is greater than a minimum rate (e.g, 6 BPM), then the rate is reduced at 3404, e.g., by 2 BPM, such as by the sound period stretching process previously described. The sound file is then repeatedly played again at 3401. If in 3403 the rate is not greater than the minimum, at 3405 a wait period is implemented while the sound file is repeatedly played. At 3406, optionally a gradual volume reduction process may be implemented (e.g., 10% every 1 minute) until the volume is zero or off within 10 minutes.

Figure 35A:
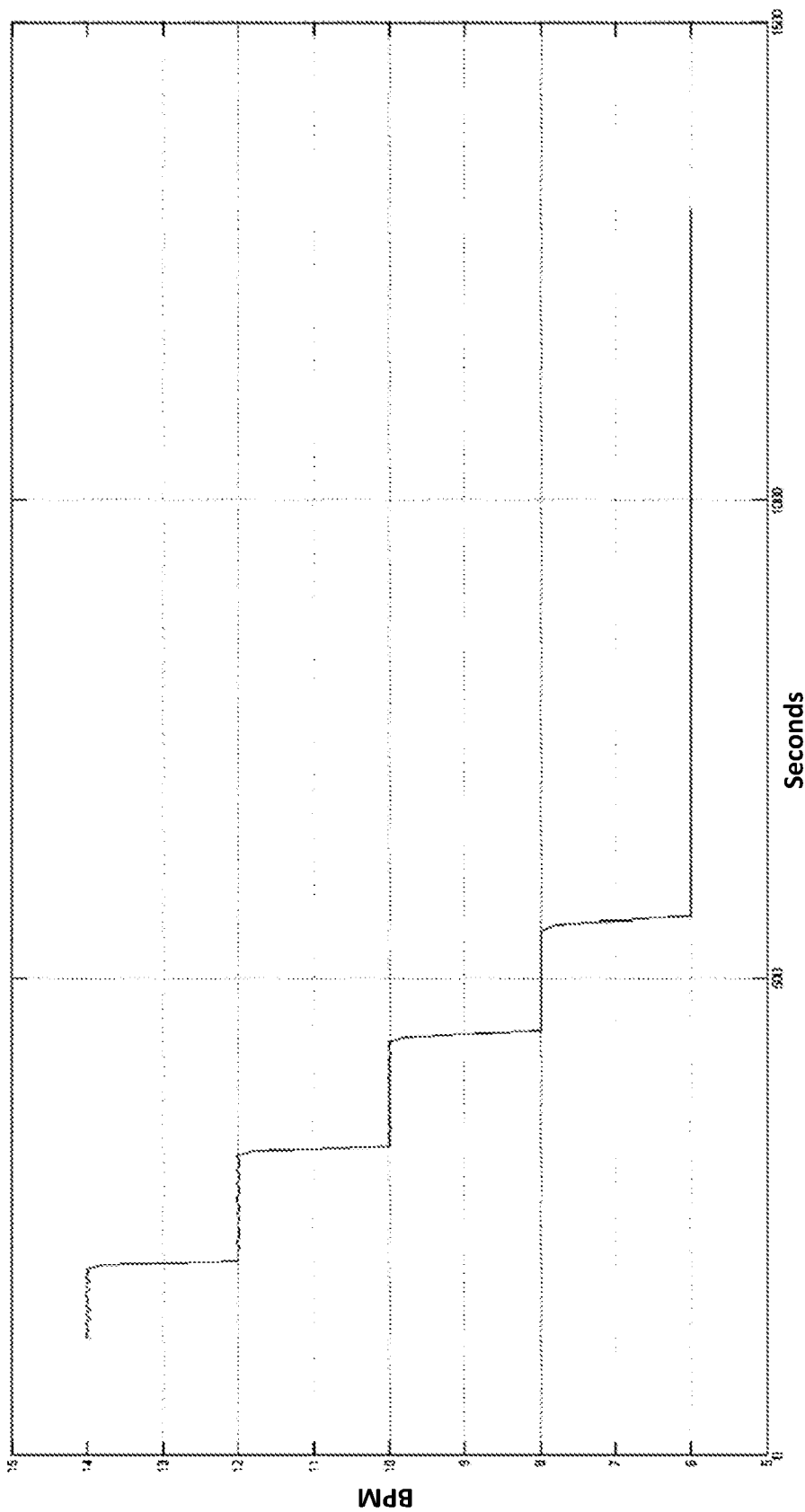
FIGS. 35a and 35b illustrate breathing rate reduction that may be implemented with the methodologies of FIGS. 33 and 34.
Figure 35B:
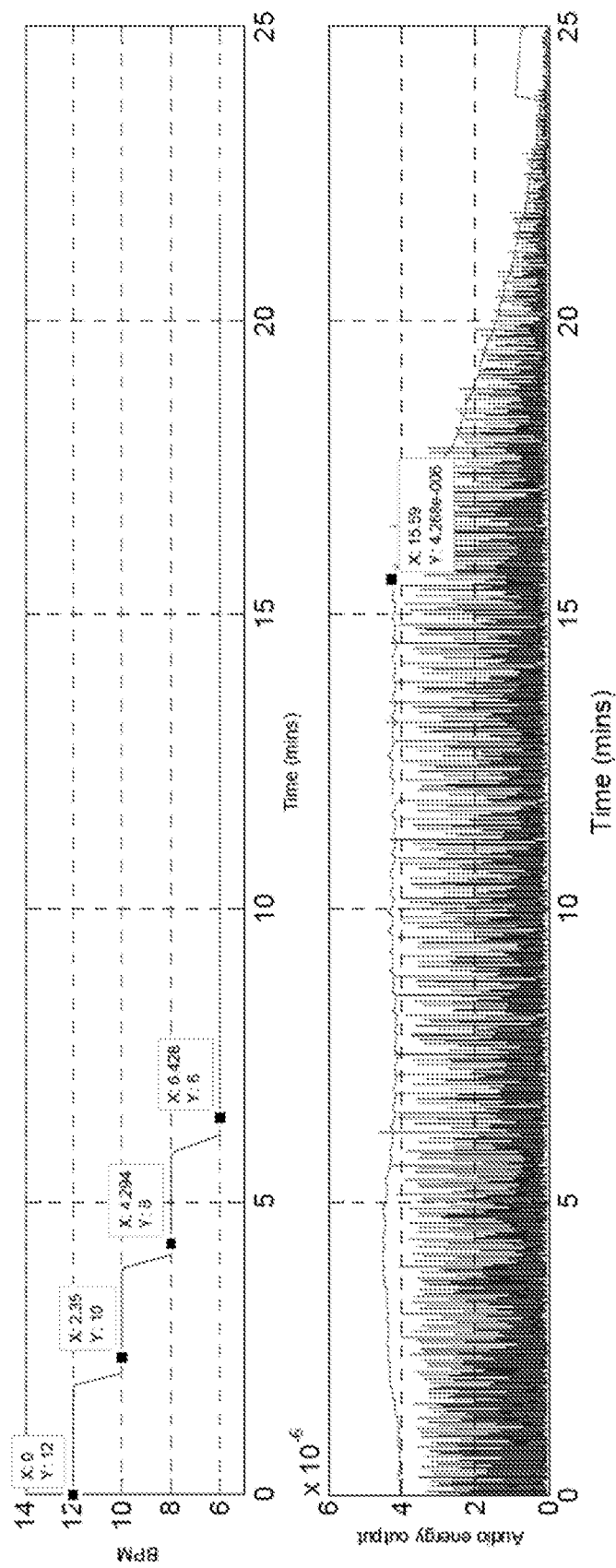

The reduction of the breathing pattern by such a process may be further considered in relation to the graphs of FIGS. 35a and 35b. This represents one embodiment of the pre-determined rate reduction path in the daytime relax feature. The graph in FIG. 35a shows a reduction from 14 br/min to 6 br/min illustrating the controlled reduction of the rate of the sound file. In FIG. 35b, the graphs correlate the 12 br/min to 6 br/min. playback reduction with a graph of the audio energy output. The graph of FIG. 35b also illustrates the volume reduction towards the end of the daytime relax process.

Software—Conceptual Personalized Sleep and Environment Advice

As previously mentioned, the system may be configured to generate messages/output to a user concerning sleep advice. For example, as the system builds an understanding of the sleep patterns of a user, such as from sleep related analysis of sensor signals and questionnaires, it may deliver customized personal advice to help improve the user's sleep through the utilization of an 'advice engine'. In some cases, diagnostic capacities can be included in the advice engine to help identify other sleep issues which can connect the user to other products such as for treatment of sleep related health issues (e.g., anti-snoring devices, sleep apnea treatments, CPAP devices, etc.). The advice, which is generated by one or more processors of the system, can be designed to inform the users of the benefits of good sleep habits, best environmental conditions for sleep, and daily activities that help sleep. It delivers credible and insightful information so as to assist the user's sleep and keep the user engaged with the overall system. The system may implement a learning classifier, such as using Bayesian methods and/or a decision tree, in order to tailor advice to the individual patterns of the user, a local population, or a global population of system users. The user can be prompted to respond to electronic queries embedded in task/advice nuggets received. The user responses can guide/trace a path through the contents of the decision tree.

The user's detected sleep pattern may also indicate a risk of a serious sleep issue. If significant sleep issues are detected, the system can recommend, and facilitate connection to professional online or offline resources (e.g., expert advice articles, access to relevant forums, or contact with sleep professional or a sleep center) to assist the user. The connection may be facilitated by a smart device (e.g., cell phone or tablet) or a PC. For example, links on the computer of phone may initiate communications with such professionals or for downloads or access to the sleep related information. For example, a prompt of the system to the user may trigger sending of a report to a professional with detected sleep information. The profession may then communicate back to the user such as through the system. For example, a medical practitioner may generate and forward a specialised report or professional opinion on the sleep health of the user, based on the sleep report generated by the herein described system, which the medical practitioner has received and reviewed. This can be facilitated via the bedside device BeD, one or more of the systems servers, such as a dedicated web page or through communications via a smart phone or SmD.

The creation of such report elements may have multiple pathways and may depend on the sleep problem detected. For example, the report feature can be delivered on the screen as a PDF, or other document format, that can be printed/saved by the user. For a user with normal sleep or (perhaps) basic insomnia, but poor sleep hygiene and/or sub optimal bedroom environment, the pathway may be via the advice engine to try to improve the user's sleep. The report may show trend data of sleep parameters, a description of what are the main sleep drivers, and any advice given and user changes (if any) arising from the advice.

For example, a typical report may contain any one or more of the following information:
Is the problem with falling asleep or staying asleep
How many nights a week
Duration of sleep
Fragmentation level
Light/REM/deep quantity A detailed example report is also illustrated in FIGS. 54a, 54b, 54c and 54d.

Figure 36:
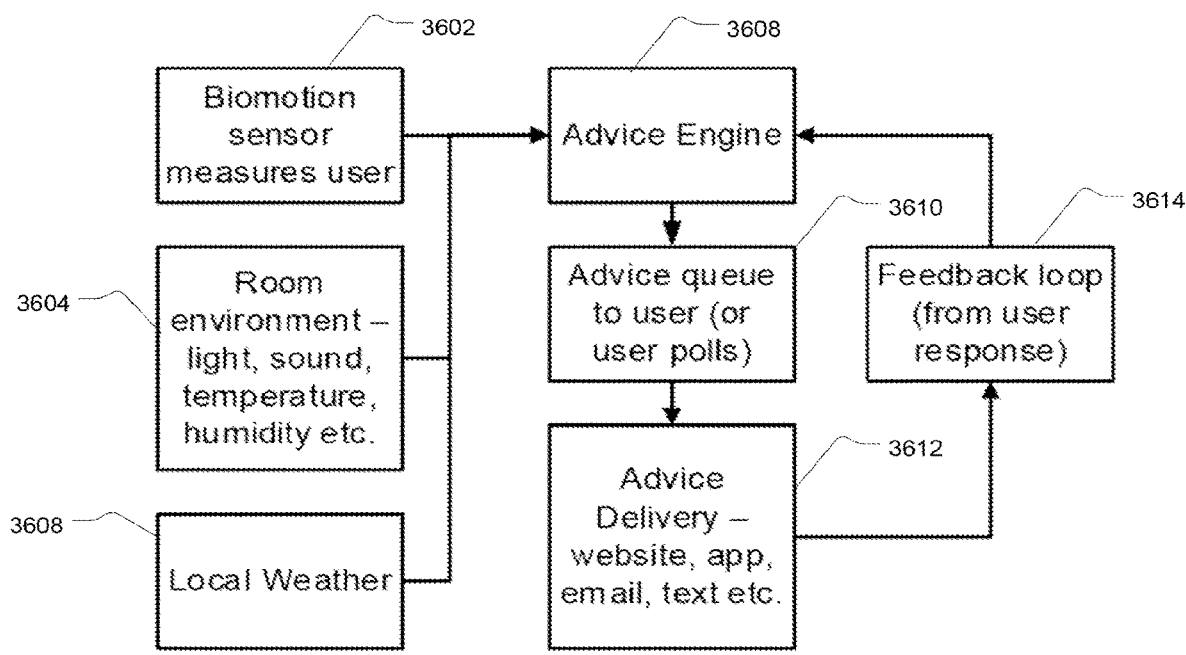
FIG. 36 shows a conceptual block diagram with example processes of one implementation with a bedside unit (e.g., processing unit)

FIG. 36 illustrates a general flow diagram concerning advice generation. The advice generation may involve any one or more of the BeD, SmD and the cloud servers(s). At 3602, respiration and movement (and optionally heart rate) data may be detected from a user. The data and/or sleep related analysis (sleep staging etc.) of the data may be sent to an advice engine. Optionally sleep room environment information (e.g., light, sound, temperature, humidity, air quality, etc.) gathered from sensors at 3604 may also be provided to the advice engine. Additional information may be accessed such as local weather (and location data if available) at 3606. At 3608, the information may be analyzed. At 3610, generated or selected advice may be queued for delivery based on the analysis. At 3612, the advice may be delivered to the user by one or more different delivery means (e.g., website, text message, push notifications, voice message, email, SmD app notification message, etc. At 3614, a user may respond to a query associated with or included within the electronic advice, which may be fed back to the advice engine for generation of further advice. During the advice processing, various characteristics and trends in the data, possibly identifying sleep characteristics and patterns, may be identified. On the basis of these features and trends, the proposed system and method provide recommendations and coaching to the user, in the "deliver" stage. The signals may be processed at least in part in a back end server.

Figure 37:
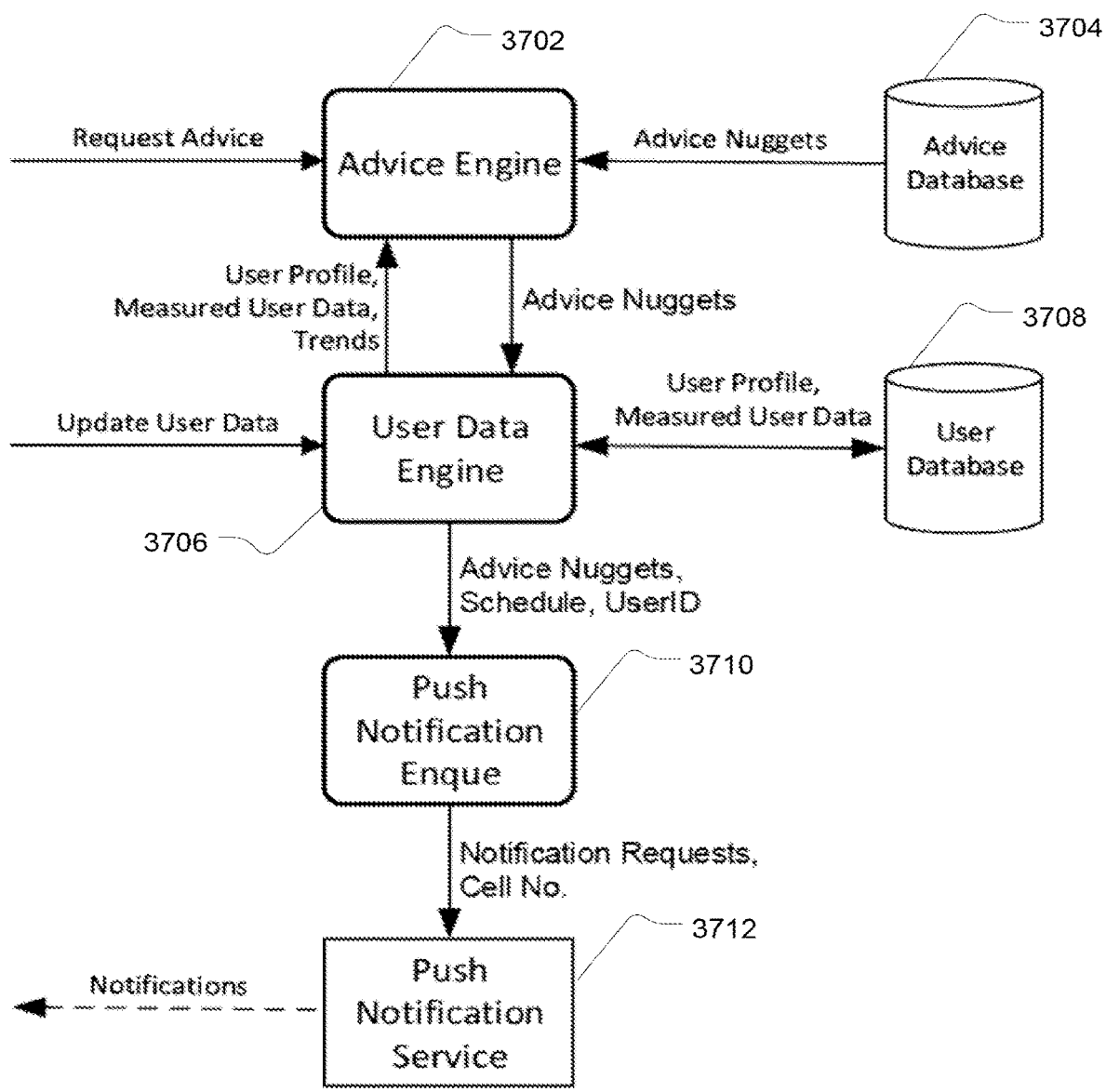
FIG. 37 illustrates example processes of a system for generating sleep advice, such as utilizing one or more servers to communicate with a processing device (e.g., smart phone) of the system of the present technology.

FIG. 37 illustrates one process that may be executed by software, such as on one or more a backend cloud servers. Thus, the advice engine may be formed by a number of services running on a number of back-end servers. This may operate in co-operation with a Push Notification Service such as one from Apple or Google, for example. The back-end services can follow a client-server model. Push Notifications may be delivered over a cellular/mobile or other wireless network. An advice database may be separated from a user database for flexibility/scalability reasons. The advice engine can be a back-end component that implements the logic of advice generation, scheduling and delivery as described in more detail herein. Thus, in this example, an advice engine service module 3702 may receive an advice request such as from an SmD. The advice engine may access user data, measured sleep information and trends, etc. from a user data engine service module 3706. This information may be stored in a user database 3708. Based on this information, the advice engine may select advice nuggets from an advice database 3704 based on advice selection logic. The selected advice nuggets, which then are associated with a particular user, may in turn be stored in the user database 3708. The user data engine may provide the advice nuggets, scheduling and delivery information for a user to a push notification queue 3710. The queue service may then provide the necessary advice communication information to a push notification service 3712 for delivery to the user.

Figure 39:
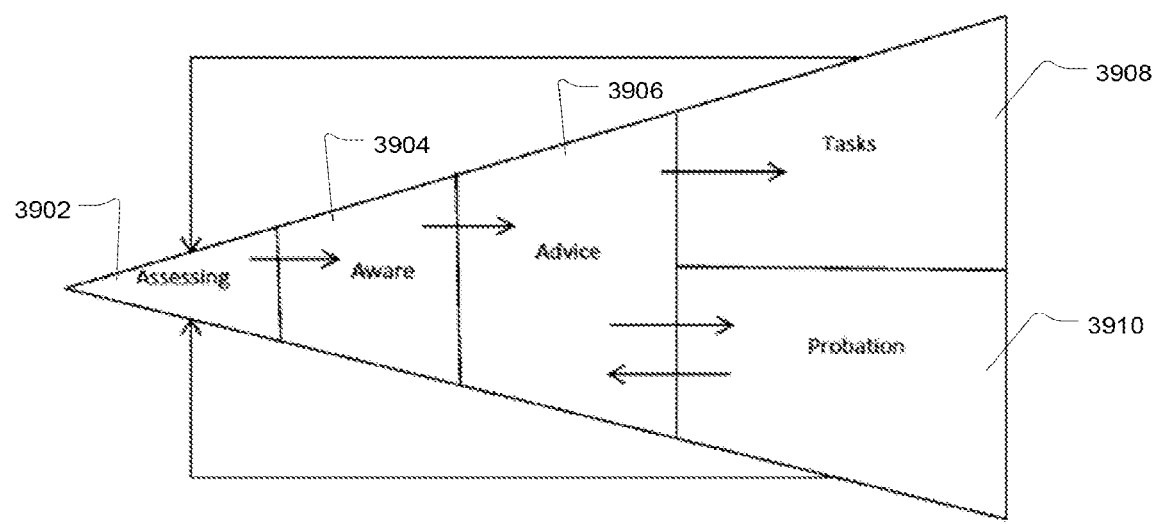
FIG. 39 shows a processing methodology for generating advice over time.
Figure 40:
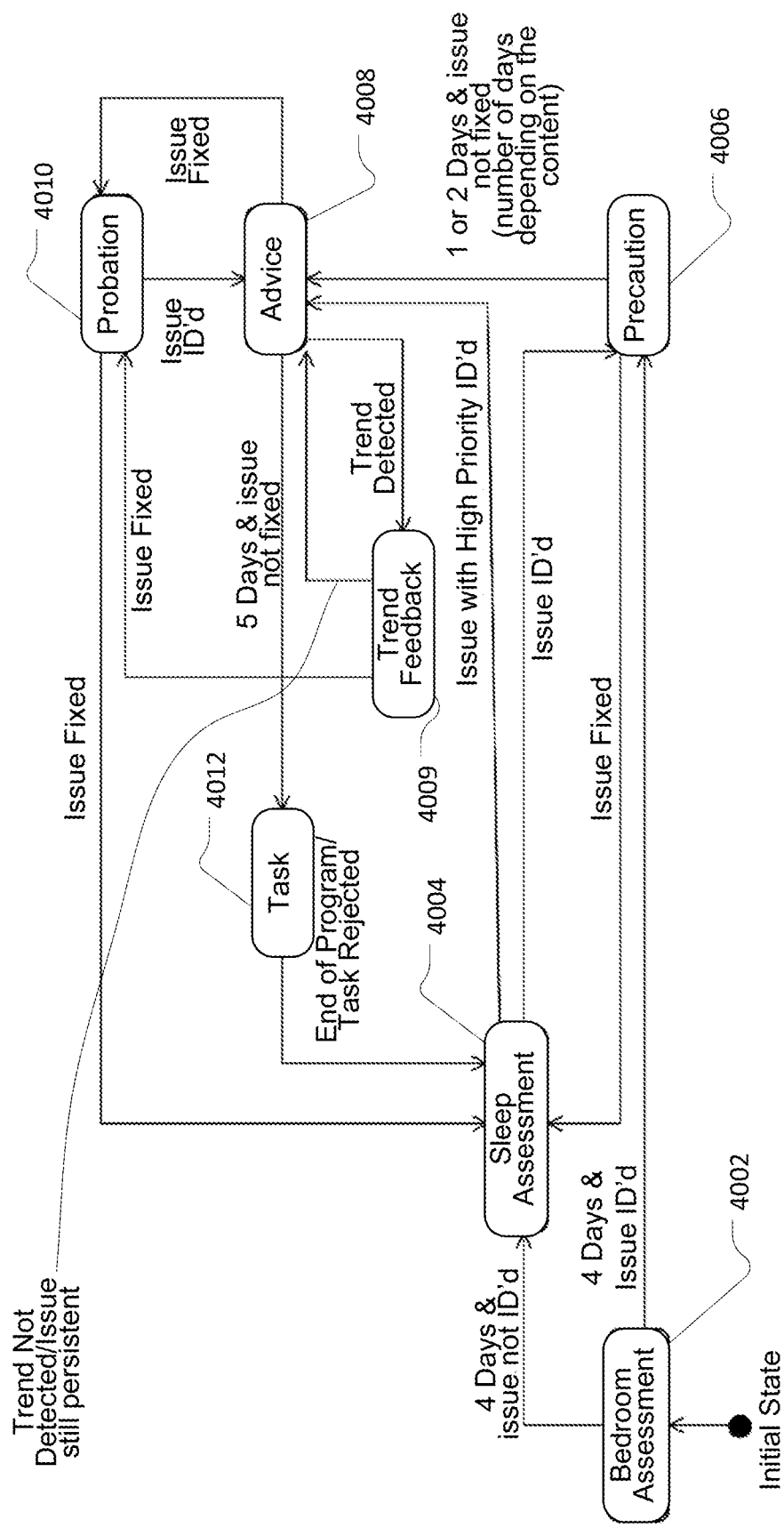
FIG. 40 illustrates a state machine for a processing methodology to generate advice over time.

A processing flow methodology for the advice engine may be considered in reference to diagram of FIG. 39 and the state diagram of FIG. 40. The process may include an assessing state 3902, an awareness state 3904, an advice state 3906, a tasks state 3908 and a probation state 3910. These states may be considered in reference to the following discussion of FIG. 40.

In an initial state, a bedroom assessment stage 4002 may be made. In this process, the user may immediately receive recommendations based on the user's first night sleep, which are specifically aimed at optimising the bedroom environment and the sleep related detections previously described. This stage may last 3-4 days (i.e., uses of the BeD and/or other sleep recordings) typically. If no issues are detected with the user's sleep, they will receive "wizard" like nuggets—which may be general information about sleep. In other words, if no issues are seen, sleep facts can be supplied as nuggets. This may avoid annoying the user who may not like to be informed about environmental factors that are not actually impacting their sleep. Thus, some specific advice may be ruled out based on a detection of satisfactory environmental conditions.

After an initial assessment, for example 4 days, the SmD may start becoming aware of more details regarding the user's sleep in a sleep assessment stage 4004 by detecting issues with the user's sleep record (e.g., a trend). If the system does not detect any unusual sleep issues, it may remain in the nightly sleep assessment phase detecting environmental conditions and sleep indicators/parameters/stages, etc.

If an issue is identified, the user moves to a precaution advice stage 4006 for a period of time (e.g., maximum of two days). This allows the user to have a transient/bad night of sleep without annoying the user or directing them into a sleep program. If the issue goes away, they move back to the sleep assessment phase. If the issue remains, the Sleep Advice phase becomes more active. This may last for a subsequent period of time (e.g., around 3-5 days, depending on the detected condition and the content available). If a positive (getting better) or negative (getting worse) trend is seen, the user may also receive trend feedback in a trend stage 4009.

In some cases, the process may advance from the advice stage 4008 to the probation phase 4010 if the device detects that the previously detected issue is fixed or no longer detected. Otherwise, the will continue or move back to advice phase where further or secondary advice suggestions may be generated.

In some cases, the process may advance to the tasks stage 4012 if the device detects that the user is showing no improvement (i.e., the sleep related problem is repeatedly detected). These tasks are longer term programs to address certain issues—e.g., increase exercise levels, reduce caffeine intake etc.

Figure 38:
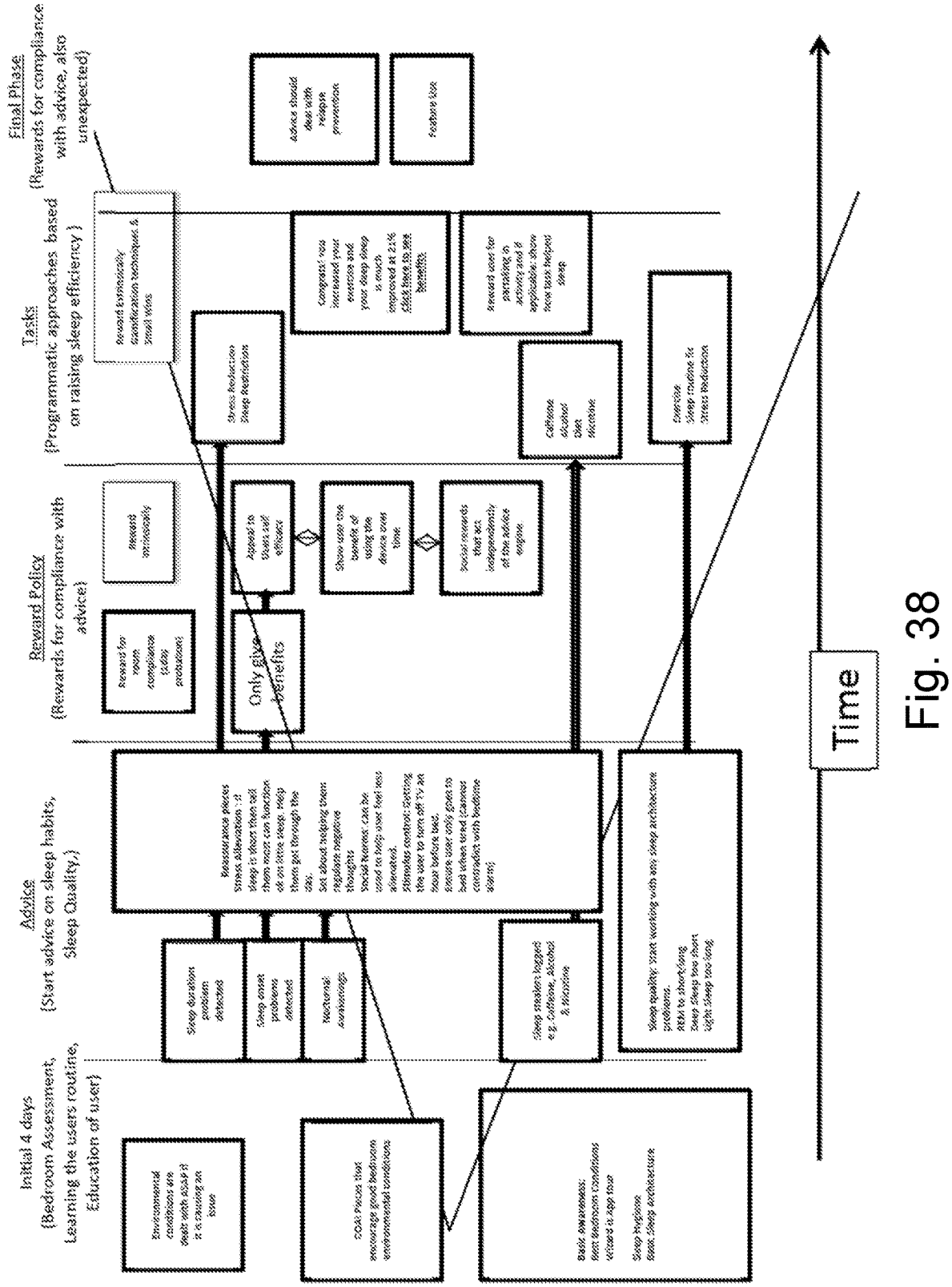
FIG. 38 illustrates an example processing methodology for generating sleep related advice for some versions of the present technology.

In short, over time, the advice engine can generate personalised advice for the user based on the user's sleep patterns, changes in sleep patterns, journal entries and a personal profile. It will gain an awareness of issues that will be monitored. If the issue remains persistent then it will move into the advice phase for informing/correcting a user with these issues utilising the advice nuggets. It may designate a task to the user to help combat the sleep issue. However, if the user does not comply with the advice or the issue is no longer detected then the system will enter a probation period for a number of days and the advice may resume addressing this problem as before. If the issue is no longer detected then the system may revert back to an assessing phase, where no sleep issue is detected but the user is monitored. On the other hand, if the user complies with advice then a reward policy may be implemented. These processes are also illustrated in the diagram of FIG. 38.

Advice

As previously mentioned, the advice engine is responsible for managing and generating all advice content, implementing business logic and scheduling advice to the push notification engine. Input to the advice engine may typically include processed data from the BeD and/or SmD, such as that stored in an accessible database to the advice engine. The input may similarly include advice feedback from the user and/or user data and state information (e.g., state of advice process, see, e.g., FIGS. 38, 39 and 40.) The output of the advice engine may include advice annotations concerning and/or overlayed on a hypnogram and advice nuggets. This may be communicated via an interface to, for example, the SmD or a cloud server or traditional server. The output may also include the advice content/nuggets and advice scheduling information such as through another communications interface (e.g., a push engine interface). Another form of the advice engine could be implemented entirely within the SmD or within the BeD device (such as one with a graphical display and/or enabled with the sleep related processing functions of the SmD).

The advice engine may typically identify combinations of parameters that trigger specific pieces (nuggets) of sleep improvement advice. These are then added to a queue for later delivery to the user—e.g., by sms text message, email or application notification (e.g., push notification). The actual advice can be text, audio, or a short video clip. As an example, it will be assumed that too much 'light sleep' (stages 1/2), restlessness and periods of awake are detected early in the morning for a user. The advice engine can identify that this detected condition coincides with elevated light levels (as detected by the light sensor). The advice content generated for the user may in this case suggest use of blackout curtains (and potentially offer the ability to purchase online). The light sensor may also detect whether this elevated light level is due to daylight or artificial light (e.g., light bulb, LED, fluorescent or other) and tailor the advice appropriately. The system may determine the location of the SmD and estimate sunrise, sunset and other parameters from online services or from a lookup table.

Thus, the advice engine may include or have access to a number of services running on a number of back-end servers. This may be in cooperation with a Push Notification Service (e.g., from Apple/Google) and other operating systems. The back-end services may then follow a client-server model. Push Notifications may be delivered by over a mobile or cellular network. The advice database may be separated from the user database for flexibility/scalability reasons. The advice engine may be a back-end component (e.g., a processor service of a cloud server) that implements the logic of the advice generation, scheduling and delivery.

By way of further example, the advice engine inputs estimates of a user's current and historical sleep data as measured by a BeD and analyzed by the SmD, lifestyle data input by the user, and a record of advice previously given to the user to deliver advice that helps a user improve their sleep. The advice is designed to inform the users of the benefits of good sleep habits, best environmental conditions for sleep, and daily activities that help sleep. It delivers credible and insightful information so as to keep a user engaged with the overall system.

In doing so, the advice engine may implement any of the following interface(s):
Advice Engine Content Interface: an interface between the advice engine library and the advice engine content from which advice may be selected with the logic process of the advice engine;
Data Access Layer: This is the interface between a back-end repository (e.g., user database server) and the advice engine;
Notification Engine—this allows notifications to be sent to a user such as via a smart device.

Advice generation by the advice engine may be further considered by the following examples:

(1) Light level and sleep disturbance advice: (a) If a higher than average ambient light is detected then a content message may be generated to suggest that a user consider covering their eyes or turning off devices with lights, LEDs etc. (b) If blue light is detected then a content message may be generated to identify the need to cover such devices and why blue light can be significant to disturbing sleep. If an increase in light level is detected around sunrise and the device detects that the user is waking or having disturbed sleep in this time frame, a message may be generated with content to recommend blackout curtains or other window covering. If blinking light is detected a message may be generated with content to suggest that the user consider checking smartphone for notifications or to turn off a notifications on the smart phone.

(2) Sound level and sleep disturbance advice. (a) If road noise, garbage/bin collection and/or elevated background noise is detected by analysis of microphone sounds, then a content message may be generated to suggest that a user consider ear plugs or other sound control/masking background white noise. If snoring is detected by analysis of microphone sounds (e.g., by snoring of user or their partner) then a content message may be generated to suggest that a user consider a snoring reduction aid or otherwise seeking assistance for such SDB in a report.

(3) Temperature and sleep disturbance advice. (a) Record room temperature and if the device detects that user is slow to fall asleep, then a content message may be generated to suggest that a user consider changing the temperature (e.g., if overheated or too cold). (b) Record room temperature and if any awakenings are detected during the night; then a content message may be generated to suggest that a user consider changing the temperature of the room which may be too cold or too warm for instance, (c) Record room temperature and if any awakenings are detected near morning in conjunction with a temperature change, then a content message may be generated to suggest that a user consider changing the boiler/heater start time as it may be disturbing sleep with sudden temperature change. A control signal could also be generated and optionally sent to a temperature (and/or humidity) control device such as a thermostat and/or air conditioner controller.

(4) Patterns of sleep advice: if the device detects, for example, short sleep duration, fragmented sleep, low efficiency sleep, then a content message may be generated to suggest that a user consider various tips with specific sleep hygiene advice, this may include environmental adjustments when the events are linked to detected issues in environmental events such as any listed above.

In some cases, location data (e.g., GPS or other location awareness information) may be accessed and the advice may be generated based on the location advice. For example, by evaluating location data, advice can be based on actual sunrise time at the user location. Similarly, the device may check if the user is travelling and offer appropriate advice to manage jetlag or their new room environment, and other weather based parameters such as pollen count, temperature and humidity during the day or at night that might affect sleep. The phases of the moon (e.g., full moon) may also be referenced, and used to tailor advice.

In some cases, an advice engine may employ any of the following: a Back-end infrastructure (e.g., one or more servers); an Advice Engine comprising a number of cooperating Advice Sub-Units running on the backend server; an Advices Database hosted on a Relational Database running on the backend server; an Advice Push mechanism running on a Push Server; a graphic user interface (GUI)-based advice display mechanism running one or more Smart Devices; and/or a comprehensive user experience design, whose implementation is distributed over the above Functional Blocks.

An advice message or advice nugget may be characterized in two forms, leading and trailing. A leading nugget may be related to a cause which the advice engine estimates is responsible for the issue being addressed. These might involve alcohol and caffeine levels being too high or exercise level too low and/or suboptimal environmental conditions. A trailing nugget may be related to particular causes of the sleep issues being addressed by the advice engine. These may be related to the user's sleep pattern as illustrated by the hypnogram such as lengths of REM and deep sleep, number of awakenings which are not conducive to restful sleep. These issues may be defined in a class implementation or list and may be mapped to a database so that the system and repository can share the same identification for each issue. Each issue may have particular detection methods for analysing the presence of the issue and evaluating relevance as well as content for messages to communicate the issues to users.

Figure 41:
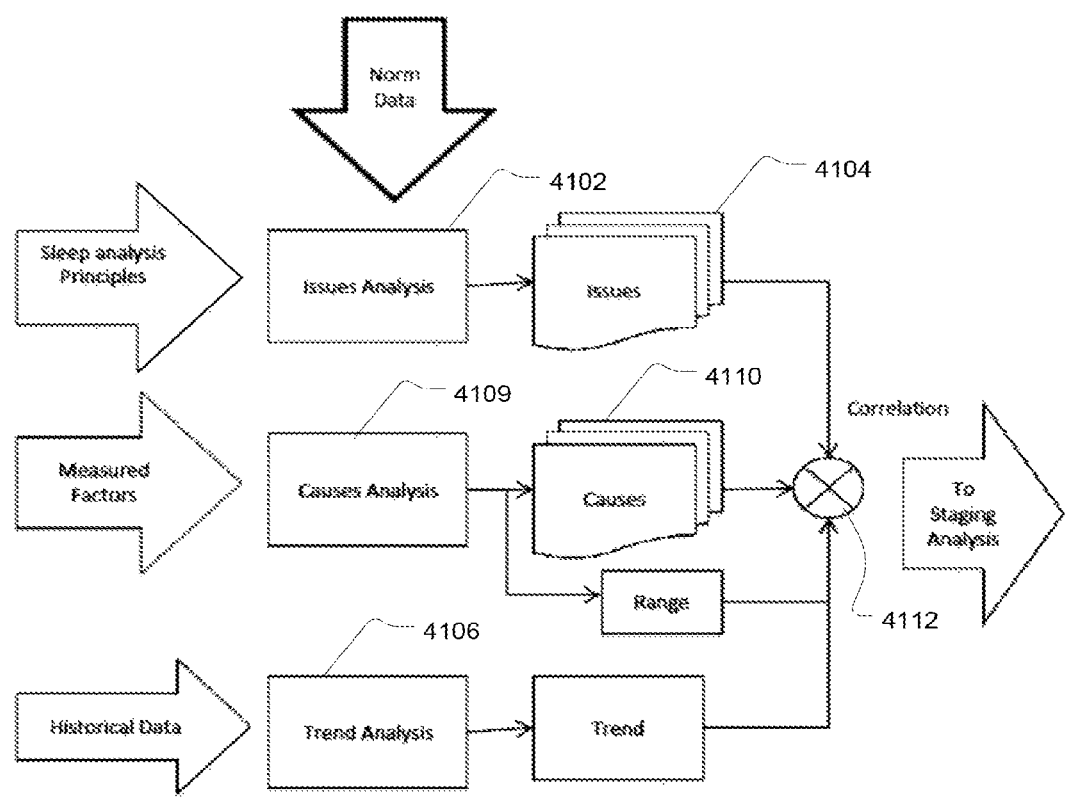
FIG. 41 illustrates a correlation process for correlation of parameters detected and recorded.
Figure 42:
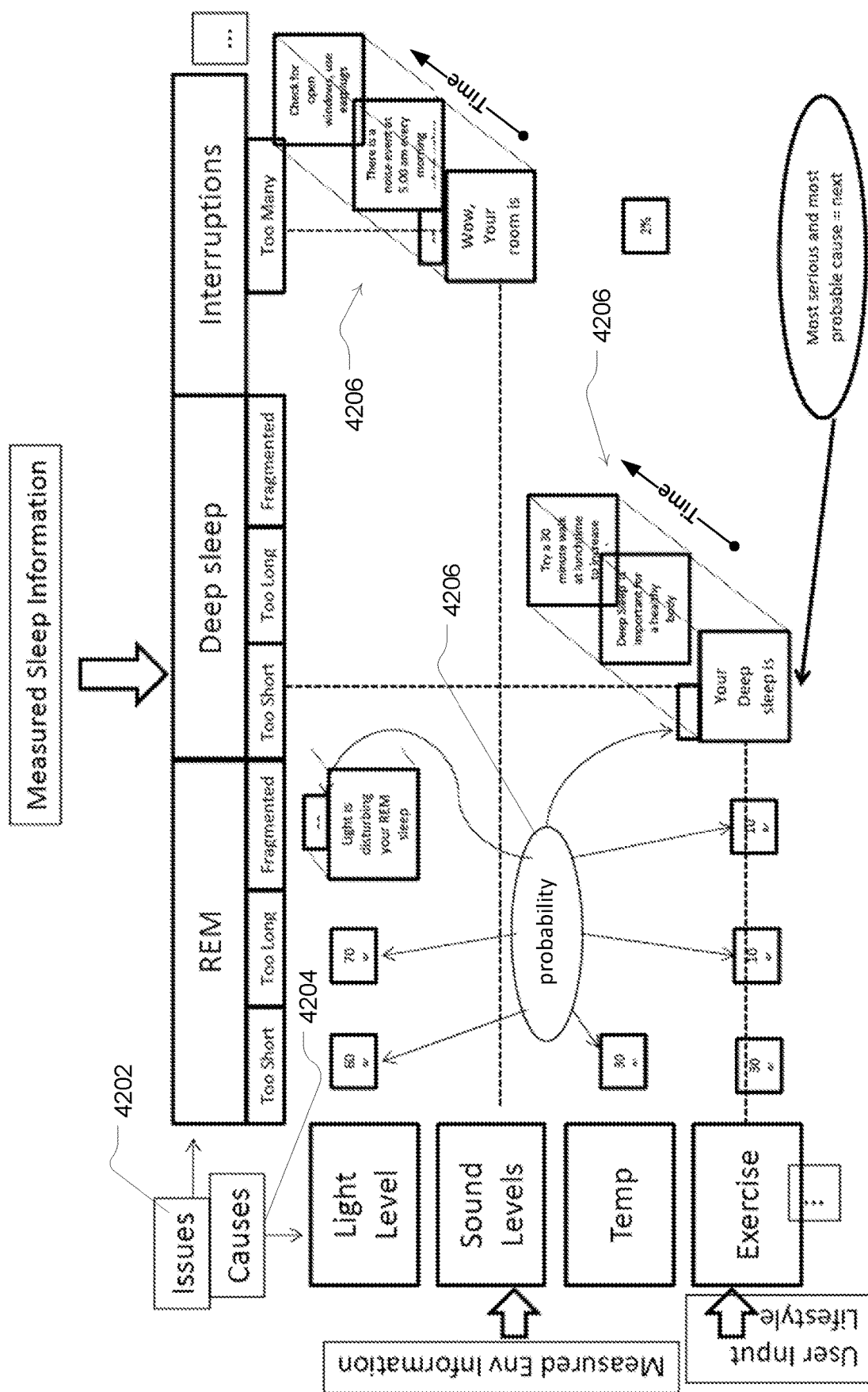
FIG. 42 illustrates an advice process showing how collected information contributes to the advice engine analysis.
Figure 43:
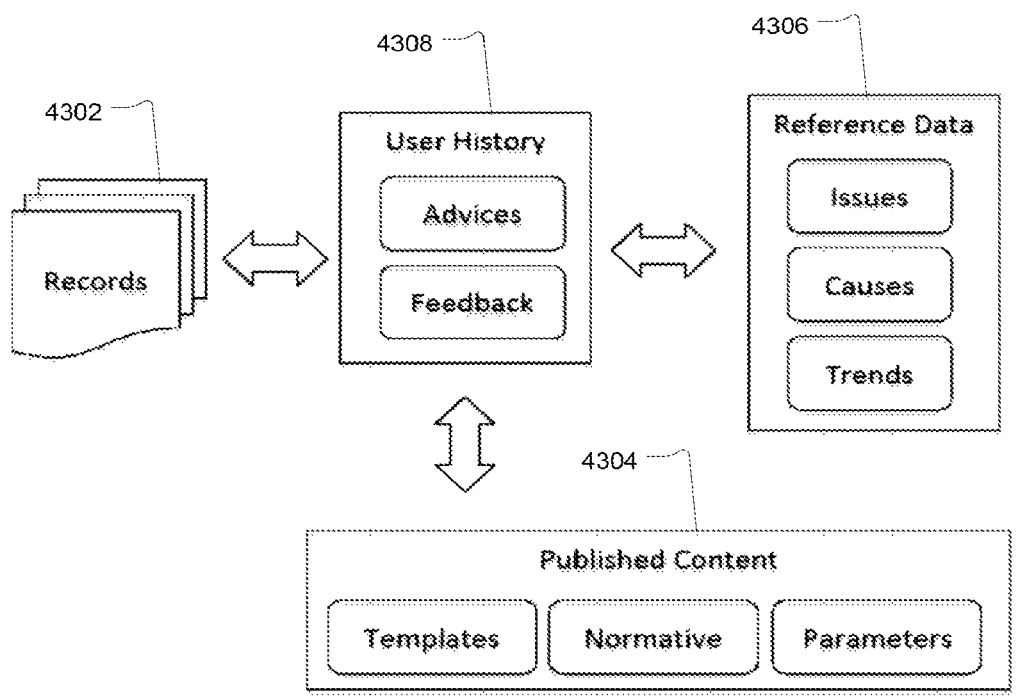
FIG. 43 illustrates a relationship between user data to advice content.

The processing of the advice engine may be further considered in reference to FIGS. 41, 42 and 43. The advice engine may include processing logic to do any one or more of the following:

(1) Adds measured sleep data to a user profile. This is required for building a user's profile and then for generating personalized advice.

(2) Solicits user profile data and adds to a user's profile. This is required for both building a user's profile and then for generating personalized advice.

(3) Delivers generic awareness advice while acquiring enough user and sleep data to generate a user profile. This engages the user until enough personalized data and advice is available. The complete user profile, in conjunction with current records of a user's previous night's sleep is used to generate personalized advice.

(4) Delivers personalized advice after the initial data gathering phase (5) Delivers personalized advice based on trends in acquired data and on previously delivered advice.

(6) Maintains a history of previously given advice which enables the user to improve their sleep to a greater, more targeted extent.

(7) Learns user's habits and the applicability of rules-of-thumb to the particular user.

As illustrated in FIG. 41, initially, the advice engine may primarily detect sleep issues by comparing detected patterns with normalized data, obtained from other users the described technology or from external sources, in issue analysis process 4102. However, over time, given increased use by a user and the collection of historical data of the user, the 'industry standard norms' may be phased out in favour of comparing recently detected sleep patterns with the particular user's normal historical data. This can allow further customizing of the advice given to a particular user. Thus, given a user's history of sleep records and advices, the most relevant advice template available on the system may be selected by the processor for addressing issues with the user's most recent sleep record. In this regard, most relevant criteria for selection may include the following parameters: presence of issue with a cause; trend; range; sequence; substitute; language; user type; and/or stage. Thus, trends from historical data may be determined in a trend analysis process 4106.

In some cases, as illustrated in FIG. 41, the advice engine library may base its logic process for advice generation on the following measured parameters (also referred as principles): REM duration; Sleep Duration; Awakenings (number and/or duration); SWS (Deep sleep) duration; and Sleep Onset duration, regularity of time to bed, among others. These principles are the basis for an issues analysis process 4102 that should identify a number of possible issues 4104 based on the comparison between those principles and the normative data. The engine will tag each user with the issue(s) that appear to be the most relevant, based on how much each underlying principle (measure principles) deviates from the standard (norm). The system will keep a user tagged with an issue until the relevance of that issue falls below a pre-defined threshold.

The processor of the engine in a correlation process 4112 may also correlate the user into a trend, which may be one of the following: None; improving a lot; improving; stable; Worsening; Worsening a lot. The trend will be based on the previous history of the user/issue. The identified trend may generate a queue of advices, selecting at least one likely cause and/or the most likely cause. Initially, the most likely cause may be attributed to the measured factor that deviate the most from the standard (norm). In a causes process 4109 causes 4110 may be evaluated for the sleep issues based on measured factors. The potential measured factors may include: (1) Environmental (enabled by default) including (a) Temperature, (b) Light and/or (c) Sound; (2) Lifestyle (enabled by specific issues): (a) Stress, (b) Diet, (c) Caffeine and/or (d) Alcohol. Initially all causes may be weighted by a 1.00 factor. As knowledge base around the way every issue is influenced by causes (or measured principles are influenced by factors) a correlation factor can be applied between issues and causes.

FIG. 42 further illustrates advice processes (such as of the SmD and/or a server processor) as detected conditions lead to generation of different advice content. It also illustrates the relationship between 'Issue' and 'Cause' in more detail. A user is educated to improve their sleep habits, and optimise their sleep environment. Behavioural improvement paths are based on the user response to advice nuggets. For example, issues 4202 may be detected with REM time, Deep Sleep time and/or number of interruptions. REM or Deep Sleep may be detected and evaluated by comparision with a threshold (either norm based and/or user trend based) to detect whether it is too short, too long or fragmented. Interruptions may be counted and compared to a threshold to decide if there are too many. A probability analysis process 4206 with respect to the issues and their relationship to cause 4204 such as measured or input information (e.g., threshold comparisions involving measured light levels, sound levels, temperature levels and other user input) may result in selection of one or more advice messages 4208 over time. The progression of delivery of different advice messages over time with respect to a detected issue may be selected based on their association with the different causes and the detected issue.

FIG. 43 further illustrates the data relationship between stored user sleep records 4302, advice content 4304 and evaluation or reference data 4306 (e.g., detected issues, causes and trends) as administered with the advice engine for generating advice and receiving feedback. User advice history data 4308 (e.g., sleep, environment, previous advice, their feedback, etc.) may be based on any one or more of this data, including detected sleep issues, causes and trends. This illustrates how issues and cause are associated with and contribute to the advice engine analysis for advice generation.

As previously mentioned, the advice engine library may move a user's status within and between various states such as those identified with reference to FIG. 40. In some versions, the following states may be implemented:

(1) Regular/101: This is a state where the advice engine does not detect anything wrong with the current user's data. It could go on forever, if all the measured sleep hygiene principles are within the expected ranges.

(2) Awareness: When the advice engine detects an issue with a user's data, it starts tracking that issue, and it enters an awareness status. The library remains in this status as long as the issue is still detected as the most relevant, for a number of record that depends on the number of stages defined in the advices content (3) Advice: If the advice engine is still detecting a specific issue for a consistent number of sessions in the user's data corresponding to the highest sequence number defined in the content data for that issue, then the system moves to the advice phase. During this phase the content can be more prescriptive, but from the perspective of the advice engine, the behavior is quite similar. The main difference is that the content is now delivered in two parts, one being associated with the issue and the second with the likely or the most likely cause detected. If the advice engine has already sent the highest sequence number available (e.g., all advice previously communicated), then the system can trigger a Task, and move to the Task phase.

(4) Task: During this phase the system will put the user through a specific program, with daily tasks. This phase will go on for the entire duration of the task program, as defined in the system. At the end of the task program the user will receive a report, showing the progression, improvements and highlights of the daily tasks. Next the system will go back to a Regular phase, and will stop monitoring the issue that originated the task program, for a number of records. If no other issues are detected will stay in regular phase, if not it will move to awareness for the new detected issue.

(5) Probation: If during an awareness or advice phase the user replies with a negative feedback for a number of times or the issue is not detected anymore, the user moves to a probation phase, where it can stay for a small number of days. From here, the issue may arise again, therefore the system will get back to where it left, or the issue may disappear completely, and have the system back to regular phase. This stage allows the advice engine to make sure that newly established environmental conditions and behaviours are maintained and successfully implemented as the user's new habit.

Figure 44:
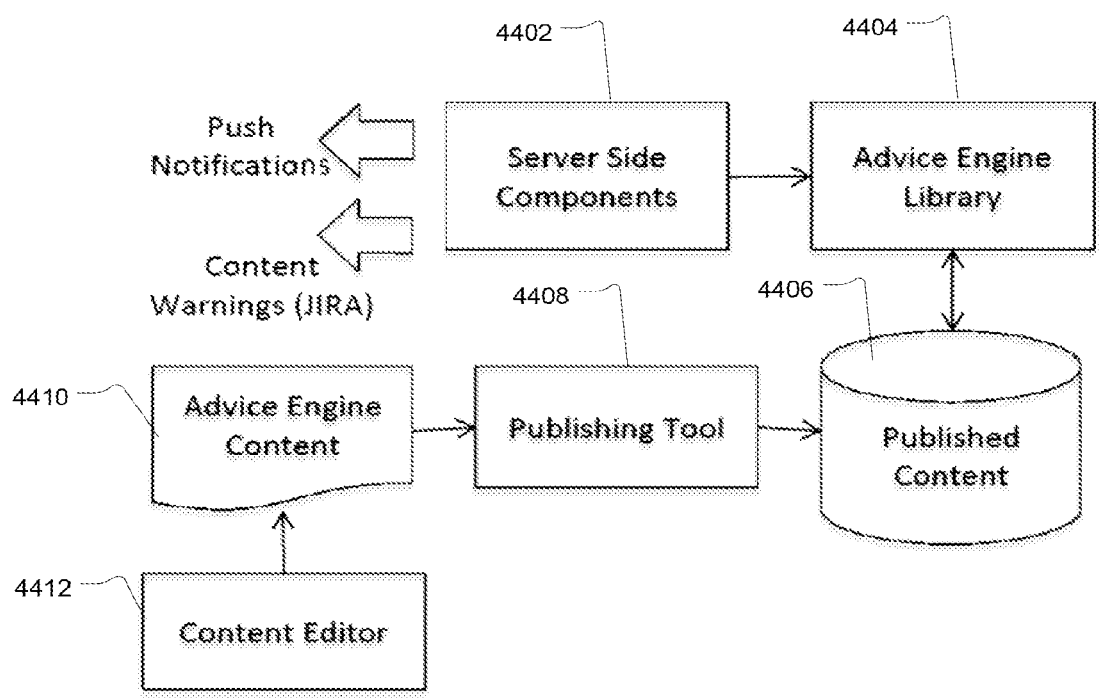
FIG. 44 illustrates a process for management of advice content in some versions of the present technology.

In reference to FIG. 44, the advice engine may include various components such as for management of the system. The components may include:

(1) Server side components 4402: This may include processes, such as with software, responsible for running the Advice Engine, scheduling and delivering advices to the users, and generating advice engine warnings, call specific functions in the Advice Engine Library 4404 which eventually accesses the published content 4406. Its components are:
(a) Advice Enqueuer
(b) Advice Dispatcher
(c) Advice Content Warning Generator The advice Enqueuer and Dispatcher form a Queue-Centric workflow pattern where the communication between the two components happens through a queue. The Advice Generator is triggered ultimately by an incoming record (Record Queued) and how this fires the Dispatcher to send advices to the Push Notification Service.

(2) Advice Engine Content and Management tools: A set of software components allow content editors 4412 to edit the advice content 4410. It may be able to access both production (live) and local data records, and provide a mechanism to playback a sequence of recordings i.e. manages the advice engine content, that is published to the various environments (production/staging) via a Publishing Tool 4408 which populates the advice engine content database.

(3) Advice Engine Publishing Tools 4408 serves as mechanism to evaluate the overall quality of the advice content, to version the current advice content and deploy it into various environment. It may allow access to both the DAL (Data Access Layer) and the Advice Engine Library 4404. It may read the content file (such as stored in XML format) and write into "Live" database (such as via SQL). The simplest form of publishing tool could be an SQL script run using an SQL server management application.

(4) Advice Engine Library 4404 is a processing module that may be responsible for online advice generation. Its main concern is to select the most appropriate template from a list, depending on a user's record and profile. The system may have logic that accepts that issues may be attributed to the most likely cause. This may not always be correct but the knowledge base for improving such causes may be improved over time as previously described. This library is the main and most important component of the advice engine.

Figure 45:
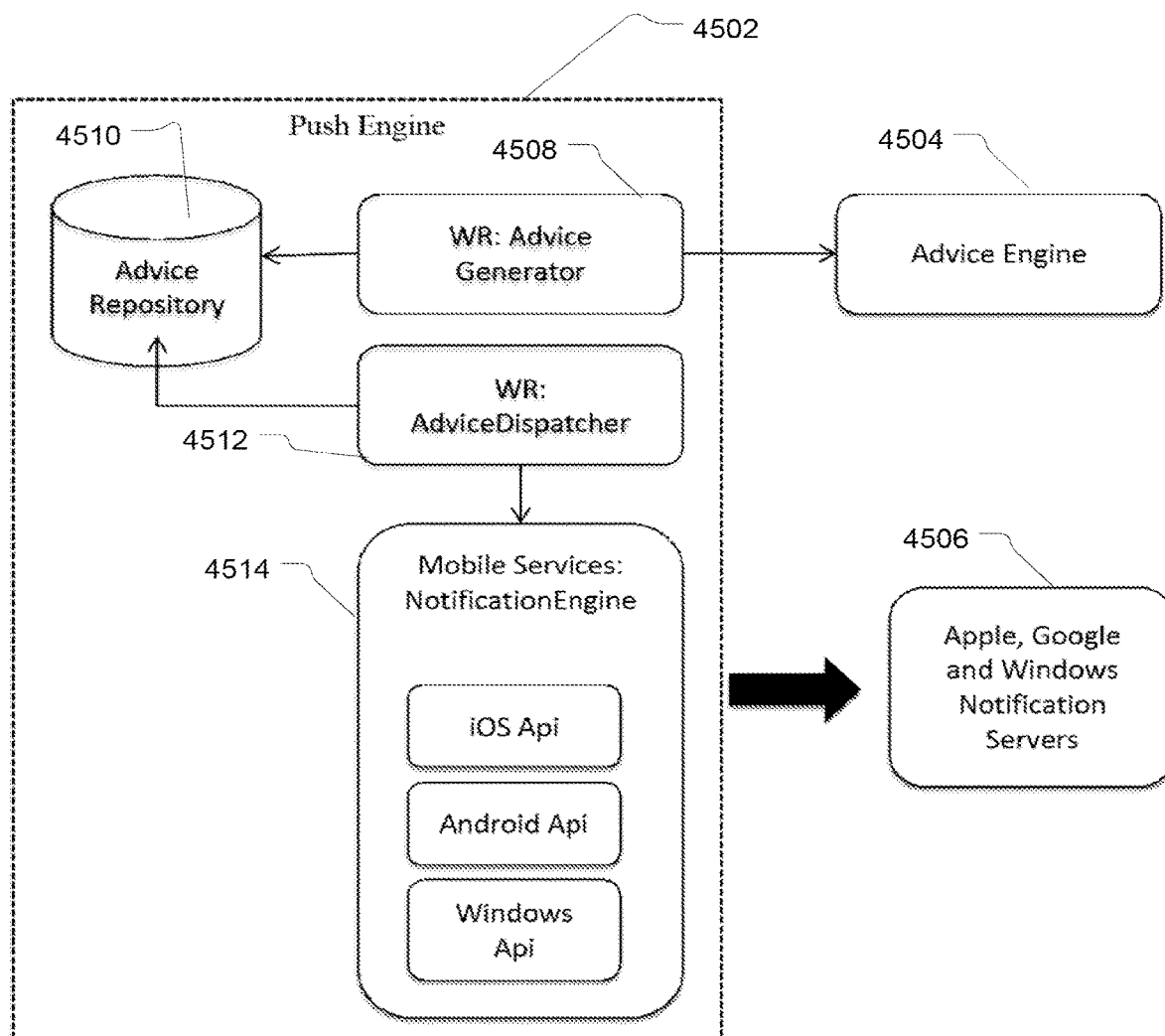
FIG. 45 illustrates an example push engine architecture and its interactions in the generation of sleep advice in some versions of the present technology.

FIG. 45 illustrates an example push engine 4502 architecture and its interactions with external components, such as the advice engine 4504 and one or more messaging notification servers 4506. Some example notification servers may include iOS, Android, and Windows operating systems. Once the advice has been determined, following backend server processing, the advice engine requires the advice to be sent to the user generated in the cloud. Sending or not sending an advice nugget to the user is based on the advice engine logic, scheduling and method of advice delivery can also be determined by the advice engine. This employs a 'transportation' method such as a push notification service to deliver the advice. The advice generator 4508 process receives advice nuggets/messages from the advice engine and queues them in the advice repository 4510. The advice dispatcher 4512 process retrieves the messages for a notification engine 4514 (e.g., via a communication service application programming interface API), which in turn communicates the message to a messaging notification server of the messaging notification servers 4506.

Advice Example Scenarios

As previously described, the system stores historical data, such as by uploading to the cloud server, which it then can draw upon to determine the user specific habits. It may also make recommendations for behaviour change such as to improve sleep. This may involve generating advice that educates a user as to improving their sleep habits, and optimising their sleep environment. As data is gathered from the user, the advice is automatically customised/personalized to their actual sleep habits, and their response to actual advice delivered to them (e.g., was the advice useful, not useful, irrelevant etc.). These behavioural improvement paths are based on the user response to "nuggets" or short pieces of advice, of which they may receive a number of these each day (and they can configure frequency of receipt). Nuggets should reinforce good sleep habits, and provide a pathway to improved sleep such as best environmental conditions for sleep, and daily activities that aid sleep. An example follows.

Consider a person using the system for one week. The following table of events summarizes a potential outcome generated by the system:

Events Tables (a) System in Initial State:

| # | Use Case | Outcome | Advice Content |
|---|---|---|---|
| 1 | On $1^{st}$ night | No advice/Welcome/intro nugget | NA |
| 2 | On upload of $1^{st}$ record | Welcome message 1-3 advices (content dependent), spaced throughout the day. | Bedroom assessment (env. data) No relation to issues detected |
| 3 | On $2^{nd}$ night | No Advice | NA |
| 4 | On upload of $2^{nd}$ record | 1-3 advices (content dependent), spaced throughout the day. | Bedroom assessment (env data) No relation to issues detected |
| 5 | same | same | same |

(b) After Initial State

| # | Use Case | Outcome | Advice Content If Issues detected | Advice Content no Issues detected |
|---|---|---|---|---|
| 1 | On $5^{th}$ night | No advice (or reminder of expected bedtime) | NA | NA |
| 2 | On upload of $5^{th}$ record | 1-3 advices (content dependent), spaced throughout the day. | Advice engine enters "precaution state" 1 night only | Advice engine enter "Sleep assessment" (env. data, sleep facts) |
| 3 | On upload of $6^{th}$ record | No Advice | NA | NA |
| 4 | On upload of $6^{th}$ record | 1-3 advices (content dependent), spaced throughout the day. | Advice engine enters "advice state" | Advice engine enter "Sleep assessment" (env. data, sleep facts) |
|   |   | Duration | 5-10 days | Indefinitely |

(c) In Advice State

| # | Use Case | Outcome | Advice Content If Issues continue | Advice Content no Issues detected |
|---|---|---|---|---|
| 1 | On upload of $1^{st}$ record | 1-3 advices (content dependant), spaced throughout the day. | Stay in "advice state"; if improvement noted but issue still present give user a reward - single nugget with compliment | Move to "probation state" |
|   |   | Duration | 5-10 days Move to "task" | 2-4 days Back to "sleep assessment" |

(d) In Task State

| # | Use Case | Outcome | Accepts | Declines |
|---|---|---|---|---|
| 1 | On upload of $1^{st}$ record | Task offer | Task request. Nugget will request an action from the user | If user declines task offer twice then go back to sleep assessment |
|   |   | Duration | 5-10 days | 2 days Back to "sleep assessment" |

Suggestions for the optimization of bedroom sleep settings or sleep habits can include one or more of the following:

(1) Immediate recommendations (i.e., first night experience) to improve the user's sleep environment, initially based on normative data and subsequently on the user's own data measurements (e.g., provided by email, in-app, on web). For example, the system checks if ambient noise is disturbing the user's sleep without the user being aware of it, checks if light levels may be affecting the user's sleep and wake-up patterns, checks ambient temperature at night etc. The system then suggests changes to the user's sleep environment, if one or more parameters of the user's environment are significantly different from statistical averaged parameters of other users or of the user's own collected data. The collected data may relate to the user's location/current weather conditions, average weather trends (i.e., baseline temperature may vary by country, area, time of year, allergy alerts). The system can also collect personal data by allowing the user to journal (input data to the system in response to a query) (e.g., ask if the user is using air conditioning, heating, humidifier, type of bedding).

(2) Generate and provide personally tailored advice based on user sleep patterns, journal entries and personal profile. The personal profile covers the users name, age, weight, gender. The system provides a personalized report and list of suggestions. Can be viewed in app or emailed.

(3) Generated and provide a risk assessment of the user's sleep pattern, and suggests if the user might need to follow-up with a sleep physician or sleep professional (e.g., "Stop-Bang" or other form of questionnaire). Risk assessment reports will be available in a PDF format that can be printed off which can be the basis of a discussion with a physician.

(4) Generate and Provide further suggestions over time to improve sleep—a combination of environment and personal routine recommendations. For example:
  (a) Prompt for checking on lighting settings, TV/gadgets, eating before going to bed (i.e., best practice).
  (b) Prompt to go to bed when a statistically determined suitable time approaches (option of bedtime alarm as a reminder).
  (c) Advise the user on what to eat and drink before bed (diet) and when the user wakes up, what to do (listen to music) and not to do (eat or watch TV) in bed and what to take to bed with the user (e.g., by email, in-app, on web).
  (d) Ask the user what settings/changes they are capable of making and remembers this so as to only recommend changes to the user that the user can implement, e.g., dimming light settings
  (e) Provide a "Willpower Index"—may warn the user that their willpower may be tested if they haven't managed to get sufficient quality or quantity of sleep.
  (f) Offer the user the opportunity to explore other products related to any problems that might help sleep better (e.g., sleep bedding, eye masks, speakers for enhanced audio experience) in-app or on web
  (g) Provide access to discussion forums to learn from sleep experts and other people's approaches—on website and via email/app.
  (h) Provide recommendations and references to interesting articles on what affects our sleep and how we can improve it—website and via email/app.

In another example use scenario, a user uses the system during one night. She wakes three times, vaguely remembers but doesn't know why. When she sees the hypnogram in the morning generated by the SmD it has annotated events with the awakenings shown. Awakenings are also shown as a single number (count) outside the hypnogram. The awakenings may be annotated by or matched with environmental factors detected by the device. Display of such annotations may be based on a comparison of a predefined threshold of a number of events detected.

| # | Use Case | Limit | Outcome |
|---|---|---|---|
| 1 | Light event | Detected level greater than (>) predefined threshold (e.g., lux) | Noted in back end service and communicated to user (such as in a message or on hypnogram) |
| 2 | Sound event | Detected level greater than (>) predefined threshold (e.g., decibels dB) | Noted in back end service and communicated to user (such as in a message or on hypnogram) |
| 3 | Temperature event | Detected level greater than (>) predefined threshold (e.g., Degrees Celcius) | Noted in back end service and communicated to user (such as in a message or on hypnogram) |
| 4 | Number of events greater than (>) predefined threshold (e.g., 15 events noted in a night) | 5 for light 5 for sound 5 for temp | Display all 15 on hypnogram. |
| 5 | Number of events less than (<) a predefined threshold (e.g., 15 events noted in a night). | 5 for light | Display none on hypnogram. |

In some cases, the system may optionally aggregate data from other sources, such as environmental data (e.g., allergy alert, humidity, air quality and related parameters). These data can be obtained from physical wired or wireless sensors, or via 'online' services such as local, regional and trending sources of weather, air pollution, and allergy (e.g., pollen) conditions data. An example of how 'environmental monitoring' information is utilized by the system is as follows.

(a) Weather forecast (and historical) data—meta environment: Short and/or long term weather data can be obtained from a variety of online sources. Cold weather can lead to significant bronchoconstriction, e.g., via facial cooling. Therefore, the algorithm analyses current temperature, predicted temperatures, and historical data to recommend suitable clothing and risk levels for the user. Local pollution levels (airborne allergens) are recorded by the algorithm; these can be related to asthma severity for example. Advice provided on internal (bedroom) temperature may be further customised if external weather reports suggest that heat wave (or very cold spell) is occurring, i.e., the system may adjust the settings to avoid providing potentially spurious advice.

(b) Allergy alerts (e.g., related to pollen count) can be communicated to the user based on forecasted and seasonal values.

Further User Scenario (Jet Lag Advice)

As previously mentioned, the system may generate location based advice, such as jet lag advice. In such a scenario, the SmD may automatically detect a possible "jetlag" event based on one or more of (a) the user's smart device timezone setting (usually auto updated), (b) large distance change in location based on location aware data (GPS or network assisted), (c) use of smart device at an unusual time of the day. The advice engine may evaluate a jetlag process to proactively assist if the user indicates that they are planning to travel.

In this process, the system may provide advice to suggest exposure to daylight at varying times of the day, moving towards the target timezone from the current timezone (i.e., by increasing exposure to daylight/white light earlier, and restricting closer to the target timezone bedtime). By reference to the typical sleeping pattern of the user based on their detected sleep cycles, the system may even suggest changes over several days (e.g., up to 2 weeks) before travel. This change can continue once the user has reached their destination, in order to move their sleep to the new time zone. The system can also provide advice when the user returns from travel.

When travelling (or just after arriving in the new time zone), the system can also provide advice concerning suggested diet changes, exercise, and light exposure in order to allow the user to adapt to the new time zone. For example, it is known that if the person is tired at an unusual time, they may be more likely to snack on "junk" foods, and the system can proactively suggest alternatives (e.g., eat fruit, drink water, etc.) at their "high risk" time periods. It can also suggest modulation to the use of caffeine and alcohol (if applicable). Using location data, advice can be linked to actual sunrise time at the user location, check if the user is travelling and offer appropriate advice to manage jetlag or their new room environment.

Additionally, in some cases the SmD may even retrieve and display different background images depending on the time of day, such as simulating a sunrise, sunset, day, night with different colour schemes, such as to give the user a simulation of the new time zone. The system may also adjust the display of previous sleep recordings to denote a period of travel.

Software—Example Data Storage Model

Figure 46:
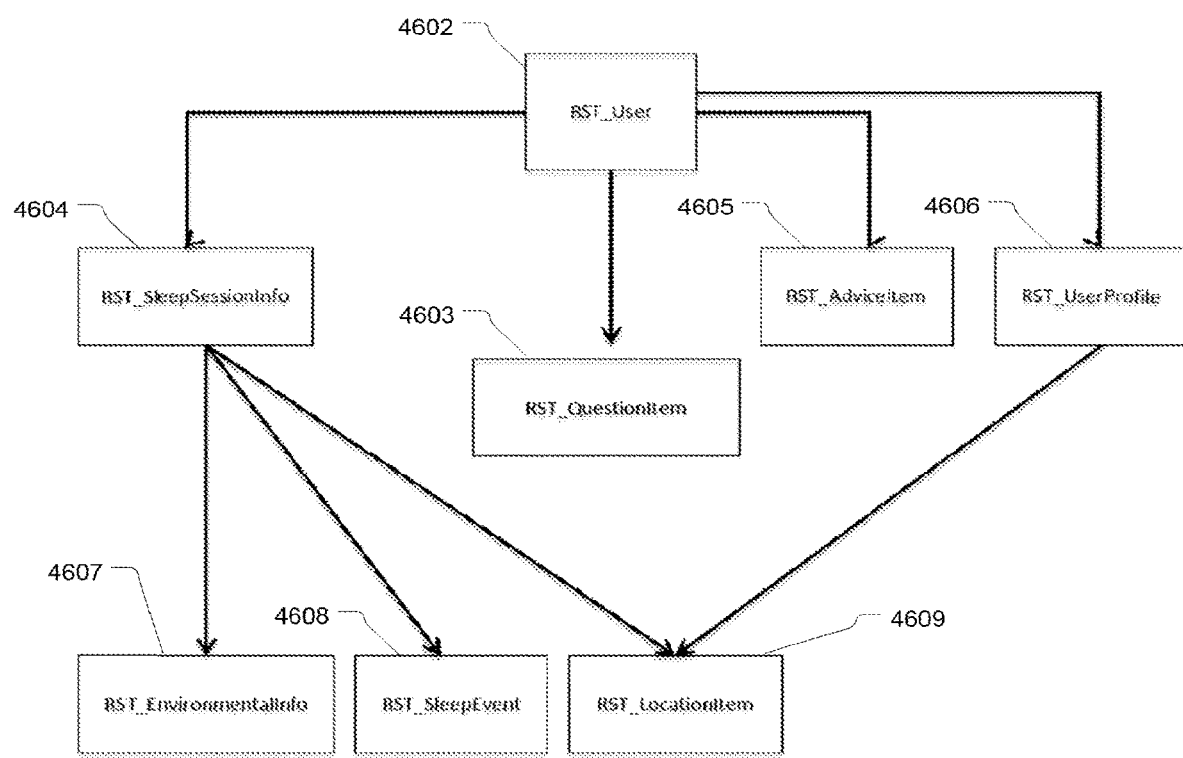
FIG. 46 illustrates example data organization suitable for implementation in some embodiments of the present technology.

As previously mentioned, the system stores data for sleep analysis and management. Such data may be included in one or more databases, such as a database accessible to the SmD and/or server(s) 3004 of the cloud system. FIG. 46 illustrates an example data storage model for some of the data of the system. For example, the data may include user information 4602, such as a user identification, name, address, etc. This may serve as an association for sleep session information 4604 (e.g., sleep patterns from one or more nights, hypnograms, etc.) of the user, questionnaire responses 4603 of the user, and advice items for the user 4605 and the user's profile 4606 (e.g., age, sex, etc.) The database may also include recorded environmental information 4607, sleep event information 4608 and sleep location information 4609 in association with sleep session information. The location information 4609 may also be associated with the user profile information. Other data model and organization may also be implemented.

Software—Example Embodiment—Mind Clear

Figure 47:
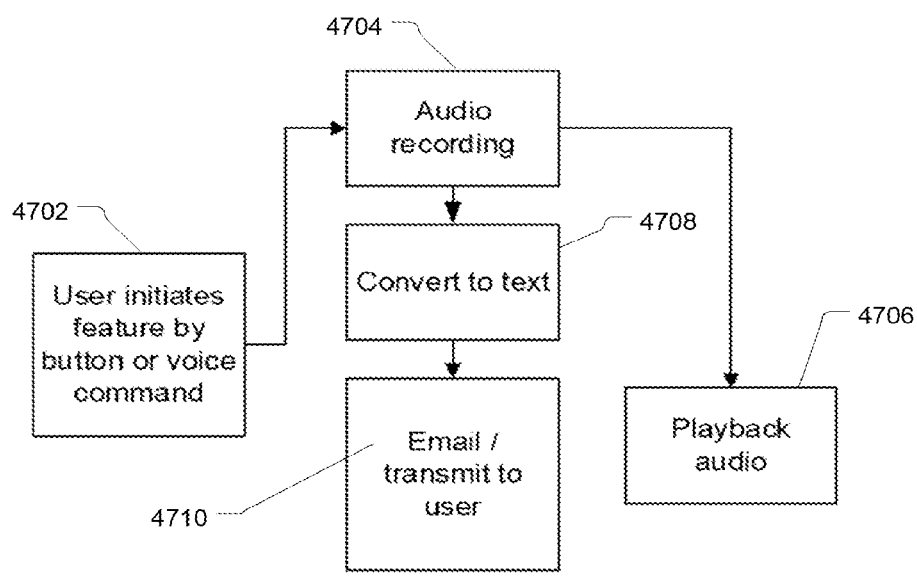
FIG. 47 illustrates a "Clear up your Mind" recording process implemented to promote sleep.

As previously mentioned, the system may implement a mind clear process such as with a processor of the SmD. FIG. 47 illustrates an example of such a process. Generally, this 'Mind Clear' process can assist the user in achieving and maintaining a state of relaxation and a peace of mind so as to assist with falling asleep.

The process permits the user to dictate (e.g., to a digital recorder), write down, or otherwise record, any thought or idea that the user has developed when resting. This helps to clear the user's mind of thoughts that otherwise might keep the user awake. In the morning the user can access their records and access the recorded thought or idea. Alternatively, the records may be sent to the user's email or telephone message box.

The recording process can be implemented so as to minimise any disruptions to the user's resting routine. For example, the use of voice recording enables the user to avoid all the disruptions associated with looking for light switches in the dark, turning a light on, looking for a pen or an access to the user's computer. The system minimises the disruption and the visual disturbance introduced by a bright light and can greatly assist the user's return to sleep after recording. Adding to this, the mind clear function may be voice activated (with the SmD) further minimalizing the sleep disruption. Whilst similar recording features can be available on some smart phones, utilising them may require handling the phone and navigating through the phone menus, again exposing the user to interruptions and light. A voice activated mind clear function can help avoid such disturbances.

Because of the reduced disruption, a user is able to record multiple "notes" to self, which the user can reply and listen to at a later time. These 'memos' can be accessed at any time. The system may also convert voice notes to text using voice recognition for delivery to the user by email or a text message.

A flow chart of an example process is shown in FIG. 47. The user initiates the process with the SmD at 4702 and makes the audio recording at 4704. The recording can be replayed at any time at 4706 such as with the SmD or other device of the system. Optionally, the message may be transmitted for a reply to a remote device, such as a mobile phone or an online server. Optionally, the message may be converted at 4708 into a text format such as with the SmD or a server. The text may be displayed on a screen such as the SmD. Optionally, at 4710, the message or converted message may be transmitted to a remote device, such as a mobile phone or an online server. Thus, the text memos/messages may be edited, saved or deleted by the user.

Thus, any one or more processors of the system may be configured to perform any one or more of the following for a user: input typed text or record a voice note/memo; edit a text note; delete voice memos and text notes; browse and navigate voice memos and text notes; listen to voice memos, read text and access other forms of communication at any time; share memos via email, SMS and AirDrop/Bluetooth; voice activate; convert voice to text memos.

In sum, the process may allow a user to capture any persistent thoughts if they are finding it difficult to fall asleep or if they wake up during the night. The reassurance of knowing that they have recorded or 'logged' their thoughts/worries aids in clearing their mind and helps them fall asleep.

Software—Example Embodiment—Nap Assist

As previously mentioned, the system may implement a nap assist process such as with a processor of the SmD. This process may assist with a user's day naps (here the expression "nap" is intended to include a relatively short period of day time sleep that is distinct and is usually in addition to the long period of sleep during night-time). Once a user has selected this process option (and perhaps specified it to days which suit a nap) the user's wake up from night sleep times and nap times, including going to bed for a nap and wake up from a nap time, will get logged by the system. Then by processing this wake-up and/or nap data, an optimum nap time is calculated. A morning notification generated by the processor will then be produced so that it can be facilitated into the user's routine. This is followed by another notification shortly before nap time to act as a reminder.

If the user is at home, a dedicated unit can act as a nap monitor. This is significant since the difference between a good and bad nap is all about timing. Nap duration of anywhere from 10-45 minutes is good, and of 90 minutes is very good. But waking up in-between 45 and 90 minutes will possibly wake the person in slow-wave sleep and they will feel tired upon awakening.

When the user lays down for a nap, the nap wake up alarm can be automatically set from the person's detected sleep onset, depending also of course, on the desired duration of the nap.

Such a system may implement multiple 'smart data' points:

It can predict the best time for the user to start a nap (e.g., 2:30 pm) based on the time that they awoke on that day. The nap wake-up time is determined by the data gathered by the sensor. The data is used to determine when the user has actually fallen asleep during their nap so as to 'start the clock' and determine the optimal time to wake. The system advises of an optimal time for napping by selecting a time (called the nap-delay), which is delayed from the user's morning/sleep wake up time. Initially, this value may be set to a fixed population average (e.g., 6 hours) based on known human circadian rhythms. The value can then be adjusted by the system based on the measured nap duration and sleep-onset latency for the nap. For example, if the system initially suggests a 6 hour offset from wake-up time, but measures that the sleep onset latency is 20 minutes, it would increase the nap-delay value to 6.5 hours. The data from the sensor is also used to, when reasonable duration of sleep (say between 30-45 mins) has been obtained, determine if the user is slipping into slow wave sleep and, if so, awake the user via the alarm so that the user can wake up refreshed from their nap.

The reminders/schedule may be determined by the processor from the data gathered via the sensor relating to the wake-up time.

Software—Example Embodiment—Setup Optimiser

In some versions, the system may implement a setup optimiser process such as with a processor of the SmD. The set up optimizer may include two parts: the setup guide and the advice feedback setup. This setup may include a graphic user interface and may include screens with static images, and may not require a flow of data. For example, the user may swipe or click through the screens. A set of images, displaying the ideal system setup may be presented, and the user may scroll through at first sign on with the system. This may optionally be accessible at other times such as from an "about" page or from within a "settings" menu.

In some versions, the system or device may detect that it is not positioned correctly such as if no motion signal is detected. This may trigger a setup up process to send a notification to the user such as by sending an advice nugget that alerts the user that the positioning of their device has been or is incorrect. The advice nugget may optionally provide a link to a video such as with content to show how to position the device correctly.

Such a nugget feedback for setup with the system may occur as follows:

(1) User sleeps and data is fed in the usual way from the Bed to SmD;

(2) The RM20 process produces "Sleep Synopsis Data" of these parameters and measures of signal quality;

(3) The Sleep Synopsis Data is uploaded to a cloud server (e.g., backend server); 1

(4) The Advice Engine analyses the result, and based on its logic, sends or does not send a push notification of an advice nugget (e.g., poor measurement signal—reposition device);

(5) The notification can be communicated via a network to the phone;

(6) The phone receives the notification which contains a unique identifier for the user and a link to the advice;

(7) The user clicks the notification, and the SmD processor is triggered to download and display the advice nugget.

In some cases, the system can implement/calculate a metric referred to as 'Signal Quality'. This may be an average (mean) version of the data signal quality that is calculated throughout the sleep session.

In an embodiment, it can take on values (also considered bins) of 1, 2, 3, 4, 5. For this particular scale, the midpoint "3" represents an ideal, with "2" and "4" being acceptable quality, while "1" and "5" indicate poor signal quality.

A value of "1" indicates that the user is too far away from the sensor to detect a good quality, consistent breathing rate—i.e., the overall signals detected are of small amplitude, and/or the detected cardiorespiratory signal(s) are of very poor quality. For example, small changes in respiratory waveform shape are very difficult to detect at "1", as the signal-to-noise ratio is very low.

At the opposite extreme, a "5" indicates that a very large (consistently) signal is detected, so much so that soft clipping is detected on the signals. This is indicative of the subject (human, animal etc.) sleeping too close to the sensor. The impact of a "5" is that subtleties of the signal may be lost due to this clipping, potentially skewing cardiorespiratory readings (e.g., clipping respiratory peaks), masking possible apnea/hypopnea behavior, and leading to excess movement being triggered. For a "1" or a "5", the user is suggested to adjust the position of the device in order to get a better quality signal.

The system also returns the percentage of the overall signal falling inside each bin—e.g., 62.7% might be in bin "3", 10.54% in bin "2", and the residue in the other three bins, leading to an overall classification of a "3". A standard deviation of the signal is returned for the overall signal quality metric.

Software—Example Embodiment—Lucid Dream Assist

In some versions, the system may implement a lucid dream assist process such as with a processor of the SmD. Webster's definition of lucidity includes the following meaning: "clearness of thought or style," and "a presumed capacity to perceive the truth directly and instantaneously." Lucidity in lucid dreaming was coined by Frederik van Eeden in 1913: referring to the perception of the truth that one is dreaming. In other words; a lucid dream refers to when someone becomes aware they are dreaming and gain some level of sovereignty over their actions in a dream. The scientific consensus on lucid dreaming is "Lucid dreaming is a rare but robust state of sleep that can be trained" (Dresler et al. 2011 p. 1; LaBerge, 1980). Snyder and Gackenbach (1988, p. 230) conclude that about 58% of the population have experienced a lucid dream once in their lifetime and 21% report them once or more per month. The first book to recognize the scientific potential of lucid dreams was Celia Green's (1968) study Lucid Dreams. The first peer-reviewed article was published by Stephen LaBerge (1980) at Stanford University, who had developed a Lucid dreaming technique as part of his doctoral dissertation. During the 1980s, further scientific evidence to confirm the existence of lucid dreaming was produced as lucid dreamers were able to demonstrate to researchers that they were consciously aware of being in a dream state by using eye movement signals (LaBerge, 1990). Dresler et al. (2011) has recently provided the first demonstration of neuro-imaging of specific dream contents using lucid dreaming. They found that if a subject is asked to clench their right or left hand within a dream, the parts of the somatosensory cortex (the part used for movement and feeling) activated.

Such a Lucid dreaming training process could be used by a user to create a course that may be presented through the SmD or the servers of the system. Such a course on Lucid dreaming can be accessed at the user's discretion. Upon initiating the training course process, the user can choice a small burst of sound or a soundscape which can act as a trigger while they are dreaming. When user then falls asleep (and also wishes to experiment with lucid dreaming that night), the device will detect at least the second round of REM or at later REM cycles (this may optionally be a setting of the training process at the user's discretion perhaps). Upon detection by the SmD of the particular REM cycles, the processor of the SmD may generate the sound or soundscape (e.g., or control playing it through a speaker) and hopefully the user will realize they are dreaming. Optionally, the processor may control activating of a small burst of light instead of, or in addition to, the sound/soundscape. The levels of sound and/or light may be a setting and may be sufficiently low in order not to wake user (e.g. <25 dB) but may be adjusted/changed by a user in settings for the process.

Further Example Advice Process—Triaging Sleep Issues

In one example, the advice engine may be configured to recognize "risky sleep" such as sleep that may be indicative of a sleep disorder and/or sleep disordered breathing (SDB) issues. Such an SDB pathway may combine information on unusual breathing and movements. Based on observed fragmented sleep and minimum deep sleep, a lifestyle questionnaire may be presented to the user (a breathing stability metric may also be included). This query connects a user to an appropriate solution logic pathway based on an automatic analysis of their setup questionnaire, advice, and sleep data into different categories such as "risky sleep" or "sleep optimiser". Additional categories may also be included.

Figure 48:
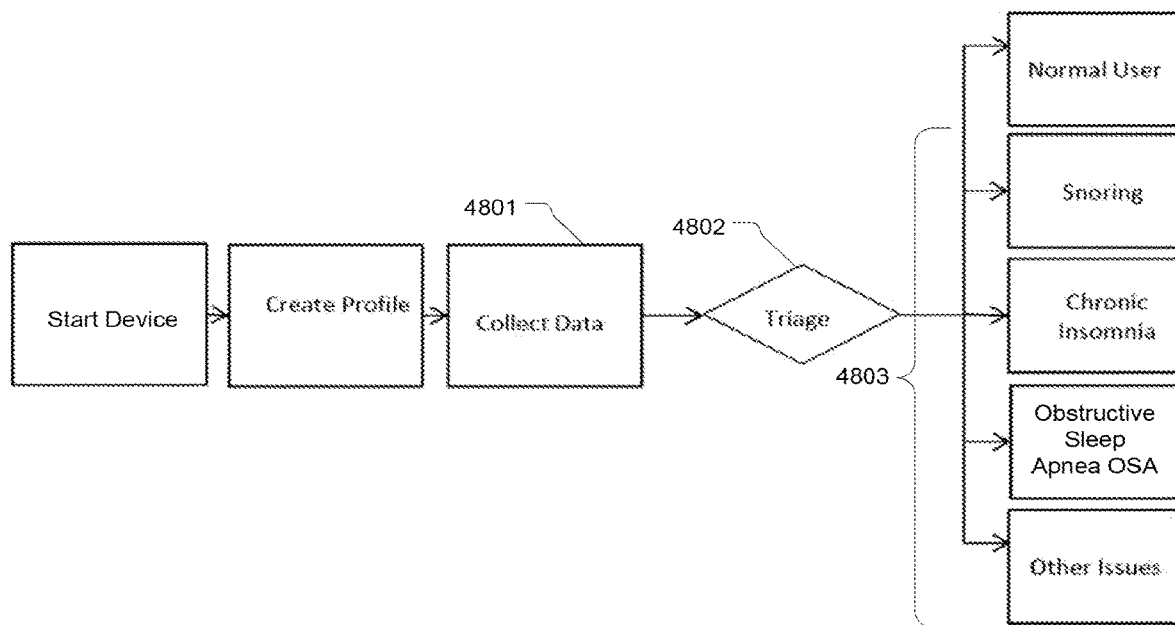
FIG. 48 shows and example triage process for analysis of data that may be implemented in some versions of the present technology.

Such a triage process 4802 may be considered with reference to the flow chart of FIG. 48. This illustrates an overall flow of 'sleep issue' identification. By combining the data gathered at process 4801 by the device/unit and responses to queries, a triage process 4802 may be initiated by a server, such as a backend system server. The triage process may decide between a risky sleep and normal sleep conditions. As a result of such flow processing logic, the triage engine may direct the advice engine to a normal user process and may as a consequence lead to a generation of the advice previously described for sleep optimization. However, the triage process may also lead to various risky sleep advice processes 4803 for generating advice for risky sleep users where detected data suggesting risky sleep. Such a detection may result in advice or reports concerning the 'risky sleep' being potentially generated. Some such risky sleep characterizations may include, for example, snoring, Chronic Insomnia, and other issues.

In one example, an optional triage process of the advice engine can be initiated, such as by a Backend server or other cloud server, and can involve sending a notification (to the app of the SmD or an email) with a link to the user to download a report. The user may then be directed to request a Report for Discussion with their Physician (doctor's report) document (printable web page and/or PDF). The user can then view their data in a visually appealing and informative manner on the website. The system may automatically select such a report to send to the user from this notification based on logic applied to their sleep related data. The triage process of one or more processors may detect, for example, either "normal sleep" or "risky sleep" and generate output for user with the classification. The methodology of this process, which may also be referred to as a "risky sleep engine," may include analysis of input from a set-up profile concerning user responses to risky sleep related questions of a questionnaire. The processing of the triage process may also evaluate any one or more of the following risky sleep indicators: Sleep duration (time asleep); Time in bed; Difference in time to bed; Deep sleep percentage and/or minutes; REM sleep percentage and/or minutes; Sleep efficiency; sleep disruptions, etc. The result of the analysis may be the output report and/or a communications link, such as via a website, to a sleep clinic or specialist, which may depend on the detected sleep issue.

Figure 49:
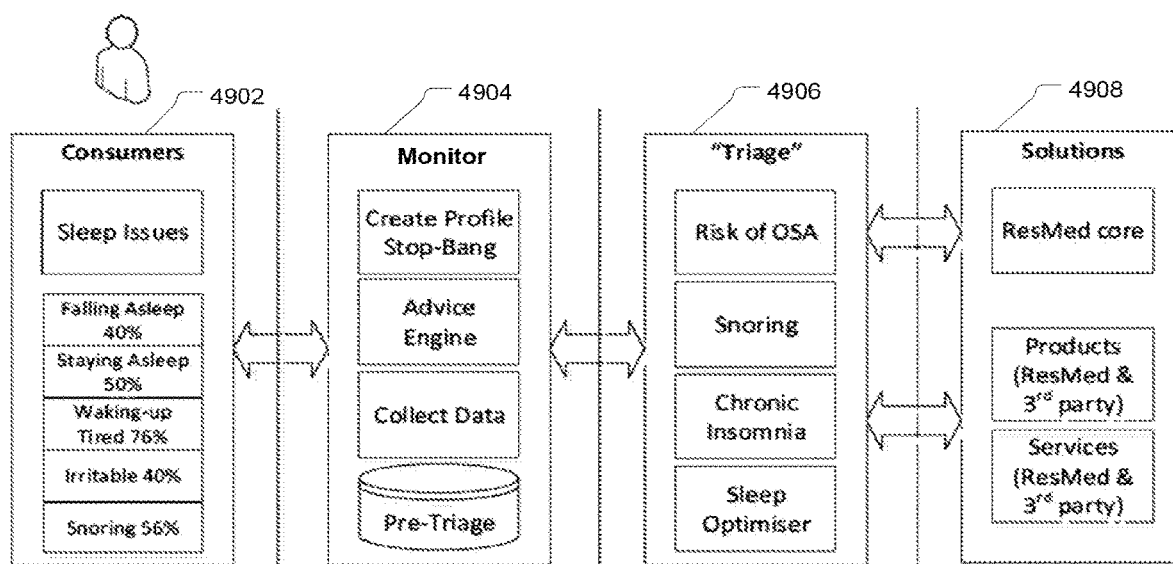
FIG. 49 illustrates an example process for data analysis in the detection of risky sleep that may be indicative of a sleep problem.

FIG. 49 illustrates a flow of information that may concern triaging risky sleep. Consumers 4902 using the present technology (e.g., sleep detection monitor 4904) may experience sleep issues such as falling asleep, staying asleep, waking up tired, irritability, snoring, etc. This may be detected with percentage threshold, e.g., falling asleep 40% of the time. Other percentages than those listed may be utilized as suitable. Such information may be input and/or detected (e.g., sleep patterns) by the BeD and SmD system (sleep detection monitor 4904). Such input may optionally include responses to an electronic "Stop-bang" or other form of questionnaire, survey or other screening information gathering tool for sleep apnea diagnosis. This monitor stage may be considered a 'Pre Triage' phase. The users that have been identified as to have 'risky sleep' may then be informed, and there may be a transition from pretriage to triage stage 4906 where further processing may occur such as further queries and information (e.g., directing risky users to further informational solutions 4908 such as those at internet or web sites so as to guide the user to solutions for the user). This may optionally include facilitating the user in contacting a clinic or specialist.

Figure 50:
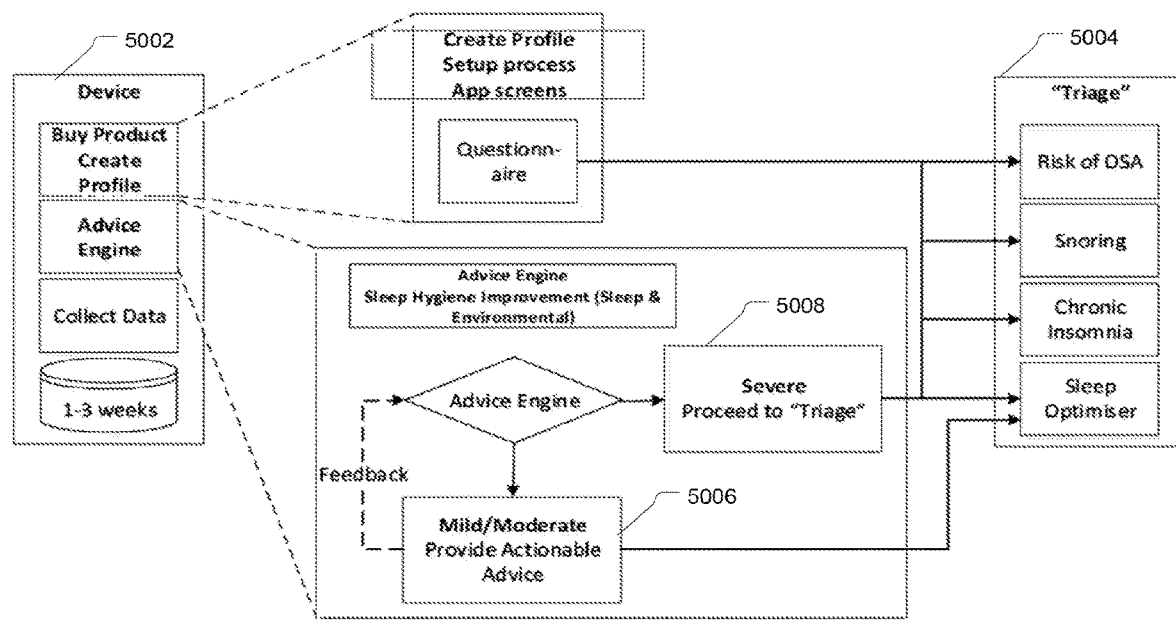
FIG. 50 illustrates a process flow that may be implemented in some version of the present technology, such as by a backend server, to implment a pre-triage advice engine processing.

Such a process may be further considered in reference to FIG. 50. Here a monitoring device 5002 (e.g., SmD and/or BeD or other server components) may include or be part of an advice engine as previously described. The advice engine based on the analysis of collected data, as described in more detail herein, may conduct a pre-triage process to categorize sleep patterns, trends and/or user input of the user as either "severe" or "mild/moderate" sleep issues. Mild or moderate classification advice process 5006 may trigger processing operations that generate advice directed to sleep optimization as previously discussed. However, a severe classification advice process 5008 may trigger processing operations, such as with triage process server 5004 that generate advice directed to sleep optimization and/or further advice processes directed to obtaining diagnosis of sleep disordered breathing or other sleep related health condition (e.g., risky sleep) such as obstructive sleep apnea processing, snoring processing, Chronic insomnia processing, etc.

Figure 51:
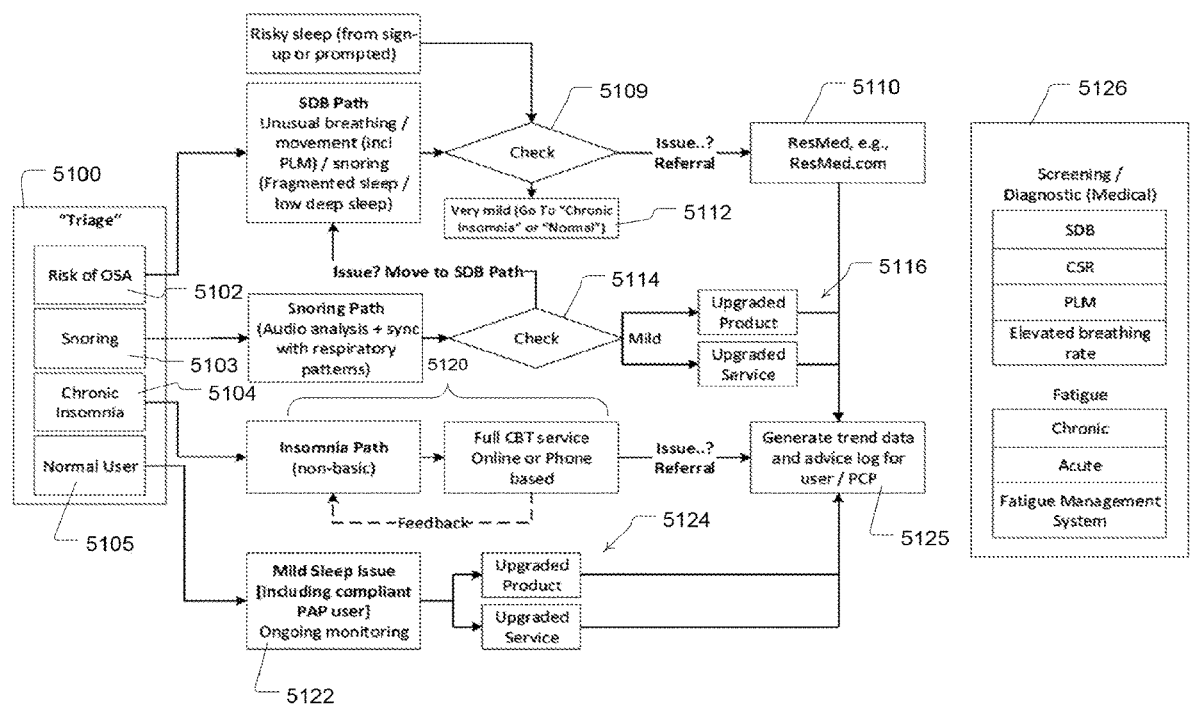
FIG. 51 illustrates a process in the detection of some example 'sleep issues' that may be implemented by a risky sleep determination engine.

FIG. 51 illustrates further operations associated with an example advice triaging process such when an OSA/SDB process 5102, snoring process 5103, chronic insomnia process 5104 and normal user process 5105 are triggered. This diagram represents some of the 'sleep issues' that may be detected by the Risky Sleep engine. Once the triage process 5100 is initiated different pathways are implemented based on the type of 'risky sleep' identified. This facilitates the user in receiving the appropriate advice and support required if a sleep issue is detected.

For example, in the risk of OSA process 5102 issues concerning unusual breathing, movement (e.g., including period leg movement), snoring, fragmented sleep and/or low deep sleep are evaluated or checked at 5109. If a significant issue relating to OSA is found, at referral process 5110 a referral notification such as to promote contact with a SDB sleep specialist. If not significant, only a mild OSA issue is detected then a different evaluation process may be considered such as by redirecting the analysis at 5112 to a chronic insomnia process 5104 or normal user process 5105.

In the snoring process 5103, audio analysis (e.g., recorded snoring audio) data and its synchronization with respiratory patterns and/or sleep disturbances may be checked at 5114. If mild snoring issues are confirmed at 5116 advice for snoring related services or products may be triggered.

In the Chronic Insomnia process 5104, sleep patterns may be assessed along with other query-based response data such as from a triggered cognitive behavioural treatment (CBT) query (e.g., electronic, online, or phone based) at 5120. If an insomnia issue is detected, an advice referral message to a sleep insomnia specialist may be generated.

In the normal user process 5105, advice as previously described for sleep optimization may be provided. Such normal users may optionally include users being treated for sleep apnea with, for example, a positive airway pressure PAP treatment device or CPAP device. At 5122, such a treatment device user may be found to have a mild sleep issue such as from the detection processes previously describe (e.g., high disturbance count). In such a case, at 5124 further devices and/or services may be recommended in a generated advice message so that the user may obtain help to assess whether a more suitable treatment device may be obtained to better promote sleep.

Outputs from the various data pathways may then be recorded for trend analysis in trend update process at 5125. As illustrated at 5126, input for the diagnostic screenings/evaluations of any of the triage processes may include information concerning identified or detected sleep disordered breathing SDB events, Chenye Stokes respiration (CSR) events, periodic leg movement events, elevated breathing rate events. It may further include identified fatigue, such as chronic or acute fatigue such as identified by a fatigue management system.

Example "Risky Sleep Engine" processing:

An example processing methodology for a risky sleep engine may now be considered.

Figure 53:
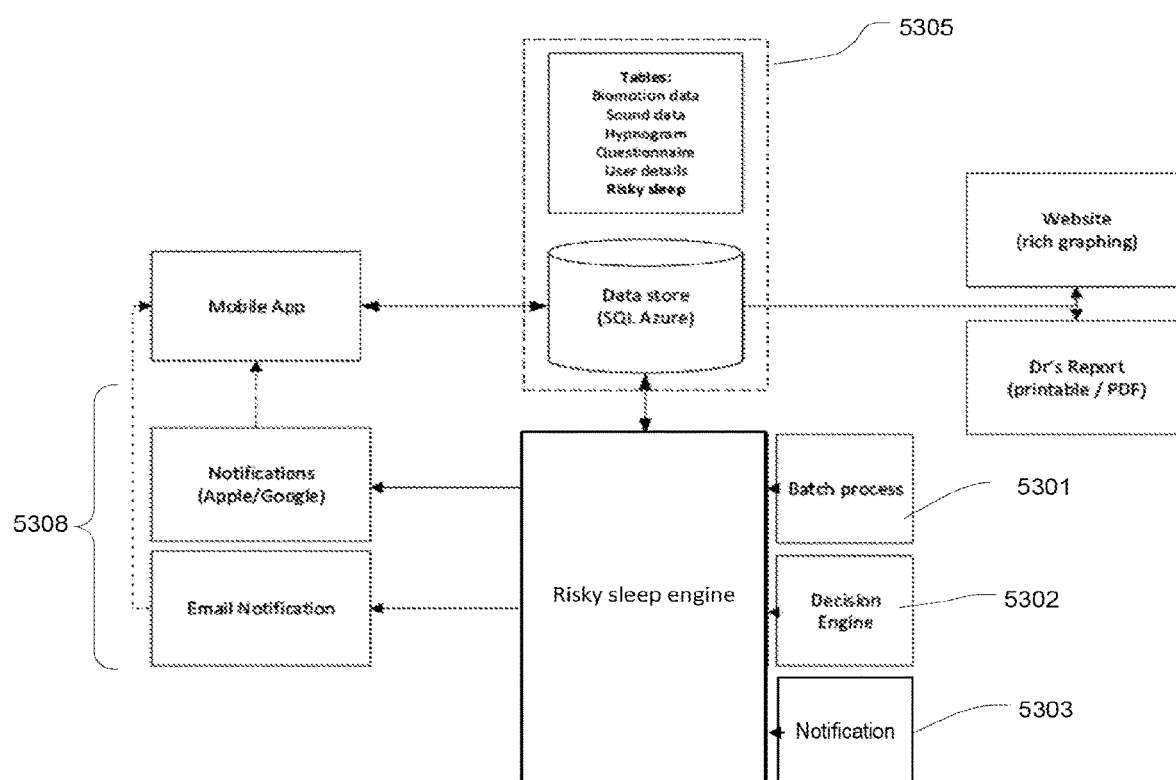
FIG. 53 is a block diagram for an example oganization of processes involved in risky sleep detection with a risky sleep engine.
Figure 54C:
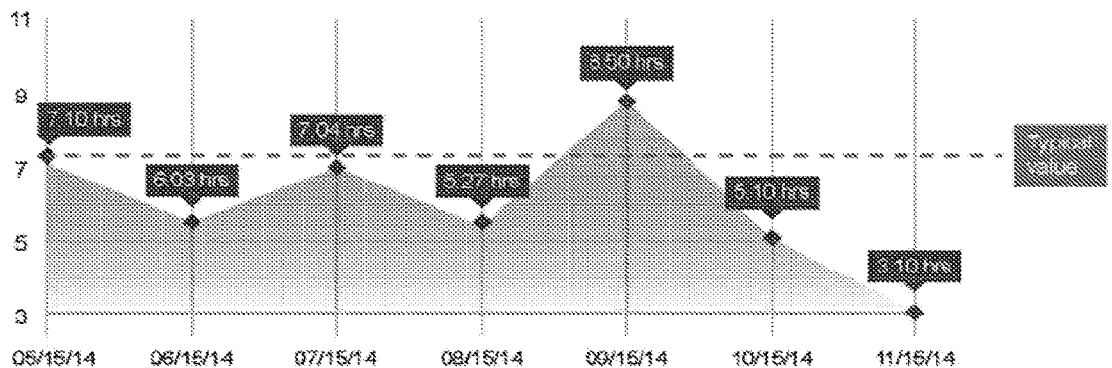
Figure 54C:
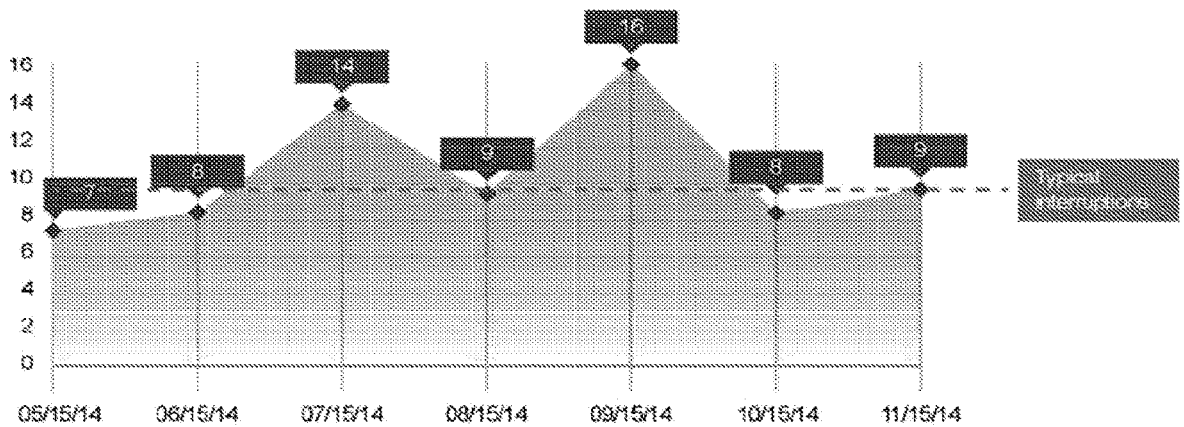
Figure 54D:
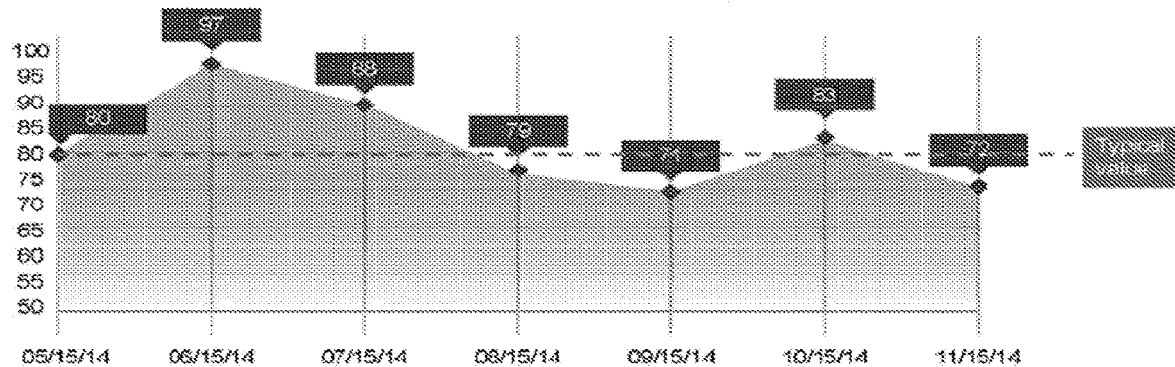

In one example illustrated in the example of FIG. 53, a risky sleep engine 5300 system capable of the risky sleep assessment methodology with one or more processors may include a batch process component 5301, a decision component 5302 and a notification component 5303. The batch process component may perform any of the following steps:
  (1) Scheduled task executes;
  (2) Check progress of last related task;
  (3) Access data from database 5305 (e.g., biomotion data, environmental data, etc.)
  (4) Begin data processing;
  (5) Add results to database (processed biomotion data, processed environmental data)
  (6) Call "Decision Engine"
  (7) Call "Notification"
  (8) Update progress record
  (9) Complete;

The decision engine process component 5302 may perform any of the following steps:
  (1) access data of database (e.g., hypnogram(s); questionnaire(s) user parameters (demographics); processed bio-motion data; processed environmental data; etc.);
  (2) apply probabilistic model to estimate "risky sleep" probability with accessed data; and
  (3) update database with results.

The notification process component 5303 may involve any of the following steps:
  (1) Check user notification flags in database "Risky sleep table";
  (2) Call notification service (e.g., Apple/Google notification/push notification to phone (to identify that a new sleep report is available and/or send the report), etc.); and
  (3) Call electronic message service 5308 (e.g., email via send grid service and/or push notification email to user (to identify that a new sleep report is available or send the report)).

Figure 52:
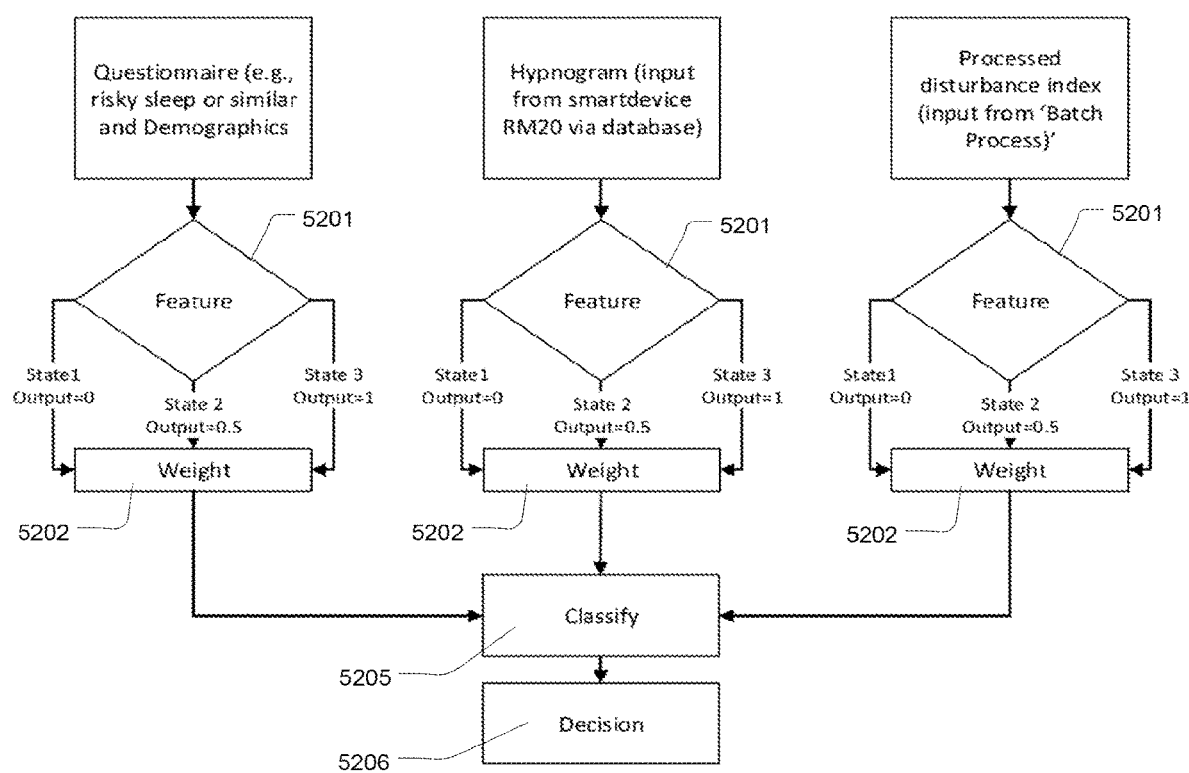
FIG. 52 illustrates a classification process in of risky sleep detection based on a number of data inputs.

An example estimate model of risky sleep for the decision engine process component may be considered with reference to the following table and the flow chart illustrated in FIG. 52. Generally, classification of risky sleep may be based on a number of data inputs, and may include questionnaires such as pre-sleep and user profiles, sleep score results and data input from the batch process. The decision engine analyses the stored user data, applies probabilistic model and estimates the probability of risky sleep. It then updates the user's database. Flags set in the database—which could be formed in a Risky Sleep Table—can initiate different methods to alert the user. For example, they may initiate a push notification or email communication.

The risky sleep table below illustrates example sleep information (parameters or features) that may be applied to detect a risky sleep. The parameters or features 5201 can be tailored to the population, and to normative values for the users (both by region, and/or gender, and/or age). Questionnaire data, demographics and other elements have not been included in this example but may also be included in the analysis. For each feature, two "bands" are implemented as low risk (a value of "0") and moderate risk (a value of "0.5"). Areas outside of these bands are defined as high risk (a value of "1"). Additionally, a weighting factor (a multiplier) by a weighting component 5202 may be applied (e.g., the weighting for "Deep Sleep Minutes" is "3" or ×3). As shown in FIG. 52, these, and additional, weighed features may then be classified (e.g., by a suitable probability classifier 5205) so that a decision as to a particular risky sleep category may be made by a decision process 5206. Collectively, the values may then serve as a trigger for selecting risky sleep advice described in more detail herein.

| Risky Sleep Table | | | | | | | |
|---|---|---|---|---|---|---|---|
| Feature/Parameter | a | b | c | d | e | f | |
| Questionnaire (for n = 8) | 0 | 3 | 3 | 5 | 8 | 8 | 12 |
| Delta to sunset (hrs) | 0 | 3 | 3 | 4 | 4 | 12+ | 0.5 |
| Difference in time to bed (hrs) | −1.5 | 1.5 | 1.5 / −1.5 | 2.0 / −2.0 | 2.0 / −2.0 | 12 / −12 | 2 |
| REM sleep % | 15 | 25 | 12 / 25 | 15 / 28 | 0 / 28 | 12 / 100 | 1 |
| Deep sleep % | 15 | 25 | 10 / 25 | 15 / 30 | 0 / 30 | 10 / 100 | 3 |
| REM sleep (mins) | 70 | 110 | 50 / 110 | 70 / 130 | 0 / 130 | 50 / 600+ | 1 |
| Deep sleep (mins) | 70 | 110 | 50 / 110 | 70 / 130 | 0 / 130 | 50 / 600+ | 3 |
| Time in bed (hrs) | 7 | 12 | 6 / 12 | 7 / 13 | 0 / 13 | 7 / 24+ | 1 |
| Time asleep (hrs) | 6 | 9 | 5.5 / 9 | 6 / 9.5 | 0 / 9.5 | 5.5 / 24+ | 2 |
| Sleep efficiency % | 80 | 100 | 75 | 80 | 0 | 75 | 3 |
| Disruptions # | 0 | 10 | 10 | 13 | 13 | 100+ | 6 |
| Processed disruption index | 0 | 14 | 14 | 17 | 17 | 180 | 24 |
| Processed breathing rate | 0 | 19 | 19 | 23 | 23 | 60 | 3 |

This disclosure details various methodologies any of which can be implemented by a system of one or more processors. It will be understood that such a processing apparatus may include integrated chips, a memory and/or other control instruction, data or information storage medium for carrying out such methodologies. For example, programmed instructions encompassing the methodologies may be coded on integrated chips in the memory of the device or apparatus to form an application specific integrated chip (ASIC). Such instructions may also or alternatively be loaded as software or firmware using an appropriate data storage medium.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology.

The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

Further examples of the technology may be considered by the following descriptive paragraphs and following claims.

Embodiment 1

A method for reducing a user's breathing rate in order to induce sleep, the method comprising:
providing at least one sensory input to the user to reduce the user's breathing rate, the at least one sensory input being characterised by at least one parameter;
monitoring the user's breathing rate to provide feedback for the sensory input; and
modifying a value of at least one of the at least one parameter based on the feedback.

Embodiment 2

The method of Embodiment 1 wherein an initial value of the at least one parameter of the sensory input is calculated on a basis of monitoring the user's breathing rate at a start of a current sleep session and/or of one or more previous sleep sessions.

Embodiment 3

The method of any one of Embodiments 1 to 2, wherein the sensory input comprises at least one of an audio signal and a video signal.

Embodiment 4

The method of Embodiment 3, wherein the sensory input comprises at least one of the following: a light of controlled colour and/or intensity, and/or a sound characterised by at least one of a controlled audio frequency, volume and rhythm, wherein a modification includes at least one of changing the colour and/or intensity of the light and/or the audio frequency, volume and/or the rhythm of the sound.

Embodiment 5

The method of any one of Embodiments 1 to 4, the method further comprising modifying the at least one parameter periodically or in a continuous manner.

Embodiment 6

The method of Embodiment 5, wherein the at least one parameter is modified at a predetermined time interval.

Embodiment 7

The method of any one of Embodiments 1 to 6 wherein the modifying the at least one parameter is paused or reset, if feedback indicates that a user's breathing rate does not decrease or that it decreases too slowly with regards to change in the parameter of the sensory input.

Embodiment 8

The method of any one of Embodiments 1 to 7, wherein the modifying the at least one parameter is paused or reset, if feedback indicates that a difference between a user's breathing rate and a rate associated with the at least one parameter stops to decrease or starts to increase.

Embodiment 9

The method of any one of Embodiments 1 to 8, wherein the monitoring is conducted by way of at least one RF sensor.

Embodiment 10

The method of any one of Embodiments 5 to 9, wherein the providing of the least one sensory input is terminated when the monitoring indicates that a predetermined breathing rate has been reached and/or maintained for a predetermined time.

Embodiment 11

The method of any one of Embodiments 1 to 10, the method further comprising monitoring in a non-contact manner at least one physiological and/or environmental parameter associated with the user, in addition to user's breathing rate.

Embodiment 12

The method of any one of Embodiments 1 to 11, wherein implementation of the method is initiated or terminated, depending on the presence/absence status of the user.

Embodiment 13

The method of any one of Embodiments 1 to 12, wherein implementation of the method is initiated or terminated, depending on a sleep status associated with the user.

Embodiment 14

The method of any one of Embodiments 1 to 13, wherein implementation of the method is started and/or terminated at a predetermined time after the start of the sleep session.

Embodiment 15

The method of any one of Embodiments 1 to 14, wherein the method further comprises an alarm function prompting the user to initiate the method at a predetermined time.

Embodiment 16

The method of Embodiment 15, further comprising measuring at least one subjective and/or at least one objective measure associated with the user to trigger the alarm function.

Embodiment 17

The method of Embodiment 16, wherein the at least one subjective measure includes one of sleep latency and sleep quality, and the at least one objective measure includes one of perceived stress level and perceived time taken to fall asleep.

Embodiment 18

A method for user data management comprising;
acquiring data associated with at least one respiratory and/or sleep parameter related to a user;
processing the acquired data;
obtaining, on a basis of the processing, an indication of a possible abnormal condition of the user; and
notifying the user of the possible abnormal condition.

Embodiment 19

The method of Embodiment 18, further comprising generating, based on at least some of the acquired and/or processed data, a report to the user in a form suitable for forwarding to a third party for diagnostic.

Embodiment 20

The method of Embodiment 18 or Embodiment 19, further comprising providing the user with a report of the possible abnormal condition of the user in a format suitable for printing or for electronic forwarding to a third party.

Embodiment 21

The method of any one of Embodiments 18 to 20, further comprising providing the user with at least one of the following:
information relevant to the possible abnormal condition;
websites relevant to the abnormal condition; and
contact information of one or more parties that may be able to assist the user with evaluating and/or treating the possible abnormal condition.

Embodiment 22

The method of any one of Embodiments 18 to 21, wherein the abnormal condition is one of a sleep disorder, cardio/respiratory disorder and/or snoring.

Embodiment 23

The method of any one of Embodiments 18 to 22, wherein the acquired data is transmitted to and processed at a data processing centre remote from the user.

Embodiment 24

The method of any one of Embodiments 18 to 23, wherein the acquired data also comprises at least one parameter associated with the user's environment.

Embodiment 25

A method for estimating sleep latency of a user, the method comprising:
measuring at least one parameter associated with a user's breathing and/or movement;
detecting a change from wakefulness to "stage 1" light sleep, based on analysis of the at least one measured parameter; and
estimating the sleep latency of the user based on a time that it takes for the change from wakefulness to "stage 1" light sleep to take place.

Embodiment 26

The method of Embodiment 25, wherein at least one parameter relates to one of breathing frequency, amplitude and burstiness.

Embodiment 27

The method of Embodiment 25 or Embodiment 26, further comprising analyzing a combined nature of movement pattern and breathing rate value and waveform shape to classify sleep onset.

Embodiment 28

A method for managing user's naps, the method comprising:
recording data associated with at least one base parameter associated with a user's sleep history; and
calculating, on a basis of the recorded data, at least one optimised parameter associated with the user's future naps.

Embodiment 29

The method of Embodiment 28, wherein at least one of the at least one base parameter or of the at least one optimized parameter is associated with one of: the time when the user wakes up from night sleep, the time when the user goes to bed for a nap, the time when the user wakes up from a nap, and the nap duration.

Embodiment 30

The method of Embodiment 28 or Embodiment 29, the method further comprising setting an automatic alarm and/or recommending the optimized parameter to the user for the purposes of one or more future naps.

Embodiment 31

The method of any one of Embodiments 28 to Embodiment 30, the method further comprising reminding the user of the optimized time when the user should go to bed for a nap, either a predetermined time before the optimized nap time or on the basis of a time determined by way of processing user historical sleep data.

Embodiment 32

The method of any one of Embodiments 28 to 31, wherein the data associated with at least one base parameter is recorded by way of a contactless sensor.

Embodiment 33

A method for controlling the operation of a contactless sensor for measuring at least one user physiological parameter and/or movement parameter, the method comprising;
measuring, with the sensor, at least one parameter associated with a presence/absence status and/or a sleep status of the user;
processing the at least one measured parameter to determine the presence/absence status and/or the sleep status of the user; and
initiating at least one of starting and terminating the operation of the sensor, depending on the determined presence/absence and/or a sleep status.

Embodiment 34

The method of Embodiment 33, wherein a probability of the user's absence/presence is determined based on the detection of characteristic breathing signals and/or gross large scale movements.

Embodiment 35

The method of Embodiment 33 or Embodiment 34, wherein a hysteresis is used to reject an ocurrence where the user enters a room for a brief period and then leaves again.

Embodiment 36

The method of any one of Embodiments 33 to 35, further comprising using a light sensor to detect if the room light is switched on or off, and comparing to previously recorded user data to assist in determining the presence/absence status and/or the sleep status of the user.

Embodiment 37

The method of any one of Embodiments 33 to 36, the method further comprising calculating a 'target time' related to the user going to bed and/or waking up, to reduce a search window for an auto-start and/or auto-stop function.

Embodiment 38

The method of any one of Embodiments 33 to 38, wherein the sleep status is associated with a current sleep stage of the user.

Embodiment 39

The method of Embodiment 38 wherein the sleep stage of the user is one of: light sleep, deep sleep and REM sleep.

Embodiment 40

An apparatus for reducing a user's breathing rate in order to induce sleep, the apparatus comprising;
an output device for providing at least one sensory input to the user, the at least one sensory input being characterised by at least one parameter;
a sensor for detecting the user's breathing rate, and a controller to receive data from the sensor, to process the sensor data and to modify, based on the processed sensor data, at least one of the at least one parameter to reduce the user's breathing rate.

Embodiment 41

An apparatus for user data management comprising;
at least one sensor for acquiring data associated with at least one respiratory and/or sleep parameter related to the user;
a processor for processing the acquired data and obtaining, on a basis of the processing, an indication of a possible abnormal condition of the user; and an interface for notifying the user of the possible abnormal condition.

Embodiment 42

The apparatus of Embodiment 41 wherein the processor is located on a remote server.

Embodiment 43

The apparatus of Embodiment 42, wherein the processor is arranged to generate, based on at least some of the acquired and/or processed data, a report to the user in a form suitable for forwarding to a third party for diagnostic.

Embodiment 44

An apparatus for estimating sleep latency of a user, the apparatus comprising:
at least one sensor for measuring at least one parameter associated with a user's breathing and/or movement; and
a processor for:
processing the measured data for detecting a change from wakefulness to "stage 1" light sleep; and
estimating sleep latency of the user based on the time that it takes for the change from wakefulness to "stage 1" light sleep to take place.

Embodiment 45

The apparatus of Embodiment 44, wherein the at least one parameter relates to one of breathing frequency, amplitude and burstiness.

Embodiment 46

An apparatus for managing user's naps, the apparatus comprising:
a sensor for detecting data associated with at least one base parameter associated with the user's sleep history;
memory for saving the detected data; and
a processor for calculating, on the basis of the saved data, at least one optimised parameter associated with the user's future naps.

Embodiment 47

An apparatus for measuring at least one user physiological parameter and/or movement parameter, the apparatus comprising;
a sensor for measuring at least one parameter associated with a presence/absence status and/or a sleep status of the user; and
a processor for:
processing the at least one measured parameter to determine the presence/absence status and/or the sleep status of the user; and
initiating at least one of starting and terminating operation of the sensor, depending on the determined presence/absence and/or a sleep status.

Embodiment 48

The apparatus of Embodiment 47, wherein the processor determines a probability of the user's absence/presence based on the detection of characteristic breathing signals and/or gross large scale movements.

Embodiment 49

An apparatus arranged to detect at least one physiological and/or environmental parameter related to a user, the apparatus comprising;
a sensor for detecting data related to the at least one physiological and/or environmental parameter,
a data storage device configured to record the detected data; and
a transmitter for transmitting data collected from a user to a remote data monitoring/processing centre, and for receiving instructions from the remote data monitoring/processing centre to the monitoring system and/or the user.

Embodiment 50

An method for detecting at least one physiological and/or environmental parameter related to a user, the method comprising:
detecting the at least one physiological and/or environmental parameter;
recording data of the detected at least one physiological and/or environmental parameter; and
with a transmitter, transmitting data collected from a user to a remote data monitoring/processing centre, and for receiving instructions from the remote data monitoring/processing centre to the monitoring system and/or the user.

Embodiment 51

A system to promote sleep comprising:
one or more processors configured to:
access measured sleep data representing user movement detected by a movement sensor, and sleep factors determined with features derived from the measured data;
access measured environmental data representing ambient sleep conditions;
access input user lifestyle data on a sleep session-by-sleep session basis; and
evaluate the sleep factors to detect a sleep issue;
evaluate the measured environmental data and the input user lifestyle data to select one as a most likely cause of the detected sleep issue; and
generate one or more advice messages associated with the selected one, the advice messages including advice content for promoting sleep.

Embodiment 52

The system of Embodiment 51 wherein the generated one or more advice messages comprise a series of advice messages over time consecutively generated upon continued detection of the sleep issue.

Embodiment 53

The system of any one of Embodiments 51 to 52 wherein the measured environmental data comprises one or more of detected light, detected sound and detected temperature.

Embodiment 54

The system of any one of Embodiments 51 to 53 wherein the sleep factors comprise one or more of sleep latency, REM sleep time, deep sleep time and number of sleep interruptions.

Embodiment 55

The system of any one of Embodiments 51 to 54 wherein a detected sleep issue comprises any one or more of a REM time too short condition, a REM time too long condition and a REM time fragmented condition.

Embodiment 56

The system of any one of Embodiments 51 to 55 wherein a detected sleep issue comprises any one or more of a deep sleep time too short condition, a deep sleep time too long condition and deep sleep time fragmented condition.

Embodiment 57

The system of any one of Embodiments 51 to 56 wherein a detected sleep issue is that the user's sleep comprises too many interruptions.

Embodiment 58

The system of any one of Embodiments 51 to 57 wherein the evaluation of the measured environmental data and the input user lifestyle data to select one as a most likely cause of the detected sleep issue comprises calculating probabilities.

Embodiment 59

The system of any one of Embodiments 51 to 58 wherein the generation of an advice message comprises triggering a push notification.

Embodiment 60

The system of any one of Embodiments 51 to 59 wherein the evaluation of the measured environmental data and the input user lifestyle data to select one as a most likely cause of the detected sleep issue further includes an evaluation of historical sleep data to detect a sleep trend.

Embodiment 61

The system of any one of Embodiments 51 to 60 further comprising one or more processors configured to execute a triage process, the triage process comprising a probability determination based on the detected sleep issue to determine a risky sleep condition, the probability determination comprising calculating a probability of one or more of a risk of sleep apnea, a risk of snoring and a risk of chronic insomnia.

Embodiment 62

The system of Embodiment 61 wherein the triage process triggers generation of a report with information concerning the risky sleep condition to facilitate access to a sleep health specialist.

Embodiment 63

The system of Embodiment 62 wherein the triage process triggers generation of the report based on a comparison of a threshold with a calculated probability value.

Embodiment 64

The system of any one of Embodiments 51 to 63 wherein the one or more processors configured to generate one or more advice messages is further configured to generate the one or more advice messages based on a detected location.

Embodiment 65

The system of Embodiment 64 wherein generated advice message comprises content to promote sleep for jet lag upon detection of a change in time zone.

Embodiment 66

The system of any one of Embodiments 51 to 64 wherein the one or more processors are in at least one server.

Embodiment 67

The system of any one of Embodiments 51 to 64 wherein the one or more processors are in at least one smart device or smart phone.

Embodiment 68

A method for an electronic system to promote sleep with one or more processors, the method comprising any one or more of:
accessing measured data representing user movement detected by a movement sensor;
accessing determined sleep factors with features derived from the measured data;
accessing measured environmental data representing ambient sleep conditions;
accessing input user lifestyle data input on a sleep session-by-sleep session basis;
evaluating the sleep factors to detect a sleep issue;
evaluating with a processor the measured environmental data and the input user lifestyle data to select one as a most likely cause of the detected sleep issue; and
generating one or more electronic advice messages associated with the selected one, the advice messages including advice content for promoting sleep.

Embodiment 69

The method of Embodiment 68 wherein generating one or more advice messages comprises generating a series of advice messages over time consecutively upon continued detection of the sleep issue

Embodiment 70

The method of any one of Embodiments 68 to 69 wherein the environmental data comprises one or more of detected light, detected sound and detected temperature.

Embodiment 71

The method of any one of Embodiments 68 to 70 wherein the sleep factors comprises one or more of: REM sleep time, deep sleep time, and too many sleep interruptions.

Embodiment 72

The method of any one of Embodiments 68 to 71 wherein a detected sleep issue comprises any one or more of a REM time too short condition, a REM time too long condition and a REM time fragmented condition.

Embodiment 73

The method of any one of Embodiments 68 to 72 wherein a detected sleep issue comprises any one or more of a Deep sleep time too short condition, a deep sleep time too long condition and deep sleep time fragmented condition.

Embodiment 74

The method of any one of Embodiments 68 to 73 wherein a detected sleep issue comprises too many interruptions.

Embodiment 75

The method of any one of Embodiments 68 to 74 wherein the evaluating of the measured environmental data and the input user lifestyle data to select one as a most likely cause of the detected sleep issue comprises calculating probabilities.

Embodiment 76

The method of any one of Embodiments 68 to 75 the generating of the advice message comprises triggering a push notification.

Embodiment 77

The method of any one of Embodiments 68 to 76 wherein (a) accessing measured data representing user movement detected by a movement sensor, (b) processing the measured data to determine sleep factors with features derived from the measured data, and (c) prompting for input of user lifestyle data on a sleep session-by-sleep session basis are each executed by processor control instructions of a smart device.

Embodiment 78

The method of any one of Embodiments 68 to 77 wherein (a) evaluating the sleep factors to detect a sleep issue, (b) evaluating the measured environmental data and the input user lifestyle data to select one as a most likely cause of the detected sleep issue and (c) generating one or more advice messages associated with the selected one, are executed by processes of one or more networked servers.

Embodiment 79

The method of any one of Embodiments 68 to 78 wherein evaluation of the measured environmental data and the input user lifestyle data to select one as a most likely cause of the detected sleep issue further includes evaluating historical sleep data to detect a sleep trend.

Embodiment 80

The method of any one of Embodiments 68 to 79 further comprising executing a triage process, the triage process comprising determining probabilities based on the detected sleep issue to determine a risky sleep condition, the determined probabilities comprising a probability of one or more of a risk of sleep apnea, a risk of snoring and a risk of chronic insomnia.

Embodiment 81

The method of Embodiment 80 wherein the triage process triggers generation of a report with information concerning the risky sleep condition to facilitate access to a sleep health specialist.

Embodiment 82

The method of Embodiment 81 wherein the triage process triggers generation of the report based on a comparison of a threshold with a calculated probability value.

Embodiment 83

The method of any one of Embodiments 68 to 82 further comprising generating one or more of the advice messages based on a detected location.

Embodiment 84

The method of Embodiment 83 further comprising detecting a change in time zone with the detected location and wherein a generated advice message comprises content to promote sleep for jet lag upon detection of a change in time zone.

Embodiment 85

The method of any one of Embodiments 68 to 84 wherein the one or more processors are in at least one server or one or more networked servers.

Embodiment 86

The method of any one of Embodiments 68 to 84 wherein the one or more processors are in at least one smart device or one smart phone.

REFERENCES

Åkerstedt, T., Kecklund, G. & Gillberg, M., 2007. Sleep and sleepiness in relation to stress and displaced work hours. Physiology & behavior, 92(1-2), pp. 250-255.

Buysse, D. J., Grunstein, R., Horne, J., & Lavie, P. (2010). Can an improvement in sleep positively impact on health? Sleep Medicine Reviews, 14(6), 405-10.

Dijk, D.-J., 2010. Slow-wave sleep deficiency and enhancement: implications for insomnia and its management. The world journal of biological psychiatry: the official journal of the World Federation of Societies of Biological Psychiatry, 11 Suppl 1, pp. 22-8.

Epstein, L. & Mardon, S., 2006. The Harvard Medical School Guide to a Good Night's Sleep. Available at:

http://www.health.harvard.edu/special_health_reports/improving-sleep-a-guide-to-a-good-nights-rest.

Iber, C. et al., 2007. The AASM manual for the scoring of sleep and associated events: rules, terminology and technical specifications, Westchester, Ill.: American Academy of Sleep Medicine.

O'Brien, J., 2009. First human gene implicated in regulating length of human sleep|ucsfedu. UCSF.

Ostrow, N., 2012. Not enough sleep leads to diabetes and obesity—Independent.ie. Available at: www.independent.ie/lifestyle/health/not-enough-sleep-leads-to-diabetes-and-obesity-26843605 html.

Patel S R, Malhotra A, White D P, Gottlieb D J, Hu F B. Association between reduced sleep and weight gain in women. Am J Epidemiol. 2006; 164:947-54.

Webster, M., 2008. Can You Catch Up on Lost Sleep?—Scientific American. Scientific American.

Young, T., Peppard, P. E. & Gottlieb, D. J., 2002. Epidemiology of obstructive sleep apnea: a population health perspective. American journal of respiratory and critical care medicine, 165(9), pp. 1217-39.

The invention claimed is:

1. A method performed by one or more processors of an electronic system to promote sleep, the method comprising:
    accessing sleep factors determined with features derived from measured data representing user movement;
    accessing measured environmental data representing ambient sleep conditions;
    accessing user lifestyle data obtained by input on a sleep session-by-sleep session basis in response to a lifestyle questionnaire presented to the user;
    evaluating the sleep factors to detect a sleep issue;
    evaluating the measured environmental data and the input user lifestyle data to select one as a most likely cause of the detected sleep issue;
    based on the detected sleep issue, triggering at least one of a plurality of assessment pathways within a triage process for assessing the detected sleep issue for detecting a risky sleep condition; and
    generating electronic advice messages associated with the selected cause, the advice messages comprising a series of different advice messages over time consecutively generated upon continued detection of the sleep issue.

2. The method of claim 1, wherein the environmental data is detected locally to the user and is selected from the group consisting of detected light, detected sound and detected temperature and wherein the sleep factors are selected from the group consisting of sleep latency, REM sleep time, deep sleep time and number of sleep interruptions.

3. The method of claim 1, wherein a detected sleep issue is selected from a group consisting: a REM time too short condition; a REM time too long condition; a REM time fragmented condition; a deep sleep time too short condition; a deep sleep time too long condition; deep sleep time fragmented condition; and too many sleep interruptions.

4. The method of claim 1, wherein the evaluating of the measured environmental data and the input user lifestyle data to select one as a most likely cause of the detected sleep issue comprises calculating probabilities.

5. The method of claim 4, wherein the generating of the advice message comprises triggering a push notification and wherein the method is executed by processes of one or more networked servers.

6. The method of claim 1, wherein the evaluating of the measured environmental data and the input user lifestyle data to select one as a most likely cause of the detected sleep issue further includes evaluating historical sleep data to detect a sleep trend.

7. The method of claim 1, wherein the triage process determines probabilities based on the detected sleep issue to determine the risky sleep condition, the determined probabilities comprising a probability of one or more of a risk of sleep apnea, a risk of snoring and a risk of chronic insomnia.

8. The method of claim 7, wherein the triage process triggers generation of a report based on a comparison of a threshold with a calculated probability value.

9. The method of claim 7, wherein the triage process triggers generation of a report with information concerning the risky sleep condition to facilitate access to a sleep health specialist.

10. The method of claim 1, wherein generating advice messages further comprises generating a further series of advice messages over time consecutively upon continued detection of another sleep issue.

11. The method of claim 1, wherein the measured data is processed, locally or at a remote server, to determine the sleep factors with features derived from the measured data, the method further comprising:
    prompting the user, by way of a local display, for input of user lifestyle data on a sleep session-by-sleep session basis;
    and the generating, at the remote server, of the electronic advice messages comprises the steps of:
        (a) receiving, at the remote server, at least some of at least one of the following types of data: the measured data, data of the determined sleep factors, the measured environmental data and the input user lifestyle data, to facilitate evaluation of the received data and selection of a likely cause, or a most likely cause, of the detected sleep issue, and
        (b) transmitting one or more generated electronic advice messages associated with the selected cause, the advice messages comprising a series of different advice messages over time consecutively generated upon continued detection of the sleep issue; and
    displaying the transmitted electronic advice messages.

12. The method of claim 11, wherein the environmental data comprises one or more of detected light, detected sound and detected temperature, the environmental data being detected locally to the user.

13. The method of claim 11, wherein the sleep factors comprise one or more of: REM sleep time; deep sleep time; too many sleep interruptions; a REM time too short condition; a REM time too short or too long condition; a REM time fragmented condition; a deep sleep time too short condition; a deep sleep time too long condition; and a deep sleep time fragmented condition.

14. The method of claim 11, wherein the evaluation of the measured environmental data and the input user lifestyle data to select one as a most likely cause of the detected sleep issue further includes evaluating historical sleep data to detect a sleep trend.

15. The method of claim 11, further comprising executing, at the remote server, the at least one of a plurality of assessment pathways within the triage process, wherein the triage process determines probabilities based on the detected sleep issue to determine the risky sleep condition, the determined probabilities comprising a probability of one or more of a risk of sleep apnea, a risk of snoring and a risk of chronic insomnia.

16. The method of claim 15, further comprising receiving, at the local display, a report indicative of a result of the triage process, the report with information concerning the risky sleep condition to facilitate access to a sleep health specialist.

17. The method of claim 1, wherein at least one of the advice messages is based on a detected location or on a detected change in location.

18. The method of claim 17, wherein a generated advice message comprises jet lag advice.

19. The method of claim 1, wherein each of the accessing, each of the evaluating and the generating are performed on a remote server.

20. An electronic system to promote sleep comprising one or more processors configured to:
   access sleep factors determined with features derived from measured sleep data representing user movement detected by a movement sensor;
   access measured environmental data representing ambient sleep conditions;
       access input user lifestyle data collected on a sleep session-by-sleep session basis in response to a lifestyle questionnaire presented to the user;
       evaluate the sleep factors to detect a sleep issue;
       evaluate data of the sleep factors, the measured environmental data and the input user lifestyle data, to select a likely cause, or a most likely cause, of the detected sleep issue;
   based on the detected sleep issue, trigger at least one of a plurality of assessment pathways within a triage process for assessing the detected sleep issue for detecting a risky sleep condition;
   generate advice messages associated with the selected cause, the advice messages comprising a series of different advice messages over time consecutively generated upon continued detection of the sleep issue; and
   transmit the generated advice messages to a display device associated with the user and/or control displaying of the generated advice messages on the display device associated with the user.

21. The system of claim 20, wherein the generated advice messages further comprise a further series of advice messages over time consecutively generated upon continued detection of another sleep issue.

22. The system of claim 20, wherein an evaluation of the measured environmental data and the input user lifestyle data to select one as a most likely cause of the detected sleep issue comprises calculating probabilities.

23. The system of claim 22, wherein generation of an advice message comprises triggering a push notification.

24. The system of claim 20, wherein an evaluation of the measured environmental data and the input user lifestyle data to select one as a most likely cause of the detected sleep issue further includes an evaluation of historical sleep data to detect a sleep trend.

25. The system of claim 20, wherein the triage process comprises a probability determination based on the detected sleep issue to determine the risky sleep condition, the probability determination comprising a calculation of a probability of one or more of a risk of sleep apnea, a risk of snoring and a risk of chronic insomnia.

26. The system of claim 25, wherein the triage process triggers generation of a report with information concerning the risky sleep condition to facilitate access to a sleep health specialist.

27. The system of claim 25, wherein the triage process triggers generation of a report based on a comparison of a threshold with a calculated probability value.

28. The system of claim 20, wherein at least one of the generated advice messages is based on a detected location and/or change in location.

29. The system of claim 28, wherein the at least one generated advice message comprises jet lag advice.

30. The system of claim 20, further configured to:
   process the measured sleep data to determine sleep factors with features derived from the measured data, and further comprising
   a transmitter configured to transmit at least some of at least one of: the measured sleep data, data of the determined sleep factors, the measured environmental data and the input user lifestyle data, so as to facilitate evaluation of the transmitted data and selection of a likely cause, or a most likely cause, of the detected sleep issue; and
   a receiver configured to receive one or more advice messages associated with the selected cause, the advice messages comprising a series of different advice messages over time consecutively generated upon continued detection of the sleep issue.

31. The system of claim 30, wherein the measured environmental data comprises one or more of detected light, detected sound and detected temperature.

32. The system of claim 31, wherein the sleep factors comprise one or more of sleep latency, REM sleep time, deep sleep time and number of sleep interruptions.

33. The system of claim 32, wherein a detected sleep issue comprises any one or more of a REM time too short condition, a REM time too long condition, a REM time fragmented condition, a deep sleep time too short condition, a deep sleep time too long condition and a deep sleep time fragmented condition.

34. The system of claim 30, wherein a detected sleep issue is that a user's sleep comprises too many interruptions.

35. The system of claim 30, wherein the evaluation of the measured environmental data and the input user lifestyle data to select one as a most likely cause of the detected sleep issue comprises calculating probabilities.

36. The system of claim 35, wherein generation of an advice message comprises triggering a push notification.

37. The system of claim 30, wherein the selected most likely cause of the detected sleep issue, associated with the received advice, is further based on an evaluation of historical sleep data to detect a sleep trend.

38. The system of claim 30, wherein the one or more processors and the receiver are configured to receive data indicative of a result of the triage process, wherein the triage process comprises a probability determination based on the detected sleep issue to determine a risky sleep condition, the probability determination comprising a calculation of a probability of one or more of a risk of sleep apnea, a risk of snoring and a risk of chronic insomnia.

39. The system of claim 38, wherein the one or more processors and the receiver are further configured to receive a generated report with information concerning the risky sleep condition to facilitate access to a sleep health specialist.

40. The system of claim 30, wherein the one or more processors and the transmitter are further configured to transmit data indicative of a user's location and receive one or more advice messages based on the transmitted location data.

41. The system of claim 40, wherein the received one or more advice messages comprises jet lag advice.

42. The system of claim 20, wherein one or more remote servers are configured to perform the evaluations and the generation of the advice messages, and to transmit the generated advice messages to the display device.

43. The system of claim 20, wherein the display device comprises the one or more processors.

* * * * *